US011371050B2

(12) United States Patent
Cigan et al.

(10) Patent No.: US 11,371,050 B2
(45) Date of Patent: Jun. 28, 2022

(54) RAPID CHARACTERIZATION OF CAS ENDONUCLEASE SYSTEMS, PAM SEQUENCES AND GUIDE RNA ELEMENTS

(71) Applicant: PIONEER HI-BRED INTERNATIONAL, INC., Johnston, IA (US)

(72) Inventors: Andrew Mark Cigan, Madison, WI (US); Giedrius Gasiunas, Vilnius (LT); Tautvydas Karvelis, Vilnius (LT); Virginijus Siksnys, Vilnius (LT); Joshua K Young, Johnston, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 524 days.

(21) Appl. No.: 15/573,862

(22) PCT Filed: May 12, 2016

(86) PCT No.: PCT/US2016/032028
§ 371 (c)(1),
(2) Date: Nov. 14, 2017

(87) PCT Pub. No.: WO2016/186946
PCT Pub. Date: Nov. 24, 2016

(65) Prior Publication Data
US 2018/0258417 A1 Sep. 13, 2018

Related U.S. Application Data

(60) Provisional application No. 62/162,377, filed on May 15, 2015, provisional application No. 62/162,353, filed on May 15, 2015, provisional application No. 62/196,535, filed on Jul. 24, 2015.

(51) Int. Cl.
| | |
|---|---|
| *C12N 15/10* | (2006.01) |
| *C12N 9/22* | (2006.01) |
| *C12N 15/82* | (2006.01) |
| *C12N 15/113* | (2010.01) |
| *C12N 15/90* | (2006.01) |
| *C12Q 1/6811* | (2018.01) |
| *C12N 15/11* | (2006.01) |
| *C40B 20/04* | (2006.01) |
| *C40B 40/06* | (2006.01) |

(52) U.S. Cl.
CPC ........... *C12N 15/8213* (2013.01); *C12N 9/22* (2013.01); *C12N 15/102* (2013.01); *C12N 15/1051* (2013.01); *C12N 15/1093* (2013.01); *C12N 15/11* (2013.01); *C12N 15/113* (2013.01); *C12N 15/902* (2013.01); *C12Q 1/6811* (2013.01); *C12N 2310/20* (2017.05); *C12N 2320/10* (2013.01); *C12N 2800/80* (2013.01); *C40B 20/04* (2013.01); *C40B 40/06* (2013.01)

(58) Field of Classification Search
CPC .. C12N 9/22; C12N 15/1093; C12N 15/1051; C12N 2525/191; C12N 2525/122; C12Q 1/6811
See application file for complete search history.

(56) References Cited

U.S. PATENT DOCUMENTS

| | | | | |
|---|---|---|---|---|
| 8,865,406 B2 * | 10/2014 | Zhang | .................... | C12N 15/63 435/6.1 |
| 9,163,284 B2 | 10/2015 | Liu et al. | | |
| 10,000,772 B2 * | 6/2018 | Doudna | ................. | C12Q 1/686 |
| 2014/0186843 A1 * | 7/2014 | Zhang | ...................... | C12N 9/22 435/6.12 |
| 2015/0044191 A1 * | 2/2015 | Liu | ...................... | C12Q 1/6869 424/94.6 |
| 2015/0045546 A1 * | 2/2015 | Siksnys | .................... | C12N 9/22 536/23.1 |
| 2016/0355795 A1 * | 12/2016 | Ran | ........................ | C12N 15/63 |

FOREIGN PATENT DOCUMENTS

| | | |
|---|---|---|
| WO | 2013/142578 A1 | 9/2013 |
| WO | 2015006294 A2 | 1/2015 |

OTHER PUBLICATIONS

Briner, et al., "Guide RNA Functional Modules Direct Cas9 Activity and Orthogonality", Mol Cell (2014) 56(2):333-339.
Briner, et al., "Guide RNA Functional Modules Direct Cas9 Activity and Orthogonality", Mol Cell (2014) Supplemental Information mmc1.
Leonard, et al., "Complete Genome Sequences of Lactobacillus johnsonii Strain N6.2 and Lactobacillus reuteri Strain TD1", Genome Announcements (2014) 2(3):e00397-14.
Xu, et al., "Efficient genome engineering in eukaryotes using Cas9 from *Streptococcus thermophilus*, Cell Mol Life Sci (2015) 72(2):383-399.
Shah, et al., "Protospacer recognition motifs", RNA Biol (2013) 10(5):891-899.

(Continued)

*Primary Examiner* — Antonio Galisteo Gonzalez

(57) ABSTRACT

Compositions and methods are provided for rapid characterization of Cas endonuclease systems and the elements comprising such systems, including, but not limiting to, rapid characterization of PAM sequences, guide RNA elements and Cas endonucleases. Type II Cas9 endonuclease systems originating from *Brevibacillus laterosporus*, *Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis*, *Sphingomonas sanxanigenens* NX02, *Epilithonimonas tenax* DSM 16811, *Sporocytophaga myxococcoides* are described herein. The present disclosure also describes methods for genome modification of a target sequence in the genome of a cell, for gene editing, and for inserting a polynucleotide of interest into the genome of a cell.

10 Claims, 50 Drawing Sheets
Specification includes a Sequence Listing.

(56) References Cited

OTHER PUBLICATIONS

Karvelis, et al., "Rapid characterization of CRISPR_Cas9 protospacer adjacent motif sequence elements", Genome Biol (2015) 30(1):1335.
Xue, et al., "CRISPR interference and priming varies with individual spacer sequences", Nucl Acids Res (2015) 43(22):10831-10847.
Leenay, et al., "Identifying and Visualizing Functional PAM Diversity across CRISPR-Cas Systems", Mol Cell (2016) 62(1):137-147.
Leenay, et al., "Identifying and Visualizing Functional PAM Diversity across CRISPR-Cas Systems", Mol Cell (2016) 62(1):Supplemental Information mmc1.
NCBI Reference Sequence WP_019251774.1.
ISR and Written Opinion for PCT/US16/32028 dated Oct. 14, 2016.
Briner, et al., "Guide RNA Functional Modules Direct Cas9 Activity and Orthogonality", Mol Cell (2014) Supplemental Information mmc2.
Briner, et al., "Guide RNA Functional Modules Direct Cas9 Activity and Orthogonality", Mol Cell (2014) Supplemental Information mmc3.
Xu, et al., Efficient genome engineering in eukaryotes using Cas9 from *Streptococcus thermophilus*, Cell Mol Life Sci (2015) Supplemental Information.
Leenay, et al., "Identifying and Visualizing Functional PAM Diversity across CRISPR-Cas Systems", Mol Cell (2016) 62(1):Supplemental Information mmc2.
Leenay, et al., "Identifying and Visualizing Functional PAM Diversity across CRISPR-Cas Systems", Mol Cell (2016) 62(1):Supplemental Information mmc4.
Leenay, et al., "Identifying and Visualizing Functional PAM Diversity across CRISPR-Cas Systems", Mol Cell (2016) 62(1):Supplemental Information mmc5.
Leenay, et al., "Identifying and Visualizing Functional PAM Diversity across CRISPR-Cas Systems", Mol Cell (2016) 62(1):Supplemental Information mmc6.

\* cited by examiner

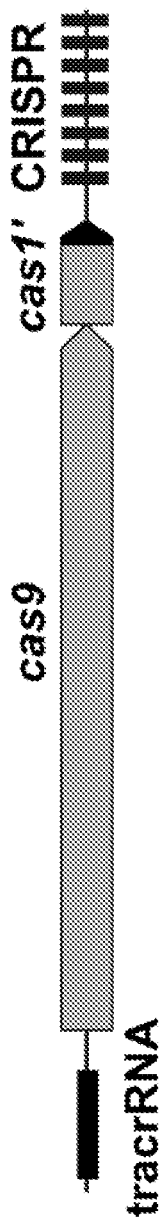

| | | |
|---|---|---|
| Repeat1 | ATCATATCATATATCGAGTTTTAGTAAGGAACTATAGC | SEQ ID NO: 37 |
| Repeat2 | ATCATATCATATATCGAGCTTTAGTAAGGAACTATAGC | SEQ ID NO: 38 |
| Repeat3 | ATCATATCATATATCGAGTTTTAGTAAGGAACCATAGC | SEQ ID NO: 39 |
| Repeat4 | ATCATATCATATATCGAGTTTTAGTAAGGAACTATAGC | SEQ ID NO: 40 |
| Repeat5 | ATCATATCATATATCGAGTTTTAGTAAGGAACTATAGC | SEQ ID NO: 41 |
| Repeat6 | ATCATATCATATATCGAGCTTCAGTAAGGAACTATAGC | SEQ ID NO: 42 |
| Repeat7 | ATCATATCATATCATAAGCTTTAGTAAGGAACTATAGC | SEQ ID NO: 43 |
| Repeat8 | ATCATATCATATATCGAGTTTTAGTAAGGAACTATAGT | SEQ ID NO: 44 |

SEQ ID NO: 68

SEQ ID NO: 69

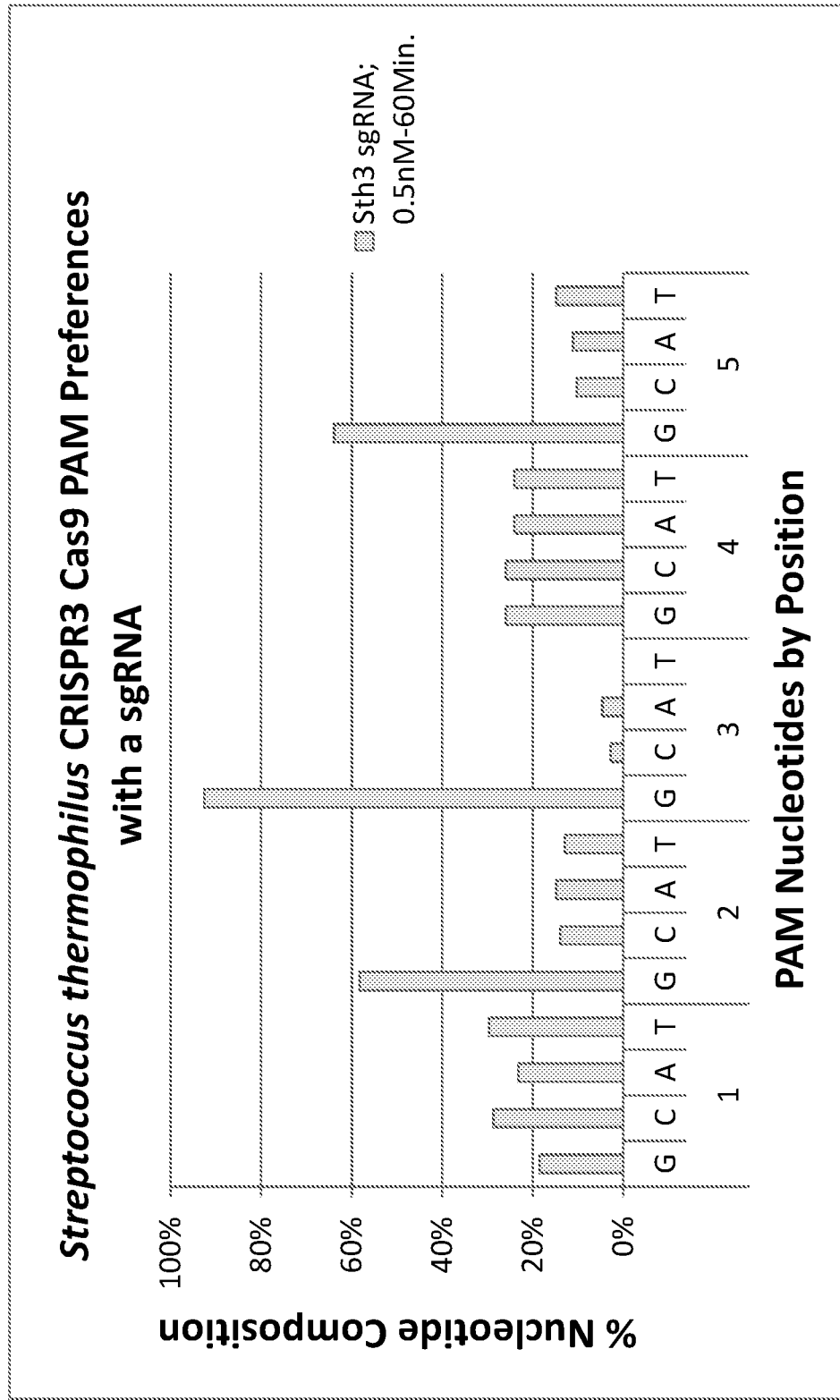

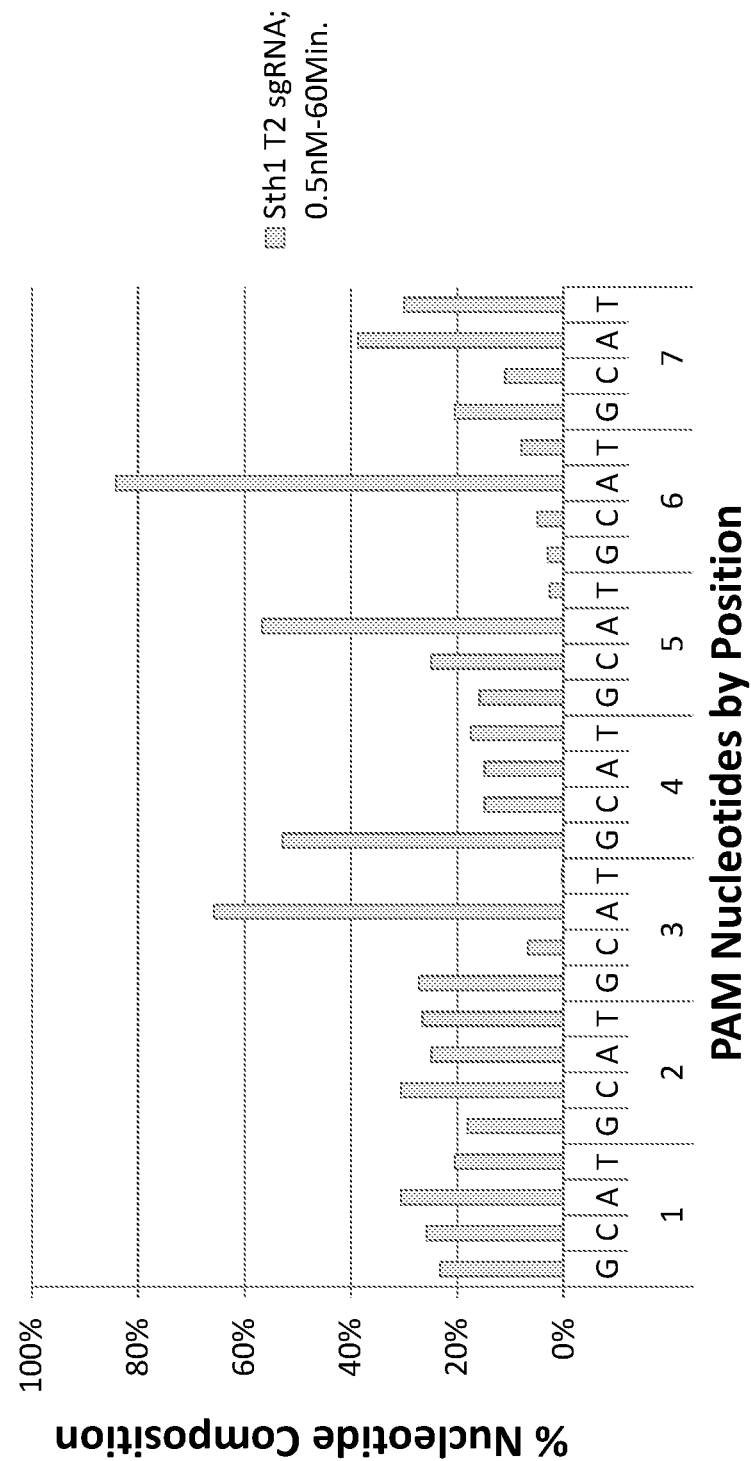

SEQ ID NO: 152

Figure 43

| | Sequence | Frequency in Treated | Frequency in Control | SEQ ID NO: |
|---|---|---|---|---|
| Reference | CCTTGACCAGGATAATGAGGTACTGGCTGGAAGGCCCAAGAGCGGGCGAGGTAGAGGTGTTCGCGAACCTGCC | | | 154 |
| Mutation 1 | CTTGACCAGGATAATGAGGTACTGGCTtGGAAGGCCCAAGAGCGGGCGAGGTAGAGGTGTTCGCGAACCTGCC | 4,553 | 0 | 155 |
| Mutation 2 | CTTGACCAGGATAATGAGGTACTGGCTaGGAAGGCCCAAGAGCGGGCGAGGTAGAGGTGTTCGCGAACCTGCC | 1,110 | 0 | 156 |
| Mutation 3 | CTTGACCAGGATAATGAGGTACTGGCTgGGAAGGCCCAAGAGCGGGCGAGGTAGAGGTGTTCGCGAACCTGCC | 281 | 0 | 157 |
| Mutation 4 | CTTGACCAGGATAATGAGGTACTGGCTcGGAAGGCCCAAGAGCGGGCGAGGTAGAGGTGTTCGCGAACCTGCC | 120 | 0 | 158 |
| Mutation 5 | CCTTGACCAGGATAATGAGGTACTGGC-GGAAGGCCCAAGAGCGGGCGAGGTAGAGGTGTTCGCGAACCTGCC | 119 | 0 | 159 |
| Mutation 6 | TTGACCAGGATAATGAGGTACTGGCTtGGAAGGCCCAAGAGCGGGCGAGGTAGAGGTGTTCGCGAACCTGCC | 112 | 0 | 160 |
| Mutation 7 | CTTGACCAGGATAATGAGGTACTGCGCTGGAAGGCCCAAGAGCGGGCGAGGTAGAGGTGTTCGCGAACCTGCC | 111 | 0 | 161 |
| Mutation 8 | CCTTGACCAGGATAATGAGGTACTGGCT--AAGGCCCAAGAGCGGGCGAGGTAGAGGTGTTCGCGAACCTGCC | 87 | 0 | 162 |
| Mutation 9 | CCTTGACCAGGATAAT-----------------------GAGGTAGAGGTGTTCGCGAACCTGCC | 79 | 0 | 163 |
| Mutation 10 | CCTTGACCAGGATAATGAGGTACT-------GGCCCAAGAGCGGGCGAGGTAGAGGTGTTCGCGAACCTGCC | 63 | 0 | 164 |
| | Total Read Depth | 450,873 | 755,448 | |

Figure 44

| | Sequence | Frequency in Treated | Frequency in Control | SEQ ID NO: |
|---|---|---|---|---|
| Reference | CCTTGACCAGGATAATGAGGTACTGGCTGGAAGGCCCAAGAGAGCGGGCGAGGTAGAGGTGTTCGCGAACCTGCC | | | 154 |
| Mutation 1 | CTTTGACCAGGATAATGAGGTACTGGCTtGGAAGGCCCAAGAGAGCGGGCGAGGTAGAGGTGTTCGCGAACCTGCC | 2,807 | 0 | 165 |
| Mutation 2 | CCTTGACCAGGATAATGAGGTACTGGC-GGAAGGCCCAAGAGAGCGGGCGAGGTAGAGGTGTTCGCGAACCTGCC | 579 | 2 | 166 |
| Mutation 3 | CCTTGACCAGGATAATGAGGTAC----TGGAAGGCCCAAGAGAGCGGGCGAGGTAGAGGTGTTCGCGAACCTGCC | 130 | 0 | 167 |
| Mutation 4 | CCTTGACCAGGATAATGAGGTACTGG-TGGAAGGCCCAAGAGAGCGGGCGAGGTAGAGGTGTTCGCGAACCTGCC | 92 | 0 | 168 |
| Mutation 5 | CTTTGACCAGGATAATGAGGTACTGGCgTGGAAGGCCCAAGAGAGCGGGCGAGGTAGAGGTGTTCGCGAACCTGCC | 85 | 0 | 169 |
| Mutation 6 | CCTTGACCAGGATAATGAGGTACT-------GGCGAGGTAGAGGTGTTCGCGAACCTGCC | 63 | 0 | 170 |
| Mutation 7 | CCTTGACCAGGATAAT------------GAGGTAGAGGTGTTCGCGAACCTGCC | 60 | 0 | 171 |
| Mutation 8 | CCTTGACCAGGATAATGAGGTAC-----GGAAGGCCCAAGAGAGCGGGCGAGGTAGAGGTGTTCGCGAACCTGCC | 48 | 0 | 172 |
| Mutation 9 | CTTTGACCAGGATAATGAGGTACTGGCTaGGAAGGCCCAAGAGAGCGGGCGAGGTAGAGGTGTTCGCGAACCTGCC | 34 | 0 | 173 |
| Mutation 10 | CCTTGACCAGGATAATGAGGTA------GGAAGGCCCAAGAGAGCGGGCGAGGTAGAGGTGTTCGCGAACCTGCC | 33 | 0 | 174 |
| | Total Read Depth | 446,634 | 828,936 | |

SEQUENCE LISTING

```
<160> NUMBER OF SEQ ID NOS: 236

<210> SEQ ID NO 1
<211> LENGTH: 20
<212> TYPE: DNA
<213> ORGANISM: Artificial Sequence
<220> FEATURE:
<223> OTHER INFORMATION: synthesized T1 sequence

<400> SEQUENCE: 1
cgctaaagag gaagaggaca                                                20

<210> SEQ ID NO 2
<211> LENGTH: 47
<212> TYPE: DNA
<213> ORGANISM: Artificial Sequence
<220> FEATURE:
<223> OTHER INFORMATION: synthesized GG-821N
<220> FEATURE:
<221> NAME/KEY: misc_feature
<222> LOCATION: (20)..(24)
<223> OTHER INFORMATION: n is a, c, g, or t

<400> SEQUENCE: 2
tgaccatgat tacgaattcn nnnntgtcct cttcctcttt agcgagc              47

<210> SEQ ID NO 3
<211> LENGTH: 44
<212> TYPE: DNA
<213> ORGANISM: Artificial Sequence
<220> FEATURE:
<223> OTHER INFORMATION: synthesized GG-820

<400> SEQUENCE: 3
aaggatcccc gggtaccgag ctgctcgcta aagaggaaga ggac                 44

<210> SEQ ID NO 4
<211> LENGTH: 22
<212> TYPE: DNA
<213> ORGANISM: Artificial Sequence
<220> FEATURE:
<223> OTHER INFORMATION: synthesized sequence TK-119

<400> SEQUENCE: 4
gagctcgcta aagaggaaga gg                                         22

<210> SEQ ID NO 5
<211> LENGTH: 22
<212> TYPE: DNA
<213> ORGANISM: Artificial Sequence
```

```
<220> FEATURE:
<223> OTHER INFORMATION: synthesized sequence pUC-dir

<400> SEQUENCE: 5
gccagggttt tcccagtcac ga                                         22

<210> SEQ ID NO 6
<211> LENGTH: 59
<212> TYPE: DNA
<213> ORGANISM: Artificial Sequence
<220> FEATURE:
<223> OTHER INFORMATION: synthesized sequence JKYS800.1

<400> SEQUENCE: 6
ctacactctt tccctacacg acgctcttcc gatctaagtg agctcgctaa agaggaaga  59

<210> SEQ ID NO 7
<211> LENGTH: 53
<212> TYPE: DNA
<213> ORGANISM: Artificial Sequence
<220> FEATURE:
<223> OTHER INFORMATION: synthesized sequence JKYS803

<400> SEQUENCE: 7
caagcagaag acggcatacg agctcttccg atctgaattc gagctcggta cct        53

<210> SEQ ID NO 8
<211> LENGTH: 43
<212> TYPE: DNA
<213> ORGANISM: Artificial Sequence
<220> FEATURE:
<223> OTHER INFORMATION: synthesized sequence Universal Forward

<400> SEQUENCE: 8
aatgatacgg cgaccaccga gatctacact ctttccctac acg                   43

<210> SEQ ID NO 9
<211> LENGTH: 18
<212> TYPE: DNA
<213> ORGANISM: Artificial Sequence
<220> FEATURE:
<223> OTHER INFORMATION: synthesized sequence Universal Reverse

<400> SEQUENCE: 9
caagcagaag acggcata                                               18

<210> SEQ ID NO 10
<211> LENGTH: 34
<212> TYPE: DNA
<213> ORGANISM: Artificial Sequence
<220> FEATURE:
<223> OTHER INFORMATION: synthesized sequence Sth1-dir

<400> SEQUENCE: 10
acgtctcaca tgactaagcc atactcaatt ggac                             34

<210> SEQ ID NO 11
<211> LENGTH: 27
<212> TYPE: DNA
<213> ORGANISM: Artificial Sequence
<220> FEATURE:
<223> OTHER INFORMATION: synthesized sequence Sth1-rev

<400> SEQUENCE: 11
actcgagacc ctctcctagt ttggcaa                                     27
```

```
<210> SEQ ID NO 12
<211> LENGTH: 26
<212> TYPE: DNA
<213> ORGANISM: Artificial Sequence
<220> FEATURE:
<223> OTHER INFORMATION: synthesized sequence Sth3-dir

<400> SEQUENCE: 12 gggggtctc acatgagtga cttagt                                        26

<210> SEQ ID NO 13
<211> LENGTH: 30
<212> TYPE: DNA
<213> ORGANISM: Artificial Sequence
<220> FEATURE:
<223> OTHER INFORMATION: synthesized sequence Sth3-rev

<400> SEQUENCE: 13
aattactcga gaaaatctag cttaggctta                                   30

<210> SEQ ID NO 14
<211> LENGTH: 38
<212> TYPE: DNA
<213> ORGANISM: Artificial Sequence
<220> FEATURE:
<223> OTHER INFORMATION: synthesized sequence Spy-dir

<400> SEQUENCE: 14
aaggtctccc atggataaga aatactcaat aggcttag                          38

<210> SEQ ID NO 15
<211> LENGTH: 32
<212> TYPE: DNA
<213> ORGANISM: Artificial Sequence
<220> FEATURE:
<223> OTHER INFORMATION: synthesized sequence Spy-rev

<400> SEQUENCE: 15
ttctcgaggt cacctcctag ctgactcaaa tc                                32

<210> SEQ ID NO 16
<211> LENGTH: 42
<212> TYPE: RNA
<213> ORGANISM: Streptococcus thermophilus

<400> SEQUENCE: 16
cgcuaaagag gaagaggaca guuuuagagc uguuuguuu cg                     42

<210> SEQ ID NO 17
<211> LENGTH: 78
<212> TYPE: RNA
<213> ORGANISM: Streptococcus thermophilus

<400> SEQUENCE: 17
gggcgaaaca acacagcgag uuaaaauaag gcuuaguccg uacucaacuu gaaaaggugg  60
caccgauucg guguuuuu                                                78

<210> SEQ ID NO 18
<211> LENGTH: 42
<212> TYPE: RNA
<213> ORGANISM: Streptococcus pyogenes

<400> SEQUENCE: 18
cgcuaaagag gaagaggaca guuuuagagc uaugcuguuu ug                    42
```

<210> SEQ ID NO 19
<211> LENGTH: 78
<212> TYPE: RNA
<213> ORGANISM: Streptococcus pyogenes

<400> SEQUENCE: 19
gggaaacagc auagcaaguu aaaauaaggc uaguccguua ucaacuugaa aaaguggcac    60
cgagucggug cuuuuuuu                                                  78

<210> SEQ ID NO 20
<211> LENGTH: 31
<212> TYPE: DNA
<213> ORGANISM: Artificial Sequence
<220> FEATURE:
<223> OTHER INFORMATION: synthesized sequence TK-117

<400> SEQUENCE: 20
cggcattcct gctgaaccgc tcttccgatc t                                   31

<210> SEQ ID NO 21
<211> LENGTH: 30
<212> TYPE: DNA
<213> ORGANISM: Artificial Sequence
<220> FEATURE:
<223> OTHER INFORMATION: synthesized sequence TK-111

<400> SEQUENCE: 21
gatcggaaga gcggttcagc aggaatgccg                                     30

<210> SEQ ID NO 22
<211> LENGTH: 56
<212> TYPE: DNA
<213> ORGANISM: Artificial Sequence
<220> FEATURE:
<223> OTHER INFORMATION: synthesized sequence JKYS807.1

<400> SEQUENCE: 22
ctacactctt tccctacacg acgctcttcc gatctaaggc ggcattcctg ctgaac        56

<210> SEQ ID NO 23
<211> LENGTH: 56
<212> TYPE: DNA
<213> ORGANISM: Artificial Sequence
<220> FEATURE:
<223> OTHER INFORMATION: synthesized sequence JKYS807.2

<400> SEQUENCE: 23
ctacactctt tccctacacg acgctcttcc gatctttccc ggcattcctg ctgaac        56

<210> SEQ ID NO 24
<211> LENGTH: 56
<212> TYPE: DNA
<213> ORGANISM: Artificial Sequence
<220> FEATURE:
<223> OTHER INFORMATION: synthesized sequence JKYS807.3

<400> SEQUENCE: 24
ctacactctt tccctacacg acgctcttcc gatctggaac ggcattcctg ctgaac        56

<210> SEQ ID NO 25
<211> LENGTH: 56
<212> TYPE: DNA
<213> ORGANISM: Artificial Sequence
<220> FEATURE:

```
<223> OTHER INFORMATION: synthesized sequence JKYS807.4

<400> SEQUENCE: 25
ctacactctt tccctacacg acgctcttcc gatctccttc ggcattcctg ctgaac        56

<210> SEQ ID NO 26
<211> LENGTH: 123
<212> TYPE: RNA
<213> ORGANISM: Artificial Sequence
<220> FEATURE:
<223> OTHER INFORMATION: synthesized sequence Sth3 sgRNA

<400> SEQUENCE: 26
gggcgcuaaa gaggaagagg acaguuuuag agcuguguug uuucgguuaa aacaacacag    60
cgaguuaaaa uaaggcuuag uccguacuca acuugaaaag guggcaccga uucggguguuu  120 uuu                                                                 123

<210> SEQ ID NO 27
<211> LENGTH: 105
<212> TYPE: RNA
<213> ORGANISM: Artificial Sequence
<220> FEATURE:
<223> OTHER INFORMATION: synthesized sequence Spy sgRNA

<400> SEQUENCE: 27
gggcgcuaaa gaggaagagg acaguuuuag agcuagaaau agcaaguuaa aauaaggcua    60
guccguuauc aacuugaaaa aguggcaccg agucggugcu uuuuu                   105

<210> SEQ ID NO 28
<211> LENGTH: 59
<212> TYPE: DNA
<213> ORGANISM: Artificial Sequence
<220> FEATURE:
<223> OTHER INFORMATION: synthesized sequence GG-940-G
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(34)
<223> OTHER INFORMATION: n is a, c, g, or t

<400> SEQUENCE: 28
gtgcacgccg gcgacgttgg gtcaactnng nnnntgtcct cttcctcttt agcgtttag    59

<210> SEQ ID NO 29
<211> LENGTH: 59
<212> TYPE: DNA
<213> ORGANISM: Artificial Sequence
<220> FEATURE:
<223> OTHER INFORMATION: synthesized sequence GG-940-C
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(34)
<223> OTHER INFORMATION: n is a, c, g, or t

<400> SEQUENCE: 29
gtgcacgccg gcgacgttgg gtcaactnnc nnnntgtcct cttcctcttt agcgtttag    59

<210> SEQ ID NO 30
<211> LENGTH: 59
```

```
<212> TYPE: DNA
<213> ORGANISM: Artificial Sequence
<220> FEATURE:
<223> OTHER INFORMATION: synthesized sequence GG-940-A
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(34)
<223> OTHER INFORMATION: n is a, c, g, or t

<400> SEQUENCE: 30
gtgcacgccg gcgacgttgg gtcaactnna nnnntgtcct cttcctcttt agcgtttag      59

<210> SEQ ID NO 31
<211> LENGTH: 59
<212> TYPE: DNA
<213> ORGANISM: Artificial Sequence
<220> FEATURE:
<223> OTHER INFORMATION: synthesized sequence GG-940-T
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(34)
<223> OTHER INFORMATION: n is a, c, g, or t

<400> SEQUENCE: 31
gtgcacgccg gcgacgttgg gtcaactnnt nnnntgtcct cttcctcttt agcgtttag      59

<210> SEQ ID NO 32
<211> LENGTH: 49
<212> TYPE: DNA
<213> ORGANISM: Artificial Sequence
<220> FEATURE:
<223> OTHER INFORMATION: synthesized sequence JKYS812

<400> SEQUENCE: 32
caagcagaag acggcatacg agctcttccg atctcggcga cgttgggtc                49

<210> SEQ ID NO 33
<211> LENGTH: 42
<212> TYPE: RNA
<213> ORGANISM: Streptococcus thermophilus

<400> SEQUENCE: 33
cgcuaaagag gaagaggaca guuuuguac ucucaagauu ua                        42

<210> SEQ ID NO 34
<211> LENGTH: 80
<212> TYPE: RNA
<213> ORGANISM: Streptococcus thermophilus

<400> SEQUENCE: 34
ggguaaaucu ugcagaagcu acaaagauaa ggcuucaugc cgaaaucaac acccugucau    60
uuuauggcag gguguuuucg                                                 80

<210> SEQ ID NO 35
<211> LENGTH: 1388
<212> TYPE: PRT
<213> ORGANISM: Streptococcus thermophilus

<400> SEQUENCE: 35
```

```
Met Thr Lys Pro Tyr Ser Ile Gly Leu Asp Ile Gly Thr Asn Ser Val
1               5                   10                  15

Gly Trp Ala Val Ile Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
            35                  40                  45

Gly Val Leu Leu Phe Asp Ser Gly Ile Thr Ala Glu Gly Arg Arg Leu
50                  55                  60

Lys Arg Thr Ala Arg Arg Tyr Thr Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
                100                 105                 110

Asp Ser Lys Tyr Pro Ile Phe Gly Asn Leu Val Glu Glu Lys Val Tyr
            115                 120                 125

His Asp Glu Phe Pro Thr Ile Tyr His Leu Arg Lys Tyr Leu Ala Asp
            130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
            195                 200                 205

Glu Glu Ile Val Lys Asp Lys Ile Ser Lys Leu Glu Lys Lys Asp Arg
            210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Cys Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Asp Tyr Ser Asp
            275                 280                 285

Val Phe Leu Lys Ala Lys Lys Leu Tyr Asp Ala Ile Leu Leu Ser Gly
            290                 295                 300

Phe Leu Thr Val Thr Asp Asn Glu Thr Glu Ala Pro Leu Ser Ser Ala
305                 310                 315                 320

Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
            340                 345                 350

Asp Asp Thr Lys Asn Gly Tyr Ala Gly Tyr Ile Asp Gly Lys Thr Asn
            355                 360                 365

Gln Glu Asp Phe Tyr Val Tyr Leu Lys Asn Leu Leu Ala Glu Phe Glu
            370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
```

```
                420             425             430
Leu Ala Lys Asn Lys Glu Arg Ile Glu Lys Ile Leu Thr Phe Arg Ile
            435             440             445
Pro Tyr Tyr Val Gly Pro Leu Ala Arg Gly Asn Ser Asp Phe Ala Trp
        450             455             460
Ser Ile Arg Lys Arg Asn Glu Lys Ile Thr Pro Trp Asn Phe Glu Asp
465             470             475             480
Val Ile Asp Lys Glu Ser Ser Ala Glu Ala Phe Ile Asn Arg Met Thr
                485             490             495
Ser Phe Asp Leu Tyr Leu Pro Glu Gly Lys Val Leu Pro Lys His Ser
            500             505             510
Leu Leu Tyr Glu Thr Phe Asn Val Tyr Asn Glu Leu Thr Lys Val Arg
        515             520             525
Phe Ile Ala Glu Ser Met Arg Asp Tyr Gln Phe Leu Asp Ser Lys Gln
        530             535             540
Lys Lys Asp Ile Val Arg Leu Tyr Phe Lys Asp Lys Arg Lys Val Thr
545             550             555             560
Asp Lys Asp Ile Ile Glu Tyr Leu His Ala Ile Tyr Gly Tyr Asp Gly
                565             570             575
Ile Glu Leu Lys Gly Ile Glu Lys Gln Phe Asn Ser Ser Leu Ser Thr
            580             585             590
Tyr His Asp Leu Leu Asn Ile Ile Asn Asp Lys Glu Phe Leu Asp Asp
        595             600             605
Ser Ser Asn Glu Ala Ile Ile Glu Ile Ile His Thr Leu Thr Ile
        610             615             620
Phe Glu Asp Arg Glu Met Ile Lys Gln Arg Leu Ser Lys Phe Glu Asn
625             630             635             640
Ile Phe Asp Lys Ser Val Leu Lys Lys Leu Ser Arg Arg His Tyr Thr
                645             650             655
Gly Trp Gly Lys Leu Ser Ala Lys Leu Ile Asn Gly Ile Arg Asp Glu
            660             665             670
Lys Ser Gly Asn Thr Ile Leu Asp Tyr Leu Ile Asp Asp Gly Ile Ser
        675             680             685
Asn Arg Asn Phe Met Gln Leu Ile His Asp Asp Ala Leu Ser Phe Lys
        690             695             700
Lys Lys Ile Gln Lys Ala Gln Ile Ile Gly Asp Glu Asp Lys Gly Asn
705             710             715             720
Ile Lys Glu Val Val Lys Ser Leu Pro Gly Ser Pro Ala Ile Lys Lys
                725             730             735
Gly Ile Leu Gln Ser Ile Lys Ile Val Asp Glu Leu Val Lys Val Met
            740             745             750
Gly Gly Arg Lys Pro Glu Ser Ile Val Glu Met Ala Arg Glu Asn
        755             760             765
Gln Tyr Thr Asn Gln Gly Lys Ser Asn Ser Gln Gln Arg Leu Lys Arg
        770             775             780
Leu Glu Lys Ser Leu Lys Glu Leu Gly Ser Lys Ile Leu Lys Glu Asn
785             790             795             800
Ile Pro Ala Lys Leu Ser Lys Ile Asp Asn Asn Ala Leu Gln Asn Asp
                805             810             815
Arg Leu Tyr Leu Tyr Tyr Leu Gln Asn Gly Lys Asp Met Tyr Thr Gly
            820             825             830
Asp Asp Leu Asp Ile Asp Arg Leu Ser Asn Tyr Asp Ile Asp His Ile
        835             840             845
```

```
Ile Pro Gln Ala Phe Leu Lys Asp Asn Ser Ile Asp Asn Lys Val Leu
    850                 855                 860

Val Ser Ser Ala Ser Asn Arg Gly Lys Ser Asp Asp Phe Pro Ser Leu
865                 870                 875                 880

Glu Val Val Lys Lys Arg Lys Thr Phe Trp Tyr Gln Leu Leu Lys Ser
                885                 890                 895

Lys Leu Ile Ser Gln Arg Lys Phe Asp Asn Leu Thr Lys Ala Glu Arg
                900                 905                 910

Gly Gly Leu Leu Pro Glu Asp Lys Ala Gly Phe Ile Gln Arg Gln Leu
            915                 920                 925

Val Glu Thr Arg Gln Ile Thr Lys His Val Ala Arg Leu Leu Asp Glu
    930                 935                 940

Lys Phe Asn Asn Lys Lys Asp Glu Asn Asn Arg Ala Val Arg Thr Val
945                 950                 955                 960

Lys Ile Ile Thr Leu Lys Ser Thr Leu Val Ser Gln Phe Arg Lys Asp
                965                 970                 975

Phe Glu Leu Tyr Lys Val Arg Glu Ile Asn Asp Phe His His Ala His
                980                 985                 990

Asp Ala Tyr Leu Asn Ala Val Ile Ala Ser Ala Leu Leu Lys Lys Tyr
            995                 1000                1005

Pro Lys Leu Glu Pro Glu Phe Val Tyr Gly Asp Tyr Pro Lys Tyr
    1010                1015                1020

Asn Ser Phe Arg Glu Arg Lys Ser Ala Thr Glu Lys Val Tyr Phe
    1025                1030                1035

Tyr Ser Asn Ile Met Asn Ile Phe Lys Lys Ser Ile Ser Leu Ala
    1040                1045                1050

Asp Gly Arg Val Ile Glu Arg Pro Leu Ile Glu Val Asn Glu Glu
    1055                1060                1065

Thr Gly Glu Ser Val Trp Asn Lys Glu Ser Asp Leu Ala Thr Val
    1070                1075                1080

Arg Arg Val Leu Ser Tyr Pro Gln Val Asn Val Val Lys Lys Val
    1085                1090                1095

Glu Glu Gln Asn His Gly Leu Asp Arg Gly Lys Pro Lys Gly Leu
    1100                1105                1110

Phe Asn Ala Asn Leu Ser Ser Lys Pro Lys Pro Asn Ser Asn Glu
    1115                1120                1125

Asn Leu Val Gly Ala Lys Glu Tyr Leu Asp Pro Lys Lys Tyr Gly
    1130                1135                1140

Gly Tyr Ala Gly Ile Ser Asn Ser Phe Ala Val Leu Val Lys Gly
    1145                1150                1155

Thr Ile Glu Lys Gly Ala Lys Lys Lys Ile Thr Asn Val Leu Glu
    1160                1165                1170

Phe Gln Gly Ile Ser Ile Leu Asp Arg Ile Asn Tyr Arg Lys Asp
    1175                1180                1185

Lys Leu Asn Phe Leu Leu Glu Lys Gly Tyr Lys Asp Ile Glu Leu
    1190                1195                1200

Ile Ile Glu Leu Pro Lys Tyr Ser Leu Phe Glu Leu Ser Asp Gly
    1205                1210                1215

Ser Arg Arg Met Leu Ala Ser Ile Leu Ser Thr Asn Asn Lys Arg
    1220                1225                1230

Gly Glu Ile His Lys Gly Asn Gln Ile Phe Leu Ser Gln Lys Phe
    1235                1240                1245
```

| Val | Lys | Leu | Leu | Tyr | His | Ala | Lys | Arg | Ile | Ser | Asn | Thr | Ile | Asn |
|---|---|---|---|---|---|---|---|---|---|---|---|---|---|---|
| 1250 | | | | | 1255 | | | | | 1260 | | | | |

| Glu | Asn | His | Arg | Lys | Tyr | Val | Glu | Asn | His | Lys | Lys | Glu | Phe | Glu |
|---|---|---|---|---|---|---|---|---|---|---|---|---|---|---|
| 1265 | | | | | 1270 | | | | | 1275 | | | | |

| Glu | Leu | Phe | Tyr | Tyr | Ile | Leu | Glu | Phe | Asn | Glu | Asn | Tyr | Val | Gly |
|---|---|---|---|---|---|---|---|---|---|---|---|---|---|---|
| 1280 | | | | | 1285 | | | | | 1290 | | | | |

| Ala | Lys | Lys | Asn | Gly | Lys | Leu | Leu | Asn | Ser | Ala | Phe | Gln | Ser | Trp |
|---|---|---|---|---|---|---|---|---|---|---|---|---|---|---|
| 1295 | | | | | 1300 | | | | | 1305 | | | | |

| Gln | Asn | His | Ser | Ile | Asp | Glu | Leu | Cys | Ser | Ser | Phe | Ile | Gly | Pro |
|---|---|---|---|---|---|---|---|---|---|---|---|---|---|---|
| 1310 | | | | | 1315 | | | | | 1320 | | | | |

| Thr | Gly | Ser | Glu | Arg | Lys | Gly | Leu | Phe | Glu | Leu | Thr | Ser | Arg | Gly |
|---|---|---|---|---|---|---|---|---|---|---|---|---|---|---|
| 1325 | | | | | 1330 | | | | | 1335 | | | | |

| Ser | Ala | Ala | Asp | Phe | Glu | Phe | Leu | Gly | Val | Lys | Ile | Pro | Arg | Tyr |
|---|---|---|---|---|---|---|---|---|---|---|---|---|---|---|
| 1340 | | | | | 1345 | | | | | 1350 | | | | |

| Arg | Asp | Tyr | Thr | Pro | Ser | Ser | Leu | Leu | Lys | Asp | Ala | Thr | Leu | Ile |
|---|---|---|---|---|---|---|---|---|---|---|---|---|---|---|
| 1355 | | | | | 1360 | | | | | 1365 | | | | |

| His | Gln | Ser | Val | Thr | Gly | Leu | Tyr | Glu | Thr | Arg | Ile | Asp | Leu | Ala |
|---|---|---|---|---|---|---|---|---|---|---|---|---|---|---|
| 1370 | | | | | 1375 | | | | | 1380 | | | | |

| Lys | Leu | Gly | Glu | Gly |
|---|---|---|---|---|
| 1385 | | | | |

<210> SEQ ID NO 36
<211> LENGTH: 3279
<212> TYPE: DNA
<213> ORGANISM: Brevibacillus laterosporus
<220> FEATURE:
<221> NAME/KEY: misc_feature
<222> LOCATION: (1)..(3279)
<223> OTHER INFORMATION: Cas9 single long open-reading-frame

<400> SEQUENCE: 36

```
atggcataca caatgggaat agatgtgggg attgcttcgt gtggatgggc cattgtagat      60
cttgaaagac aacgaataat agatataggt gttcgaactt ttgagaaagc agagaatccg     120
aaaaatggag aggctcttgc tgttccaagg agagaagcta gatcaagccg taggagatta     180
cggagaaaaa aacatcgcat tgaaagatta aagcatatgt ttgttcggaa tggactggcg     240
gttgatattc aacatcttga gcagacgtta cgtagtcaaa atgaaataga gtatggcaa      300
ttacgagtag atggtttgga tcgaatgtta actcaaaaag agtggcttcg tgtattaatt     360
catcttgcac aacgtcgtgg ttttcaatca atcgaaaaa cagatggttc aagtgaagat      420
ggacaggttc ttgtaaatgt aacggagaat gacagattaa tggaagagaa agattataga     480
accgtagcgg aaatgatggt aaaagatgaa aaattttctg accataagcg aaataaaaat     540
ggaaattatc atggagtagt gagcagatct tctttactag ttgaaataca tacattattt     600
gaaacccaaa gacagcacca taattctttg gcatcgaaag atttcgagct ggaatatgtt     660
aatatttggt ctgcacaacg gcctgttgca acaaaagatc aaatagaaaa atgattggt      720
acatgtactt tcttaccgaa agaaaagaga gctccaaagg catcttggca ttttcaatat     780
tttatgcttt tgcaaacgat caatcatatc cgtataacaa atgtacaagg cacgagatca     840
ttgaataaag aagaaattga acaagtggtc aatatggcac ttaccaaatc aaaggtatct     900
taccatgata ctagaaagat ccttgattta tcagaagaat atcaatttgt tggcttggat     960
tatggaaaag aggatgaaaa aagaaagtt gaagtaaggg aacgatcat caaattagat    1020
gattaccata gttaaataa gattttaat gaagtggaat tagctaaagg agaaacgtgg    1080
gaagctgatg attatgatac agtagcgtat gccctcactt tctttaaaga tgatgaagat    1140
```

```
attagagatt atttgcagaa taaatataaa gatagtaaaa atcgtcttgt taagaacttg    1200
gctaataaag aatacacaaa tgaattgata ggaaaagtga gtacgctatc ttttcgtaaa    1260
gtggggcatt tatcattgaa agccttacga aagatcatcc cgttttttgga acaaggtatg   1320 acgtatgata aggcgtgcca agcggctggt tttgactttc aaggtatatc aaaaaagaag    1380
agatctgtcg tcttgccagt cattgaccaa atttccaacc cagtagtaaa tcgtgctctt    1440
actcaaacac gtaaagtaat taatgctcta atcaaaaaat atggttcacc tgaaaccata    1500
cacattgaaa cagcaagaga gttatcaaag acatttgatg aacgaaagaa tattaccaag    1560
gattataagg agaatagaga caagaacgaa catgcaaaaa aacacttatc tgaattgggg    1620
attattaatc ctactggtct tgatatagta aagtacaagt tgtggtgtga gcaacaaggg    1680
cgctgtatgt acagcaatca acccatctcc tttgaaagac tgaaagaatc aggttatacc    1740
gaggtagatc acattattcc atacagccga agtatgaatg atagttataa caatcgcgta    1800
ttggttatga ctagagaaaa tcgtgaaaag ggtaatcaaa ctccttttcga atatatgggg    1860 aatgatacgc aaagatggta tgagtttgaa cagagagtca caacaaatcc acaaataaaa    1920
aaggagaaac gacagaacct cttgctaaaa ggattcacta atcgtcggga actagaaatg    1980
ttagaaagaa acttaaatga tacacgttat ataactaagt atctttcaca ttttattagt    2040
acgaatttgg aattctctcc tagtgataaa aagaaaaagg tagttaatac aagcggtcgt    2100
atcacttccc atttaagaag tagatgggga ttagaaaaaa atcgtgggca aaatgaccta    2160
caccatgcaa tggatgcgat cgtcattgct gtcacctcag actcgtttat tcaacaggta    2220
acgaattact ataaacggaa agaaagaaga gagttgaatg gggatgataa gttccctcta    2280
ccttggaagt ttttttagaga agaagtcata gcaagattaa gccctaaccc aaaagaacaa    2340
attgaagcat tgcccaacca tttttatagc gaagatgaac ttgctgatct tcaaccgata    2400
tttgtgtcaa gaatgcccaa gcgtagtata actggagagg cgcatcaggc acagtttcgt    2460
cgagttgtgg gtaaaactaa agagggtaaa aatattactg caaagaaaac tgctttagtt    2520
gatattagct atgataaaaa tggtgatttt aatatgtatg gaagagaaac agatcctgct    2580
acttatgaag caattaaaga aagatatctc gaatttggag gaaatgttaa aaaagcattt    2640
tcgacggatt tacataaacc gaaaaaagat ggcaccaaag gtccactgat aaaatctgtg    2700
agaataatgg aaaataaaac attggtacat cccgtaaata aaggaaaagg cgttgtgtat    2760
aacagctcta ttgtaaggac agatgtattt caaagaaaag agaaatatta tttactacct    2820
gtgtacgtaa cagatgtaac caaggggaaa ctaccaaata aggtgatcgt tgccaaaaag    2880
ggatatcatg attggattga ggttgatgat agcttcacat ttttattcag tctatatccg    2940
aatgatttaa tattcatcag acaaaatcca aaaagaaaa tatcattaaa aaaacgtatt    3000
gagagtcatt ctatttctga tagtaaagag gttcaggaaa ttcacgccta ttataaaggg    3060
gttgatagtt caactgctgc tatagagttt attattcatg atggtagtta ctatgcaaaa    3120
ggtgttggtg tccaaaatct agattgtttt gaaaaatatc aagttgatat tctaggtaat    3180
tatttcaaag tgaaaggaga aaacgacttt gagttggaga catctgatag taaccacaaa    3240
ggcaaagatg tcaattcgat taaatcaact agtcgttaa                         3279
```

<210> SEQ ID NO 37
<211> LENGTH: 36
<212> TYPE: DNA
<213> ORGANISM: Brevibacillus laterosporus
<220> FEATURE:

```
<221> NAME/KEY: misc_feature
<222> LOCATION: (1)..(36)
<223> OTHER INFORMATION: Repeat1

<400> SEQUENCE: 37
atcatatcat atcgagtttt agtaaggaac tatagc                                 36

<210> SEQ ID NO 38
<211> LENGTH: 36
<212> TYPE: DNA
<213> ORGANISM: Brevibacillus laterosporus
<220> FEATURE:
<221> NAME/KEY: misc_feature
<222> LOCATION: (1)..(36)
<223> OTHER INFORMATION: Repeat2

<400> SEQUENCE: 38
atcatatcat atcgagcttt agtaaggaac tatagc                                 36

<210> SEQ ID NO 39
<211> LENGTH: 36
<212> TYPE: DNA
<213> ORGANISM: Brevibacillus laterosporus
<220> FEATURE:
<221> NAME/KEY: misc_feature
<222> LOCATION: (1)..(36)
<223> OTHER INFORMATION: Repeat3

<400> SEQUENCE: 39
atcatatcat atcgagtttt agtaaggaac catagc                                 36

<210> SEQ ID NO 40
<211> LENGTH: 36
<212> TYPE: DNA
<213> ORGANISM: Brevibacillus laterosporus
<220> FEATURE:
<221> NAME/KEY: misc_feature
<222> LOCATION: (1)..(36)
<223> OTHER INFORMATION: Repeat4

<400> SEQUENCE: 40
atcatatcat atcgagtttt agtaaggaac tatagc                                 36

<210> SEQ ID NO 41
<211> LENGTH: 36
<212> TYPE: DNA
<213> ORGANISM: Brevibacillus laterosporus

<400> SEQUENCE: 41
atcatatcat atcgagtttt agtaaggaac tatagc                                 36

<210> SEQ ID NO 42
<211> LENGTH: 36
<212> TYPE: DNA
<213> ORGANISM: Brevibacillus laterosporus
<220> FEATURE:
<221> NAME/KEY: misc_feature
<222> LOCATION: (1)..(36)
<223> OTHER INFORMATION: Repeat6

<400> SEQUENCE: 42
atcatatcat atcgagcttc agtaaggaac tatagc                                 36

<210> SEQ ID NO 43
<211> LENGTH: 36
<212> TYPE: DNA
<213> ORGANISM: Brevibacillus laterosporus
```

```
<220> FEATURE:
<221> NAME/KEY: misc_feature
<222> LOCATION: (1)..(36)
<223> OTHER INFORMATION: Repeat7

<400> SEQUENCE: 43
atcatatcat atcaagcttt agtaaggaac tatagc                                    36

<210> SEQ ID NO 44
<211> LENGTH: 36
<212> TYPE: DNA
<213> ORGANISM: Brevibacillus laterosporus
<220> FEATURE:
<221> NAME/KEY: misc_feature
<222> LOCATION: (1)..(36)
<223> OTHER INFORMATION: Repeat8

<400> SEQUENCE: 44
atcatatcat atcgagtttt agtaaggaac tatagt                                    36

<210> SEQ ID NO 45
<211> LENGTH: 29
<212> TYPE: DNA
<213> ORGANISM: Artificial Sequence
<220> FEATURE:
<223> OTHER INFORMATION: synthesized sequence Blat-Cas9-dir

<400> SEQUENCE: 45
taccatggca tacacaatgg gaatagatg                                            29

<210> SEQ ID NO 46
<211> LENGTH: 35
<212> TYPE: DNA
<213> ORGANISM: Artificial Sequence
<220> FEATURE:
<223> OTHER INFORMATION: synthesized sequence Blat-Cas9-rev

<400> SEQUENCE: 46
ttctcgagac gactagttga tttaatcgaa ttgac                                     35

<210> SEQ ID NO 47
<211> LENGTH: 177
<212> TYPE: RNA
<213> ORGANISM: Artificial Sequence
<220> FEATURE:
<223> OTHER INFORMATION: synthesized sequence Blat sgRNA Direct

<400> SEQUENCE: 47
gggcgcuaaa gaggaagagg acagcuauag uuccuuacug aaagguaagu ugcuauagua          60
agggcaacag acccgaggcg uuggggaucg ccuagcccgu uuuuacgggc ucuccccaua         120
uucaaaauaa ugacagacga gcaccuugga gcauuuauuu ccgaggugcu uuuuuu            177

<210> SEQ ID NO 48
<211> LENGTH: 118
<212> TYPE: RNA
<213> ORGANISM: Artificial Sequence
<220> FEATURE:
<223> OTHER INFORMATION: synthesized sequence Blat sgRNA Reverse

<400> SEQUENCE: 48
gggcgcuaaa gaggaagagg acaaucauau cauaucgagg aaacuugaua ugauaugaua          60
cuuucauuuu auaccauau aucaucgaag ucaaucucau uuaucugucu auuuuaug            118

<210> SEQ ID NO 49
```

```
<211> LENGTH: 68
<212> TYPE: DNA
<213> ORGANISM: Artificial Sequence
<220> FEATURE:
<223> OTHER INFORMATION: synthesized sequence GG-969

<400> SEQUENCE: 49
gggcgctaaa gaggaagagg acagctatag ttccttactg aaaggtaagt tgctatagta      60
agggcaac                                                              68

<210> SEQ ID NO 50
<211> LENGTH: 62
<212> TYPE: DNA
<213> ORGANISM: Artificial Sequence
<220> FEATURE:
<223> OTHER INFORMATION: synthesized sequence GG-839

<400> SEQUENCE: 50
ctaaaaacgg gctaggcgat ccccaacgcc tcgggtctgt tgcccttact atagcaactt      60
ac                                                                    62

<210> SEQ ID NO 51
<211> LENGTH: 55
<212> TYPE: DNA
<213> ORGANISM: Artificial Sequence
<220> FEATURE:
<223> OTHER INFORMATION: synthesized sequence TK-149

<400> SEQUENCE: 51
gatcgcctag cccgttttta cgggctctcc ccatattcaa ataatgaca gacga           55

<210> SEQ ID NO 52
<211> LENGTH: 62
<212> TYPE: DNA
<213> ORGANISM: Artificial Sequence
<220> FEATURE:
<223> OTHER INFORMATION: synthesized sequence TK-150

<400> SEQUENCE: 52
aaaaaaaagc acctcggaaa taaatgctcc aaggtgctcg tctgtcatta ttttgaatat     60
gg                                                                    62

<210> SEQ ID NO 53
<211> LENGTH: 71
<212> TYPE: DNA
<213> ORGANISM: Artificial Sequence
<220> FEATURE:
<223> OTHER INFORMATION: synthesized sequence GG-840

<400> SEQUENCE: 53
gggcgctaaa gaggaagagg acaatcatat catatcgagg aaacttgata tgatatgata    60
ctttcatttt a                                                          71

<210> SEQ ID NO 54
<211> LENGTH: 75
<212> TYPE: DNA
<213> ORGANISM: Artificial Sequence
<220> FEATURE:
<223> OTHER INFORMATION: synthesized sequence GG-841

<400> SEQUENCE: 54
cataaaatag acagataaat gagattgact tcgatgatat atggatataa aatgaaagta    60
tcatatcata tcaag                                                      75
```

```
<210> SEQ ID NO 55
<211> LENGTH: 37
<212> TYPE: DNA
<213> ORGANISM: Artificial Sequence
<220> FEATURE:
<223> OTHER INFORMATION: synthesized sequence TK-124

<400> SEQUENCE: 55
taatacgact cactataggg cgctaaagag gaagagg                              37

<210> SEQ ID NO 56
<211> LENGTH: 26
<212> TYPE: DNA
<213> ORGANISM: Artificial Sequence
<220> FEATURE:
<223> OTHER INFORMATION: synthesized sequence TK-151

<400> SEQUENCE: 56
aaaaaaaagc acctcggaaa taaatg                                         26

<210> SEQ ID NO 57
<211> LENGTH: 32
<212> TYPE: DNA
<213> ORGANISM: Artificial Sequence
<220> FEATURE:
<223> OTHER INFORMATION: synthesized sequence TK-126

<400> SEQUENCE: 57
ataaaataga cagataaatg agattgactt cg                                  32

<210> SEQ ID NO 58
<211> LENGTH: 37
<212> TYPE: DNA
<213> ORGANISM: Artificial Sequence
<220> FEATURE:
<223> OTHER INFORMATION: synthesized sequence GG-935

<400> SEQUENCE: 58
caaattctaa acgctaaaga ggaagaggac agtcccg                             37

<210> SEQ ID NO 59
<211> LENGTH: 45
<212> TYPE: DNA
<213> ORGANISM: Artificial Sequence
<220> FEATURE:
<223> OTHER INFORMATION: synthesized sequence GG-936

<400> SEQUENCE: 59
aattcgggac tgtcctcttc ctctttagcg tttagaattt gagct                    45

<210> SEQ ID NO 60
<211> LENGTH: 21
<212> TYPE: DNA
<213> ORGANISM: Artificial Sequence
<220> FEATURE:
<223> OTHER INFORMATION: synthesized sequence pUC-EheD

<400> SEQUENCE: 60
ccgcatcagg cgccattcgc c                                              21

<210> SEQ ID NO 61
<211> LENGTH: 22
<212> TYPE: DNA
<213> ORGANISM: Artificial Sequence
<220> FEATURE:
```

<223> OTHER INFORMATION: synthesized sequence pUC-LguR

<400> SEQUENCE: 61
gcgaggaagc ggaagagcgc cc                                      22

<210> SEQ ID NO 62
<211> LENGTH: 21
<212> TYPE: DNA
<213> ORGANISM: Artificial Sequence
<220> FEATURE:
<223> OTHER INFORMATION: synthesized sequence Sense DNA Strand of
      Cleaved Sequencing Template

<400> SEQUENCE: 62
gaggaagagg accagtcccg t                                       21

<210> SEQ ID NO 63
<211> LENGTH: 11
<212> TYPE: DNA
<213> ORGANISM: Artificial Sequence
<220> FEATURE:
<223> OTHER INFORMATION: synthesized Anti-Sense DNA Strand Sequencing
      Read
<220> FEATURE:
<221> NAME/KEY: misc_feature
<222> LOCATION: (11)..(11)
<223> OTHER INFORMATION: n is a, c, g, or t

<400> SEQUENCE: 63
acgggactgt n                                                  11

<210> SEQ ID NO 64
<211> LENGTH: 21
<212> TYPE: DNA
<213> ORGANISM: Artificial Sequence
<220> FEATURE:
<223> OTHER INFORMATION: synthesized  Anti-Sense DNA Strand of Cleaved
      Sequencing Template

<400> SEQUENCE: 64
acgggacctg tcctcttcct c                                       21

<210> SEQ ID NO 65
<211> LENGTH: 11
<212> TYPE: DNA
<213> ORGANISM: Artificial Sequence
<220> FEATURE:
<223> OTHER INFORMATION: synthesized  Sense DNA Strand of DNA Sequencing
      Read
<220> FEATURE:
<221> NAME/KEY: misc_feature
<222> LOCATION: (11)..(11)
<223> OTHER INFORMATION: n is a, c, g, or t

<400> SEQUENCE: 65
gaggaagagg n                                                  11

<210> SEQ ID NO 66
<211> LENGTH: 27
<212> TYPE: DNA
<213> ORGANISM: Artificial Sequence
<220> FEATURE:
<223> OTHER INFORMATION: synthesized  Sense DNA Strand of Target and PAM

<400> SEQUENCE: 66
cgctaaagag gaagaggaca gtcccgt                                 27

```
<210> SEQ ID NO 67
<211> LENGTH: 27
<212> TYPE: DNA
<213> ORGANISM: Artificial Sequence
<220> FEATURE:
<223> OTHER INFORMATION: synthesized  Anti-Sense DNA Strand of Target
      and PAM

<400> SEQUENCE: 67
acgggactgt cctcttcctc tttagcg                                          27

<210> SEQ ID NO 68
<211> LENGTH: 118
<212> TYPE: RNA
<213> ORGANISM: Brevibacillus laterosporus
<220> FEATURE:
<221> NAME/KEY: misc_feature
<222> LOCATION: (1)..(118)
<223> OTHER INFORMATION: "Direct" tracrRNA region downstream of the
      anti-repeat

<400> SEQUENCE: 68
aagggcaaca gacccgaggc guuggggauc gccuagcccg uuuuuacggg cucuccccau      60
auucaaaaua augacagacg agcaccuugg agcauuuauu uccgaggugc uuuuuuuu       118

<210> SEQ ID NO 69
<211> LENGTH: 58
<212> TYPE: RNA
<213> ORGANISM: Brevibacillus laterosporus
<220> FEATURE:
<221> NAME/KEY: misc_feature
<222> LOCATION: (1)..(58)
<223> OTHER INFORMATION: "Reverse" tracrRNA region downstream of the
      anti-repeat

<400> SEQUENCE: 69
acuuucauuu uauauccaua uaucaucgaa gucaaucuca uuuaucuguc uauuuuau        58

<210> SEQ ID NO 70
<211> LENGTH: 4107
<212> TYPE: DNA
<213> ORGANISM: Lactobacillus reuteri
<220> FEATURE:
<221> NAME/KEY: misc_feature
<222> LOCATION: (1)..(4107)
<223> OTHER INFORMATION: Lreu Cas9 Open Reading Frame

<400> SEQUENCE: 70
atgataaaga aagactataa tattggactt gatattgggg caacttcagt cggctttgct      60
ggtattgatg aacagtatga cccaattaag ttaaagggaa aaacagtagt ggggggttaac    120 ctatttgaag aagggcaaac agcggcagat cggcgttcct ttcgcactac ccgtcggcga     180
ttgaaccggc gtaaatggcg cttatcatta ttagaagagt ttttttgaccc atatattacg    240 cctgttgatc ccgcattctt tgcacgtttg aaggaatcaa atctttcacc aaaggataat    300
aacaaaaatt ttagtagatc attactttt cctgatatta cagatcagaa attttatgaa     360
gaatatccga caatttatca tctgcgatat gcattgatga ctgaaaataa aaaatttgat    420
cttcgggcta tcttcttagc aattcaccat atgatcaagt accggggaaa ttcttaaat     480 tccacccctg tagcacattt tgatacgagt aagattgatt ttgcgaatga ttttagtaaa    540
ctaaatcgtc tttacttgaa tgaagatcct aataatattt ttgaaattaa tttacaaaat    600
gtaaaagaaa taagtgatat tttactggat catagtatta agaagtttga taagcaaaag    660
caagttgcta agcttttact tacatctcaa aatgataagg aactggataa aagaaataag    720
```

```
cagattgcta ctcagatcag taaagcaatt cttggctata attttcact aaatgaaatt      780
ttgaaacttg aagcagtaaa taaaagcaaa tggaaactaa actttagtag cgccgacatt      840
gatgatacgt tacccgactt aatttccgaa cttgatgaaa gtcaagaatc aattttaaat      900
attattttaa gtttgtactc acggttgact ttaaatggaa ttgtcccaag tggaatgagt      960
ctttccgaat caatgattga taaatatggt actcataagg aacaccttga tttattaaag     1020
aaatatttaa aaacccttcc tataaaaaat cggaaagaga ttgctgaagc ctatgccgaa     1080
tatgttggaa attctttgaa gaaaagcgga catatttctc aagaagaatt ttataaagca     1140
gtaaagaaga atcttgataa atccgaaaca gctcaaaaaa ttcttagctt aattagtgaa     1200
gagaagttta tgcctaagca acggaccaat caaaatgggg tcattccata tcaacttcac     1260
caaaaggaac ttgatcagat tattgtaaac caatctcaat attatccatg gttagcagaa     1320
ttaaatccag ttacggagca taaagatgca agtataaac tagatgaatt gattgctttc     1380
cgggtaccgt attatgttgg accgttaatt gatcctaaaa caatccctca aacagaacaa     1440
ggaaataaaa atgcttcatt tgcgtggatg gttcgtaaag aaaatggtca ataacgcca      1500
tggaatttg ataaaaagt agatagaatt tcgtctgcaa ataactttat taagcggatg        1560
actactaagg atacgtattt aatcggcgaa gatgtattac ctgctcatag ccttatttat     1620
gaacgtttta aggtattaaa tgaactaaat atgattcggg taaatggtaa aaaactctct     1680
gtttcggtta acaaaatct ttataatgac ctatttaaac aacaaagac aattaatagg       1740
aagaagttag ctaattatct ccaagcaaat cttggtatcc ctgaacgacc tcaaattaca     1800
ggtctctcag atcctgaaaa atttaattca caattaagct catatattga tttacaaaaa     1860
atactaggaa gtgaaattgt tgatgatcct aataagcagg atgatttaga aaagattat       1920
gaatggtcaa ctgttttga agattcacgg atctataagg ttaagttaca agaaattgga      1980
tggttcactg aaaaacaaaa gaatgagtta gtaagtcatc gctatcaagg ctggggacga     2040
ttatcaaaga aattactagt tgagctaaaa gataagaatg ggagatcaat tattgatttg     2100
ctttggaatt cacagcgaac atttatggag attcaaagtc gtccagagtt tgctgaacag     2160
attactaatg agaaccaaga taaattaact gaggataatt acgaagacgt actggccgat     2220
gcctatactt caccgcaaaa caaaaaggca attcgtcagg taattaaagt tgtcgatgat     2280
attgttaagg caactggaaa agcaccgaag tttatttcgt tagagtttgc tcgctcggat     2340
gaacggtcag atcgtgtaaa atcaaggaaa acacatatcc aaaaaattta tgaaactacc     2400
gctaaagaat tactgaaaga tgatcagtta attaaagagt taggtagcgt ttcagattta     2460
tcagatcggt tatacttata ctttacccag cttggtcgtg atatgtatac aggtaagcca     2520
attaatattg atgaaatttc gactatgtat gacattgacc atatccttcc gcaggcgttt     2580
cttaaggacg attcattaga taaccgggta cttgtaagac gacaggataa taacgctaaa     2640
tctgacactg ttccggcttt gaatttggaa agatgaaac catttggaa caaattacaa       2700
aagcacggct tgattagtaa acgtaaactt aataacttgc aaactaatcc tgaaagtatc     2760
gataagttta aagcagttgg ttttgtgaac cgtcagttag ttgaaacacg ccaagttata     2820
aaattagctg caaatatttt agcaagccgt atcctgatt ctaagattat tgaagttaaa      2880
gcaagtttaa ctcatcaaat gcgtgaatca tttaacctaa ttaagaatcg ggatgttaat     2940
gactatcatc atgctgttga tgcgtattta agtgcatttg tagggcaata cctatataat     3000
cgttatccta aattgcagcc atattttgtt tatggtcagt ttaaaaaatt tgataaacaa     3060
```

```
agtactcgga ttgggatgaa aactaaccac tttaattttt tgtatgatct tgagcccgaa    3120
ggtaaaaatg taaaaataaa gaaaccaact aagattataa acaaggaaac tggtgaaatt    3180
attggtgatc gtgatgaatt agttgccaaa ttgaaccgtg tttataattt taagtacatg    3240
ttagtttcac aagaagtata tacgcgaagt ggtgcattgt ttgatcagac aatttaccca    3300
gctaattcag gtaagaaatt aatcccgctg aagcaaaata aaactacagc aatttatggt    3360
ggatacagtg gaagtaaagc agcgtatatg tctatcatta ggttacgaga taaaaagggt    3420
ggaacttacc gtatcgttgg aatcccagta agagcagtta ataaattaaa tcaagcgaag    3480
aaaaagagta atgaaaaata tcttgcagaa ttaaaggcag tcattgagcc acaaattgct    3540
aagacaaaga aggatcgaaa gactggtcaa agggttcttg taccacaaga atttgatgtg    3600
attatccctg aagttatgta tcgtcagtta atagttgatg gtgaccagaa atttacgttg    3660
ggtggaacta ttgatagata taatgctgtt caattagttt tgaatcaaga atattgaca    3720
ttccttgagc aacctactaa atataaggac gccgatacaa aattgttgga tatatatgat    3780
caaatagtaa atttagtaga gaaatatttt atgctgtttg atagcaaacg acttgctgca    3840
ggtcgagttg cgtttgaaaa attacctact ttacaacctg tcgataaaat gccttctaaa    3900
ttaataataa ttagaagaat tattcaggga cttcatgaca atgctgctcg aacagattta    3960
aaggcgatta atggaagttc gtcatttggt aggttacaaa aagaaatgg aattatacta    4020
tcacctaatg catgcctgat ttaccagtca ccaactggct tatttgagag aaaagtttat    4080
ctaaatacta tttcaccatt aaaatag                                        4107
```

<210> SEQ ID NO 71
<211> LENGTH: 4110
<212> TYPE: DNA
<213> ORGANISM: Lactobacillus rossiae
<220> FEATURE:
<221> NAME/KEY: misc_feature
<222> LOCATION: (1)..(4110)
<223> OTHER INFORMATION: Lros Cas9 Open Reading Frame

<400> SEQUENCE: 71

```
atggataaat caaaaccata tggaattggc ctagatattg gtacaaattc tgtcgggttc     60
gtggcgactg atgctgaggg gcaccttatc cgattgaaag gaaagacggt tattggagcg    120
tacctgttta atgctggaat atcggcagcg gaaagacggg ggtttcggac gacaagacgt    180
cgattatcgc gggttaaatg gcgcctagga cttcttagag aaatatttga gactcatttt    240
caggaaagta tgggagaaaa tgaggataat gatttctttt tacgtttcaa atactcgaat    300
atttcaccta aagacccaca attttcgacg gctaaggggtt tatttaatga tcgaacggat    360
aaggaatttt atgatcagta tccgactatt tatcatttgc gtcgggcttt gatgactgaa    420
gaccatcagt ttgatattcg ggaaatatac atcgcaatgc atcacattgt gaaatatcgt    480
ggtcattttt taaagaagg acgcgccaaa gactttaaag ttggggattt aagactgctg    540
gataaatttca aaatgatgaa tgaacaaatt gaagaaatta atcctttgtg gcagttgaaa    600
ttaccaactg atgacgcctc tattaagtcg ataaccgcta ttttactaga caatactcag    660
agccaaaatg atcgtcaaaa agcagtgacg aaagtaattc tggcaacact tgttaaggcg    720
agtgacaaag acattaacgc tgcacgtaaa cggtttgttg gcgaattgag taaggctatg    780
gttggccttta aacaaaaact ttgggttctt gcagatgttt cgcagaatgg tgattgggaa    840
attaagtatg aaaactacgc tgactttgcg gaaacgatcg gttccggtga agtgacacc     900
attcaaagtc ttttaacga gattaatgat ctatatgggg ttattacgtt ggctggcatt     960
```

```
attcccaaag aagctgagtc attttctgac ggaatggtcc gcaagtatga acatcatcgt   1020
aaaaatctag aactgttaaa agtttattgt gcggaacaat cagatggtaa acggggacga   1080
cagattcgtc agacttatga taaatatatt gatggggtag atagcaaaca gtttacgcag   1140
gaagactttt ataaggcatt aagcaagttc actgcgaagg atgaagcgac tagtgaaaat   1200
gccaaattaa ttgctcagga aattgcagtt ggaactttca tgcctaagct gcgaacaaag   1260
gctaatggca ccattccaca tcagttgcac caaaaagaat tggatgcaat tattgaaaat   1320 caaaaaagt attacccatg gcttggtgaa gtcaatcccg ttgagagtca tcgtcgcgca   1380
ttgccataca aattggatga attagtcagt tttaggattc catattatgt tggaccaatg   1440
gttacgccaa caagggaga tccagaaaaa agtaaatttg cctggatggt tcgaaaggaa   1500
ccgggtacca ttacgccatg gaatttcgat caaaaagtag accgatcggc gtctggtgaa   1560
gcgtttattc aacgaatgaa acgactgat acattttaa ttggcgaaga tgtattgcca   1620
caacaaagtc tgctgtatca gaaatttgaa gtactaaatg aattaaacaa aattatgata   1680
aacggtaagc caatttgcag agaacagaaa caacggcttt tcaaacaact gtttatgcaa   1740
tataagactg tgacagtgaa gaaagttcaa caaaatttaa ttgcgaatgg tgaagagtct   1800
gaaaatgtgc caattactgg cttgtcagat cctttacggt ttaatagttc attcagcact   1860
tatatcgatt acaaagatat tttgggtaca gctgctgtta acgataatgc aaagcaaagc   1920
gatattgagc agataattgc atggtccaca atttttgaag atgcagccat tttccgagag   1980
aagttaaatg atattacttg gcttaatgac gatcaacgca ataagctcag tcataaacgt   2040
tatcgcggtt ggggtcgtca ttctcgcaaa ttgttagctg gtcttcgtga cggagaaggc   2100
cagactatca tcgaacggct atggaacaca aatgacaact tcatgcagat tcaaaacgat   2160
agtgaaatag cgcgtcaaat taccgaagca aactcaagca agatggcaac cgctgaggga   2220
acagacgaaa ttatcgatgg cttctacact tcacccgaaa acaaaaaggc cctgcgtgaa   2280
gtaatgaaag ttgtgaagga tattcaacgt gcgcatcatg gtcaggcacc tgcttgggtt   2340
tatattgaaa gtccgcgaga gacaccaaga cccggtcagc ggacagttag tcgagaacaa   2400
cagttaacag atttgtatga gggtgcagca aaagaaatcg ttgatgatgc cgttttaaat   2460
gaactaaagg acaaggttaa atccaaggaa aactttacgg ataaattagt tttgtatttc   2520
ttgcaaaatg gacatgatat ttatgcgaat gacagtatca acattgataa ccttaatgca   2580
tatgatatcg atcatgtttt accgcaaagt ttgataaaag atgatagcct agacaatcgg   2640
gttctcacaa cacatgaaag aaatcttaaa aaatctaatc ggtttgctac agaactgttt   2700
gccgatcaaa ggaaaaaatg ggaaaaatgg catcgattag gattgatttc gtcacgtaaa   2760
ttaaaacatt taactatgca gcccaattca gtagaaaaat ttgcacatgg atttattgca   2820
cgtcaactca ctgaaacgag gcaaataatt catttaacgg cgaatgtact ttcaaattta   2880
tatcaagaaa atgacactaa aatcgttatg attaaggcgg gattaaactc ggagtttagg   2940
cgtacatttg attttccaaa gaatcgtagt gtaaatgatt accaccatgc ctttgatgca   3000
tttttaacgg ccaaaattgg acgttactta ttagcgagat atccaaaatt agaaccctt   3060 tttgtttatg gaaacttcgt taagaatcct aaagcaatga agcgattgag tagttttgat   3120
ttcattgctc agttagctgc taaaactgat gatactagtc atatagatca acgcagttta   3180
aaacaagttc ccgttgttaa tgaagaaaca ggggaaattg tttgggataa ggatattgag   3240
cttgctgaac tggacaagac gtataactac aaaactatgt tagtgaaacg tgctcagact   3300
```

```
gaaaataatg ctcaaatgtt caaacaaaca gttttttaagg ctcgtgacaa tcaaaataaa    3360
acgctaattc ctgtcaaaaa tggattatct actgacgttt atggtggtca ttcacaacag    3420
gcgatttctt acttatgtat cgtttgggtt ggacaaaaga aaaaatatcg cgttttggga    3480
attagtaccg cccatgcagg catattgaac aatttcgaaa aaaactacgg ccggtttgaa    3540
gcgaaaaaga aactacaaga aattgtctcc aatacactag ataatgcgga cagaaacgat    3600
tttaagatag ttgctcctaa agttttgttt gaacaagtgg ttgaggacga taacatgaag    3660
tttgggttgg gtagtgctag tgactataga aatgttcaac agttgttttt atcccggaaa    3720
aatcagttgc tattggctaa tatgatgact gaccaaatac acgaccaaga tttagtccac    3780 cttttttgacg aaatagttgg tcaaatgaat gcgcattttc ccattttttga tcgcggaggc    3840 tatcgaagtt cattgaccca atctcgtgat aaatttttga aattacccttt taaaaagaat    3900 gaggatttga tcacgaaaca agaggttatt cgaagaattt tagatggatt acatgctaat    3960
gcaaatcgta aagatcttaa aatcattggt agtaaaggtg attttgggag attgggaaca    4020
aagaaaatct acttatcgaa agatgcgaag cttatttaca cctcaccaac atgtcttttt    4080
actcgtactg ttccactcag ttcttttgtaa                                    4110

<210> SEQ ID NO 72
<211> LENGTH: 4041
<212> TYPE: DNA
<213> ORGANISM: Pediococcus pentosaceus
<220> FEATURE:
<221> NAME/KEY: misc_feature
<222> LOCATION: (1)..(4041)
<223> OTHER INFORMATION: Ppen Cas9 Open Reading Frame

<400> SEQUENCE: 72
atggaaaaag taccatataa tattggtctc gatattggga cgtcatcaat tggttttgca      60
gcaaccgata atcttaacaa gcctattcgg gcaaaaggta aaaccgttat tggagtacga     120
ttatttgaag agggtaaaac tgcagctgat cgacgtggat ttagaacaac acgtcggcga     180
ttatcaagaa gaaagtggcg tttaaggtta cttgatgaga ttttcgataa agaaatggct     240
aaggtagata taccttttt tgctcgtttg aaggagtcga atctttcacc aaaagatgct     300
aataagaaat atttaggatc attattattt ccagaaaaga aggattttaa gttttatgaa     360
gattatccaa cgatatatca tctacgttat gctctaatgc atgaaaaacg tcaatttgat     420
attcgtgaag tttatttagc aatgcatcat attatcaaat atcgtggtaa ttttttttaaat     480 tcagccccaa tgaattcttt taaaacacaa gattttgatt ttgtggctaa atttgaaaaa     540
ttaaacgaac tctttgaaag tattgatgcg gaacatgaaa cgaaatttga tattgaaaat     600
atttctaagt ttagagatat catgctaaat caagatattc gtaagttaga ccgaaaaaaa     660
caagccgcta aaatttttaat cctagatagt acagataaga cggctaaaaa gattaataat     720
aaaattgcaa ctgcagtagc caattcagct ttaggatata gtttgcgtt ggatgctatt     780 ttgaaattag atgtagaaga gtctaaagat tggtcgatta gtttaaacga tgaagaaatc     840
gatagtattt tagataactt aactagtgat ctggatgcgg aacgcatcga aatcattgag     900
atattgagag atttatacag tcatattgct ttaaatgaaa ttgtacccaa cggacaatcc     960
ttgtctaaat ccatgatgga taaatacgat aagcatcatg cggatttaga tgtattgaaa    1020
aaagttattt ctaatatgga cgatcgaaaa aaagctaaat cttttaaaaaa tatttacaat    1080 cagtatgtgg gtaaaactaa tgataaagtt ttggataaag atgaattcta taacaaatc    1140 caaaagaatt tagatgagtc tgaagatgct atgaagattg tcaatgaaat tgaacttgat    1200
```

```
caatttatgc caaaacagcg tacatctcaa aatggagtga ttccgcatca acttcaccaa    1260
aaagaattag atgaaatcat tgaaaatcaa aagcaatact atccattttt agcagagcct    1320
aaccctaacg agaaaagaaa acctcatgct caatttaaat tagatgagtt gatagctttc    1380
aaaattcctt actatgttgg tcctttgatt acaaaagaag aacaacaagc ccaatctggt    1440
gctaaatttg cctggatgaa gcgtaagcaa gatggggtga taactccttg gaatttcgat    1500
gaaaaagtgg atcgaatggc gtcagctaat gaatttattc gccgaatgac gactaaagac    1560
acgtatttgt taggtgaaga tgtacttcca gacgaaagct taatctatca aaaatttaaa    1620
gttttgaatg aattgaataa tgtcaaagtt aacgataaaa aactgacagt ttctgataag    1680
caggatattt tcaatgacct gtttaagaaa cagaaaactg tttccgtaag taaacttcaa    1740
aagtactttg ttacagaaaa gcattacttg acagagccaa cgatcaaggg gttatcagat    1800
acgaagaaat tttctaatag cttatcaact tatattgatt ttgaaaaaat atttggaaat    1860
gaaattcttg ctgatcaaaa taagcaaaat gatttagaaa aaattattga gtggtcaact    1920 attttgaag atcgtaaaat ttttgaagat aaattgcatg agattgaatg gttaactgaa    1980
aagcagatta aagctgttcg gagatatcgt ggatggggac ggcttttctaa aaagctacta    2040 gtcgatttaa gaaataatga aggtaaaagc attttagatg aactttggcg taccaatgat    2100
aactttatgc agattcaagc acgtgaggaa tttgctaagt cgattgtcga agctaaccaa    2160
aagttaatga atcttggtgg agctgccagt gttcaaaata ctgtggaaag taccttagag    2220
gatgcctata cctctcccca aaataaaaag gctattcgtc aagttattaa agttgttgaa    2280
gacatagtca aagcggttgg ctacgctcca gagaaaatca caattgaatt tactcgaggg    2340
gcagataaaa atcctagacg gactcaaaat cgtcaaaagc aaatcatgga agtatataaa    2400
accgcggcta aggaaatcgt agatgcaact ttgaagggac aacttgaaaa tgaggaaaag    2460
ttaactgata agttatattt gtatttcacc cagttaggta agatatttta tagtggcgaa    2520
acaattaata tcgatcaact taataattat gatattgacc atattttgcc acaagctttt    2580
attaaagatg attctctgga taatcgagtg ttaacaagtc gggatttaaa caacggtaaa    2640
agtgatagtg tgcctgtgaa gcagtttggt gcaaacatga aatcattttg gatgagactc    2700
caagcacatg gattaatctc aaaaagaaag cttaataatt taatgacaga tccagacagt    2760
attggaaaat ataccatgca aggatttgtt agaagacagc tagttgaaac tagccaagtt    2820
attaagttga ctgcaaatat actaggtgcc atctatgggg aaaatactga tattgtggaa    2880
atcccagcga agctgactca tcaaatgcgg agaagttca atctgtataa ggtgcgtgag    2940
gtaaatgatt atcatcacgc ctttgatgcg tatttaacga cctttgttgg taactattta    3000
ttcaaacgct atccaaaact acgtcctat tttgtatatg cgcatttcaa aatgactgat    3060
aatgccttga agggatgcg tagattcaat ttcttacatg acttaaaaga tgatgaagta    3120
ttagtagata cgaaactgg tgaagtttta tgggaaggtc aaaagtctat tgaagagttg    3180
aagaagattt atggttataa gtttatgtta acgactcatg aagcatatac gcaacatggt    3240
ccaatgttta agcaaactgt atatagttct gatacgcctg gcaaactaat taagataaag    3300
aacaataagc ctactgaaat atatggtgga tacttcga atacagatgc ttatatggcg    3360
attgtaagaa taaaagctag aaaggggat acttataagg ttgtcggagt acctagaaaa    3420
gaaggagatg ctttaagtcg aatcaagtta ttagacgaaa gtaaatacca tgagaacttg    3480
aagaatattt tagcaattaa tttgaataaa tctttgaaca agtttgatgt ggttctcgat    3540
```

| | |
|---|---:|
| aaagttaaat atcggcaggt tatttatgac ggtacagatc atttaatgtt aggtagttca | 3600 |
| aaatataaat atagtactaa acaattagta ttatcagacc aatctatgaa aattttaagc | 3660 |
| tctactggtg aattctcgga cgaggaactt atcaaggtgt tcgacgagat tatgtacatt | 3720 |
| gttaataaga actttagttt gtatgatacc cgaggatttc gtgataagtt aaataatgct | 3780 |
| agggaaaatt tcataaaatt gcctaataaa acattgttcg aaaagggaaa attaaaacaa | 3840 |
| catagcaagt tagaaatatt aaaacaaatt ttaattggac tgcatgcgaa tgctggtcga | 3900 |
| ggtgatttaa aagatattgg agttaataat tttggagcta tggttgttac tgctggggta | 3960 |
| acgttatcac ctgacgctac aattgtttat caatccccaa ccgggctatt tgaacgcaaa | 4020 |
| gttaaattga gcgacccttta a | 4041 |

<210> SEQ ID NO 73
<211> LENGTH: 3393
<212> TYPE: DNA
<213> ORGANISM: Lactobacillus nodensis
<220> FEATURE:
<221> NAME/KEY: misc_feature
<222> LOCATION: (1)..(3393)
<223> OTHER INFORMATION: Lnod Cas9 Open Reading Frame

<400> SEQUENCE: 73

| | |
|---|---:|
| atggaaaaca aaattagctt aggattagat attggagttg cttctgttgg ttttagtgta | 60 |
| attgatgcac aagaaggtaa agtactggag ttaggggcca gactattcaa tagttcagtt | 120 |
| tccgcggaga atcaaactcg tcgagatatg cgagggtcca aagactaag taatcgcaag | 180 |
| aaacaacgtc gtaagatgt agctcaacta tttaagactt ttggattaat aaattatttt | 240 |
| gataaagaaa attattttga taactttcaa aataatttaa attcttatga attgagagtt | 300 |
| aaaggattat cagagaaatt atcaaaagaa gaactggtga atagtttgta tcatattgtc | 360 |
| aaaaggcgtg gtatcagtta tgacttggca gatgctgaca ctgatttcga tggttctgat | 420 |
| tactcatcta gtttgaatca gaatcaattg gaattacaga cgaagactcc agctgaaata | 480 |
| caacttactc gcttgaatgt acatggagct gtacgtggaa aagttacgat caatggcgag | 540 |
| gatgaggaca ctatgcaagt attgttgaat gtgttcccca ccaaatcatt tgtatctgaa | 600 |
| gcaaaaaaga ttattcaaac acaacaacaa tattatcctg atattttgac ggatatattt | 660 |
| gaaactaagt atttagaaat tctagaacgt aaaagagaat attttgtcgg acctggtagc | 720 |
| gaaaaatcta gaactgattt tggtatctat aagaaagatg gtagaacttt ggataatttg | 780 |
| ttcgaagagt taattggtca tgacaaaata tatcctgatg agttacgtgc gtctggtgca | 840 |
| tcttatactg cacaggtttt taatgtctta aatgatttaa ataatttacg tatttctagt | 900 |
| tatgaaaacg ggaaaatttc tacgaagat aaaataaaga ttgttgaaga tttaagaaac | 960 |
| aatatcggca atgtaattat aatgaaaatc attaaaaagg ttgccggttg tgaagatgat | 1020 |
| gatattaaag gctatagatt ggatagcaag gacaaaccgg atattcattc aatggccgtt | 1080 |
| tatcgaaaag ttcatcgtga tttattgaaa tatgatgtgg atattattaa gtggccaacg | 1140 |
| gaatttattg atgaattaag tccaatatta actttgaata cggagaacgg tgaaattcgg | 1200 |
| aaacaaatgg tcaataagtt gcaaccaaag tattcatttt taacggatga acttattcaa | 1260 |
| gttattatta ataacaaatc tagttttgac gttacttcca ataataaatg gcatcgtttc | 1320 |
| tcattgaaaa caatgaatgt tttgatcgaa gaaatgttca gacgaccagt tgaacaaatg | 1380 |
| actcttattc aagaactggg attgattaaa gactcaggta agagatttga aaattgtaaa | 1440 |
| cttttgccat ataggaaaat ctcaaaggat attttttaatc cggtagcgtc caagtcagtt | 1500 |

```
cgtgaggctc ttaaaattgt taatgccgta atgaagaagt atggtcaaat tgattatctg   1560
gttatcgaga tgcctcgtga taagaatgaa gaagaaatga agaaacaaat tgaaaaattc   1620
caaaaggaaa ataataagca aaaagatgaa gcaataaatg agtttgttaa aaaaattggg   1680
aataagaatg ctgttgatga tggactaaga cgatatggtg gtaaattata tttcaagatt   1740
agattgtggt atcaacaaga tggaattgat ttatataatg gcaaagtaat tgaaccgttt   1800
gacttattga ataatattaa taaatttgaa gtggatcata ttattccaga atcaatttca   1860
tttgacgaca gtattaataa caagacactt tgctatgctg atatgaatca aatcaaagga   1920
caaaagacac cgtttgaatt tatgaacgag ggacatggcc agggctttgc aaaaatgaag   1980
gctatggtaa ataagaattc aaagttaaaa ggtaaacgaa aaaattattt atttgatgaa   2040
aatattagtg atattgaaac cagaaaaagg tttatatctc gtaaccttgt tgatactcag   2100
tattcgtcaa gagtggtttt gaatagtttg caagagttct ttaaggaaaa agaaaccgga   2160
actaaggtga ctgtcgtccg aggtaagttt acttctaatt tacgcaagca ttggcatatc   2220
aataagacac gtgatacatt tcatcatcac gccatcgatg catcaataat tgccgcgaca   2280 ccattttaa gaatttggaa aaaagatgcc agtttattcc ccatgcatgt ctctgaaaat   2340
actgttgata ttgaaactgg tgagattctt aatgatactg aatttaaaaa agacttttac   2400
ggattaccgt atagcagttt tattgaagaa ctgaacggtg ctgatgaccg gattaagttt   2460
tcgcatcagg ttgataggaa gatgaatcgt aaggtaagtg atgcgacaat ttattcgaca   2520
cgtaaaggaa tgttgaataa agataaagaa gaaactgatt atgtcttggg aaaaatcaaa   2580
aatatttatg atgttagtga gtataacaaa ttcaaacgaa tttacgataa agatccaaat   2640
aaatttctgt tggctcatca tgatccaaaa agctttgatg aacttagaaa aatcatgcag   2700
gaatatccta gtaaaattga taaagtaatg actaatggta agtaaaatc tgtggatatt   2760 tctccatttg aattgtatcg tcgcaaacat ggaatggtac agaaatactc taataaaaat   2820
aaaggccctg ttattaaaca acttaagtat ttagacaaga agttgggatc tcacattgat   2880
attactccga aggatacatt gaatgatagg catgttgtat tacagtcact gaagccgtgg   2940
agaactgatg tgtattacaa tagtgtgacc ggtgaatatg aaattatggg tattaagtat   3000
tctgatttga agttcaatgg tggtgagtat ggaatcaaga tgagcaaata tttggaaata   3060
aaagagcgtg aacaggtttc agatgagtct gagtttctgt ttactcttta taagagagat   3120
agaatccaaa ttataaattg tgaaaatgac gaaattgtag aaatgctttt ctggtctaga   3180
aataattcta atattgggta tgccgaactt aaaccggtgt ataaatataa aactgaggat   3240
gaaagttggc cggtatacgg atatggaaaa aatcaaatcc taaaaagatt ggtaccaaag   3300
aattgtaaaa tattgaaagt aaataccgat atactgggca atccatacta tattaaaaaa   3360
gaatccaaaa acccaaaaaa tattcttgat taa                                3393
```

<210> SEQ ID NO 74
<211> LENGTH: 4086
<212> TYPE: DNA
<213> ORGANISM: Artificial Sequence
<220> FEATURE:
<223> OTHER INFORMATION: sequence from Sulfurospirillum sp. SCADC (Sspe)
<220> FEATURE:
<221> NAME/KEY: misc_feature
<222> LOCATION: (1)..(4086)
<223> OTHER INFORMATION: Sspe Cas9 Open Reading Frame

<400> SEQUENCE: 74

```
atgacatcgt tgatttcact ggatttgggt gggaaaaata cgggattttt tagttttaca    60
gctaaagacg tttcaataat agatactttt caatcaggaa cgattatcta tgatgaaagc   120
tttgtgctct cacaagtcgc acgacgaggc aaacgacacg gtaaacgtaa caacctacgc   180
aacacgctag tcaagcgact ttttttgctt cttttacaaa agcattatgg gcttagtctt   240 gatttttac ccgacgaaat tttgggactt tttaataaac gaggttacac ttatgcaagt    300
tttgaaatca agaagatga aaagaaaat cttgaaagcg atattttaaa agagttttg     360 aatgacaaac tcaattacac tatacaaaat gatgacgaag tagaagagtt tttaaatcag   420
atagcttcaa atgaagagac gttcaagaac tataaaaagg attttgaaaa tttatttgga   480
gcttcgacgc atcagccaaa aaaacaaatt gaacttattg atgagataaa aaaagacctt   540
gaaaaagaag atgccaaaga acttttagat gggttaaaag tcataaaaaa aattatagac   600
gaatttcaca aacaacaaaa ccaaggcaat ctcccacggg ctaagtattt tgaagaactt   660
tatcttgaaa tagaatacaa tctaaaaatc caaaaattct ttacatgtaa ccatcttcac   720
atcaatgaca tgcaatatct catcggcaat ctctcaaact atcagctcaa agagctaaga   780
cgctacttta acgatgaagc tatggcaaaa gaagactttt ggtcttgcga aaaactgcat   840
cgcatcacat ggcgatttat ccaaagttgg caccccaaaa gtcctgaaga caaacaaagg   900
caaaaagaga atcttgcaaa ccttaaaacc aaaagtatta ttgagttttt aaccaccacc   960
aacccactga tgaccattcc gccgtatgac gatatgaaca accgtggagc ggtcaaatgc  1020
caaacattgc gactcaatga ggagtatttg gataagcatc taccacattg gagagccata  1080
gcacatacgc ttgcaagtga gactcaaaaa gaaaatcttg agggtgtgac cgtaaaaggc  1140
tacagtgaag atagcacgct tttacaccgc attttggaca cctctagcat cattgaccct  1200
tatagactta gaagtgatga gatagatagt tattgtgatg tattgaccaa agacaatgct  1260
tttgcattga aaaaatttgc aaaagagtac tatcaacttg tcaaagaaaa agtacgaaca  1320
ggtatttgga caaaagacga tgatatgttc aaaaagtgtg accacaatcc accacacaaa  1380
aacaatcaaa tccacaattt agtcgcagga atcttaggca aacccatcgc aaaagagcgg  1440
tttgaagcgt ttgaaaatga acttggaat gtaaaatttg gcaacaaaaa actctcaagc   1500
tattgtaaaa acattgaaga gtttagaaaa tcaaacggca accttttaa gcagattgta   1560 gaattgggtg aagataaaga ggtacaaaaa tatcaaaaag agttaaacga atgggtacga  1620
aaaatcggtg agttttttaa catcgaaacg ccttatagag cacgctttaa caacctttt   1680 tccatggcgc aacttcatac catcatcgat accacacgca gtggttttaa cgctacatgt  1740
aaatggtgta gctgcgaaaa tcaataccga gctagcacaa gaatagagat agatgagcaa  1800
acaggggaaa ttactaccaa tgccaactgc caacggctcc cagccgatac acaaagacct  1860
tttagtggca agattgagcg gtacatcgac aaactaggtt acgagatagc caaagtcaaa  1920
gccaaagagt tggagggcat caagaagat acgatagatt taaaaatcat cttagagcaa  1980
aacgcttttg cgtatgaaga gtctattcga aatgccaaaa tcaaaaatgc caatgcaaaa  2040
gctaaaaaag ctcttgaaga agcacaaaaa agagggctta aaatattga agacaaaacc  2100 aaagaatta aagattttag caacagcatt tgccctatt gtgggcaaag tttaggcgaa  2160
gatggcgaga tagaccatat cttatcacga agttacaccc ttaaaaagta tgataccgtt  2220
ttcaacagcg aaggcaatct tttgtatgtt caccaaaaat gcaatcaagc aaaacttgca  2280
aaaacagatt attctttaca agatttaaaa atagatattt ctcaaaaatg gatagaagaa  2340
caaatcgcta ctatcaaaac ctacaaaact ttttcagttc ttacgcaaga acaacaaaaa  2400
```

```
gcttttaaat atgccctatt tttagataac tcaaatgaag cttaccaaaa agtaataagt    2460
tggcttagaa ccgaccaaag ctcacgagta acggtacgc aaaatatttt ggctaaaaaa     2520
atccaagaaa agctcaaagc gatgtttcca gctaaaacat ttaactttga gtttatctta    2580
gccgatgcca atgatgtgca tgatttgaga attaaagcgt atcaattgcc agaaaagcca    2640
aaagactcta acaagaaac ctacagtcat actatagatg cggttatgag tttggtcagt     2700
gtatgggata aggtattgcc aaaaacagaa aaacctacaa agaagatat tttaaaattt     2760 gccaatgtcg aaaattggag tgccctcaat aatgaatttt taaccaaagg caaatcagca    2820
aatcaaaaaa tagaagagat gatacaagcc aatgattttg gtcaaaaaaa tatgaggcaa    2880
gtttttagta agcccatttt taaagatgaa tcaataggag aaaggtataa gccatttgtt    2940
cgctatcaca atcaatttta cataggctat ccgataagca taaagacgg atacgatatg     3000 cagcattgtc aagcaatgat ttcaaagaac gatatttcaa gggtagagga gattcttaaa    3060
gacacctctt tatgcactct ttaaaagaa aagaatggca ttaaacttta ttctattaac     3120
aagcaaagta tcaatgaact gtcaaatcag ttctttaatt taaactatca aaacttaaac    3180
gatgcacaga gaaaaaaatc tgaactggca gaatttgtca tcaatcattg taaatattat    3240
gtcaaaaaaa catcggttat caatgcgcca caatttattg ataaagattc gatgaagccg    3300
tacccgtttt ataaagactg gcaaaaattt cacgaagctt acaaaaaaga gcttgatgct    3360
gaaccaaaaa ccaaaaaaga taacgggaaa ttagtttatg atatatcagg catagatgac    3420
ttctggactg aattttgcaa aaaatatttt ggtataaaaa caaagacaa tcgaaacaaa     3480 gcgagaaagg ttttttctat tgtggcgctt acttcagccc caggaacagt ctttagaatc    3540
aaacgaaaaa cgcctaaagg acacatatac caagcaacgg cgattgacaa tcaacaaatc    3600
agcggagatt atgcaaatgt tctgttagct ggtaactcaa aaacacttgc gttggcaggt    3660 caaaaaccctt catctgactt gaaaaaagag ttgagtgtca aagagtcaaa agatattcga    3720
gatataaagc ttgagccatc aagatttttc aaagagggt ttgattgtcg tggcattgaa     3780
gttattgtca ataaaacaag tgcgaccatt aaaaatttcc cacttacaaa aattgataaa    3840
aaaatcaaaa aacttatttt taaaactctc tttgaaaaaa aagatggtaa acgacaaaag    3900
caaaaaacat caatttcatt gaaagaaaaa aatacaatgc aagagacact aaaaaaatta    3960
ttaaaagata gtataaaagt tactattaga gatggtagca tttcgggtat tgaaattagc    4020
aaaaaaactg ttaatttac tttgccgttc aaaagtgaaa acttggcaaa actcttagat    4080
gactaa                                                              4086
```

<210> SEQ ID NO 75
<211> LENGTH: 3444
<212> TYPE: DNA
<213> ORGANISM: Bifidobacterium thermophilum
<220> FEATURE:
<221> NAME/KEY: misc_feature
<222> LOCATION: (1)..(3444)
<223> OTHER INFORMATION: Bthe Cas9 Open Reading Frame

<400> SEQUENCE: 75

```
atgtctgata agacatatcg tatcggtatc gacgttggtt tgtactctgt tggcttgtct    60
gccattcagg taaatgatga tgacgatcca gtaagaatac tgaacgcaca gagtgtcatc    120
catgatggcg gtgtcgatcc gaatgctcag aaaagcgctg atagccgacg tgctcagtct    180
gggattgccc gtcgcacgcg tcgtatgcgc cgtaatagga agaaacgtct gaagcgtctt    240
```

```
gatcaaattc ttgtggaatc tggtttccct gtgagcagtg agaatgatct tgaaggattt    300
gaaccgtggc ttcttagggc gcaagcggct gatgccttca ttgaagatga ggatattcgc    360
aagcgtgcaa tttcggtttc atgtcgccat atcgcgcgcc atcgtggatg agaaatcct     420 tatttggatg ttcgaacgct gctggcggtt gactcgcctt cctcggcatt ctatgacaag    480
ctcgtggaga atgctgctct tgaaatggac ggccagatgc ctgacagcga tgccacgccg    540
gcacagattg tgcgcgatgt gcttgagtac aagcgtggtg aagctgctat ccgtcttcga    600
aagtcaacgg ctgagaataa gaaaaatcgc ctcgctttgt tccctgagaa gatgatgcag    660
gatgactatg cttatgaatt gcgtttgatt ctggcgaagc aagcggttcc caaagatatc    720
gctcgcaagc tcattttggc ggtgttccaa tcgcagtcgc caaaaggttc tgcggagaag    780
cgtgttggga agatcccct tgatccgtct cagcctcggg cttgaaggc ttctctggca     840 ttccaagaat atcgaatatt gaatattctt accaatctgc gtttgcagga tggtggcgcg    900
gagcgtcgtc tgtctattga ggaaaagcag aagctctaca agatgctcgt ggaagatacg    960
ggtcgcgaaa agaagtacga gacatggaca gatatcgcat cggccatgga gtggaagcga   1020
aattggctca agggagttgg gagtttgacg gccgatggcg atgaccgagt cactagtcgc   1080
cctcctcata tcgatattgt agaaaagctc aacggcatta aggatacgaa attcagaaag   1140
agtattttgt cgtggtggaa atctgcgact gatgtcaacc gtgaagcgat gattgccctg   1200 cttttccaata cagtcgatat cgccaagaaa caggatgacc cggatttctc atccgccgtg   1260
gatttcattg attcgatgga tgatagcgat ttgcagattc tcgataccat cagcattcag   1320
cctggtcgtg ctgcgtattc gtcgaagacg ttgcgcgcat tatcaaaacg catgtattcc   1380
acggatgacg atttacacga tgcaagaaag catgtttttg gtgtagatga ttcatggcgt   1440
cctccacagc ctgcaattgg ggcgccattg ggtaatccgt cagttgatcg agtcgcgaaa   1500
attgtcaatc gttggcttct tgcatgccag tcccggtggg gaaacccgtt gtctatccaa   1560
atcgaacatg tacagagatgc gttgtcttcg gcagcgactg caaccgctga caagcgtgca   1620
tatgaacggg cgttaggcaa gcggaacgcc gagaaaatga agtcaagaa tgagcttcgg   1680 ttgcaaggac tcaatgaacc gcatgaatct gatgtccggc gtcaagaagc tatcactcgt   1740
caacagggca aatgcttgta ctgtggcgat gatatcacat tcagtacctg tgagatggat   1800
cacatcgttc ctcgaaaggg gcatggctct acaaatacgc gcgataatct cgctgctgta   1860
tgtattcagt gtaatcggca aagagtaat acgccgtttg ctctatggtg ccagactcca    1920
gaggcaaaaa gccgcggcgt gagtcttgaa gctgcaattc atcgcgtgaa aggtttcttc   1980
accgaatcga aggagctaac agggcggcag gcgaaggttt tcaccagctc gatgataatg   2040
cgtttgaagc agacgacagc tgacgatcct attgatagtc gctcgataga atcggtggca   2100
tggatggctg atgagttgca tcgtcgcatc gattggcatt tcaatggaga tgcctctgaa   2160
agcgaccatg tcgtagagt gctggttgct gtataccaag gcgtattac ttctgaagcg    2220 cgcaatgtca tgcgtttcca agcgggtggt gatttccact tgttggcgg acatggcaaa   2280 acacgcctcg atagaagaca ccacgcagtc gatgcgtcgg tgattgccat gatgactcct   2340
gcggcagcac ttacgctggc ggaacgtatc aatctccgag atagccaacg gtgcattgga   2400
cgtataagag agggggagat tgactggaaa cagtggccca acgagcctac agaaaaatat   2460
cagcattggc ttgataatgg gaaacgcctc ttcgcattga tcaatgatgc gctggataat   2520
gaccgtattc caataaccca ttggcagcgc tatgcgttgg gcaattctat tgcacacgaa   2580
gcaacgattc accctctgcg gaagattcca ctgggcagtg ccattgatta tgagacaatt   2640
```

```
agtcgagctg caactcctgc cctgtattgc gccttgacgc gttgcccgga ctattcggtg    2700
aatgatggtt tgccggagaa caaacagagg catattacag tgaatggcaa agtttatggg    2760
ccggaagatg aggtagcgtt ctttgcttct gaccatgtgg agcttgctgt gcaaggtggt    2820
tcggcagata ttgggaaaac tatccatcat gctcgggttt accgttgtta ctttgttgat    2880
cgtaggggac agaaaaagtg gttttacggg atgattcgtg tcttccgagt tgatttgata    2940
catgcaaggc atgagaacct attcacttat cctttgccct ctcaatcaat atcaatgaga    3000
tatgcggaaa caagaacggc tgaggcggtg ttatgcggac atgccgaaca tgtcggtaac    3060
ctggtagctg gagatgaaat cgaagttcca atgattggaa agctgacagg caaaatcgat    3120
acgtttgcaa aattctttaa tgaatctttg aataatgaat atgttgcaga acggtggagc    3180
attgatggtt tcgatagtga atcgaagttg ttgcttcgcc cgctaatgct ggctgaagag    3240
ggcatagcga attgggaaga taactctcac ttatctattc ccgatgatgt caagggactc    3300
attgctagag gctggcggcc atcggtggac acggtatttg cgaagaaacc gcggattgtc    3360
cgtcgaaatg tcctaggaga acccagatgg aagtcgcgtt caggcatgcc cgtttcttgg    3420
cgagtcacag gctctgaggc atag    3444
```

<210> SEQ ID NO 76
<211> LENGTH: 3216
<212> TYPE: DNA
<213> ORGANISM: Loktanella vestfoldensis
<220> FEATURE:
<221> NAME/KEY: misc_feature
<222> LOCATION: (1)..(3216)
<223> OTHER INFORMATION: Lves Cas9 Open Reading Frame

<400> SEQUENCE: 76

```
atgcgtcttg gttttgatat tggaacgaat tcgattggct ggtggttgta tgcgaccgac      60
ggcaacgaga tcaccggggt gatcgacggg ggcgtgcgga ttttctcgga cgggcgcgat     120
cctaaatcca aggcctcttt ggccgttgat cgccgcggcg cccgcgctca acgccgccgc     180
cgtgaccgtt acctgcggcg caaggcggcg ttgatgaaac gaatggccgc cgccggtttg     240
atgcccgccg atcctgtcgc ggcaaaggcg ttggaacagc ttgatcccta tgctttgcgc     300
gcttcgggat tggatcagga attgcccttg acccatctcg gccgtgcctt gttccacctg     360
aaccagcggc gcggctttaa gtccaaccgc aagacggaca agggcgacaa cgaaagcggc     420
aagatcaagg atgcgacagc acgtcttgat caggcgatga tagccaaggg tgcgcgtact     480
tacggcgaat tctacatat gcggcgcgct tcagccccgg acccaaaatg cgtgccgact     540
gtacgtaccc gactgtccat cgcaccgcgt gataacgccg aaaaggcaga ggcgggttat     600
gacttctacc cggaccggcg gcatttgttc gaagaattta ccaaactctg gcggcgcag     660 gccgcaaatt ccccggatat tcttaccgat gagctacgcg atgaaatctc ggtgatcatc     720
tttcaccagc gcccgctgaa acacccgag gtcggcctgt gcctgttctc aggatctcat     780
ggcgttccgc agaatgataa gcgcatcccg agcgcgcatc cgcagaacca cgccgtatt     840 cttttgaga cagtgaacaa cctgaaggtg gctgcacggg gcgaactggc acgcgggctg     900
acgcgcgatg agcgggacac aattgctcat gcgttagata caaggcgca taccaagtcg     960 ctgtccggca tgtcgatgaa gctcaaggcg cttggcaagc tgatcaagct gcgtcccgaa    1020
caatcattca cactggaaac tgccaaccgc gattccatcg tctgcgatcc ggtgcgggcc    1080
agcctgtcgc atcccgaccg gttcgggtcg cgttggtcca cactggacgc cgaagcacaa    1140
```

```
tgggatttgg tgcagcgcat ccgcgccgtg cagagcgatg cagaacataa cgcgttggtc    1200
gcatggctga tcgcgacgca cggacttgac cgcgtgcacg ccgagaacgt ggcaaatgcc    1260
ccactgcccg aaggccacgg ccgtctggga atgacggcga caaagcggat attggcggcg    1320
ctggaagccg aagtgatccc ctatagcgcg gcggtggcgg cttgtgggtg gcaccattcg    1380
gatgggcgta ccggcgaggt tctgactgaa ctgccctatt acggccagat cctcgaccgt    1440
cacgtgatcc ccggcacata cgacgagaac gacgacgaag tgacgcgcta tggccgcatc    1500
accaacccga cggttcatat cggcctgaac cagctgcggc gtttggtgaa caaaattgtc    1560
accgtttacg gcaagcctga tgaaatcgtc gttgagctag cgcgcgatct gaagctgtcc    1620
gaagatcaga agcgcgacgt gcagcgcgat atcaagaaga acaccgaagc tgcgattacc    1680
agaggtcaaa agatcgaaga attgggctat gcaaacacag gtgccaatcg ggtgatgtat    1740
cgcctttggg aggaactcgg cccggcaatc ggcccgcgct gttgcccata ttccggcaag    1800
ccgatcagtg cctcgatgat ctttgacggc tcctgtgatg tcgatcatat ccttccctat    1860
tcgcgcacgc tggaggacgg attttccaac cgtactctgt gcctgaagga gttcaatcgc    1920
cagaaaacca acaagactcc atgggaggca tggggcaata ccccggcctg ggatgccatc    1980
gaagccaacc tcaaaaatct gcccgcgaac aaggcttggc gttttgcccc cgatgcgatg    2040
gagcgtttcg agggcgagaa cgatttctct gcccgcgctc tgaaagacac tcaatacctg    2100
tcgcgcatcg cccgcagcta tctcgatgcg ctttacgatg gggcggacgg caagagccat    2160 gtctggttg tgcctggccg cctgaccgaa atgctgcgcc gccattgggg gctgaacagc    2220
ctgcttcctg ataaggatgg cgcggtcaaa gccaaaaacc gcagcgacca ccgtcaccac    2280
gcgatagatg ctgccgttgt cgcggctacc gaccggtcct tggtccagcg gatcagtaaa    2340
atggcgcaaa gggacgaagt gaatgggcc gaagaggttg cccgctccgt ccctcctcct    2400
tgggacgact ttcgaaccga tatcaaatcg caactagacc gtatcatcgt cagccaccgc    2460
gccgatcacg gccgaattga cttttgccgca cggcaaacgg gcaacgacag caccagcggc    2520
gcgttgcacg aggcgacggc actctcaatt attgacgacc agaacgtcgc agtccgcatt    2580
ccgctcttgt ctttgtccgc agcacagttt gaggaaggcg ggcggtcagg ctgggttcgt    2640
gacccgcagc tacgcggcgc tttgcatttg gcaaccaagg gcaaggacaa aaaagacttc    2700
gaggcggcgc tcctatcatt cgctgccaag cccgggccat atcacggaat atcaagggta    2760
cgtatcgaaa aacctttgca agatactgcc cgggtctacg tgcccgccga tgcgccgatt    2820
aaggcttacc aaggcggtag caatcatcgc tacgaagttt ggaagcttcc cgatggtaaa    2880
gtcctccatc acgttgtttc aatgtttgtt gcccatcagg gaaacctgac acgccccat     2940 cctgccgcaa aacgaattta tcaattcatg aagggtgatc tggtgagact tgaggacagc    3000
aagtttggac cagtgatcgc aacggtggag aagttcaacg gaaaggggat gattgagctg    3060
gttccgcata acgaagctaa tgcctcggac cgatatcgca aaaccaagga agatctctat    3120
atccgcctcg gcgcaacaac ccttctcagg gccaaagccc gccgtgtcca tgtcgatgaa    3180
atggggcgtc tgcgcgatcc tggcccaccg caatag                              3216
```

<210> SEQ ID NO 77
<211> LENGTH: 3318
<212> TYPE: DNA
<213> ORGANISM: Sphingomonas sanxanigenens
<220> FEATURE:
<221> NAME/KEY: misc_feature
<222> LOCATION: (1)..(3318)
<223> OTHER INFORMATION: Ssan Cas9 Open Reading Frame

<400> SEQUENCE: 77

```
atggatatgg cgtggcggct cgggctcgat cttggcacca attcgcttgg ctgggcggcg    60
ctgtcgctcg atgcggcggg ggcgccggat gccattctgg cagccggatc gcgcatcttc   120
ggtgatggcc gcgatccgca gtcgggcacg tcgctggcgg tggatcgccg cgcggcgcgg   180
gcggcgcggc ggcggcggga ccggttcaag caaaggcagc gcgcgctgct gaagcatctc   240
gaggcggacg ggctgttccc cgccgatccc gaggtgcagc aggcgctggc cgcgctcgat   300
ccctatgcgt tgcgcgcgcg ggcgctggac gaggcgctga gcctgcatga gatcggccgg   360
gcgctgttcc acctcaacca gcggcggggc ttccagtcca accgcaaggc ggatcgcggc   420
aaggatgagg atgcgggcaa gatcgcgatc ggcgtcgatc ggctgaagga tgccatcgcg   480
gcggcgggcg cgcggacgtt cggcgaattc ctccgccagc gccgtgcggg cgccaccggc   540
gagaatcaga tacccagcgt gcggacgcgg ctgcgcgccg agacgggcga ggggcgaag   600
ggcagcggct atgatttcta tcccagccgc gcgctgctga agacgagtt cgacgcgatc   660
tggcatgcgc aggcggagca tcatcccaag gtgctgaccg acgaggccta tcaccgcctc   720
cacgagatcg tcttccgcca gcgcccgttg agggcgccga aggtgggcgc ctgcaccctg   780
gtgccgggcg aagcgcggct gcccaaggcg cacccgctgt tccagcgccg ccggctgctt   840
gaggaactga cgcgctgat gatcgtccgc gccggcgcgg tcgcggaacg gctgacgccg   900
gagcagcgcg acctgctgct gctcaagctg aaggacaagg gtaaggtcac gttcaagagc   960
ctgcgcgaga aggtgctgaa gctggacggc gatgcgcgtt ttaacaagga aagcgagcac  1020
cgcaccgagt tgaagggcga tgaggtcgcc gcggaaatgg gcggcaagac gcgcttcggc  1080
tccttgtggc cgcaccttc cacggagcag caatggacgg tgatcgagcg gcagcaggcg  1140
ctggagagcg atgccgacga ggcggcgttc cgcacctggc tggtcgagac gcacaagctg  1200
acagccgagc aggcgagggc ggtggcgggc gcgcggctgc cgctgggca tggccgcttc  1260
gggctcaccg ccaccgcggc cctgctcgcc gcgttgcgcg atggccgcac gcccgagggg  1320
cgcggcccga atgcgcccgc gaccgaagcg ggccgggtgg tggtctatag cgaggcggcg  1380
gcgatcgccg gctatcatca cagcgatcac cgcagtggcc aggtcttcac ggacgccaag  1440
ggccgcccgg ccttgccta ttatggcgtg ccgctggatc ggcatatcgt gccgggcacc  1500
gcagaccccg acgagccgga tgaggcggcg cgcatcggcc ggctgaccaa cccgaccgtg  1560
catatcgcgc tcaaccaact ccgtcgcgtc gtcaaccggc tgatccgcgt ctatggcccg  1620
cccgccgagg tcgcgctgga actggcgcgc gaactcaagc tgtccgagga tgagaagaag  1680
gagcgcaacc gggagaacag ccgcaaccgc ctcgatgccg agaagcggtc ctccaagctc  1740
gccgaactcg gccagcgcga caatggcggc aaccgcgcgc tgctcaagct gtgggaggaa  1800
ctgaaccccg agaatatcct cgatcggcgc tgcatctatt cggggcggca gatctcgatc  1860
ggcatgatct tctcgggcgc ggcggaggtg gaccatatcc tgcctttcga cgccacgctg  1920
gatgattcca acgccaacaa gatcctctgc ctgcgcgagg ccaatcgcga caagcgcaag  1980
cgatccccgt tcgaggcgtg gggcggcacc ccgcaatggg aagagatcgc cgagcgcgct  2040
tcccgcctgc cgcgcaacaa gcgctggcgg ttcgagcccg acgcgatgga gcgcttcgcc  2100
gaggagggcg gcttcctcgc ccgccatctc gtcgacacgc aatatctcgg ccggatcgct  2160
catgactatc tgcgctgcct ctatcccgac aagggagacg gcagcagcca tgtgtgggtt  2220
tcgccaggcc ggctgaccga gatggtgcgc cgcaagctgg ggctgaacgg tctgctcggc  2280
```

| | |
|---|---|
| gaccataatc tcggcgccga acagcccaag aaccgcaagg atcatcgcca ccacgcgatc | 2340 |
| gacgcggtcg tcactgcgat cctcgatcgc tcgatgctcc agcgtatcca gcgggcttcg | 2400 |
| ggcgagggg cgagcgatgc cgagctgctg cgcatcatcg tgcccgaacc ctggacgggg | 2460 |
| tttcgggacg acctgcaacg cgcggttgac cgcatcgtcg tggcgcaccg tgcggaccat | 2520 |
| ggcacggtgg ccaaggccgc gacgcgggga cgggaccaga ccgcggcccg gctgcacaac | 2580 |
| gatactgcct acggcttcac cggcgaggcg gatgccaagg gcacgccgat tgtggtccat | 2640 |
| cgggcgccgc tgggggcgct caaaaagccc gagcatatcg atcaggtgcg cgatccgctg | 2700 |
| ctgcgcgcgg cattgcacga tttcacggcg gggctgagcg gcaagccttt cgaggatcgc | 2760 |
| atcgccgcct cccccggct tgggccgctc gactatcgcg gcatccgccg ggtgcgcgtg | 2820 |
| gtggagccgc tgcaggtgat cccgatccgc gacgccgccg gccgcgccta caagggctat | 2880 |
| aaaggcgatt ccaactatcg ctacgatgtg tgggaactgc ccgacggtaa atgggagcag | 2940 |
| cgtgtgctgc aaatgtacta cgcgcatcag tccggcgagc caccgcgccc gcatccagcg | 3000 |
| gcgcgcaagg ttctgagcct gcaccggac gatgtgctcg cgatcgagcg aggggagggg | 3060 |
| gggcgagaac tcgtccgcgt cgtgaaattc tcgaccaatg agttcacgct agcgccgctg | 3120 |
| aatgagggcg gggcgctgaa gtcgcgtcat gcggacaagg gagatccgtt cagatatctt | 3180 |
| tatccctcac cctcgacttt gaaagcgtgg cgcgcacggg aggtgcgcgt ggacgaactc | 3240 |
| ggccgggtgc tcgatcccgg cttccccgcg cgcaagcggc ggcgggtcac gcggcccggc | 3300 |
| cgcgcggacg cggattga | 3318 |

<210> SEQ ID NO 78
<211> LENGTH: 4200
<212> TYPE: DNA
<213> ORGANISM: Epilithonimonas tenax
<220> FEATURE:
<221> NAME/KEY: misc_feature
<222> LOCATION: (1)..(4200)
<223> OTHER INFORMATION: Eten Cas9 Open Reading Frame

<400> SEQUENCE: 78

| | |
|---|---|
| atgacaaaaa atattcttgg attagacttg ggagtttcat caatcggttg ggcttatgtt | 60 |
| caggaagatg ataaaaattc tgcgaataat aaaatcatca gttaggagt tcgtgtaaat | 120 |
| cctttgactt ttgatgaaca ataaatttc gaaaaggaa aaccgattac aaccaatgcg | 180 |
| ggaagaactt tagcaagagg agcaagaaga atctgcaaa ggtttaagtt gaggagagct | 240 |
| aatgttattg atgttttgac aaagggaaat atcttgaaag atggtgattt gcttacagaa | 300 |
| gttgggaaaa actctacgtt tcaaactcag gaattaagag caaaatctgc gaaagaaaaa | 360 |
| atcgaacttt cagattttgt gagggtttta cttttaatta ataaaaaaag aggctataaa | 420 |
| agcagtagaa aagcaaagaa cgaagatgaa ggacaaatca ttgacggaat ggcggttgct | 480 |
| aaaaaattat atgaagaaag cctgactcca ggagaatatt cttaccaact tttaatagaa | 540 |
| gggaagaagc aattgccaga tttttatcgt tctgatttac aatctgaatt tgataaagta | 600 |
| tggaaatttc aaaagcaatt ttattctgaa atcttaattg atgaacttta taagaacta | 660 |
| caagcaaaaa ataaaaatgc gacgtgggca atttttgaaag aaccgttttc tcttgttgga | 720 |
| atcaaacaaa tgggaactat gcaggagaaa aagattgaaa aatatctttg gagaagtgaa | 780 |
| gctgcaaaaa aacaattgga ttttgaaagc ttagctgtcg tgtttcaaga gattaacagt | 840 |
| aacctaaata attctagcgg ctatctcggc gcaataagtg atcgaagtaa agaattgtat | 900 |
| tttaatcata tgactgttgg tgaatatctt tatcaacaac ttaaagcaaa ccctcatacc | 960 |

```
aaacttaaaa atcaagtttt ttatcgacag gattatttgg atgaatttga aaaaatatgg   1020
gagacacaat ctcaatatca ttcagaatta accaaggaat taaaagaaca agttcgtgat   1080
gtcgtgattt tctatcagag aaaactcaaa tcccaaaaag gtttaattag tatttgcgaa   1140
tttgagaaca gagaaattga aatcatgaaa acggaaaaa caaagaagaa aacagtagga   1200
ttaaaggttg ctcctaaatc ttcgccattg ttccaagagt ttaaaatttg gcaagtttta   1260
aataatctgc aatttcaaaa tttagaaaca aagaaatttt tcccaatcga tttagatttc   1320
aaacaatcaa ttttttgatga agttaatgtc aaaggaagac tttctgcaaa agaggtttta   1380
gatattgtag gttattccgg taaagaatgg aaaactaatt ttaaagatat tgaaggcaat   1440
aataccaatg aaaatctata cactgctttt ctgaaaatta ttgctaatga aggaaaagaa   1500
ttcccaaaag agtttaagtt aacgattgaa gacgatatta agttactaa gattcattct   1560 tctgcaagta aaataaaaga atttgtaaaa gagaattttt cgtcattagg aataaataca   1620
tcaatattag atttaatcc agaatttgac ggaaaagatt ttgagaagca agttcctat   1680 cagctttggc atttattgta ttcttacgaa ggcgatgatt ctgcttctgg taatgaaaaa   1740
ttatatgagc ttctggagaa gaaatttagc tttaaaaaag aacattccaa atattggca   1800 gaaattggtt tctctccaga ttatggaagt ttgagttcaa aagcgatgcg aaagatttgc   1860
acttatatca aagagcataa atacagcgac gcttgtaatt tagctggtta taatcactct   1920
aaaaattcat tgactaaaga acaattagca aatagaattt taaaagaaaa actagaaatt   1980
cttccaaaaa attctttgag aaatcctgtg gttgaaaaga ttttgaatca aatgataaat   2040
gtggtcaatg aagtatccaa agaatacgga agaccagacg aaataagaat tgagctagca   2100
agagaactga aaaaaaatgc agaggagcgt gcaaatatga cttctgaaat tggcaaagca   2160
accttgcttc atcaaaaata tgcagaaata ttacagaaag aatatgggat aaaagtacca   2220
tcaagaaacg atattattcg gtacaaactg tatttggagc tggcaaataa cggtttaaa   2280 gatttataca caggtcaaaa aatagaaaag gaaaacattt ttaccgacaa atatgatatt   2340
gaccatatta tcccgcaatc tcgatttttt gatgacagtt tttcaaataa agttttggta   2400
ccgagaggtg caaatcttaa aaaaggaaac gcaactgcat tgattatttt ggaaatggaa   2460
gggaaagatc aactggaaaa attcctcaac accatcaaag atttgtttga taaaagtttg   2520
atttctaaag ctaaatttga aaaacttcag aaaaaaggaa gtgaaattgg agatggtttt   2580
atacaaagag atttacgaga tacacagtat atagcgaaaa aagcaaaaga gattcttttc   2640
gaaattacca attctgtggt ttctacatca ggaagaatca cagataaatt acgtgaggat   2700
tggaatctcg tcaacacaat gaaagaactt aatctcgata aatacaggaa attaggttta   2760
acggaaacgg taattaattc taaaggagaa gaaaagaaa gaattacgga ttggagtaaa   2820
agaaatgatc atcgccatca cgcaatggac gctttgacag tagcttttac gacgcataat   2880
catatacaat atttgaatca tttgaatgct agaaaagatg aaaagcataa tcagcatatc   2940
attatttcaa acattgaaaa tcttattaca aaagtctatg aaaagaaaaa tggttctact   3000
aaaagaaagt ttgtagaacc gattcataat tttagaattg aagccaaaaa gcatttagat   3060
gaaatattga tttctcacaa aacgaaaaat aaggttgtta ccaaaaacat caataaaacc   3120
aagaaaaagg gtggagtagt tgctaaagta gtgttgacac cgagaggtca acttcataaa   3180
gaaactattt atgaagctc gaaatttctt aaaactaaag aagaaaaagt atcgggaaa   3240 tttgatttgg aaaccattaa caaagttcag aatgagaaat ttagaattgc tttattagaa   3300
```

```
agattaaaag aatttaatgg agattctaaa aaagcattta caggaaaaaa tgtgttggca    3360
aaaaatccga tttatttgaa tgaagaaaag actgaacaag tttctgaaag tgtaattctg    3420
gcttggtacg aaaaggctta taccattagg aaagcagtaa attctgataa ttttaaagat    3480
tataaaaacc ttgaaaaagt aattgataat ggcgtaaaag aaatcttaaa aaatcgtctg    3540
gatgcattta agggtaatgc aaaagaagca ttttctgatt tagaaaaaaa tccgatttgg    3600
ttgaatgagt ccaaaggaat agccataaaa acagttacca taacgggaat caataatgca    3660
gaaactttgc attacaaaaa agaccatttt ggaaaagaaa ttctagatga aatggtaaaa    3720
agaatagccg ttgattttgt aagtactgga aataatcatc acgttgctat ttatgaagat    3780
gcagatggaa atttgcagga agagtagtg agtttctacg aagctgttga agagtgaat     3840
```
```
cagggggcttt caattatcga taaagaatat aattctggat taggatggaa gtttctttt    3900 acaatgaagc agaatgaaat gttttgtt ccatcagaag attttaatcc aaagaaaat     3960 gatttatttg atgaaagaa tctgagtttg atttctaaga atatgtttag agtacaaaag    4020
tttggggaat tatctaagtc aggttttggg tttagacatc atttggaaac atcagtggaa    4080
cttaaaaaag aattgagaag tacttcttat ttagattttt acagtaaaga ttttatgaaa    4140
actattgtta aagtaagatt gaatcatctt ggaaaaatag ttcaaatagg cgaatattaa    4200
```

<210> SEQ ID NO 79
<211> LENGTH: 4362
<212> TYPE: DNA
<213> ORGANISM: Sporocytophaga myxococcoides
<220> FEATURE:
<221> NAME/KEY: misc_feature
<222> LOCATION: (1)..(4362)
<223> OTHER INFORMATION: Smyx Cas9 Open Reading Frame

<400> SEQUENCE: 79

```
atgaaaacag ttcttggtct tgatttaggt acaaactcta ttggttgggc attgattcaa      60
catgattttg atagtaaaaa aggtgaaata cttggaatgg gtagccggat aattccaatg     120
agtcaggata ttttaggtga atttggaaag ggaaattctg tttctcaaac agctgacagg     180
actaaattca ggagtgcaag aaggctccgg gaacgtcatc ttttaagacg agagcgttta     240
catcgcgttt taaatatcct tggttttctt cctcgtcatt atgccgctga tattgatttt     300
gaaaaacgat tagggcaatt ttttgaagga aagaaccta aactagctta tgacaacaat      360
cagttcattt ttacaaaatc ctttggaaaa atgctggctg attttcgtca gcatcagcct     420 gatttttaa aggatgaaaa aagtaatgat ttattaatac cttatgattg gtctattat       480 tatttgcgta agaagcttt aacaaaaaaa atagagaagg aagagcttgc atggataatt      540 ctcaattta atcagaagcg tggatactac caattacggg gagaggagga agaggagaat      600
ttaaacaagt tggtagagtt tcattcttta aagattatag atgtagttgc ggatgaaaaa     660
cttaataata aaggtgagac atggtattcg cttcttcttg aaaatggatg gacatacaga     720
cgttcaagta aggttccatt atttgattgg aagagaaag tcagagattt tattgttact      780
actgatataa atgatgacgg gtctgtaaaa acagataaag agggaaatga aaaagaagc       840 ttcagagcgc ccagtgatga tgattggact ttactgaaaa agaaaacgga acaggatatc     900
gacaagtcaa ggaaaccaat tggggcttat atttatgatg caatacttaa aaaccccaag    960
caaaaaataa atggtaagct tgtacgtaca gttgaacgta aattctataa ggaagagctt   1020
aaactgattc tacagaagca aaaggaattt catcctgaat tgcagagtac agatttgtat    1080
aatgaatgta ttcgggagtt gtataaaaat aatgatgcac atcaattaca gttaaataaa    1140
```

```
aaagattttg ttcatctatt tttggaagat attattttt atcagcgtcc gcttcgaagt    1200
cagaaatctt ctgttggtaa ttgtccttta gaattcagaa atttaaaga tagtgagggg    1260 attgagaagg tagaatattt gaagacaatt cctaagtcca atccatattt tcaggagttc    1320
cgcatttggc agtggatgta taatctttca atatacaaga aggatgatga tgaaaatgtt    1380
acccgtgatt ttctgaaaac tatagaagat tgggaggatc tattcgaatt tcttaatcat    1440
cgaaaagata ttgagcaaga gacattgttg aagttttgt taggaaagaa tggggtaaaa    1500
ggaaaggctc ttaaagtaga agcagggaaa tttcgttgga attatgtatc agataagatt    1560
tatccatgta atgagaccaa agctcttatt atttctaagc ttgaaaaagt aaaaggtgta    1620
gaggagaaat ttttgacaga agagatagag tataagcttt ggcatcttat ttattctgta    1680
acagataaag ttgagtatga aaaggctcta aaggcttttg ctggtaaaca aaagttggat    1740
ttggtttcct ttgtagattc atttaaaagg tttccaccat ttaaaaatga gtatggtgct    1800
tattctgaga aagcaattaa aaagattctg cccttattac ggacgggaaa atcttggaat    1860
tggatggcta ttgatagcaa agtaagggat agaatcaata aaataattac tggagaattt    1920
gatgaagaaa taaagaataa agttcgtgag aaggcggaaa agcatagttt aaagaaggaa    1980
aacgattttc aaggcttacc attatggttg gcgcaatatg tagtatatgg aagacattca    2040
gaagcaagtt tttcaggtaa atggaactcc gttgatgatt taaaaaagta tctcgaagaa    2100
tttaagcaac attcattgag aaacccgata gtagaacaag tattgacgga gactttacgg    2160
gttgttgctg atatttggca attttatgga aaggagaaaa aagatttctt tagtgagatt    2220
catattgaac tcggaagaga aatgaaaaat acagctgaag accgtaaaga aatgagtgcc    2280
ataatacagg cgaacgaaac aactaacctt agaataaaag ctctattaaa tgaactgttg    2340
caagacaaga aggtggaaaa tgtaagacct tattctcctt ctcaacagga aattttaaag    2400
atatatgaag atggcgtttt aagttctgat attgaaattc cagatgatat tcagaaaatc    2460
agtaaagcag cccaaccaac gaaatcagaa cttcagagat ataagttatg gcttgagcaa    2520
aaatatcgat ctccatacac tggagcaatg attccattgg gcaagttgtt tacatctgaa    2580
tatgaaattg aacatatcat tcctcagagt cttattttg acgatagttt tagtaataaa    2640
gtaatttgtg agtcggccgt caataaactt aaagatagta ggttgggaat ggaatttata    2700
aaagaatgcc atgggatggt tgtggaaaca ggctttggta agtcggttac tgttttgag    2760 gaagaaactt atagagattt tgtggttcaa aattatagta agaatcattc caaaaaagt    2820 aagcttcttt tggaagaaat tcctgagaag atgatcgaaa ggcagatgaa tgacactcgt    2880
tatataagta agtttatatc atctgtatta tctaatatag tgcgtgagga ggtcaatgat    2940
gatggagtta actcaaaaaa tattgttccg ggtaatggta aaattacaac acagttaaaa    3000
caggactggg gtttaaatga tatttggaat gaattgattt taccacgctt tgaacgtttg    3060
aatgttttga ctgattcaaa acatttaca gcttggagtg aaaatcatca gaggctattg    3120
ccaactgtac cgataggget ttctaaagga ttttccaaga aagaattga tcatagacat    3180 catgctttgg atgccttggt tatagcctgt gcctccagaa atcatatcaa tttttttgaac    3240 aatgcacatg caatagataa aaagaaaaat tcggaggaaa acaaaaaatt tagacatgat    3300
ttaaaagcga ttctttgtga taaaaagtat agtgataaat ccgaaaagaa ttacaggtgg    3360
atattcaaga aaccttggga taattttact attgattcaa aaaacgcttt ggataaaatt    3420
attgtaagct ttaaacaaaa tcttcgaatt atcaataagg caacaaaccg ttatgaaaaa    3480
```

```
tgggtagata gagatgggat aaaagtaaaa gaatggcata agcaagaagg aataaactgg       3540
gctactagaa agcctttgca taaggataca gtttcaggta aagttgattt aaaaagggta       3600
acagttccag aaggaaagat attgaccgct accaggaaaa gcttagatac atcgtttgac       3660
ttgaaggtca ttgaatctat tacagatacc ggtattcaaa aaattctaaa aaattatctt       3720
actagtaaat caaataatcc ggagctcgca ttttcttcgg agggtgttga ggatatgaat       3780
aagaatatca gaaatataa tgatggaaaa ttgcatcaac ctatatataa agttagaata       3840
tttgagttgg ggagtaaatt tccattggga caatttggta ataaaaagtt aagtatgta       3900 gaaacagcaa aagggactaa tcttttcttt gctgtatatg aagatgaaaa taaaaatagg       3960
aattatgaaa cgattccttt aaatgtagtt attgaaaggc aaaaacaagg actctcttct       4020
gtgccaataa aaagtgaaaa aagggcataaa ttgttattct atttgtcccc aaatgatata       4080
gtctatgttc ctggtagtaa tgaagaattc agtatagata ggctttatag atttacagat       4140
tccagcgata agactgctaa ttttataccca cttagtgttt caagtttaat tttttagctca      4200 aataaaaatg agcaaaaaaa aatagggatt agctatccaa ttcaagatga gtttggtcta       4260
ggaagtccac agtcaaaaaa tcaaaagtcg atcgacggaa taatgattaa agagaaatgt       4320
gtaaaagtga atatagacag gcttggtagg gtgtcatttt ga                         4362
```

<210> SEQ ID NO 80
<211> LENGTH: 4530
<212> TYPE: DNA
<213> ORGANISM: Psychroflexus torquis
<220> FEATURE:
<221> NAME/KEY: misc_feature
<222> LOCATION: (1)..(4530)
<223> OTHER INFORMATION: Ptor Cas9 Open Reading Frame

<400> SEQUENCE: 80

```
atgaaaagaa ttttagggtt agatttagga acaaactcga ttgggtggag tctaattgaa        60
catgatttta aaataagca aggacaaatt gaaggattag gtgttcgtat aattcctatg        120
agtcaagaga tactaggtaa atttgatgct gggcaatcaa tctctcaaac cgcagataga       180
acaaaatata gaggcgttag acgattgtat caaagagaca atcttcgaag agaacgtcta       240
catagagtgt taaaaatttt agactttctt ccaaagcatt atagcgaaag cattgacttt       300
caggataaag taggtcaatt caaacctaaa caagaggtta aactcaatta tcgcaaaaat       360
gagaaaaata agcacgaatt tgttttttatg aattcattta ttgaaatggt aagtgaattc       420
aaaaatgccc aaccagagct tttttacaat aaaggtaatg gagaagaaac aaaaaatacca       480 tatgactgga cattatacta tctccgtaaa aaagccttaa ctcaacaaat tactaaagaa       540
gaactagcct ggttaatttt aaatttcaat caaaaacgag ctattatca attacgtgga       600 gaagacatag atgaggacaa gaacaagaaa tacatgcaac ttaaagtcaa caatttgatt       660
gattctggtg caaaagtgaa aggaaaagta ttgtataatg taattttttga taatgggtgg       720 aaatatgaaa acaaattgt caataaagat gaatgggaag aaggacaaaa ggaatttatt        780
attaccacta aaacactgaa aaatggtaat attaaaagaa catataagc tgtagactcg       840 gaaatagatt gggctgcgat caaagctaaa actgaacaag acattaataa agcaaataaa       900
acagtaggcg aatatattta cgaatctcta ttagacaatc cttctcaaaa aataagaggg      960
aaattggtta aaactataga acgaaaattt tataagagg aatttgaaaa gctactttct       1020
aaacaaattg aattacaacc tgaactattt aatgagtcac tgtacaaagc ttgtattaaa       1080
gaattatacc ctagaaatga aaatcatcaa agtaataata aaaaacaagg gtttgagtat      1140
```

```
ttatttacgg aggatattat cttttatcaa agaccactta aaagtcaaaa atctaatatt    1200
tctggttgtc aatttgagca taaaatttat aagcaaaaaa ataaaaaaac aggtaagctt    1260
gaattaataa aagaacctat aaaaaccatt tccagatcac atcccttatt tcaggaattt    1320
agaatttggc aatggttaca aaatcttaaa atctataata aagaaaaaat agaaaacgga    1380
aagttagaag atgtaacaac tcaactatta cctaataatg aggcctatgt taccttattt    1440
gattttttga acactaaaaa agaacttgag caaaagcaat ttatcgagta ttttgtaaaa    1500
aagaaattaa tagataaaaa agaaaaagag catttccgtt ggaactttgt agaagataaa    1560
aaatatcctt tttctgaaac cagagcccaa tttttatcac gcttagccaa agttaaagga    1620
ataaaaaata ctgaagattt tttaaataaa aatacgcaag taggaagcaa agaaaatagt    1680
ccatttatta aacgaataga gcaattatgg cacatcatat attcggtttc tgatctaaaa    1740
gagtatgaaa aagcactcga aaaatttgca gaaaaacaca acttagaaaa ggactccttt    1800
ttaaaaaact tcaaaaaatt tcctccattt gttagcgatt atgccagcta ctctaagaaa    1860
gctatatcaa aactattacc aattatgcgc atgggtaaat attggagtga aagcgccgtt    1920
ccaacccaag tgaaagagcg ttccttatca attatggaaa gagtaaaagt cttacccta    1980 aaagaaggtt actctgacaa agatttagct gatttgcttt caagagtaag tgacgatgat    2040
ataccgaagc aattaataaa aagttttatt tcttttaaag acaaaaaccc attaaaaggc    2100
ttaaatacat accaagccaa ttatttagta tatggtagac actcagaaac tggagatata    2160
caacattgga aaacacctga ggatattgac aggtatttaa ataatttcaa acagcattcc    2220
ctacgcaatc ctattgtaga gcaagtggtt atggaaacct gcgtgtagt gagggacatt    2280 tgggagcatt atggtaataa tgaaaaagac ttctttaagg aaatccatgt ggaattaggc    2340
agagagatga aaagccctgc tggtaaacga gaaaaattat cacaaagaaa taccgaaaat    2400
gaaaacacta atcatcgtat ccgggaagtt ttaaagaat tgatgaatga tgcctctgtt    2460
gaaggtggtg tacgcgatta ttctccgagc cagcaggaga ttcttaaact ttatgaggag    2520
ggcatttacc aaaatcccaa caccaattat ttaaaagttg atgaagatga aatactaaaa    2580
atacgcaaaa agaataatcc tactcaaaaa gagatacaac gctacaaact atggttagaa    2640
caaggatata tctcaccctta tacaggaaag attattccct taacaaaact gtttactcac    2700
gaatatcaaa ttgaacatat cataccacaa tctaggtatt atgataattc tctaggaaat    2760
aaaatcatct gcgaaagcga agtcaatgaa gataaggata ataaacagc ttatgaatat    2820 ttaaaggttg aaaaaggaag tattgttttt gggcataagc ttctcaattt ggacgaatat    2880
gaagctcacg tgaacaaata tttcaaaaaa aataaaacaa aactaaaaaa tttattaagc    2940
gaagatatcc ctgaaggttt tattaaccga caacttaatg atagtagata catcagtaag    3000
ctggtaaaag gactattgag taatattgta cgagaaaatg gggaacaaga agcaacatca    3060 aaaaaccttta ttccagtaac tggtgtagtc acctcaaaac taaacaaga ttggggggctt    3120 aatgataaat ggaatgaaat cattgctcct cgttttaagc gattaaataa actcacaaat    3180
tcaaatgatt ttggttttttg ggataatgac attaacgcct ttagaattca ggttccagat    3240
agtcttatca aaggttttag caaaaaaaga atagaccatc gccaccatgc cttagatgcc    3300
ttggtggtag cttgtacttc aagaaatcat acacattact tgagtgcatt aaatgccgaa    3360
aataaaaatt acagcttgcg tgacaaactt gtaatcaaaa atgagaacgg tgactatact    3420
aagacctttc aaataccgtg gcaaggtttt acaatagaag ctaaaaacaa cttagaaaaa    3480
```

-continued

```
acggttgtaa gctttaaaaa gaacctgcgt gttattaaca aaaccaataa taaattttgg    3540
tcttacaaag atgaaaacgg aaatctaaac cttggaaaag atggaaaacc taagaagaaa    3600
cttcgcaaac agaccaaagg ttataactgg gcgattcgca aacctttgca taagaaaact    3660
gtatcgggaa tttataatat taatgcgcca aaaataaaa ttgcaacttc agtaaggact    3720
ttattaacag aaatcaaaaa tgaaaaacat ttagcaaaaa taaccgattt acgtattaga    3780
gaaacgattc tacctaatca tctaaagcat tacctaaaca ataaaggga agcaaatttt    3840 agtgaagcat ttagccaagg gggtattgaa gatttaaaca aaaaaattac gactttaaac    3900
gaaggaaaaa aacatcaacc tatttataga gtgaaaatat ttgaagtagg cagtaagttt    3960
tcaatttcag aggatgaaaa ctctgcaaaa agtaagaaat atgtagaagc tgcaaaaggc    4020
accaacttgt tctttgctat ttatttggat gaggagaata aaaaacggaa ctatgagacc    4080
attccgctta atgaagtaat cacccatcaa aaacaagtag caggttttcc taaatctgaa    4140
agattatctg tacaacctga ttctcaaaaa ggcacattct tattcaccct ttctcctaat    4200
gatttagttt atgtaccaaa taatgaggaa cttgaaaatc gtgatttatt taatttgggg    4260
aatttgaatg tcgaacaaat aagtagaatt tacaaaattca ctgactcaag tgataaaact    4320
tgtaatttta taccatttca agtatcaaaa ttgatattta atttaaaaaa aaaggagcaa    4380
aaaaaattag atgttgattt tattattcaa aatgagtttg gcttaggaag tcctcaatct    4440
aaaaatcaaa aatcaattga tgatgttatg ataaagaaa aatgcattaa actcaaaata    4500
gacagattag ggaacatttc aaaagcctag                                     4530
```

<210> SEQ ID NO 81
<211> LENGTH: 1368
<212> TYPE: PRT
<213> ORGANISM: Lactobacillus reuteri

<400> SEQUENCE: 81

```
Met Ile Lys Lys Asp Tyr Asn Ile Gly Leu Asp Ile Gly Ala Thr Ser
1               5                   10                  15

Val Gly Phe Ala Gly Ile Asp Glu Gln Tyr Asp Pro Ile Lys Leu Lys
            20                  25                  30

Gly Lys Thr Val Val Gly Val Asn Leu Phe Glu Glu Gly Gln Thr Ala
        35                  40                  45

Ala Asp Arg Arg Ser Phe Arg Thr Thr Arg Arg Leu Asn Arg Arg
    50                  55                  60

Lys Trp Arg Leu Ser Leu Leu Glu Glu Phe Phe Asp Pro Tyr Ile Thr
65                  70                  75                  80

Pro Val Asp Pro Ala Phe Phe Ala Arg Leu Lys Glu Ser Asn Leu Ser
                85                  90                  95

Pro Lys Asp Asn Asn Lys Asn Phe Ser Arg Ser Leu Leu Phe Pro Asp
            100                 105                 110

Ile Thr Asp Gln Lys Phe Tyr Glu Glu Tyr Pro Thr Ile Tyr His Leu
        115                 120                 125

Arg Tyr Ala Leu Met Thr Glu Asn Lys Lys Phe Asp Leu Arg Ala Ile
    130                 135                 140

Phe Leu Ala Ile His His Met Ile Lys Tyr Arg Gly Asn Phe Leu Asn
145                 150                 155                 160

Ser Thr Pro Val Ala His Phe Asp Thr Ser Lys Ile Asp Phe Ala Asn
                165                 170                 175

Asp Phe Ser Lys Leu Asn Arg Leu Tyr Leu Asn Glu Asp Pro Asn Asn
            180                 185                 190
```

-continued

```
Ile Phe Glu Ile Asn Leu Gln Asn Val Lys Glu Ile Ser Asp Ile Leu
        195                 200                 205
Leu Asp His Ser Ile Lys Lys Phe Asp Lys Gln Lys Gln Val Ala Lys
    210                 215                 220
Leu Leu Leu Thr Ser Gln Asn Asp Lys Glu Leu Asp Lys Arg Asn Lys
225                 230                 235                 240
Gln Ile Ala Thr Gln Ile Ser Lys Ala Ile Leu Gly Tyr Asn Phe Ser
                245                 250                 255
Leu Asn Glu Ile Leu Lys Leu Glu Ala Val Asn Lys Ser Lys Trp Lys
            260                 265                 270
Leu Asn Phe Ser Ser Ala Asp Ile Asp Asp Thr Leu Pro Asp Leu Ile
            275                 280                 285
Ser Glu Leu Asp Glu Ser Gln Glu Ser Ile Leu Asn Ile Ile Leu Ser
        290                 295                 300
Leu Tyr Ser Arg Leu Thr Leu Asn Gly Ile Val Pro Ser Gly Met Ser
305                 310                 315                 320
Leu Ser Glu Ser Met Ile Asp Lys Tyr Gly Thr His Lys Glu His Leu
                325                 330                 335
Asp Leu Leu Lys Lys Tyr Leu Lys Thr Leu Pro Ile Lys Asn Arg Lys
            340                 345                 350
Glu Ile Ala Glu Ala Tyr Ala Glu Tyr Val Gly Asn Ser Leu Lys Lys
            355                 360                 365
Ser Gly His Ile Ser Gln Glu Glu Phe Tyr Lys Ala Val Lys Lys Asn
        370                 375                 380
Leu Asp Lys Ser Glu Thr Ala Gln Lys Ile Leu Ser Leu Ile Ser Glu
385                 390                 395                 400
Glu Lys Phe Met Pro Lys Gln Arg Thr Asn Gln Asn Gly Val Ile Pro
                405                 410                 415
Tyr Gln Leu His Gln Lys Glu Leu Asp Gln Ile Ile Val Asn Gln Ser
            420                 425                 430
Gln Tyr Tyr Pro Trp Leu Ala Glu Leu Asn Pro Val Thr Glu His Lys
        435                 440                 445
Asp Ala Lys Tyr Lys Leu Asp Glu Leu Ile Ala Phe Arg Val Pro Tyr
        450                 455                 460
Tyr Val Gly Pro Leu Ile Asp Pro Lys Thr Ile Pro Gln Thr Glu Gln
465                 470                 475                 480
Gly Asn Lys Asn Ala Ser Phe Ala Trp Met Val Arg Lys Glu Asn Gly
                485                 490                 495
Gln Ile Thr Pro Trp Asn Phe Asp Lys Lys Val Asp Arg Ile Ser Ser
            500                 505                 510
Ala Asn Asn Phe Ile Lys Arg Met Thr Thr Lys Asp Thr Tyr Leu Ile
            515                 520                 525
Gly Glu Asp Val Leu Pro Ala His Ser Leu Ile Tyr Glu Arg Phe Lys
        530                 535                 540
Val Leu Asn Glu Leu Asn Met Ile Arg Val Asn Gly Lys Lys Leu Ser
545                 550                 555                 560
Val Ser Val Lys Gln Asn Leu Tyr Asn Asp Leu Phe Lys Gln Gln Lys
                565                 570                 575
Thr Ile Asn Arg Lys Lys Leu Ala Asn Tyr Leu Gln Ala Asn Leu Gly
            580                 585                 590
Ile Pro Glu Arg Pro Gln Ile Thr Gly Leu Ser Asp Pro Glu Lys Phe
            595                 600                 605
```

```
Asn Ser Gln Leu Ser Ser Tyr Ile Asp Leu Gln Lys Ile Leu Gly Ser
    610                 615                 620

Glu Ile Val Asp Asp Pro Asn Lys Gln Asp Asp Leu Glu Lys Ile Ile
625                 630                 635                 640

Glu Trp Ser Thr Val Phe Glu Asp Ser Arg Ile Tyr Lys Val Lys Leu
                645                 650                 655

Gln Glu Ile Gly Trp Phe Thr Glu Lys Gln Lys Asn Glu Leu Val Ser
            660                 665                 670

His Arg Tyr Gln Gly Trp Gly Arg Leu Ser Lys Lys Leu Leu Val Glu
        675                 680                 685

Leu Lys Asp Lys Asn Gly Arg Ser Ile Ile Asp Leu Leu Trp Asn Ser
690                 695                 700

Gln Arg Thr Phe Met Glu Ile Gln Ser Arg Pro Glu Phe Ala Glu Gln
705                 710                 715                 720

Ile Thr Asn Glu Asn Gln Asp Lys Leu Thr Glu Asp Asn Tyr Glu Asp
                725                 730                 735

Val Leu Ala Asp Ala Tyr Thr Ser Pro Gln Asn Lys Lys Ala Ile Arg
                740                 745                 750

Gln Val Ile Lys Val Val Asp Asp Ile Val Lys Ala Thr Gly Lys Ala
            755                 760                 765

Pro Lys Phe Ile Ser Leu Glu Phe Ala Arg Ser Asp Glu Arg Ser Asp
770                 775                 780

Arg Val Lys Ser Arg Lys Thr His Ile Gln Lys Ile Tyr Glu Thr Thr
785                 790                 795                 800

Ala Lys Glu Leu Leu Lys Asp Asp Gln Leu Ile Lys Glu Leu Gly Ser
                805                 810                 815

Val Ser Asp Leu Ser Asp Arg Leu Tyr Leu Tyr Phe Thr Gln Leu Gly
                820                 825                 830

Arg Asp Met Tyr Thr Gly Lys Pro Ile Asn Ile Asp Glu Ile Ser Thr
        835                 840                 845

Met Tyr Asp Ile Asp His Ile Leu Pro Gln Ala Phe Leu Lys Asp Asp
    850                 855                 860

Ser Leu Asp Asn Arg Val Leu Val Arg Arg Gln Asp Asn Asn Ala Lys
865                 870                 875                 880

Ser Asp Thr Val Pro Ala Leu Lys Phe Gly Lys Met Lys Pro Phe Trp
            885                 890                 895

Asn Lys Leu Gln Lys His Gly Leu Ile Ser Lys Arg Lys Leu Asn Asn
                900                 905                 910

Leu Gln Thr Asn Pro Glu Ser Ile Asp Lys Phe Lys Ala Val Gly Phe
        915                 920                 925

Val Asn Arg Gln Leu Val Glu Thr Arg Gln Val Ile Lys Leu Ala Ala
    930                 935                 940

Asn Ile Leu Ala Ser Arg Tyr Pro Asp Ser Lys Ile Ile Glu Val Lys
945                 950                 955                 960

Ala Ser Leu Thr His Gln Met Arg Glu Ser Phe Asn Leu Ile Lys Asn
                965                 970                 975

Arg Asp Val Asn Asp Tyr His His Ala Val Asp Ala Tyr Leu Ser Ala
                980                 985                 990

Phe Val Gly Gln Tyr Leu Tyr Asn Arg Tyr Pro Lys Leu Gln Pro Tyr
            995                 1000                1005

Phe Val  Tyr Gly Gln Phe Lys  Lys Phe Asp Lys Gln  Ser Thr Arg
         1010                 1015                 1020

Ile Gly Met Lys Thr Asn His  Phe Asn Phe Leu Tyr  Asp Leu Glu
```

```
                1025                1030                1035
Pro Glu Gly Lys Asn Val Lys Ile Lys Pro Thr Lys Ile Ile
        1040                1045                1050

Asn Lys Glu Thr Gly Glu Ile Ile Gly Asp Arg Asp Glu Leu Val
        1055                1060                1065

Ala Lys Leu Asn Arg Val Tyr Asn Phe Lys Tyr Met Leu Val Ser
        1070                1075                1080

Gln Glu Val Tyr Thr Arg Ser Gly Ala Leu Phe Asp Gln Thr Ile
        1085                1090                1095

Tyr Pro Ala Asn Ser Gly Lys Lys Leu Ile Pro Leu Lys Gln Asn
        1100                1105                1110

Lys Thr Thr Ala Ile Tyr Gly Gly Tyr Ser Gly Ser Lys Ala Ala
        1115                1120                1125

Tyr Met Ser Ile Ile Arg Leu Arg Asp Lys Lys Gly Gly Thr Tyr
        1130                1135                1140

Arg Ile Val Gly Ile Pro Val Arg Ala Val Asn Lys Leu Asn Gln
        1145                1150                1155

Ala Lys Lys Lys Ser Asn Glu Lys Tyr Leu Ala Glu Leu Lys Ala
        1160                1165                1170

Val Ile Glu Pro Gln Ile Ala Lys Thr Lys Lys Asp Arg Lys Thr
        1175                1180                1185

Gly Gln Arg Val Leu Val Pro Gln Glu Phe Asp Val Ile Ile Pro
        1190                1195                1200

Glu Val Met Tyr Arg Gln Leu Ile Val Asp Gly Asp Gln Lys Phe
        1205                1210                1215

Thr Leu Gly Gly Thr Ile Asp Arg Tyr Asn Ala Val Gln Leu Val
        1220                1225                1230

Leu Asn Gln Glu Ile Leu Thr Phe Leu Glu Gln Pro Thr Lys Tyr
        1235                1240                1245

Lys Asp Ala Asp Thr Lys Leu Leu Asp Ile Tyr Asp Gln Ile Val
        1250                1255                1260

Asn Leu Val Glu Lys Tyr Phe Met Leu Phe Asp Ser Lys Arg Leu
        1265                1270                1275

Ala Ala Gly Arg Val Ala Phe Glu Lys Leu Pro Thr Leu Gln Pro
        1280                1285                1290

Val Asp Lys Met Pro Ser Lys Leu Ile Ile Ile Arg Arg Ile Ile
        1295                1300                1305

Gln Gly Leu His Asp Asn Ala Ala Arg Thr Asp Leu Lys Ala Ile
        1310                1315                1320

Asn Gly Ser Ser Ser Phe Gly Arg Leu Gln Lys Arg Asn Gly Ile
        1325                1330                1335

Ile Leu Ser Pro Asn Ala Cys Leu Ile Tyr Gln Ser Pro Thr Gly
        1340                1345                1350

Leu Phe Glu Arg Lys Val Tyr Leu Asn Thr Ile Ser Pro Leu Lys
        1355                1360                1365

<210> SEQ ID NO 82
<211> LENGTH: 1369
<212> TYPE: PRT
<213> ORGANISM: Lactobacillus rossiae

<400> SEQUENCE: 82

Met Asp Lys Ser Lys Pro Tyr Gly Ile Gly Leu Asp Ile Gly Thr Asn
1               5                   10                  15
```

```
Ser Val Gly Phe Val Ala Thr Asp Ala Glu Gly His Leu Ile Arg Leu
             20                  25                  30
Lys Gly Lys Thr Val Ile Gly Ala Tyr Leu Phe Asn Ala Gly Ile Ser
         35                  40                  45
Ala Ala Glu Arg Arg Gly Phe Arg Thr Thr Arg Arg Arg Leu Ser Arg
 50                  55                  60
Val Lys Trp Arg Leu Gly Leu Leu Arg Glu Ile Phe Glu Thr His Phe
 65                  70                  75                  80
Gln Glu Ser Met Gly Glu Asn Glu Asp Asn Asp Phe Phe Leu Arg Phe
                 85                  90                  95
Lys Tyr Ser Asn Ile Ser Pro Lys Asp Pro Gln Phe Ser Thr Ala Lys
             100                 105                 110
Gly Leu Phe Asn Asp Arg Thr Asp Lys Glu Phe Tyr Asp Gln Tyr Pro
         115                 120                 125
Thr Ile Tyr His Leu Arg Arg Ala Leu Met Thr Glu Asp His Gln Phe
130                 135                 140
Asp Ile Arg Glu Ile Tyr Ile Ala Met His His Ile Val Lys Tyr Arg
145                 150                 155                 160
Gly His Phe Leu Lys Glu Gly Arg Ala Lys Asp Phe Lys Val Gly Asp
                 165                 170                 175
Leu Arg Leu Leu Asp Asn Phe Lys Met Met Asn Glu Gln Ile Glu Glu
             180                 185                 190
Ile Asn Pro Leu Trp Gln Leu Lys Leu Pro Thr Asp Asp Ala Ser Ile
         195                 200                 205
Lys Ser Ile Thr Ala Ile Leu Leu Asp Asn Thr Gln Ser Gln Asn Asp
210                 215                 220
Arg Gln Lys Ala Val Thr Lys Val Ile Leu Ala Thr Leu Val Lys Ala
225                 230                 235                 240
Ser Asp Lys Asp Ile Asn Ala Ala Arg Lys Arg Phe Val Gly Glu Leu
                 245                 250                 255
Ser Lys Ala Met Val Gly Leu Lys Thr Lys Leu Trp Val Leu Ala Asp
             260                 265                 270
Val Ser Gln Asn Gly Asp Trp Glu Ile Lys Tyr Glu Asn Tyr Ala Asp
         275                 280                 285
Phe Ala Glu Thr Ile Gly Ser Gly Glu Ser Asp Thr Ile Gln Ser Leu
290                 295                 300
Phe Asn Glu Ile Asn Asp Leu Tyr Gly Val Ile Thr Leu Ala Gly Ile
305                 310                 315                 320
Ile Pro Lys Glu Ala Glu Ser Phe Ser Asp Gly Met Val Arg Lys Tyr
                 325                 330                 335
Glu His His Arg Lys Asn Leu Glu Leu Leu Lys Val Tyr Cys Ala Glu
             340                 345                 350
Gln Ser Asp Gly Lys Arg Gly Arg Gln Ile Arg Gln Thr Tyr Asp Lys
         355                 360                 365
Tyr Ile Asp Gly Val Asp Ser Lys Gln Phe Thr Gln Glu Asp Phe Tyr
370                 375                 380
Lys Ala Leu Ser Lys Phe Thr Ala Lys Asp Glu Ala Thr Ser Glu Asn
385                 390                 395                 400
Ala Lys Leu Ile Ala Gln Glu Ile Ala Val Gly Thr Phe Met Pro Lys
                 405                 410                 415
Leu Arg Thr Lys Ala Asn Gly Thr Ile Pro His Gln Leu His Gln Lys
             420                 425                 430
Glu Leu Asp Ala Ile Ile Glu Asn Gln Lys Lys Tyr Tyr Pro Trp Leu
```

-continued

```
                435                 440                 445
Gly Glu Val Asn Pro Val Glu Ser His Arg Ala Leu Pro Tyr Lys
    450                 455                 460

Leu Asp Glu Leu Val Ser Phe Arg Ile Pro Tyr Val Gly Pro Met
465                 470                 475                 480

Val Thr Pro Thr Lys Gly Asp Pro Glu Lys Ser Lys Phe Ala Trp Met
                485                 490                 495

Val Arg Lys Glu Pro Gly Thr Ile Thr Pro Trp Asn Phe Asp Gln Lys
            500                 505                 510

Val Asp Arg Ser Ala Ser Gly Glu Ala Phe Ile Gln Arg Met Lys Thr
            515                 520                 525

Thr Asp Thr Phe Leu Ile Gly Glu Asp Val Leu Pro Gln Gln Ser Leu
        530                 535                 540

Leu Tyr Gln Lys Phe Glu Val Leu Asn Glu Leu Asn Lys Ile Met Ile
545                 550                 555                 560

Asn Gly Lys Pro Ile Cys Arg Glu Gln Lys Gln Arg Leu Phe Lys Gln
                565                 570                 575

Leu Phe Met Gln Tyr Lys Thr Val Thr Val Lys Lys Val Gln Gln Asn
                580                 585                 590

Leu Ile Ala Asn Gly Glu Glu Ser Glu Asn Val Pro Ile Thr Gly Leu
            595                 600                 605

Ser Asp Pro Leu Arg Phe Asn Ser Ser Phe Ser Thr Tyr Ile Asp Tyr
        610                 615                 620

Lys Asp Ile Leu Gly Thr Ala Ala Val Asn Asp Asn Ala Lys Gln Ser
625                 630                 635                 640

Asp Ile Glu Gln Ile Ile Ala Trp Ser Thr Ile Phe Glu Asp Ala Ala
                645                 650                 655

Ile Phe Arg Glu Lys Leu Asn Asp Ile Thr Trp Leu Asn Asp Asp Gln
                660                 665                 670

Arg Asn Lys Leu Ser His Lys Arg Tyr Arg Gly Trp Gly Arg His Ser
            675                 680                 685

Arg Lys Leu Leu Ala Gly Leu Arg Asp Gly Glu Gly Gln Thr Ile Ile
        690                 695                 700

Glu Arg Leu Trp Asn Thr Asn Asp Asn Phe Met Gln Ile Gln Asn Asp
705                 710                 715                 720

Ser Glu Ile Ala Arg Gln Ile Thr Glu Ala Asn Ser Ser Lys Met Ala
                725                 730                 735

Thr Ala Glu Gly Thr Asp Glu Ile Ile Asp Gly Phe Tyr Thr Ser Pro
                740                 745                 750

Glu Asn Lys Lys Ala Leu Arg Glu Val Met Lys Val Lys Asp Ile
            755                 760                 765

Gln Arg Ala His His Gly Gln Ala Pro Ala Trp Val Tyr Ile Glu Ser
        770                 775                 780

Pro Arg Glu Thr Pro Arg Pro Gly Gln Arg Thr Val Ser Arg Glu Gln
785                 790                 795                 800

Gln Leu Thr Asp Leu Tyr Gly Ala Ala Lys Glu Ile Val Asp Asp
                805                 810                 815

Ala Val Leu Asn Glu Leu Lys Asp Lys Val Lys Ser Lys Glu Asn Phe
            820                 825                 830

Thr Asp Lys Leu Val Leu Tyr Phe Leu Gln Asn Gly His Asp Ile Tyr
        835                 840                 845

Ala Asn Asp Ser Ile Asn Ile Asp Asn Leu Asn Ala Tyr Asp Ile Asp
    850                 855                 860
```

-continued

```
His Val Leu Pro Gln Ser Leu Ile Lys Asp Asp Ser Leu Asp Asn Arg
865                 870                 875                 880

Val Leu Thr Thr His Glu Arg Asn Leu Lys Lys Ser Asn Arg Phe Ala
            885                 890                 895

Thr Glu Leu Phe Ala Asp Gln Arg Lys Lys Trp Glu Lys Trp His Arg
        900                 905                 910

Leu Gly Leu Ile Ser Ser Arg Lys Leu Lys His Leu Thr Met Gln Pro
            915                 920                 925

Asn Ser Val Glu Lys Phe Ala His Gly Phe Ile Ala Arg Gln Leu Thr
        930                 935                 940

Glu Thr Arg Gln Ile Ile His Leu Thr Ala Asn Val Leu Ser Asn Leu
945                 950                 955                 960

Tyr Gln Glu Asn Asp Thr Lys Ile Val Met Ile Lys Ala Gly Leu Asn
                965                 970                 975

Ser Glu Phe Arg Arg Thr Phe Asp Phe Pro Lys Asn Arg Ser Val Asn
            980                 985                 990

Asp Tyr His His Ala Phe Asp Ala Phe Leu Thr Ala Lys Ile Gly Arg
        995                 1000                1005

Tyr Leu Leu Ala Arg Tyr Pro Lys Leu Glu Pro Phe Phe Val Tyr
1010                1015                1020

Gly Asn Phe Val Lys Asn Pro Lys Ala Met Lys Arg Leu Ser Ser
1025                1030                1035

Phe Asp Phe Ile Ala Gln Leu Ala Ala Lys Thr Asp Asp Thr Ser
1040                1045                1050

His Ile Asp Gln Arg Ser Leu Lys Gln Val Pro Val Val Asn Glu
1055                1060                1065

Glu Thr Gly Glu Ile Val Trp Asp Lys Asp Ile Glu Leu Ala Glu
1070                1075                1080

Leu Asp Lys Thr Tyr Asn Tyr Lys Thr Met Leu Val Lys Arg Ala
1085                1090                1095

Gln Thr Glu Asn Asn Ala Gln Met Phe Lys Gln Thr Val Phe Lys
1100                1105                1110

Ala Arg Asp Asn Gln Asn Lys Thr Leu Ile Pro Val Lys Asn Gly
1115                1120                1125

Leu Ser Thr Asp Val Tyr Gly Gly His Ser Gln Gln Ala Ile Ser
1130                1135                1140

Tyr Leu Cys Ile Val Trp Val Gly Gln Lys Lys Tyr Arg Val
1145                1150                1155

Leu Gly Ile Ser Thr Ala His Ala Gly Ile Leu Asn Asn Phe Glu
1160                1165                1170

Lys Asn Tyr Gly Arg Phe Glu Ala Lys Lys Leu Gln Glu Ile
1175                1180                1185

Val Ser Asn Thr Leu Asp Asn Ala Asp Arg Asn Asp Phe Lys Ile
1190                1195                1200

Val Ala Pro Lys Val Leu Phe Glu Gln Val Val Glu Asp Asp Asn
1205                1210                1215

Met Lys Phe Gly Leu Gly Ser Ala Ser Asp Tyr Arg Asn Val Gln
1220                1225                1230

Gln Leu Phe Leu Ser Arg Lys Asn Gln Leu Leu Leu Ala Asn Met
1235                1240                1245

Met Thr Asp Gln Ile His Asp Gln Asp Leu Val His Leu Phe Asp
1250                1255                1260
```

-continued

```
Glu Ile Val Gly Gln Met Asn Ala His Phe Pro Ile Phe Asp Arg
    1265                1270                1275

Gly Gly Tyr Arg Ser Ser Leu Thr Gln Ser Arg Asp Lys Phe Leu
    1280                1285                1290

Lys Leu Pro Phe Lys Lys Asn Glu Asp Leu Ile Thr Lys Gln Glu
    1295                1300                1305

Val Ile Arg Arg Ile Leu Asp Gly Leu His Ala Asn Ala Asn Arg
    1310                1315                1320

Lys Asp Leu Lys Ile Ile Gly Ser Lys Gly Asp Phe Gly Arg Leu
    1325                1330                1335

Gly Thr Lys Lys Ile Tyr Leu Ser Lys Asp Ala Lys Leu Ile Tyr
    1340                1345                1350

Thr Ser Pro Thr Cys Leu Phe Thr Arg Thr Val Pro Leu Ser Ser
    1355                1360                1365

Leu
```

<210> SEQ ID NO 83
<211> LENGTH: 1346
<212> TYPE: PRT
<213> ORGANISM: Pediococcus pentosaceus

<400> SEQUENCE: 83

```
Met Glu Lys Val Pro Tyr Asn Ile Gly Leu Asp Ile Gly Thr Ser Ser
1               5                   10                  15

Ile Gly Phe Ala Ala Thr Asp Asn Leu Asn Lys Pro Ile Arg Ala Lys
                20                  25                  30

Gly Lys Thr Val Ile Gly Val Arg Leu Phe Glu Gly Lys Thr Ala
            35                  40                  45

Ala Asp Arg Arg Gly Phe Arg Thr Thr Arg Arg Leu Ser Arg Arg
        50                  55                  60

Lys Trp Arg Leu Arg Leu Leu Asp Glu Ile Phe Asp Lys Glu Met Ala
65                  70                  75                  80

Lys Val Asp Asn Thr Phe Phe Ala Arg Leu Lys Glu Ser Asn Leu Ser
                85                  90                  95

Pro Lys Asp Ala Asn Lys Lys Tyr Leu Gly Ser Leu Leu Phe Pro Glu
            100                 105                 110

Lys Lys Asp Phe Lys Phe Tyr Glu Asp Tyr Pro Thr Ile Tyr His Leu
        115                 120                 125

Arg Tyr Ala Leu Met His Glu Lys Arg Gln Phe Asp Ile Arg Glu Val
    130                 135                 140

Tyr Leu Ala Met His His Ile Ile Lys Tyr Arg Gly Asn Phe Leu Asn
145                 150                 155                 160

Ser Ala Pro Met Asn Ser Phe Lys Thr Gln Asp Phe Asp Phe Val Ala
                165                 170                 175

Lys Phe Glu Lys Leu Asn Glu Leu Phe Glu Ser Ile Asp Ala Glu His
            180                 185                 190

Glu Thr Lys Phe Asp Ile Glu Asn Ile Ser Lys Phe Arg Asp Ile Met
        195                 200                 205

Leu Asn Gln Asp Ile Arg Lys Leu Asp Arg Lys Gln Ala Ala Lys
    210                 215                 220

Ile Leu Ile Leu Asp Ser Thr Asp Lys Thr Ala Lys Lys Ile Asn Asn
225                 230                 235                 240

Lys Ile Ala Thr Ala Val Ala Asn Ser Ala Leu Gly Tyr Lys Phe Ala
                245                 250                 255
```

```
Leu Asp Ala Ile Leu Lys Leu Asp Val Glu Ser Lys Asp Trp Ser
            260                 265                 270

Ile Ser Leu Asn Asp Glu Glu Ile Asp Ser Ile Leu Asp Asn Leu Thr
        275                 280                 285

Ser Asp Leu Asp Ala Glu Arg Ile Glu Ile Ile Glu Ile Leu Arg Asp
    290                 295                 300

Leu Tyr Ser His Ile Ala Leu Asn Glu Ile Val Pro Asn Gly Gln Ser
305                 310                 315                 320

Leu Ser Lys Ser Met Met Asp Lys Tyr Asp Lys His His Ala Asp Leu
                325                 330                 335

Asp Val Leu Lys Lys Val Ile Ser Asn Met Asp Asp Arg Lys Lys Ala
            340                 345                 350

Lys Ser Leu Lys Asn Ile Tyr Asn Gln Tyr Val Gly Lys Thr Asn Asp
        355                 360                 365

Lys Val Leu Asp Lys Asp Glu Phe Tyr Lys Gln Ile Gln Lys Asn Leu
    370                 375                 380

Asp Glu Ser Glu Asp Ala Met Lys Ile Val Asn Glu Ile Glu Leu Asp
385                 390                 395                 400

Gln Phe Met Pro Lys Gln Arg Thr Ser Gln Asn Gly Val Ile Pro His
                405                 410                 415

Gln Leu His Gln Lys Glu Leu Asp Glu Ile Ile Glu Asn Gln Lys Gln
            420                 425                 430

Tyr Tyr Pro Phe Leu Ala Glu Pro Asn Pro Asn Glu Lys Arg Lys Pro
        435                 440                 445

His Ala Gln Phe Lys Leu Asp Glu Leu Ile Ala Phe Lys Ile Pro Tyr
    450                 455                 460

Tyr Val Gly Pro Leu Ile Thr Lys Glu Gln Gln Ala Gln Ser Gly
465                 470                 475                 480

Ala Lys Phe Ala Trp Met Lys Arg Lys Gln Asp Gly Val Ile Thr Pro
                485                 490                 495

Trp Asn Phe Asp Glu Lys Val Asp Arg Met Ala Ser Ala Asn Glu Phe
            500                 505                 510

Ile Arg Arg Met Thr Thr Lys Asp Thr Tyr Leu Leu Gly Glu Asp Val
        515                 520                 525

Leu Pro Asp Glu Ser Leu Ile Tyr Gln Lys Phe Lys Val Leu Asn Glu
    530                 535                 540

Leu Asn Asn Val Lys Val Asn Asp Lys Lys Leu Thr Val Ser Asp Lys
545                 550                 555                 560

Gln Asp Ile Phe Asn Asp Leu Phe Lys Lys Gln Lys Thr Val Ser Val
                565                 570                 575

Ser Lys Leu Gln Lys Tyr Phe Val Thr Glu Lys His Tyr Leu Thr Glu
            580                 585                 590

Pro Thr Ile Lys Gly Leu Ser Asp Thr Lys Lys Phe Ser Asn Ser Leu
        595                 600                 605

Ser Thr Tyr Ile Asp Phe Glu Lys Ile Phe Gly Asn Glu Ile Leu Ala
    610                 615                 620

Asp Gln Asn Lys Gln Asn Asp Leu Glu Lys Ile Ile Glu Trp Ser Thr
625                 630                 635                 640

Ile Phe Glu Asp Arg Lys Ile Phe Glu Asp Lys Leu His Glu Ile Glu
                645                 650                 655

Trp Leu Thr Glu Lys Gln Ile Lys Ala Val Arg Arg Tyr Arg Gly Trp
            660                 665                 670

Gly Arg Leu Ser Lys Lys Leu Leu Val Asp Leu Arg Asn Asn Glu Gly
```

675                 680                 685
Lys Ser Ile Leu Asp Glu Leu Trp Arg Thr Asn Asp Asn Phe Met Gln
    690                 695                 700

Ile Gln Ala Arg Glu Glu Phe Ala Lys Ser Ile Val Glu Ala Asn Gln
705                 710                 715                 720

Lys Leu Met Asn Leu Gly Gly Ala Ala Ser Val Gln Asn Thr Val Glu
                725                 730                 735

Ser Thr Leu Glu Asp Ala Tyr Thr Ser Pro Gln Asn Lys Lys Ala Ile
            740                 745                 750

Arg Gln Val Ile Lys Val Val Glu Asp Ile Val Lys Ala Val Gly Tyr
        755                 760                 765

Ala Pro Glu Lys Ile Thr Ile Glu Phe Thr Arg Gly Ala Asp Lys Asn
770                 775                 780

Pro Arg Arg Thr Gln Asn Arg Gln Lys Gln Ile Met Glu Val Tyr Lys
785                 790                 795                 800

Thr Ala Ala Lys Glu Ile Val Asp Ala Thr Leu Lys Gly Gln Leu Glu
                805                 810                 815

Asn Glu Glu Lys Leu Thr Asp Lys Leu Tyr Leu Tyr Phe Thr Gln Leu
            820                 825                 830

Gly Lys Asp Ile Tyr Ser Gly Glu Thr Ile Asn Ile Asp Gln Leu Asn
        835                 840                 845

Asn Tyr Asp Ile Asp His Ile Leu Pro Gln Ala Phe Ile Lys Asp Asp
850                 855                 860

Ser Leu Asp Asn Arg Val Leu Thr Ser Arg Asp Leu Asn Asn Gly Lys
865                 870                 875                 880

Ser Asp Ser Val Pro Val Lys Gln Phe Gly Ala Asn Met Lys Ser Phe
                885                 890                 895

Trp Met Arg Leu Gln Ala His Gly Leu Ile Ser Lys Arg Lys Leu Asn
            900                 905                 910

Asn Leu Met Thr Asp Pro Asp Ser Ile Gly Lys Tyr Thr Met Gln Gly
        915                 920                 925

Phe Val Arg Arg Gln Leu Val Glu Thr Ser Gln Val Ile Lys Leu Thr
930                 935                 940

Ala Asn Ile Leu Gly Ala Ile Tyr Gly Glu Asn Thr Asp Ile Val Glu
945                 950                 955                 960

Ile Pro Ala Lys Leu Thr His Gln Met Arg Glu Lys Phe Asn Leu Tyr
                965                 970                 975

Lys Val Arg Glu Val Asn Asp Tyr His His Ala Phe Asp Ala Tyr Leu
            980                 985                 990

Thr Thr Phe Val Gly Asn Tyr Leu Phe Lys Arg Tyr Pro Lys Leu Arg
        995                 1000                1005

Pro Tyr Phe Val Tyr Gly Asp Phe Lys Met Thr Asp Asn Ala Leu
    1010                1015                1020

Lys Gly Met Arg Arg Phe Asn Phe Leu His Asp Leu Lys Asp Asp
    1025                1030                1035

Glu Val Leu Val Asp Asn Glu Thr Gly Glu Val Leu Trp Glu Gly
    1040                1045                1050

Gln Lys Ser Ile Glu Glu Leu Lys Lys Ile Tyr Gly Tyr Lys Phe
    1055                1060                1065

Met Leu Thr Thr His Glu Ala Tyr Thr Gln His Gly Pro Met Phe
    1070                1075                1080

Lys Gln Thr Val Tyr Ser Ser Asp Thr Pro Gly Lys Leu Ile Lys
    1085                1090                1095

```
Ile Lys Asn Asn Lys Pro Thr Glu Ile Tyr Gly Gly Tyr Thr Ser
    1100                1105                1110

Asn Thr Asp Ala Tyr Met Ala Ile Val Arg Ile Lys Ala Arg Lys
    1115                1120                1125

Gly Asp Thr Tyr Lys Val Val Gly Val Pro Arg Lys Glu Gly Asp
    1130                1135                1140

Ala Leu Ser Arg Ile Lys Leu Leu Asp Glu Ser Lys Tyr His Glu
    1145                1150                1155

Asn Leu Lys Asn Ile Leu Ala Ile Asn Leu Asn Lys Ser Leu Asn
    1160                1165                1170

Lys Phe Asp Val Val Leu Asp Lys Val Lys Tyr Arg Gln Val Ile
    1175                1180                1185

Tyr Asp Gly Thr Asp His Leu Met Leu Gly Ser Ser Lys Tyr Lys
    1190                1195                1200

Tyr Ser Thr Lys Gln Leu Val Leu Ser Asp Gln Ser Met Lys Ile
    1205                1210                1215

Leu Ser Ser Thr Gly Glu Phe Ser Asp Glu Glu Leu Ile Lys Val
    1220                1225                1230

Phe Asp Glu Ile Met Tyr Ile Val Asn Lys Asn Phe Ser Leu Tyr
    1235                1240                1245

Asp Thr Arg Gly Phe Arg Asp Lys Leu Asn Asn Ala Arg Glu Asn
    1250                1255                1260

Phe Ile Lys Leu Pro Asn Lys Thr Leu Phe Glu Lys Gly Lys Leu
    1265                1270                1275

Lys Gln His Ser Lys Leu Glu Ile Leu Lys Gln Ile Leu Ile Gly
    1280                1285                1290

Leu His Ala Asn Ala Gly Arg Gly Asp Leu Lys Asp Ile Gly Val
    1295                1300                1305

Asn Asn Phe Gly Ala Met Val Val Thr Ala Gly Val Thr Leu Ser
    1310                1315                1320

Pro Asp Ala Thr Ile Val Tyr Gln Ser Pro Thr Gly Leu Phe Glu
    1325                1330                1335

Arg Lys Val Lys Leu Ser Asp Leu
    1340                1345

<210> SEQ ID NO 84
<211> LENGTH: 1130
<212> TYPE: PRT
<213> ORGANISM: Lactobacillus nodensis

<400> SEQUENCE: 84

Met Glu Asn Lys Ile Ser Leu Gly Leu Asp Ile Gly Val Ala Ser Val
1               5                   10                  15

Gly Phe Ser Val Ile Asp Ala Gln Glu Gly Lys Val Leu Glu Leu Gly
                20                  25                  30

Ala Arg Leu Phe Asn Ser Ser Val Ser Ala Glu Asn Gln Thr Arg Arg
            35                  40                  45

Asp Met Arg Gly Ser Arg Arg Leu Ser Asn Arg Lys Lys Gln Arg Arg
        50                  55                  60

Lys Asp Val Ala Gln Leu Phe Lys Thr Phe Gly Leu Ile Asn Tyr Phe
65                  70                  75                  80

Asp Lys Glu Asn Tyr Phe Asp Asn Phe Gln Asn Asn Leu Asn Ser Tyr
                85                  90                  95

Glu Leu Arg Val Lys Gly Leu Ser Glu Lys Leu Ser Lys Glu Glu Leu
```

-continued

```
                100                 105                 110
Val Asn Ser Leu Tyr His Ile Val Lys Arg Gly Ile Ser Tyr Asp
            115                 120                 125

Leu Ala Asp Ala Asp Thr Asp Phe Asp Gly Ser Asp Tyr Ser Ser
130                 135                 140

Leu Asn Gln Asn Gln Leu Glu Leu Gln Thr Lys Thr Pro Ala Glu Ile
145                 150                 155                 160

Gln Leu Thr Arg Leu Asn Val His Gly Ala Val Arg Gly Lys Val Thr
                165                 170                 175

Ile Asn Gly Glu Asp Glu Asp Thr Met Gln Val Leu Leu Asn Val Phe
            180                 185                 190

Pro Thr Lys Ser Phe Val Ser Glu Ala Lys Lys Ile Ile Gln Thr Gln
                195                 200                 205

Gln Gln Tyr Tyr Pro Asp Ile Leu Thr Asp Ile Phe Glu Thr Lys Tyr
    210                 215                 220

Leu Glu Ile Leu Glu Arg Lys Arg Glu Tyr Phe Val Gly Pro Gly Ser
225                 230                 235                 240

Glu Lys Ser Arg Thr Asp Phe Gly Ile Tyr Lys Lys Asp Gly Arg Thr
                245                 250                 255

Leu Asp Asn Leu Phe Glu Glu Leu Ile Gly His Asp Lys Ile Tyr Pro
            260                 265                 270

Asp Glu Leu Arg Ala Ser Gly Ala Ser Tyr Thr Ala Gln Val Phe Asn
        275                 280                 285

Val Leu Asn Asp Leu Asn Asn Leu Arg Ile Ser Ser Tyr Glu Asn Gly
    290                 295                 300

Lys Ile Ser Thr Glu Asp Lys Ile Lys Ile Val Glu Asp Leu Arg Asn
305                 310                 315                 320

Asn Ile Gly Asn Val Ile Met Lys Ile Ile Lys Lys Val Ala Gly
                325                 330                 335

Cys Glu Asp Asp Ile Lys Gly Tyr Arg Leu Asp Ser Lys Asp Lys
            340                 345                 350

Pro Asp Ile His Ser Met Ala Val Tyr Arg Lys Val His Arg Asp Leu
        355                 360                 365

Leu Lys Tyr Asp Val Asp Ile Ile Lys Trp Pro Thr Glu Phe Ile Asp
    370                 375                 380

Glu Leu Ser Pro Ile Leu Thr Leu Asn Thr Glu Asn Gly Glu Ile Arg
385                 390                 395                 400

Lys Gln Met Val Asn Lys Leu Gln Pro Lys Tyr Ser Phe Leu Thr Asp
                405                 410                 415

Glu Leu Ile Gln Val Ile Asn Asn Lys Ser Ser Phe Asp Val Thr
            420                 425                 430

Ser Asn Asn Lys Trp His Arg Phe Ser Leu Lys Thr Met Asn Val Leu
        435                 440                 445

Ile Glu Glu Met Phe Arg Arg Pro Val Glu Gln Met Thr Leu Ile Gln
    450                 455                 460

Glu Leu Gly Leu Ile Lys Asp Ser Gly Lys Arg Phe Glu Asn Cys Lys
465                 470                 475                 480

Leu Leu Pro Tyr Arg Glu Ile Ser Lys Asp Ile Phe Asn Pro Val Ala
                485                 490                 495

Ser Lys Ser Val Arg Glu Ala Leu Lys Ile Val Asn Ala Val Met Lys
            500                 505                 510

Lys Tyr Gly Gln Ile Asp Tyr Leu Val Ile Glu Met Pro Arg Asp Lys
        515                 520                 525
```

-continued

```
Asn Glu Glu Met Lys Lys Gln Ile Glu Lys Phe Gln Lys Glu Asn
    530                 535                 540
Asn Lys Gln Lys Asp Glu Ala Ile Asn Glu Phe Val Lys Lys Ile Gly
545                 550                 555                 560
Asn Lys Asn Ala Val Asp Asp Gly Leu Arg Arg Tyr Gly Gly Lys Leu
                565                 570                 575
Tyr Phe Lys Ile Arg Leu Trp Tyr Gln Gln Asp Gly Ile Asp Leu Tyr
            580                 585                 590
Asn Gly Lys Val Ile Glu Pro Phe Asp Leu Leu Asn Asn Ile Asn Lys
        595                 600                 605
Phe Glu Val Asp His Ile Ile Pro Glu Ser Ile Ser Phe Asp Asp Ser
    610                 615                 620
Ile Asn Asn Lys Thr Leu Cys Tyr Ala Asp Met Asn Gln Ile Lys Gly
625                 630                 635                 640
Gln Lys Thr Pro Phe Glu Phe Met Asn Glu Gly His Gly Gln Gly Phe
                645                 650                 655
Ala Lys Met Lys Ala Met Val Asn Lys Asn Ser Lys Leu Lys Gly Lys
            660                 665                 670
Arg Lys Asn Tyr Leu Phe Asp Glu Asn Ile Ser Asp Ile Glu Thr Arg
        675                 680                 685
Lys Arg Phe Ile Ser Arg Asn Leu Val Asp Thr Gln Tyr Ser Ser Arg
    690                 695                 700
Val Val Leu Asn Ser Leu Gln Glu Phe Phe Lys Glu Lys Glu Thr Gly
705                 710                 715                 720
Thr Lys Val Thr Val Val Arg Gly Lys Phe Thr Ser Asn Leu Arg Lys
                725                 730                 735
His Trp His Ile Asn Lys Thr Arg Asp Thr Phe His His His Ala Ile
            740                 745                 750
Asp Ala Ser Ile Ile Ala Ala Thr Pro Phe Leu Arg Ile Trp Lys Lys
        755                 760                 765
Asp Ala Ser Leu Phe Pro Met His Val Ser Glu Asn Thr Val Asp Ile
    770                 775                 780
Glu Thr Gly Glu Ile Leu Asn Asp Thr Glu Phe Lys Lys Asp Phe Tyr
785                 790                 795                 800
Gly Leu Pro Tyr Ser Ser Phe Ile Glu Glu Leu Asn Gly Ala Asp Asp
                805                 810                 815
Arg Ile Lys Phe Ser His Gln Val Asp Arg Lys Met Asn Arg Lys Val
            820                 825                 830
Ser Asp Ala Thr Ile Tyr Ser Thr Arg Lys Gly Met Leu Asn Lys Asp
        835                 840                 845
Lys Glu Glu Thr Asp Tyr Val Leu Gly Lys Ile Lys Asn Ile Tyr Asp
    850                 855                 860
Val Ser Glu Tyr Asn Lys Phe Lys Arg Ile Tyr Asp Lys Asp Pro Asn
865                 870                 875                 880
Lys Phe Leu Leu Ala His His Asp Pro Lys Ser Phe Asp Glu Leu Arg
                885                 890                 895
Lys Ile Met Gln Glu Tyr Pro Ser Lys Ile Asp Lys Val Met Thr Asn
            900                 905                 910
Gly Lys Val Lys Ser Val Asp Ile Ser Pro Phe Glu Leu Tyr Arg Arg
        915                 920                 925
Lys His Gly Met Val Gln Lys Tyr Ser Asn Lys Asn Lys Gly Pro Val
    930                 935                 940
```

```
Ile Lys Gln Leu Lys Tyr Leu Asp Lys Lys Leu Gly Ser His Ile Asp
945                 950                 955                 960

Ile Thr Pro Lys Asp Thr Leu Asn Asp Arg His Val Val Leu Gln Ser
                965                 970                 975

Leu Lys Pro Trp Arg Thr Asp Val Tyr Tyr Asn Ser Val Thr Gly Glu
            980                 985                 990

Tyr Glu Ile Met Gly Ile Lys Tyr Ser Asp Leu Lys Phe Asn Gly Gly
        995                 1000                1005

Glu Tyr Gly Ile Lys Met Ser Lys Tyr Leu Glu Ile Lys Glu Arg
    1010                1015                1020

Glu Gln Val Ser Asp Glu Ser Glu Phe Leu Phe Thr Leu Tyr Lys
    1025                1030                1035

Arg Asp Arg Ile Gln Ile Ile Asn Cys Glu Asn Asp Glu Ile Val
    1040                1045                1050

Glu Met Leu Phe Trp Ser Arg Asn Asn Ser Asn Ile Gly Tyr Ala
    1055                1060                1065

Glu Leu Lys Pro Val Tyr Lys Tyr Lys Thr Glu Asp Glu Ser Trp
    1070                1075                1080

Pro Val Tyr Gly Tyr Gly Lys Asn Gln Ile Leu Lys Arg Leu Val
    1085                1090                1095

Pro Lys Asn Cys Lys Ile Leu Lys Val Asn Thr Asp Ile Leu Gly
    1100                1105                1110

Asn Pro Tyr Tyr Ile Lys Lys Glu Ser Lys Asn Pro Lys Asn Ile
    1115                1120                1125

Leu Asp
    1130

<210> SEQ ID NO 85
<211> LENGTH: 1361
<212> TYPE: PRT
<213> ORGANISM: Sulfurospirillum sp.

<400> SEQUENCE: 85

Met Thr Ser Leu Ile Ser Leu Asp Leu Gly Gly Lys Asn Thr Gly Phe
1               5                   10                  15

Phe Ser Phe Thr Ala Lys Asp Val Ser Ile Ile Asp Thr Phe Gln Ser
                20                  25                  30

Gly Thr Ile Ile Tyr Asp Glu Ser Phe Val Leu Ser Gln Val Ala Arg
            35                  40                  45

Arg Gly Lys Arg His Gly Lys Arg Asn Asn Leu Arg Asn Thr Leu Val
        50                  55                  60

Lys Arg Leu Phe Leu Leu Leu Gln Lys His Tyr Gly Leu Ser Leu
65                  70                  75                  80

Asp Phe Leu Pro Asp Glu Ile Leu Gly Leu Phe Asn Lys Arg Gly Tyr
                85                  90                  95

Thr Tyr Ala Ser Phe Glu Ile Lys Glu Asp Glu Lys Glu Asn Leu Glu
            100                 105                 110

Ser Asp Ile Leu Lys Glu Phe Leu Asn Asp Lys Leu Asn Tyr Thr Ile
        115                 120                 125

Gln Asn Asp Asp Glu Val Glu Glu Phe Leu Asn Gln Ile Ala Ser Asn
    130                 135                 140

Glu Glu Thr Phe Lys Asn Tyr Lys Lys Asp Phe Glu Asn Leu Phe Gly
145                 150                 155                 160

Ala Ser Thr His Gln Pro Lys Lys Gln Ile Glu Leu Ile Asp Glu Ile
                165                 170                 175
```

```
Lys Lys Asp Leu Glu Lys Glu Asp Ala Lys Glu Leu Leu Asp Gly Leu
            180                 185                 190

Lys Val Ile Lys Lys Ile Ile Asp Glu Phe His Lys Gln Gln Asn Gln
        195                 200                 205

Gly Asn Leu Pro Arg Ala Lys Tyr Phe Glu Leu Tyr Leu Glu Ile
    210                 215                 220

Glu Tyr Asn Leu Lys Ile Gln Lys Phe Phe Thr Cys Asn His Leu His
225                 230                 235                 240

Ile Asn Asp Met Gln Tyr Leu Ile Gly Asn Leu Ser Asn Tyr Gln Leu
                245                 250                 255

Lys Glu Leu Arg Arg Tyr Phe Asn Asp Glu Ala Met Ala Lys Glu Asp
            260                 265                 270

Phe Trp Ser Cys Glu Lys Leu His Arg Ile Thr Trp Arg Phe Ile Gln
        275                 280                 285

Ser Trp His Pro Lys Ser Pro Glu Asp Lys Gln Arg Gln Lys Glu Asn
    290                 295                 300

Leu Ala Asn Leu Lys Thr Lys Ser Ile Ile Glu Phe Leu Thr Thr Thr
305                 310                 315                 320

Asn Pro Leu Met Thr Ile Pro Pro Tyr Asp Asp Met Asn Asn Arg Gly
                325                 330                 335

Ala Val Lys Cys Gln Thr Leu Arg Leu Asn Glu Glu Tyr Leu Asp Lys
            340                 345                 350

His Leu Pro His Trp Arg Ala Ile Ala His Thr Leu Ala Ser Glu Thr
        355                 360                 365

Gln Lys Glu Asn Leu Glu Gly Val Thr Val Lys Gly Tyr Ser Glu Asp
    370                 375                 380

Ser Thr Leu Leu His Arg Ile Leu Asp Thr Ser Ser Ile Ile Asp Pro
385                 390                 395                 400

Tyr Arg Leu Arg Ser Asp Glu Ile Asp Ser Tyr Cys Asp Val Leu Thr
                405                 410                 415

Lys Asp Asn Ala Phe Ala Leu Lys Lys Phe Ala Lys Glu Tyr Tyr Gln
            420                 425                 430

Leu Val Lys Glu Lys Val Arg Thr Gly Ile Trp Thr Lys Asp Asp Asp
        435                 440                 445

Met Phe Lys Lys Cys Asp His Asn Pro Pro His Lys Asn Asn Gln Ile
    450                 455                 460

His Asn Leu Val Ala Gly Ile Leu Gly Lys Pro Ile Ala Lys Glu Arg
465                 470                 475                 480

Phe Glu Ala Phe Glu Asn Glu Leu Trp Asn Val Lys Phe Gly Asn Lys
                485                 490                 495

Lys Leu Ser Ser Tyr Cys Lys Asn Ile Glu Glu Phe Arg Lys Ser Asn
            500                 505                 510

Gly Asn Leu Phe Lys Gln Ile Val Glu Leu Gly Glu Asp Lys Glu Val
        515                 520                 525

Gln Lys Tyr Gln Lys Glu Leu Asn Glu Trp Val Arg Lys Ile Gly Glu
    530                 535                 540

Phe Phe Asn Ile Glu Thr Pro Tyr Arg Ala Arg Phe Asn Asn Leu Phe
545                 550                 555                 560

Ser Met Ala Gln Leu His Thr Ile Ile Asp Thr Thr Arg Ser Gly Phe
                565                 570                 575

Asn Ala Thr Cys Lys Trp Cys Ser Cys Glu Asn Gln Tyr Arg Ala Ser
            580                 585                 590
```

-continued

Thr Arg Ile Glu Ile Asp Glu Gln Thr Gly Glu Ile Thr Thr Asn Ala
        595                 600                 605

Asn Cys Gln Arg Leu Pro Ala Asp Thr Gln Arg Pro Phe Ser Gly Lys
        610                 615                 620

Ile Glu Arg Tyr Ile Asp Lys Leu Gly Tyr Glu Ile Ala Lys Val Lys
625                 630                 635                 640

Ala Lys Glu Leu Glu Gly Ile Lys Glu Asp Thr Ile Asp Leu Lys Ile
                645                 650                 655

Ile Leu Glu Gln Asn Ala Phe Ala Tyr Glu Ser Ile Arg Asn Ala
        660                 665                 670

Lys Ile Lys Asn Ala Asn Ala Lys Ala Lys Ala Leu Glu Glu Ala
        675                 680                 685

Gln Lys Arg Gly Leu Lys Asn Ile Glu Asp Lys Thr Lys Arg Ile Lys
        690                 695                 700

Asp Phe Ser Asn Ser Ile Cys Pro Tyr Cys Gly Gln Ser Leu Gly Glu
705                 710                 715                 720

Asp Gly Glu Ile Asp His Ile Leu Ser Arg Ser Tyr Thr Leu Lys Lys
                725                 730                 735

Tyr Asp Thr Val Phe Asn Ser Glu Gly Asn Leu Leu Tyr Val His Gln
                740                 745                 750

Lys Cys Asn Gln Ala Lys Leu Ala Lys Thr Asp Tyr Ser Leu Gln Asp
        755                 760                 765

Leu Lys Ile Asp Ile Ser Gln Lys Trp Ile Glu Glu Gln Ile Ala Thr
        770                 775                 780

Ile Lys Thr Tyr Lys Thr Phe Ser Val Leu Thr Gln Glu Gln Lys
785                 790                 795                 800

Ala Phe Lys Tyr Ala Leu Phe Leu Asp Asn Ser Asn Glu Ala Tyr Gln
                805                 810                 815

Lys Val Ile Ser Trp Leu Arg Thr Asp Gln Ser Ser Arg Val Asn Gly
                820                 825                 830

Thr Gln Lys Tyr Leu Ala Lys Lys Ile Gln Glu Lys Leu Lys Ala Met
        835                 840                 845

Phe Pro Ala Lys Thr Phe Asn Phe Glu Phe Ile Leu Ala Asp Ala Asn
850                 855                 860

Asp Val His Asp Leu Arg Ile Lys Ala Tyr Gln Leu Pro Glu Lys Pro
865                 870                 875                 880

Lys Asp Ser Lys Gln Glu Thr Tyr Ser His Thr Ile Asp Ala Val Met
                885                 890                 895

Ser Leu Val Ser Val Trp Asp Lys Val Leu Pro Lys Thr Glu Lys Pro
        900                 905                 910

Thr Lys Glu Asp Ile Leu Lys Phe Ala Asn Val Glu Asn Trp Ser Ala
        915                 920                 925

Leu Asn Asn Glu Phe Leu Thr Lys Gly Lys Ser Ala Asn Gln Lys Ile
        930                 935                 940

Glu Glu Met Ile Gln Ala Asn Asp Phe Gly Lys Asn Met Arg Gln
945                 950                 955                 960

Val Phe Ser Lys Pro Ile Phe Lys Asp Glu Ser Ile Gly Glu Arg Tyr
                965                 970                 975

Lys Pro Phe Val Arg Tyr His Asn Gln Phe Tyr Ile Gly Tyr Pro Ile
                980                 985                 990

Ser Ile Lys Asp Gly Tyr Asp Met Gln His Cys Gln Ala Met Ile Ser
        995                 1000                1005

Lys Asn Asp Ile Ser Arg Val Glu Glu Ile Leu Lys Asp Thr Ser 1010                1015                1020

Leu Cys Thr Leu Leu Lys Glu Lys Asn Gly Ile Lys Leu Tyr Ser
    1025                1030                1035

Ile Asn Lys Gln Ser Ile Asn Glu Leu Ser Asn Gln Phe Phe Asn
    1040                1045                1050

Leu Asn Tyr Gln Asn Leu Asn Asp Ala Gln Lys Lys Lys Ser Glu
    1055                1060                1065

Leu Ala Glu Phe Val Ile Asn His Cys Lys Tyr Tyr Val Lys Lys
    1070                1075                1080

Thr Ser Val Ile Asn Ala Pro Gln Phe Ile Asp Lys Asp Ser Met
    1085                1090                1095

Lys Pro Tyr Pro Phe Tyr Lys Asp Trp Gln Lys Phe His Glu Ala
    1100                1105                1110

Tyr Lys Lys Glu Leu Asp Ala Glu Pro Lys Thr Lys Lys Asp Asn
    1115                1120                1125

Gly Lys Leu Val Tyr Asp Ile Ser Gly Ile Asp Asp Phe Trp Thr
    1130                1135                1140

Glu Phe Cys Lys Lys Tyr Phe Gly Ile Lys Thr Lys Asp Asn Arg
    1145                1150                1155

Asn Lys Ala Arg Lys Val Phe Ser Ile Val Ala Leu Thr Ser Ala
    1160                1165                1170

Pro Gly Thr Val Phe Arg Ile Lys Arg Lys Thr Pro Lys Gly His
    1175                1180                1185

Ile Tyr Gln Ala Thr Ala Ile Asp Asn Gln Gln Ile Ser Gly Asp
    1190                1195                1200

Tyr Ala Asn Val Leu Leu Ala Gly Asn Ser Lys Thr Leu Ala Leu
    1205                1210                1215

Ala Gly Gln Lys Pro Ser Ser Asp Leu Lys Lys Glu Leu Ser Val
    1220                1225                1230

Lys Glu Ser Lys Asp Ile Arg Asp Ile Lys Leu Glu Pro Ser Arg
    1235                1240                1245

Phe Phe Lys Glu Gly Phe Asp Cys Arg Gly Ile Glu Val Ile Val
    1250                1255                1260

Asn Lys Thr Ser Ala Thr Ile Lys Asn Phe Pro Leu Thr Lys Ile
    1265                1270                1275

Asp Lys Lys Ile Lys Lys Leu Ile Phe Lys Thr Leu Phe Glu Lys
    1280                1285                1290

Lys Asp Gly Lys Arg Gln Lys Gln Lys Thr Ser Ile Ser Leu Lys
    1295                1300                1305

Glu Lys Asn Thr Met Gln Glu Thr Leu Lys Lys Leu Leu Lys Asp
    1310                1315                1320

Ser Ile Lys Val Thr Ile Arg Asp Gly Ser Ile Ser Gly Ile Glu
    1325                1330                1335

Ile Ser Lys Lys Thr Val Asn Phe Thr Leu Pro Phe Lys Ser Glu
    1340                1345                1350

Asn Leu Ala Lys Leu Leu Asp Asp
    1355                1360

<210> SEQ ID NO 86
<211> LENGTH: 1147
<212> TYPE: PRT
<213> ORGANISM: Bifidobacterium thermophilum

<400> SEQUENCE: 86

-continued

```
Met Ser Asp Lys Thr Tyr Arg Ile Gly Ile Asp Val Gly Leu Tyr Ser
1               5                   10                  15

Val Gly Leu Ser Ala Ile Gln Val Asn Asp Asp Asp Pro Val Arg
            20                  25                  30

Ile Leu Asn Ala Gln Ser Val Ile His Asp Gly Gly Val Asp Pro Asn
            35                  40                  45

Ala Gln Lys Ser Ala Asp Ser Arg Arg Ala Gln Ser Gly Ile Ala Arg
        50                  55                  60

Arg Thr Arg Arg Met Arg Arg Asn Arg Lys Arg Leu Lys Arg Leu
65                  70                  75                  80

Asp Gln Ile Leu Val Glu Ser Gly Phe Pro Val Ser Ser Glu Asn Asp
                85                  90                  95

Leu Glu Gly Phe Glu Pro Trp Leu Leu Arg Ala Gln Ala Ala Asp Ala
            100                 105                 110

Phe Ile Glu Asp Glu Asp Ile Arg Lys Arg Ala Ile Ser Val Ser Cys
            115                 120                 125

Arg His Ile Ala Arg His Arg Gly Trp Arg Asn Pro Tyr Leu Asp Val
            130                 135                 140

Arg Thr Leu Leu Ala Val Asp Ser Pro Ser Ser Ala Phe Tyr Asp Lys
145                 150                 155                 160

Leu Val Glu Asn Ala Ala Leu Glu Met Asp Gly Gln Met Pro Asp Ser
                165                 170                 175

Asp Ala Thr Pro Ala Gln Ile Val Arg Asp Val Leu Glu Tyr Lys Arg
            180                 185                 190

Gly Glu Ala Ala Ile Arg Leu Arg Lys Ser Thr Ala Glu Asn Lys Lys
            195                 200                 205

Asn Arg Leu Ala Leu Phe Pro Glu Lys Met Met Gln Asp Asp Tyr Ala
210                 215                 220

Tyr Glu Leu Arg Leu Ile Leu Ala Lys Gln Ala Val Pro Lys Asp Ile
225                 230                 235                 240

Ala Arg Lys Leu Ile Leu Ala Val Phe Gln Ser Gln Ser Pro Lys Gly
            245                 250                 255

Ser Ala Glu Lys Arg Val Gly Lys Asp Pro Leu Asp Pro Ser Gln Pro
            260                 265                 270

Arg Ala Leu Lys Ala Ser Leu Ala Phe Gln Glu Tyr Arg Ile Leu Asn
            275                 280                 285

Ile Leu Thr Asn Leu Arg Leu Gln Asp Gly Gly Ala Glu Arg Arg Leu
            290                 295                 300

Ser Ile Glu Glu Lys Gln Lys Leu Tyr Lys Met Leu Val Glu Asp Thr
305                 310                 315                 320

Gly Arg Glu Lys Lys Tyr Glu Thr Trp Thr Asp Ile Ala Ser Ala Met
            325                 330                 335

Glu Trp Lys Arg Asn Trp Leu Lys Gly Val Gly Ser Leu Thr Ala Asp
            340                 345                 350

Gly Asp Asp Arg Val Thr Ser Arg Pro His Ile Asp Ile Val Glu
            355                 360                 365

Lys Leu Asn Gly Ile Lys Asp Thr Lys Phe Arg Lys Ser Ile Leu Ser
            370                 375                 380

Trp Trp Lys Ser Ala Thr Asp Val Asn Arg Glu Ala Met Ile Ala Leu
385                 390                 395                 400

Leu Ser Asn Thr Val Asp Ile Ala Lys Lys Gln Asp Asp Pro Asp Phe
                405                 410                 415

Ser Ser Ala Val Asp Phe Ile Asp Ser Met Asp Asp Ser Asp Leu Gln
```

```
            420                 425                 430
Ile Leu Asp Thr Ile Ser Ile Gln Pro Gly Arg Ala Ala Tyr Ser Ser
            435                 440                 445
Lys Thr Leu Arg Ala Leu Ser Lys Arg Met Tyr Ser Thr Asp Asp Asp
            450                 455                 460
Leu His Asp Ala Arg Lys His Val Phe Gly Val Asp Asp Ser Trp Arg
465                 470                 475                 480
Pro Pro Gln Pro Ala Ile Gly Ala Pro Leu Gly Asn Pro Ser Val Asp
                    485                 490                 495
Arg Val Ala Lys Ile Val Asn Arg Trp Leu Leu Ala Cys Gln Ser Arg
                500                 505                 510
Trp Gly Asn Pro Leu Ser Ile Gln Ile Glu His Val Arg Asp Ala Leu
            515                 520                 525
Ser Ser Ala Ala Thr Ala Thr Ala Asp Lys Arg Ala Tyr Glu Arg Ala
            530                 535                 540
Leu Gly Lys Arg Asn Ala Glu Lys Met Lys Val Lys Asn Glu Leu Arg
545                 550                 555                 560
Leu Gln Gly Leu Asn Glu Pro His Glu Ser Asp Val Arg Arg Gln Glu
                    565                 570                 575
Ala Ile Thr Arg Gln Gln Gly Lys Cys Leu Tyr Cys Gly Asp Asp Ile
                580                 585                 590
Thr Phe Ser Thr Cys Glu Met Asp His Ile Val Pro Arg Lys Gly His
            595                 600                 605
Gly Ser Thr Asn Thr Arg Asp Asn Leu Ala Ala Val Cys Ile Gln Cys
            610                 615                 620
Asn Arg Gln Lys Ser Asn Thr Pro Phe Ala Leu Trp Cys Gln Thr Pro
625                 630                 635                 640
Glu Ala Lys Ser Arg Gly Val Ser Leu Glu Ala Ile His Arg Val
                    645                 650                 655
Lys Gly Phe Phe Thr Glu Ser Lys Glu Leu Thr Gly Arg Gln Ala Lys
                660                 665                 670
Val Phe Thr Ser Ser Met Ile Met Arg Leu Lys Gln Thr Thr Ala Asp
            675                 680                 685
Asp Pro Ile Asp Ser Arg Ser Ile Glu Ser Val Ala Trp Met Ala Asp
            690                 695                 700
Glu Leu His Arg Arg Ile Asp Trp His Phe Asn Gly Asp Ala Ser Glu
705                 710                 715                 720
Ser Asp His Gly Arg Arg Val Leu Val Ala Val Tyr Gln Gly Arg Ile
                    725                 730                 735
Thr Ser Glu Ala Arg Asn Val Met Arg Phe Gln Ala Gly Gly Asp Phe
                740                 745                 750
His Phe Val Gly Gly His Gly Lys Thr Arg Leu Asp Arg His His
            755                 760                 765
Ala Val Asp Ala Ser Val Ile Ala Met Met Thr Pro Ala Ala Ala Leu
            770                 775                 780
Thr Leu Ala Glu Arg Ile Asn Leu Arg Asp Ser Gln Arg Cys Ile Gly
785                 790                 795                 800
Arg Ile Arg Glu Gly Glu Ile Asp Trp Lys Gln Trp Pro Asn Glu Pro
                    805                 810                 815
Thr Glu Lys Tyr Gln His Trp Leu Asp Asn Gly Lys Arg Leu Phe Ala
                820                 825                 830
Leu Ile Asn Asp Ala Leu Asp Asn Asp Arg Ile Pro Ile Thr His Trp
            835                 840                 845
```

Gln Arg Tyr Ala Leu Gly Asn Ser Ile Ala His Glu Ala Thr Ile His
            850                 855                 860

Pro Leu Arg Lys Ile Pro Leu Gly Ser Ala Ile Asp Tyr Glu Thr Ile
865                 870                 875                 880

Ser Arg Ala Ala Thr Pro Ala Leu Tyr Cys Ala Leu Thr Arg Cys Pro
                885                 890                 895

Asp Tyr Ser Val Asn Asp Gly Leu Pro Glu Asn Lys Gln Arg His Ile
            900                 905                 910

Thr Val Asn Gly Lys Val Tyr Gly Pro Glu Asp Glu Val Ala Phe Phe
            915                 920                 925

Ala Ser Asp His Val Glu Leu Ala Val Gln Gly Gly Ser Ala Asp Ile
            930                 935                 940

Gly Lys Thr Ile His His Ala Arg Val Tyr Arg Cys Tyr Phe Val Asp
945                 950                 955                 960

Arg Arg Gly Gln Lys Lys Trp Phe Tyr Gly Met Ile Arg Val Phe Arg
                965                 970                 975

Val Asp Leu Ile His Ala Arg His Glu Asn Leu Phe Thr Tyr Pro Leu
            980                 985                 990

Pro Ser Gln Ser Ile Ser Met Arg Tyr Ala Glu Thr Arg Thr Ala Glu
            995                 1000                1005

Ala Val Leu Cys Gly His Ala Glu His Val Gly Asn Leu Val Ala
            1010                1015                1020

Gly Asp Glu Ile Glu Val Pro Met Ile Gly Lys Leu Thr Gly Lys
        1025                1030                1035

Ile Asp Thr Phe Ala Lys Phe Phe Asn Glu Ser Leu Asn Asn Glu
        1040                1045                1050

Tyr Val Ala Glu Arg Trp Ser Ile Asp Gly Phe Asp Ser Glu Ser
        1055                1060                1065

Lys Leu Leu Leu Arg Pro Leu Met Leu Ala Glu Glu Gly Ile Ala
        1070                1075                1080

Asn Trp Glu Asp Asn Ser His Leu Ser Ile Pro Asp Asp Val Lys
        1085                1090                1095

Gly Leu Ile Ala Arg Gly Trp Arg Pro Ser Val Asp Thr Val Phe
        1100                1105                1110

Ala Lys Lys Pro Arg Ile Val Arg Arg Asn Val Leu Gly Glu Pro
        1115                1120                1125

Arg Trp Lys Ser Arg Ser Gly Met Pro Val Ser Trp Arg Val Thr
        1130                1135                1140

Gly Ser Glu Ala
        1145

<210> SEQ ID NO 87
<211> LENGTH: 1071
<212> TYPE: PRT
<213> ORGANISM: Loktanella vestfoldensis

<400> SEQUENCE: 87

Met Arg Leu Gly Phe Asp Ile Gly Thr Asn Ser Ile Gly Trp Trp Leu
1               5                   10                  15

Tyr Ala Thr Asp Gly Asn Glu Ile Thr Gly Val Ile Asp Gly Gly Val
                20                  25                  30

Arg Ile Phe Ser Asp Gly Arg Asp Pro Lys Ser Lys Ala Ser Leu Ala
            35                  40                  45

Val Asp Arg Arg Gly Ala Arg Ala Gln Arg Arg Arg Asp Arg Tyr

```
                50                  55                  60
Leu Arg Arg Lys Ala Ala Leu Met Lys Arg Met Ala Ala Gly Leu
 65                  70                  75                  80

Met Pro Ala Asp Pro Val Ala Lys Ala Leu Glu Gln Leu Asp Pro
                 85                  90                  95

Tyr Ala Leu Arg Ala Ser Gly Leu Asp Gln Glu Leu Pro Leu Thr His
                100                 105                 110

Leu Gly Arg Ala Leu Phe His Leu Asn Gln Arg Gly Phe Lys Ser
                115                 120                 125

Asn Arg Lys Thr Asp Lys Gly Asp Asn Glu Ser Gly Lys Ile Lys Asp
130                 135                 140

Ala Thr Ala Arg Leu Asp Gln Ala Met Ile Ala Lys Gly Ala Arg Thr
145                 150                 155                 160

Tyr Gly Glu Phe Leu His Met Arg Arg Ala Ser Ala Pro Asp Pro Lys
                165                 170                 175

Cys Val Pro Thr Val Arg Thr Arg Leu Ser Ile Ala Pro Arg Asp Asn
                180                 185                 190

Ala Glu Lys Ala Glu Ala Gly Tyr Asp Phe Tyr Pro Asp Arg Arg His
                195                 200                 205

Leu Phe Glu Glu Phe Thr Lys Leu Trp Ala Ala Gln Ala Ala Asn Ser
210                 215                 220

Pro Asp Ile Leu Thr Asp Glu Leu Arg Asp Glu Ile Ser Val Ile Ile
225                 230                 235                 240

Phe His Gln Arg Pro Leu Lys Thr Pro Glu Val Gly Leu Cys Leu Phe
                245                 250                 255

Ser Gly Ser His Gly Val Pro Gln Asn Asp Lys Arg Ile Pro Ser Ala
                260                 265                 270

His Pro Gln Asn Gln Arg Arg Ile Leu Phe Glu Thr Val Asn Asn Leu
                275                 280                 285

Lys Val Ala Ala Arg Gly Glu Leu Ala Arg Gly Leu Thr Arg Asp Glu
                290                 295                 300

Arg Asp Thr Ile Ala His Ala Leu Asp Asn Lys Ala His Thr Lys Ser
305                 310                 315                 320

Leu Ser Gly Met Ser Met Lys Leu Lys Ala Leu Gly Lys Leu Ile Lys
                325                 330                 335

Leu Arg Pro Glu Gln Ser Phe Thr Leu Glu Thr Ala Asn Arg Asp Ser
                340                 345                 350

Ile Val Cys Asp Pro Val Arg Ala Ser Leu Ser His Pro Asp Arg Phe
                355                 360                 365

Gly Ser Arg Trp Ser Thr Leu Asp Ala Glu Ala Gln Trp Asp Leu Val
                370                 375                 380

Gln Arg Ile Arg Ala Val Gln Ser Asp Ala Glu His Asn Ala Leu Val
385                 390                 395                 400

Ala Trp Leu Ile Ala Thr His Gly Leu Asp Arg Val His Ala Glu Asn
                405                 410                 415

Val Ala Asn Ala Pro Leu Pro Glu Gly His Gly Arg Leu Gly Met Thr
                420                 425                 430

Ala Thr Lys Arg Ile Leu Ala Ala Leu Glu Ala Glu Val Ile Pro Tyr
                435                 440                 445

Ser Ala Ala Val Ala Ala Cys Gly Trp His His Ser Asp Gly Arg Thr
                450                 455                 460

Gly Glu Val Leu Thr Glu Leu Pro Tyr Tyr Gly Gln Ile Leu Asp Arg
465                 470                 475                 480
```

```
His Val Ile Pro Gly Thr Tyr Asp Glu Asn Asp Asp Glu Val Thr Arg
            485                 490                 495

Tyr Gly Arg Ile Thr Asn Pro Thr Val His Ile Gly Leu Asn Gln Leu
            500                 505                 510

Arg Arg Leu Val Asn Lys Ile Val Thr Val Tyr Gly Lys Pro Asp Glu
            515                 520                 525

Ile Val Val Glu Leu Ala Arg Asp Leu Lys Leu Ser Glu Asp Gln Lys
            530                 535                 540

Arg Asp Val Gln Arg Asp Ile Lys Lys Asn Thr Glu Ala Ala Ile Thr
545                 550                 555                 560

Arg Gly Gln Lys Ile Glu Glu Leu Gly Tyr Ala Asn Thr Gly Ala Asn
            565                 570                 575

Arg Val Met Tyr Arg Leu Trp Glu Glu Leu Gly Pro Ala Ile Gly Pro
            580                 585                 590

Arg Cys Cys Pro Tyr Ser Gly Lys Pro Ile Ser Ala Ser Met Ile Phe
            595                 600                 605

Asp Gly Ser Cys Asp Val Asp His Ile Leu Pro Tyr Ser Arg Thr Leu
            610                 615                 620

Glu Asp Gly Phe Ser Asn Arg Thr Leu Cys Leu Lys Glu Phe Asn Arg
625                 630                 635                 640

Gln Lys Thr Asn Lys Thr Pro Trp Glu Ala Trp Gly Asn Thr Pro Ala
            645                 650                 655

Trp Asp Ala Ile Glu Ala Asn Leu Lys Asn Leu Pro Ala Asn Lys Ala
            660                 665                 670

Trp Arg Phe Ala Pro Asp Ala Met Glu Arg Phe Glu Gly Glu Asn Asp
            675                 680                 685

Phe Ser Ala Arg Ala Leu Lys Asp Thr Gln Tyr Leu Ser Arg Ile Ala
            690                 695                 700

Arg Ser Tyr Leu Asp Ala Leu Tyr Asp Gly Ala Asp Gly Lys Ser His
705                 710                 715                 720

Val Trp Val Val Pro Gly Arg Leu Thr Glu Met Leu Arg Arg His Trp
            725                 730                 735

Gly Leu Asn Ser Leu Leu Pro Asp Lys Asp Gly Ala Val Lys Ala Lys
            740                 745                 750

Asn Arg Ser Asp His Arg His His Ala Ile Asp Ala Ala Val Val Ala
            755                 760                 765

Ala Thr Asp Arg Ser Leu Val Gln Arg Ile Ser Lys Met Ala Gln Arg
            770                 775                 780

Asp Glu Val Asn Gly Ala Glu Val Ala Arg Ser Val Pro Pro Pro
785                 790                 795                 800

Trp Asp Asp Phe Arg Thr Asp Ile Lys Ser Gln Leu Asp Arg Ile Ile
            805                 810                 815

Val Ser His Arg Ala Asp His Gly Arg Ile Asp Phe Ala Ala Arg Gln
            820                 825                 830

Thr Gly Asn Asp Ser Thr Ser Gly Ala Leu His Glu Ala Thr Ala Leu
            835                 840                 845

Ser Ile Ile Asp Asp Gln Asn Val Ala Val Arg Ile Pro Leu Leu Ser
            850                 855                 860

Leu Ser Ala Ala Gln Phe Glu Glu Gly Gly Arg Ser Gly Trp Val Arg
865                 870                 875                 880

Asp Pro Gln Leu Arg Gly Ala Leu His Leu Ala Thr Lys Gly Lys Asp
            885                 890                 895
```

```
Lys Lys Asp Phe Glu Ala Ala Leu Leu Ser Phe Ala Ala Lys Pro Gly
                900                 905                 910

Pro Tyr His Gly Ile Ser Arg Val Arg Ile Glu Lys Pro Leu Gln Asp
            915                 920                 925

Thr Ala Arg Val Tyr Val Pro Ala Asp Ala Pro Ile Lys Ala Tyr Gln
        930                 935                 940

Gly Gly Ser Asn His Arg Tyr Glu Val Trp Lys Leu Pro Asp Gly Lys
945                 950                 955                 960

Val Leu His His Val Ser Met Phe Val Ala His Gln Gly Asn Leu
                965                 970                 975

Thr Arg Pro His Pro Ala Ala Lys Arg Ile Tyr Gln Phe Met Lys Gly
            980                 985                 990

Asp Leu Val Arg Leu Glu Asp Ser Lys Phe Gly Pro Val Ile Ala Thr
        995                 1000                1005

Val Glu Lys Phe Asn Gly Lys Gly Met Ile Glu Leu Val Pro His
    1010                1015                1020

Asn Glu Ala Asn Ala Ser Asp Arg Tyr Arg Lys Thr Lys Glu Asp
    1025                1030                1035

Leu Tyr Ile Arg Leu Gly Ala Thr Thr Leu Leu Arg Ala Lys Ala
    1040                1045                1050

Arg Arg Val His Val Asp Glu Met Gly Arg Leu Arg Asp Pro Gly
    1055                1060                1065

Pro Pro Gln
    1070

<210> SEQ ID NO 88
<211> LENGTH: 1105
<212> TYPE: PRT
<213> ORGANISM: Sphingomonas sanxanigenens

<400> SEQUENCE: 88

Met Asp Met Ala Trp Arg Leu Gly Leu Asp Leu Gly Thr Asn Ser Leu
1               5                   10                  15

Gly Trp Ala Ala Leu Ser Leu Asp Ala Ala Gly Ala Pro Asp Ala Ile
            20                  25                  30

Leu Ala Ala Gly Ser Arg Ile Phe Gly Asp Gly Arg Asp Pro Gln Ser
        35                  40                  45

Gly Thr Ser Leu Ala Val Asp Arg Arg Ala Ala Arg Ala Ala Arg Arg
    50                  55                  60

Arg Arg Asp Arg Phe Lys Gln Arg Gln Arg Ala Leu Leu Lys His Leu
65                  70                  75                  80

Glu Ala Asp Gly Leu Phe Pro Ala Asp Pro Glu Val Gln Gln Ala Leu
                85                  90                  95

Ala Ala Leu Asp Pro Tyr Ala Leu Arg Ala Arg Ala Leu Asp Glu Ala
            100                 105                 110

Leu Ser Leu His Glu Ile Gly Arg Ala Leu Phe His Leu Asn Gln Arg
        115                 120                 125

Arg Gly Phe Gln Ser Asn Arg Lys Ala Asp Arg Gly Lys Asp Glu Asp
    130                 135                 140

Ala Gly Lys Ile Ala Ile Gly Val Asp Arg Leu Lys Asp Ala Ile Ala
145                 150                 155                 160

Ala Ala Gly Ala Arg Thr Phe Gly Glu Phe Leu Arg Gln Arg Ala
                165                 170                 175

Gly Ala Thr Gly Glu Asn Gln Ile Pro Ser Val Arg Thr Arg Leu Arg
            180                 185                 190
```

```
Ala Glu Thr Gly Glu Gly Ala Lys Gly Ser Gly Tyr Asp Phe Tyr Pro
        195                 200                 205

Ser Arg Ala Leu Leu Lys Asp Glu Phe Asp Ala Ile Trp His Ala Gln
    210                 215                 220

Ala Glu His His Pro Lys Val Leu Thr Asp Glu Ala Tyr His Arg Leu
225                 230                 235                 240

His Glu Ile Val Phe Arg Gln Arg Pro Leu Arg Ala Pro Lys Val Gly
                245                 250                 255

Ala Cys Thr Leu Val Pro Gly Glu Ala Arg Leu Pro Lys Ala His Pro
                260                 265                 270

Leu Phe Gln Arg Arg Leu Leu Glu Glu Leu Asn Ala Leu Met Ile
        275                 280                 285

Val Arg Ala Gly Ala Val Ala Glu Arg Leu Thr Pro Glu Gln Arg Asp
    290                 295                 300

Leu Leu Leu Leu Lys Leu Lys Asp Lys Gly Lys Val Thr Phe Lys Ser
305                 310                 315                 320

Leu Arg Glu Lys Val Leu Lys Leu Asp Gly Asp Ala Arg Phe Asn Lys
                325                 330                 335

Glu Ser Glu His Arg Thr Glu Leu Lys Gly Asp Glu Val Ala Ala Glu
                340                 345                 350

Met Gly Gly Lys Thr Arg Phe Gly Ser Leu Trp Pro His Leu Ser Thr
        355                 360                 365

Glu Gln Gln Trp Thr Val Ile Glu Arg Gln Gln Ala Leu Glu Ser Asp
        370                 375                 380

Ala Asp Glu Ala Ala Phe Arg Thr Trp Leu Val Glu Thr His Lys Leu
385                 390                 395                 400

Thr Ala Glu Gln Ala Arg Ala Val Ala Gly Ala Arg Leu Pro Ala Gly
                405                 410                 415

His Gly Arg Phe Gly Leu Thr Ala Thr Ala Ala Leu Leu Ala Ala Leu
                420                 425                 430

Arg Asp Gly Arg Thr Pro Glu Gly Arg Gly Pro Asn Ala Pro Ala Thr
                435                 440                 445

Glu Ala Gly Arg Val Val Val Tyr Ser Glu Ala Ala Ile Ala Gly
    450                 455                 460

Tyr His His Ser Asp His Arg Ser Gly Glu Val Phe Thr Asp Ala Lys
465                 470                 475                 480

Gly Arg Pro Ala Leu Pro Tyr Tyr Gly Val Pro Leu Asp Arg His Ile
                485                 490                 495

Val Pro Gly Thr Ala Asp Pro Asp Glu Pro Asp Glu Ala Ala Arg Ile
                500                 505                 510

Gly Arg Leu Thr Asn Pro Thr Val His Ile Ala Leu Asn Gln Leu Arg
                515                 520                 525

Arg Val Val Asn Arg Leu Ile Arg Val Tyr Gly Pro Pro Ala Glu Val
    530                 535                 540

Ala Leu Glu Leu Ala Arg Glu Leu Lys Leu Ser Glu Asp Glu Lys Lys
545                 550                 555                 560

Glu Arg Asn Arg Glu Asn Ser Arg Asn Arg Leu Asp Ala Glu Lys Arg
                565                 570                 575

Ser Ser Lys Leu Ala Glu Leu Gly Gln Arg Asp Asn Gly Gly Asn Arg
        580                 585                 590

Ala Leu Leu Lys Leu Trp Glu Glu Leu Asn Pro Glu Asn Ile Leu Asp
        595                 600                 605
```

-continued

Arg Arg Cys Ile Tyr Ser Gly Arg Gln Ile Ser Ile Gly Met Ile Phe
610                 615                 620

Ser Gly Ala Ala Glu Val Asp His Ile Leu Pro Phe Asp Ala Thr Leu
625                 630                 635                 640

Asp Asp Ser Asn Ala Asn Lys Ile Leu Cys Leu Arg Glu Ala Asn Arg
            645                 650                 655

Asp Lys Arg Lys Arg Ser Pro Phe Glu Ala Trp Gly Thr Pro Gln
        660                 665                 670

Trp Glu Glu Ile Ala Glu Arg Ala Ser Arg Leu Pro Arg Asn Lys Arg
            675                 680                 685

Trp Arg Phe Glu Pro Asp Ala Met Glu Arg Phe Ala Glu Glu Gly Gly
690                 695                 700

Phe Leu Ala Arg His Leu Val Asp Thr Gln Tyr Leu Gly Arg Ile Ala
705                 710                 715                 720

His Asp Tyr Leu Arg Cys Leu Tyr Pro Asp Lys Gly Asp Gly Ser Ser
            725                 730                 735

His Val Trp Val Ser Pro Gly Arg Leu Thr Glu Met Val Arg Arg Lys
            740                 745                 750

Leu Gly Leu Asn Gly Leu Leu Gly Asp His Asn Leu Gly Ala Glu Gln
        755                 760                 765

Pro Lys Asn Arg Lys Asp His Arg His His Ala Ile Asp Ala Val Val
770                 775                 780

Thr Ala Ile Leu Asp Arg Ser Met Leu Gln Arg Ile Gln Arg Ala Ser
785                 790                 795                 800

Gly Glu Gly Ala Ser Asp Ala Glu Leu Leu Arg Ile Ile Val Pro Glu
                805                 810                 815

Pro Trp Thr Gly Phe Arg Asp Asp Leu Gln Arg Ala Val Asp Arg Ile
                820                 825                 830

Val Val Ala His Arg Ala Asp His Gly Thr Val Ala Lys Ala Ala Thr
            835                 840                 845

Arg Gly Arg Asp Gln Thr Ala Ala Arg Leu His Asn Asp Thr Ala Tyr
    850                 855                 860

Gly Phe Thr Gly Glu Ala Asp Ala Lys Gly Thr Pro Ile Val Val His
865                 870                 875                 880

Arg Ala Pro Leu Gly Ala Leu Lys Lys Pro Glu His Ile Asp Gln Val
                885                 890                 895

Arg Asp Pro Leu Leu Arg Ala Ala Leu His Asp Phe Thr Ala Gly Leu
        900                 905                 910

Ser Gly Lys Pro Phe Gly Asp Arg Ile Ala Ala Phe Pro Arg Leu Gly
    915                 920                 925

Pro Leu Asp Tyr Arg Gly Ile Arg Arg Val Arg Val Glu Pro Leu
930                 935                 940

Gln Val Ile Pro Ile Arg Asp Ala Ala Gly Arg Ala Tyr Lys Gly Tyr
945                 950                 955                 960

Lys Gly Asp Ser Asn Tyr Arg Tyr Asp Val Trp Glu Leu Pro Asp Gly
                965                 970                 975

Lys Trp Glu Gln Arg Val Leu Gln Met Tyr Tyr Ala His Gln Ser Gly
            980                 985                 990

Glu Pro Pro Arg Pro His Pro Ala Ala Arg Lys Val Leu Ser Leu His
                995                 1000                1005

Arg Asp Asp Val Leu Ala Ile Glu Arg Gly Glu Gly Gly Arg Glu
        1010                1015                1020

Leu Val Arg Val Val Lys Phe Ser Thr Asn Glu Phe Thr Leu Ala

-continued

```
               1025                1030                1035

Pro Leu Asn Glu Gly Gly Ala Leu Lys Ser Arg His Ala Asp Lys
        1040                1045                1050

Gly Asp Pro Phe Arg Tyr Leu Tyr Pro Ser Pro Ser Thr Leu Lys
    1055                1060                1065

Ala Trp Arg Ala Arg Glu Val Arg Val Asp Glu Leu Gly Arg Val
    1070                1075                1080

Leu Asp Pro Gly Phe Pro Ala Arg Lys Arg Arg Val Thr Arg
    1085                1090                1095

Pro Gly Arg Ala Asp Ala Asp
    1100                1105

<210> SEQ ID NO 89
<211> LENGTH: 1399
<212> TYPE: PRT
<213> ORGANISM: Epilithonimonas tenax

<400> SEQUENCE: 89

Met Thr Lys Asn Ile Leu Gly Leu Asp Leu Gly Val Ser Ser Ile Gly
1               5                   10                  15

Trp Ala Tyr Val Gln Glu Asp Lys Asn Ser Ala Asn Asn Lys Ile
            20                  25                  30

Ile Lys Leu Gly Val Arg Val Asn Pro Leu Thr Val Asp Glu Gln Ile
        35                  40                  45

Asn Phe Glu Lys Gly Lys Pro Ile Thr Thr Asn Ala Gly Arg Thr Leu
    50                  55                  60

Ala Arg Gly Ala Arg Arg Asn Leu Gln Arg Phe Lys Leu Arg Arg Ala
65                  70                  75                  80

Asn Val Ile Asp Val Leu Thr Lys Gly Asn Ile Leu Lys Asp Gly Asp
                85                  90                  95

Leu Leu Thr Glu Val Gly Lys Asn Ser Thr Phe Gln Thr Gln Glu Leu
            100                 105                 110

Arg Ala Lys Ser Ala Lys Glu Lys Ile Glu Leu Ser Asp Phe Val Arg
        115                 120                 125

Val Leu Leu Ile Asn Lys Lys Arg Gly Tyr Lys Ser Ser Arg Lys
    130                 135                 140

Ala Lys Asn Glu Asp Glu Gly Gln Ile Ile Asp Gly Met Ala Val Ala
145                 150                 155                 160

Lys Lys Leu Tyr Glu Glu Ser Leu Thr Pro Gly Glu Tyr Ser Tyr Gln
                165                 170                 175

Leu Leu Ile Glu Gly Lys Lys Gln Leu Pro Asp Phe Tyr Arg Ser Asp
            180                 185                 190

Leu Gln Ser Glu Phe Asp Lys Val Trp Lys Phe Gln Lys Gln Phe Tyr
        195                 200                 205

Ser Glu Ile Leu Ile Asp Glu Leu Tyr Lys Glu Leu Gln Ala Lys Asn
    210                 215                 220

Lys Asn Ala Thr Trp Ala Ile Leu Lys Glu Pro Phe Ser Leu Val Gly
225                 230                 235                 240

Ile Lys Gln Met Gly Thr Met Gln Glu Lys Lys Ile Glu Lys Tyr Leu
                245                 250                 255

Trp Arg Ser Glu Ala Ala Lys Lys Gln Leu Asp Phe Glu Ser Leu Ala
            260                 265                 270

Val Val Phe Gln Glu Ile Asn Ser Asn Leu Asn Asn Ser Ser Gly Tyr
        275                 280                 285
```

```
Leu Gly Ala Ile Ser Asp Arg Ser Lys Glu Leu Tyr Phe Asn His Met
    290                 295                 300
Thr Val Gly Glu Tyr Leu Tyr Gln Gln Leu Lys Ala Asn Pro His Thr
305                 310                 315                 320
Lys Leu Lys Asn Gln Val Phe Tyr Arg Gln Asp Tyr Leu Asp Glu Phe
                325                 330                 335
Glu Lys Ile Trp Glu Thr Gln Ser Gln Tyr His Ser Glu Leu Thr Lys
                340                 345                 350
Glu Leu Lys Glu Gln Val Arg Asp Val Val Ile Phe Tyr Gln Arg Lys
            355                 360                 365
Leu Lys Ser Gln Lys Gly Leu Ile Ser Ile Cys Glu Phe Glu Asn Arg
    370                 375                 380
Glu Ile Glu Ile Ile Glu Asn Gly Lys Thr Lys Lys Thr Val Gly
385                 390                 395                 400
Leu Lys Val Ala Pro Lys Ser Pro Leu Phe Gln Glu Phe Lys Ile
                405                 410                 415
Trp Gln Val Leu Asn Asn Leu Gln Phe Gln Asn Leu Glu Thr Lys Glu
                420                 425                 430
Ile Phe Pro Ile Asp Leu Asp Phe Lys Gln Ser Ile Phe Asp Glu Val
                435                 440                 445
Asn Val Lys Gly Arg Leu Ser Ala Lys Glu Val Leu Asp Ile Val Gly
    450                 455                 460
Tyr Ser Gly Lys Glu Trp Lys Thr Asn Phe Lys Asp Ile Glu Gly Asn
465                 470                 475                 480
Asn Thr Asn Glu Asn Leu Tyr Thr Ala Phe Leu Lys Ile Ile Ala Asn
                485                 490                 495
Glu Gly Lys Glu Phe Pro Lys Glu Phe Lys Leu Thr Ile Glu Asp Asp
                500                 505                 510
Ile Lys Val Thr Lys Ile His Ser Ser Ala Ser Lys Ile Lys Glu Phe
                515                 520                 525
Val Lys Glu Asn Phe Ser Ser Leu Gly Ile Asn Thr Ser Ile Leu Asp
    530                 535                 540
Phe Asn Pro Glu Phe Asp Gly Lys Asp Phe Glu Lys Gln Ser Ser Tyr
545                 550                 555                 560
Gln Leu Trp His Leu Leu Tyr Ser Tyr Glu Gly Asp Asp Ser Ala Ser
                565                 570                 575
Gly Asn Glu Lys Leu Tyr Glu Leu Leu Glu Lys Lys Phe Ser Phe Lys
                580                 585                 590
Lys Glu His Ser Lys Ile Leu Ala Glu Ile Gly Phe Ser Pro Asp Tyr
            595                 600                 605
Gly Ser Leu Ser Ser Lys Ala Met Arg Lys Ile Cys Thr Tyr Ile Lys
    610                 615                 620
Glu His Lys Tyr Ser Asp Ala Cys Asn Leu Ala Gly Tyr Asn His Ser
625                 630                 635                 640
Lys Asn Ser Leu Thr Lys Glu Gln Leu Ala Asn Arg Ile Leu Lys Glu
                645                 650                 655
Lys Leu Glu Ile Leu Pro Lys Asn Ser Leu Arg Asn Pro Val Val Glu
                660                 665                 670
Lys Ile Leu Asn Gln Met Ile Asn Val Val Asn Glu Val Ser Lys Glu
            675                 680                 685
Tyr Gly Arg Pro Asp Glu Ile Arg Ile Glu Leu Ala Arg Glu Leu Lys
    690                 695                 700
Lys Asn Ala Glu Glu Arg Ala Asn Met Thr Ser Glu Ile Gly Lys Ala
```

```
            705                 710                 715                 720
        Thr Leu Leu His Gln Lys Tyr Ala Glu Ile Leu Gln Lys Glu Tyr Gly
                        725                 730                 735
        Ile Lys Val Pro Ser Arg Asn Asp Ile Ile Arg Tyr Lys Leu Tyr Leu
                        740                 745                 750
        Glu Leu Ala Asn Asn Gly Phe Lys Asp Leu Tyr Thr Gly Gln Lys Ile
                        755                 760                 765
        Glu Lys Glu Asn Ile Phe Thr Asp Lys Tyr Asp Ile Asp His Ile Ile
                        770                 775                 780
        Pro Gln Ser Arg Phe Phe Asp Asp Ser Phe Ser Asn Lys Val Leu Val
        785                 790                 795                 800
        Pro Arg Gly Ala Asn Leu Lys Lys Gly Asn Ala Thr Ala Phe Asp Tyr
                        805                 810                 815
        Leu Glu Met Glu Gly Lys Asp Gln Leu Glu Lys Phe Leu Asn Thr Ile
                        820                 825                 830
        Lys Asp Leu Phe Asp Lys Ser Leu Ile Ser Lys Ala Lys Phe Glu Lys
                        835                 840                 845
        Leu Gln Lys Lys Gly Ser Glu Ile Gly Asp Gly Phe Ile Gln Arg Asp
                        850                 855                 860
        Leu Arg Asp Thr Gln Tyr Ile Ala Lys Lys Ala Lys Glu Ile Leu Phe
        865                 870                 875                 880
        Glu Ile Thr Asn Ser Val Val Ser Thr Ser Gly Arg Ile Thr Asp Lys
                        885                 890                 895
        Leu Arg Glu Asp Trp Asn Leu Val Asn Thr Met Lys Glu Leu Asn Leu
                        900                 905                 910
        Asp Lys Tyr Arg Lys Leu Gly Leu Thr Glu Thr Val Ile Asn Ser Lys
                        915                 920                 925
        Gly Glu Glu Lys Glu Arg Ile Thr Asp Trp Ser Lys Arg Asn Asp His
                        930                 935                 940
        Arg His His Ala Met Asp Ala Leu Thr Val Ala Phe Thr Thr His Asn
        945                 950                 955                 960
        His Ile Gln Tyr Leu Asn His Leu Asn Ala Arg Lys Asp Glu Lys His
                        965                 970                 975
        Asn Gln His Ile Ile Ile Ser Asn Ile Glu Asn Leu Ile Thr Lys Val
                        980                 985                 990
        Tyr Glu Lys Lys Asn Gly Ser Thr  Lys Arg Lys Phe Val  Glu Pro Ile
                        995                 1000                1005
        His Asn  Phe Arg Ile Glu Ala  Lys Lys His Leu Asp  Glu Ile Leu
            1010                1015                1020
        Ile Ser  His Lys Thr Lys Asn  Lys Val Val Thr Lys  Asn Ile Asn
            1025                1030                1035
        Lys Thr  Lys Lys Lys Gly Gly  Val Val Ala Lys Val  Val Leu Thr
            1040                1045                1050
        Pro Arg  Gly Gln Leu His Lys  Glu Thr Ile Tyr Gly  Ser Ser Lys
            1055                1060                1065
        Phe Leu  Lys Thr Lys Glu Glu  Lys Val Ser Gly Lys  Phe Asp Leu
            1070                1075                1080
        Glu Thr  Ile Asn Lys Val Gln  Asn Glu Lys Phe Arg  Ile Ala Leu
            1085                1090                1095
        Leu Glu  Arg Leu Lys Glu Phe  Asn Gly Asp Ser Lys  Lys Ala Phe
            1100                1105                1110
        Thr Gly  Lys Asn Val Leu Ala  Lys Asn Pro Ile Tyr  Leu Asn Glu
            1115                1120                1125
```

Glu Lys Thr Glu Gln Val Ser Glu Ser Val Ile Leu Ala Trp Tyr
    1130                1135                1140

Glu Lys Ala Tyr Thr Ile Arg Lys Ala Val Asn Ser Asp Asn Phe
    1145                1150                1155

Lys Asp Tyr Lys Asn Leu Glu Lys Val Ile Asp Asn Gly Val Lys
    1160                1165                1170

Glu Ile Leu Lys Asn Arg Leu Asp Ala Phe Lys Gly Asn Ala Lys
    1175                1180                1185

Glu Ala Phe Ser Asp Leu Glu Lys Asn Pro Ile Trp Leu Asn Glu
    1190                1195                1200

Ser Lys Gly Ile Ala Ile Lys Thr Val Thr Ile Thr Gly Ile Asn
    1205                1210                1215

Asn Ala Glu Thr Leu His Tyr Lys Lys Asp His Phe Gly Lys Glu
    1220                1225                1230

Ile Leu Asp Glu Asn Gly Lys Arg Ile Ala Val Asp Phe Val Ser
    1235                1240                1245

Thr Gly Asn Asn His His Val Ala Ile Tyr Glu Asp Ala Asp Gly
    1250                1255                1260

Asn Leu Gln Glu Arg Val Val Ser Phe Tyr Glu Ala Val Glu Arg
    1265                1270                1275

Val Asn Gln Gly Leu Ser Ile Ile Asp Lys Glu Tyr Asn Ser Gly
    1280                1285                1290

Leu Gly Trp Lys Phe Leu Phe Thr Met Lys Gln Asn Glu Met Phe
    1295                1300                1305

Leu Phe Pro Ser Glu Asp Phe Asn Pro Lys Glu Asn Asp Leu Phe
    1310                1315                1320

Asp Glu Lys Asn Leu Ser Leu Ile Ser Lys Asn Met Phe Arg Val
    1325                1330                1335

Gln Lys Phe Gly Glu Leu Ser Lys Ser Gly Phe Trp Phe Arg His
    1340                1345                1350

His Leu Glu Thr Ser Val Glu Leu Lys Lys Glu Leu Arg Ser Thr
    1355                1360                1365

Ser Tyr Leu Asp Phe Tyr Ser Lys Asp Phe Met Lys Thr Ile Val
    1370                1375                1380

Lys Val Arg Leu Asn His Leu Gly Lys Ile Val Gln Ile Gly Glu
    1385                1390                1395

Tyr

<210> SEQ ID NO 90
<211> LENGTH: 1453
<212> TYPE: PRT
<213> ORGANISM: Sporocytophaga myxococcoides

<400> SEQUENCE: 90

Met Lys Thr Val Leu Gly Leu Asp Leu Gly Thr Asn Ser Ile Gly Trp
1               5                   10                  15

Ala Leu Ile Gln His Asp Phe Asp Ser Lys Lys Gly Glu Ile Leu Gly
                20                  25                  30

Met Gly Ser Arg Ile Ile Pro Met Ser Gln Asp Ile Leu Gly Glu Phe
            35                  40                  45

Gly Lys Gly Asn Ser Val Ser Gln Thr Ala Asp Arg Thr Lys Phe Arg
        50                  55                  60

Ser Ala Arg Arg Leu Arg Glu Arg His Leu Leu Arg Arg Glu Arg Leu
65                  70                  75                  80

```
His Arg Val Leu Asn Ile Leu Gly Phe Leu Pro Arg His Tyr Ala Ala
                85                  90                  95

Asp Ile Asp Phe Glu Lys Arg Leu Gly Gln Phe Glu Gly Lys Glu
            100                 105                 110

Pro Lys Leu Ala Tyr Asp Asn Asn Gln Phe Ile Phe Thr Lys Ser Phe
            115                 120                 125

Gly Lys Met Leu Ala Asp Phe Arg Gln His Gln Pro Asp Phe Leu Lys
            130                 135             140

Asp Glu Lys Ser Asn Asp Leu Leu Ile Pro Tyr Asp Trp Ser Ile Tyr
145                 150                 155                 160

Tyr Leu Arg Lys Glu Ala Leu Thr Lys Lys Ile Glu Lys Glu Glu Leu
                165                 170                 175

Ala Trp Ile Ile Leu Asn Phe Asn Gln Lys Arg Gly Tyr Tyr Gln Leu
            180                 185                 190

Arg Gly Glu Glu Glu Glu Asn Leu Asn Lys Leu Val Glu Phe His
            195                 200                 205

Ser Leu Lys Ile Ile Asp Val Val Ala Asp Glu Lys Leu Asn Asn Lys
            210                 215                 220

Gly Glu Thr Trp Tyr Ser Leu Leu Glu Asn Gly Trp Thr Tyr Arg
225                 230                 235                 240

Arg Ser Ser Lys Val Pro Leu Phe Asp Trp Lys Glu Lys Val Arg Asp
                245                 250                 255

Phe Ile Val Thr Thr Asp Ile Asn Asp Asp Gly Ser Val Lys Thr Asp
                260                 265                 270

Lys Glu Gly Asn Glu Lys Arg Ser Phe Arg Ala Pro Ser Asp Asp Asp
            275                 280                 285

Trp Thr Leu Leu Lys Lys Thr Gln Asp Ile Asp Lys Ser Arg
            290                 295                 300

Lys Pro Ile Gly Ala Tyr Ile Tyr Asp Ala Ile Leu Lys Asn Pro Lys
305                 310                 315                 320

Gln Lys Ile Asn Gly Lys Leu Val Arg Thr Val Glu Arg Lys Phe Tyr
                325                 330                 335

Lys Glu Glu Leu Lys Leu Ile Leu Gln Lys Gln Lys Glu Phe His Pro
            340                 345                 350

Glu Leu Gln Ser Thr Asp Leu Tyr Asn Glu Cys Ile Arg Glu Leu Tyr
            355                 360                 365

Lys Asn Asn Asp Ala His Gln Leu Gln Leu Asn Lys Lys Asp Phe Val
            370                 375                 380

His Leu Phe Leu Glu Asp Ile Ile Phe Tyr Gln Arg Pro Leu Arg Ser
385                 390                 395                 400

Gln Lys Ser Ser Val Gly Asn Cys Pro Leu Glu Phe Arg Lys Phe Lys
                405                 410                 415

Asp Ser Glu Gly Ile Glu Lys Val Glu Tyr Leu Lys Thr Ile Pro Lys
            420                 425                 430

Ser Asn Pro Tyr Phe Gln Glu Phe Arg Ile Trp Gln Trp Met Tyr Asn
            435                 440                 445

Leu Ser Ile Tyr Lys Lys Asp Asp Glu Asn Val Thr Arg Asp Phe
450                 455                 460

Leu Lys Thr Ile Glu Asp Trp Glu Asp Leu Phe Glu Phe Leu Asn His
465                 470                 475                 480

Arg Lys Asp Ile Glu Gln Glu Thr Leu Leu Lys Phe Leu Leu Gly Lys
                485                 490                 495
```

```
Asn Gly Val Lys Gly Lys Ala Leu Lys Val Glu Ala Gly Lys Phe Arg
            500                 505                 510
Trp Asn Tyr Val Ser Asp Lys Ile Tyr Pro Cys Asn Glu Thr Lys Ala
        515                 520                 525
Leu Ile Ile Ser Lys Leu Glu Lys Val Lys Gly Val Glu Glu Lys Phe
        530                 535                 540
Leu Thr Glu Glu Ile Glu Tyr Lys Leu Trp His Leu Ile Tyr Ser Val
545                 550                 555                 560
Thr Asp Lys Val Glu Tyr Glu Lys Ala Leu Lys Ala Phe Ala Gly Lys
                565                 570                 575
Gln Lys Leu Asp Leu Val Ser Phe Val Asp Ser Phe Lys Arg Phe Pro
            580                 585                 590
Pro Phe Lys Asn Glu Tyr Gly Ala Tyr Ser Glu Lys Ala Ile Lys Lys
        595                 600                 605
Ile Leu Pro Leu Leu Arg Thr Gly Lys Ser Trp Asn Trp Met Ala Ile
        610                 615                 620
Asp Ser Lys Val Arg Asp Arg Ile Asn Lys Ile Ile Thr Gly Glu Phe
625                 630                 635                 640
Asp Glu Glu Ile Lys Asn Lys Val Arg Glu Lys Ala Glu Lys His Ser
                645                 650                 655
Leu Lys Lys Glu Asn Asp Phe Gln Gly Leu Pro Leu Trp Leu Ala Gln
            660                 665                 670
Tyr Val Val Tyr Gly Arg His Ser Glu Ala Ser Phe Ser Gly Lys Trp
        675                 680                 685
Asn Ser Val Asp Asp Leu Lys Lys Tyr Leu Glu Glu Phe Lys Gln His
        690                 695                 700
Ser Leu Arg Asn Pro Ile Val Glu Gln Val Leu Thr Glu Thr Leu Arg
705                 710                 715                 720
Val Val Ala Asp Ile Trp Gln Phe Tyr Gly Lys Gly Glu Lys Asp Phe
                725                 730                 735
Phe Ser Glu Ile His Ile Glu Leu Gly Arg Glu Met Lys Asn Thr Ala
            740                 745                 750
Glu Asp Arg Lys Glu Met Ser Ala Ile Ile Gln Ala Asn Glu Thr Thr
        755                 760                 765
Asn Leu Arg Ile Lys Ala Leu Leu Asn Glu Leu Leu Gln Asp Lys Lys
        770                 775                 780
Val Glu Asn Val Arg Pro Tyr Ser Pro Ser Gln Gln Glu Ile Leu Lys
785                 790                 795                 800
Ile Tyr Glu Asp Gly Val Leu Ser Ser Asp Ile Glu Ile Pro Asp Asp
                805                 810                 815
Ile Gln Lys Ile Ser Lys Ala Ala Gln Pro Thr Lys Ser Glu Leu Gln
            820                 825                 830
Arg Tyr Lys Leu Trp Leu Glu Gln Lys Tyr Arg Ser Pro Tyr Thr Gly
        835                 840                 845
Ala Met Ile Pro Leu Gly Lys Leu Phe Thr Ser Glu Tyr Glu Ile Glu
        850                 855                 860
His Ile Ile Pro Gln Ser Leu Tyr Phe Asp Asp Ser Phe Ser Asn Lys
865                 870                 875                 880
Val Ile Cys Glu Ser Ala Val Asn Lys Leu Lys Asp Ser Arg Leu Gly
                885                 890                 895
Met Glu Phe Ile Lys Glu Cys His Gly Met Val Val Glu Thr Gly Phe
            900                 905                 910
Gly Lys Ser Val Thr Val Phe Glu Glu Glu Thr Tyr Arg Asp Phe Val
```

```
                915                 920                 925
Val Gln Asn Tyr Ser Lys Asn His Ser Lys Ser Lys Leu Leu Leu
        930                 935                 940
Glu Glu Ile Pro Glu Lys Met Ile Glu Arg Gln Met Asn Asp Thr Arg
945                 950                 955                 960
Tyr Ile Ser Lys Phe Ile Ser Ser Val Leu Ser Asn Ile Val Arg Glu
                965                 970                 975
Glu Val Asn Asp Asp Gly Val Asn Ser Lys Asn Ile Val Pro Gly Asn
                980                 985                 990
Gly Lys Ile Thr Thr Gln Leu Lys Gln Asp Trp Gly Leu Asn Asp Ile
        995                 1000                1005
Trp Asn Glu Leu Ile Leu Pro Arg Phe Glu Arg Leu Asn Val Leu
    1010                1015                1020
Thr Asp Ser Lys His Phe Thr Ala Trp Ser Glu Asn His Gln Arg
    1025                1030                1035
Leu Leu Pro Thr Val Pro Ile Gly Leu Ser Lys Gly Phe Ser Lys
    1040                1045                1050
Lys Arg Ile Asp His Arg His Ala Leu Asp Ala Leu Val Ile
    1055                1060                1065
Ala Cys Ala Ser Arg Asn His Ile Asn Phe Leu Asn Asn Ala His
    1070                1075                1080
Ala Ile Asp Lys Lys Asn Ser Glu Glu Lys Gln Lys Phe Arg
    1085                1090                1095
His Asp Leu Lys Ala Ile Leu Cys Asp Lys Lys Tyr Ser Asp Lys
    1100                1105                1110
Ser Glu Lys Asn Tyr Arg Trp Ile Phe Lys Lys Pro Trp Asp Asn
    1115                1120                1125
Phe Thr Ile Asp Ser Lys Asn Ala Leu Asp Lys Ile Ile Val Ser
    1130                1135                1140
Phe Lys Gln Asn Leu Arg Ile Ile Asn Lys Ala Thr Asn Arg Tyr
    1145                1150                1155
Glu Lys Trp Val Asp Arg Asp Gly Ile Lys Val Lys Glu Trp His
    1160                1165                1170
Lys Gln Glu Gly Ile Asn Trp Ala Thr Arg Lys Pro Leu His Lys
    1175                1180                1185
Asp Thr Val Ser Gly Lys Val Asp Leu Lys Arg Val Thr Val Pro
    1190                1195                1200
Glu Gly Lys Ile Leu Thr Ala Thr Arg Lys Ser Leu Asp Thr Ser
    1205                1210                1215
Phe Asp Leu Lys Val Ile Glu Ser Ile Thr Asp Thr Gly Ile Gln
    1220                1225                1230
Lys Ile Leu Lys Asn Tyr Leu Thr Ser Lys Ser Asn Asn Pro Glu
    1235                1240                1245
Leu Ala Phe Ser Ser Glu Gly Val Glu Asp Met Asn Lys Asn Ile
    1250                1255                1260
Arg Lys Tyr Asn Asp Gly Lys Leu His Gln Pro Ile Tyr Lys Val
    1265                1270                1275
Arg Ile Phe Glu Leu Gly Ser Lys Phe Pro Leu Gly Gln Phe Gly
    1280                1285                1290
Asn Lys Lys Phe Lys Tyr Val Glu Thr Ala Lys Gly Thr Asn Leu
    1295                1300                1305
Phe Phe Ala Val Tyr Glu Asp Glu Asn Lys Asn Arg Asn Tyr Glu
    1310                1315                1320
```

Thr Ile Pro Leu Asn Val Val Ile Glu Arg Gln Lys Gln Gly Leu
    1325            1330                1335

Ser Ser Val Pro Ile Lys Ser Glu Lys Gly His Lys Leu Leu Phe
    1340            1345                1350

Tyr Leu Ser Pro Asn Asp Ile Val Tyr Val Pro Gly Ser Asn Glu
    1355            1360                1365

Glu Phe Ser Ile Asp Arg Leu Tyr Arg Phe Thr Asp Ser Ser Asp
    1370            1375                1380

Lys Thr Ala Asn Phe Ile Pro Leu Ser Val Ser Ser Leu Ile Phe
    1385            1390                1395

Ser Ser Asn Lys Asn Glu Gln Lys Lys Ile Gly Ile Ser Tyr Pro
    1400            1405                1410

Ile Gln Asp Glu Phe Gly Leu Gly Ser Pro Gln Ser Lys Asn Gln
    1415            1420                1425

Lys Ser Ile Asp Gly Ile Met Ile Lys Glu Lys Cys Val Lys Val
    1430            1435                1440

Asn Ile Asp Arg Leu Gly Arg Val Ser Phe
    1445            1450

<210> SEQ ID NO 91
<211> LENGTH: 1509
<212> TYPE: PRT
<213> ORGANISM: Psychroflexus torquis

<400> SEQUENCE: 91

Met Lys Arg Ile Leu Gly Leu Asp Leu Gly Thr Asn Ser Ile Gly Trp
1               5                   10                  15

Ser Leu Ile Glu His Asp Phe Lys Asn Lys Gln Gly Gln Ile Glu Gly
                20                  25                  30

Leu Gly Val Arg Ile Ile Pro Met Ser Gln Glu Ile Leu Gly Lys Phe
            35                  40                  45

Asp Ala Gly Gln Ser Ile Ser Gln Thr Ala Asp Arg Thr Lys Tyr Arg
        50                  55                  60

Gly Val Arg Arg Leu Tyr Gln Arg Asp Asn Leu Arg Arg Glu Arg Leu
65                  70                  75                  80

His Arg Val Leu Lys Ile Leu Asp Phe Leu Pro Lys His Tyr Ser Glu
                85                  90                  95

Ser Ile Asp Phe Gln Asp Lys Val Gly Gln Phe Lys Pro Lys Gln Glu
                100                 105                 110

Val Lys Leu Asn Tyr Arg Lys Asn Glu Lys Asn Lys His Glu Phe Val
            115                 120                 125

Phe Met Asn Ser Phe Ile Glu Met Val Ser Glu Phe Lys Asn Ala Gln
        130                 135                 140

Pro Glu Leu Phe Tyr Asn Lys Gly Asn Gly Glu Glu Thr Lys Ile Pro
145                 150                 155                 160

Tyr Asp Trp Thr Leu Tyr Tyr Leu Arg Lys Lys Ala Leu Thr Gln Gln
                165                 170                 175

Ile Thr Lys Glu Glu Leu Ala Trp Leu Ile Leu Asn Phe Asn Gln Lys
            180                 185                 190

Arg Gly Tyr Tyr Gln Leu Arg Gly Glu Asp Ile Asp Glu Asp Lys Asn
        195                 200                 205

Lys Lys Tyr Met Gln Leu Lys Val Asn Asn Leu Ile Asp Ser Gly Ala
    210                 215                 220

Lys Val Lys Gly Lys Val Leu Tyr Asn Val Ile Phe Asp Asn Gly Trp

```
              225                 230                 235                 240
Lys Tyr Glu Lys Gln Ile Val Asn Lys Asp Glu Trp Glu Gly Arg Thr
                    245                 250                 255
Lys Glu Phe Ile Ile Thr Thr Lys Thr Leu Lys Asn Gly Asn Ile Lys
                260                 265                 270
Arg Thr Tyr Lys Ala Val Asp Ser Glu Ile Asp Trp Ala Ala Ile Lys
            275                 280                 285
Ala Lys Thr Glu Gln Asp Ile Asn Lys Ala Asn Lys Thr Val Gly Glu
        290                 295                 300
Tyr Ile Tyr Glu Ser Leu Leu Asp Asn Pro Ser Gln Lys Ile Arg Gly
305                 310                 315                 320
Lys Leu Val Lys Thr Ile Glu Arg Lys Phe Tyr Lys Glu Phe Glu
                    325                 330                 335
Lys Leu Leu Ser Lys Gln Ile Glu Leu Gln Pro Glu Leu Phe Asn Glu
                340                 345                 350
Ser Leu Tyr Lys Ala Cys Ile Lys Glu Leu Tyr Pro Arg Asn Glu Asn
            355                 360                 365
His Gln Ser Asn Asn Lys Lys Gln Gly Phe Glu Tyr Leu Phe Thr Glu
        370                 375                 380
Asp Ile Ile Phe Tyr Gln Arg Pro Leu Lys Ser Gln Lys Ser Asn Ile
385                 390                 395                 400
Ser Gly Cys Gln Phe Glu His Lys Ile Tyr Lys Gln Lys Asn Lys Lys
                    405                 410                 415
Thr Gly Lys Leu Glu Leu Ile Lys Glu Pro Ile Lys Thr Ile Ser Arg
                420                 425                 430
Ser His Pro Leu Phe Gln Glu Phe Arg Ile Trp Gln Trp Leu Gln Asn
            435                 440                 445
Leu Lys Ile Tyr Asn Lys Glu Lys Ile Glu Asn Gly Lys Leu Glu Asp
        450                 455                 460
Val Thr Thr Gln Leu Leu Pro Asn Asn Glu Ala Tyr Val Thr Leu Phe
465                 470                 475                 480
Asp Phe Leu Asn Thr Lys Lys Glu Leu Glu Gln Lys Gln Phe Ile Glu
                    485                 490                 495
Tyr Phe Val Lys Lys Leu Ile Asp Lys Lys Glu Lys Glu His Phe
                500                 505                 510
Arg Trp Asn Phe Val Glu Asp Lys Lys Tyr Pro Phe Ser Glu Thr Arg
            515                 520                 525
Ala Gln Phe Leu Ser Arg Leu Ala Lys Val Lys Gly Ile Lys Asn Thr
        530                 535                 540
Glu Asp Phe Leu Asn Lys Asn Thr Gln Val Gly Ser Lys Glu Asn Ser
545                 550                 555                 560
Pro Phe Ile Lys Arg Ile Glu Gln Leu Trp His Ile Ile Tyr Ser Val
                    565                 570                 575
Ser Asp Leu Lys Glu Tyr Glu Lys Ala Leu Glu Lys Phe Ala Glu Lys
                580                 585                 590
His Asn Leu Glu Lys Asp Ser Phe Leu Lys Asn Phe Lys Lys Phe Pro
            595                 600                 605
Pro Phe Val Ser Asp Tyr Ala Ser Tyr Ser Lys Ala Ile Ser Lys
        610                 615                 620
Leu Leu Pro Ile Met Arg Met Gly Lys Tyr Trp Ser Glu Ser Ala Val
625                 630                 635                 640
Pro Thr Gln Val Lys Glu Arg Ser Leu Ser Ile Met Glu Arg Val Lys
                    645                 650                 655
```

Val Leu Pro Leu Lys Glu Gly Tyr Ser Asp Lys Asp Leu Ala Asp Leu
             660                 665                 670

Leu Ser Arg Val Ser Asp Asp Ile Pro Lys Gln Leu Ile Lys Ser
         675                 680                 685

Phe Ile Ser Phe Lys Asp Lys Asn Pro Leu Lys Gly Leu Asn Thr Tyr
    690                 695                 700

Gln Ala Asn Tyr Leu Val Tyr Gly Arg His Ser Glu Thr Gly Asp Ile
705                 710                 715                 720

Gln His Trp Lys Thr Pro Glu Asp Ile Asp Arg Tyr Leu Asn Asn Phe
             725                 730                 735

Lys Gln His Ser Leu Arg Asn Pro Ile Val Glu Gln Val Val Met Glu
             740                 745                 750

Thr Leu Arg Val Val Arg Asp Ile Trp Glu His Tyr Gly Asn Asn Glu
         755                 760                 765

Lys Asp Phe Phe Lys Glu Ile His Val Glu Leu Gly Arg Glu Met Lys
    770                 775                 780

Ser Pro Ala Gly Lys Arg Glu Lys Leu Ser Gln Arg Asn Thr Glu Asn
785                 790                 795                 800

Glu Asn Thr Asn His Arg Ile Arg Glu Val Leu Lys Glu Leu Met Asn
             805                 810                 815

Asp Ala Ser Val Glu Gly Gly Val Arg Asp Tyr Ser Pro Ser Gln Gln
             820                 825                 830

Glu Ile Leu Lys Leu Tyr Glu Glu Gly Ile Tyr Gln Asn Pro Asn Thr
         835                 840                 845

Asn Tyr Leu Lys Val Asp Glu Asp Glu Ile Leu Lys Ile Arg Lys Lys
    850                 855                 860

Asn Asn Pro Thr Gln Lys Glu Ile Gln Arg Tyr Lys Leu Trp Leu Glu
865                 870                 875                 880

Gln Gly Tyr Ile Ser Pro Tyr Thr Gly Lys Ile Ile Pro Leu Thr Lys
             885                 890                 895

Leu Phe Thr His Glu Tyr Gln Ile Glu His Ile Ile Pro Gln Ser Arg
             900                 905                 910

Tyr Tyr Asp Asn Ser Leu Gly Asn Lys Ile Ile Cys Glu Ser Glu Val
         915                 920                 925

Asn Glu Asp Lys Asp Asn Lys Thr Ala Tyr Glu Tyr Leu Lys Val Glu
    930                 935                 940

Lys Gly Ser Ile Val Phe Gly His Lys Leu Leu Asn Leu Asp Glu Tyr
945                 950                 955                 960

Glu Ala His Val Asn Lys Tyr Phe Lys Lys Asn Lys Thr Lys Leu Lys
             965                 970                 975

Asn Leu Leu Ser Glu Asp Ile Pro Glu Gly Phe Ile Asn Arg Gln Leu
             980                 985                 990

Asn Asp Ser Arg Tyr Ile Ser Lys Leu Val Lys Gly Leu Leu Ser Asn
         995                 1000                1005

Ile Val Arg Glu Asn Gly Glu Gln Glu Ala Thr Ser Lys Asn Leu
    1010                1015                1020

Ile Pro Val Thr Gly Val Val Thr Ser Lys Leu Lys Gln Asp Trp
    1025                1030                1035

Gly Leu Asn Asp Lys Trp Asn Glu Ile Ile Ala Pro Arg Phe Lys
    1040                1045                1050

Arg Leu Asn Lys Leu Thr Asn Ser Asn Asp Phe Gly Phe Trp Asp
    1055                1060                1065

```
Asn Asp Ile Asn Ala Phe Arg Ile Gln Val Pro Asp Ser Leu Ile
    1070                1075                1080

Lys Gly Phe Ser Lys Lys Arg Ile Asp His Arg His Ala Leu
    1085                1090                1095

Asp Ala Leu Val Val Ala Cys Thr Ser Arg Asn His Thr His Tyr
    1100                1105                1110

Leu Ser Ala Leu Asn Ala Glu Asn Lys Asn Tyr Ser Leu Arg Asp
    1115                1120                1125

Lys Leu Val Ile Lys Asn Glu Asn Gly Asp Tyr Thr Lys Thr Phe
    1130                1135                1140

Gln Ile Pro Trp Gln Gly Phe Thr Ile Glu Ala Lys Asn Asn Leu
    1145                1150                1155

Glu Lys Thr Val Val Ser Phe Lys Lys Asn Leu Arg Val Ile Asn
    1160                1165                1170

Lys Thr Asn Asn Lys Phe Trp Ser Tyr Lys Asp Glu Asn Gly Asn
    1175                1180                1185

Leu Asn Leu Gly Lys Asp Gly Lys Pro Lys Lys Lys Leu Arg Lys
    1190                1195                1200

Gln Thr Lys Gly Tyr Asn Trp Ala Ile Arg Lys Pro Leu His Lys
    1205                1210                1215

Glu Thr Val Ser Gly Ile Tyr Asn Ile Asn Ala Pro Lys Asn Lys
    1220                1225                1230

Ile Ala Thr Ser Val Arg Thr Leu Leu Thr Glu Ile Lys Asn Glu
    1235                1240                1245

Lys His Leu Ala Lys Ile Thr Asp Leu Arg Ile Arg Glu Thr Ile
    1250                1255                1260

Leu Pro Asn His Leu Lys His Tyr Leu Asn Asn Lys Gly Glu Ala
    1265                1270                1275

Asn Phe Ser Glu Ala Phe Ser Gln Gly Gly Ile Glu Asp Leu Asn
    1280                1285                1290

Lys Lys Ile Thr Thr Leu Asn Glu Gly Lys Lys His Gln Pro Ile
    1295                1300                1305

Tyr Arg Val Lys Ile Phe Glu Val Gly Ser Lys Phe Ser Ile Ser
    1310                1315                1320

Glu Asp Glu Asn Ser Ala Lys Ser Lys Lys Tyr Val Glu Ala Ala
    1325                1330                1335

Lys Gly Thr Asn Leu Phe Phe Ala Ile Tyr Leu Asp Glu Glu Asn
    1340                1345                1350

Lys Lys Arg Asn Tyr Glu Thr Ile Pro Leu Asn Glu Val Ile Thr
    1355                1360                1365

His Gln Lys Gln Val Ala Gly Phe Pro Lys Ser Glu Arg Leu Ser
    1370                1375                1380

Val Gln Pro Asp Ser Gln Lys Gly Thr Phe Leu Phe Thr Leu Ser
    1385                1390                1395

Pro Asn Asp Leu Val Tyr Val Pro Asn Asn Glu Glu Leu Glu Asn
    1400                1405                1410

Arg Asp Leu Phe Asn Leu Gly Asn Leu Asn Val Glu Gln Ile Ser
    1415                1420                1425

Arg Ile Tyr Lys Phe Thr Asp Ser Ser Asp Lys Thr Cys Asn Phe
    1430                1435                1440

Ile Pro Phe Gln Val Ser Lys Leu Ile Phe Asn Leu Lys Lys Lys
    1445                1450                1455

Glu Gln Lys Lys Leu Asp Val Asp Phe Ile Ile Gln Asn Glu Phe
```

|  | 1460 | 1465 | 1470 |

Gly Leu Gly Ser Pro Gln Ser Lys Asn Gln Lys Ser Ile Asp Asp
    1475                  1480                1485

Val Met Ile Lys Glu Lys Cys Ile Lys Leu Lys Ile Asp Arg Leu
    1490                  1495                1500

Gly Asn Ile Ser Lys Ala
    1505

<210> SEQ ID NO 92
<211> LENGTH: 36
<212> TYPE: DNA
<213> ORGANISM: Lactobacillus reuteri

<400> SEQUENCE: 92
gttttagatg tacttcaaat caataatgtt tagaac                                  36

<210> SEQ ID NO 93
<211> LENGTH: 36
<212> TYPE: DNA
<213> ORGANISM: Lactobacillus rossiae

<400> SEQUENCE: 93
gttttagatg tatgtcagat caatagggtt aagaac                                  36

<210> SEQ ID NO 94
<211> LENGTH: 36
<212> TYPE: DNA
<213> ORGANISM: Pediococcus pentosaceus

<400> SEQUENCE: 94
gtttcagaag agtgttaaat caataagttc aagtac                                  36

<210> SEQ ID NO 95
<211> LENGTH: 36
<212> TYPE: DNA
<213> ORGANISM: Lactobacillus nodensis

<400> SEQUENCE: 95
gttttagtac tctcaagaat ttagtaacag taaaac                                  36

<210> SEQ ID NO 96
<211> LENGTH: 37
<212> TYPE: DNA
<213> ORGANISM: Artificial sequence
<220> FEATURE:
<223> OTHER INFORMATION: sequence from Sulfurospirillum sp. SCADC (Sspe)

<400> SEQUENCE: 96
acgacacttt acaacaccat cgcttagcaa ctgraac                               37

<210> SEQ ID NO 97
<211> LENGTH: 36
<212> TYPE: DNA
<213> ORGANISM: Bifidobacterium thermophilum

<400> SEQUENCE: 97
caagtctatc aagaaggaag gatgctaatt ctcagc                                  36

<210> SEQ ID NO 98
<211> LENGTH: 36
<212> TYPE: DNA
<213> ORGANISM: Loktanella vestfoldensis

<400> SEQUENCE: 98
attatagctg ttcaaaattc gcggtccagc cgcaac                                    36

<210> SEQ ID NO 99
<211> LENGTH: 36
<212> TYPE: DNA
<213> ORGANISM: Sphingomonas sanxanigenens

<400> SEQUENCE: 99
accatagctg ttcagagatc gcggtccagc ggcaac                                    36

<210> SEQ ID NO 100
<211> LENGTH: 47
<212> TYPE: DNA
<213> ORGANISM: Epilithonimonas tenax DSM

<400> SEQUENCE: 100
gttgttgtgt atcccaaaga tacttaaaaa tgaaagcaat tcacaac                        47

<210> SEQ ID NO 101
<211> LENGTH: 47
<212> TYPE: DNA
<213> ORGANISM: Sporocytophaga myxococcoides

<400> SEQUENCE: 101
gttgtgattt gctttcaaac aacgatcttt gaattatcgg aaacaac                        47

<210> SEQ ID NO 102
<211> LENGTH: 46
<212> TYPE: DNA
<213> ORGANISM: Psychroflexus torquis

<400> SEQUENCE: 102
cctgtgaatt atcactaaaa atacaatttt gaaagcaatt cacaac                         46

<210> SEQ ID NO 103
<211> LENGTH: 36
<212> TYPE: DNA
<213> ORGANISM: Lactobacillus reuteri

<400> SEQUENCE: 103
tttaactctg tacttcaaat caataatatt tagtag                                    36

<210> SEQ ID NO 104
<211> LENGTH: 37
<212> TYPE: DNA
<213> ORGANISM: Lactobacillus rossiae

<400> SEQUENCE: 104
tttaacgctg tatgtcagat caatagggtc aaaagtt                                   37

<210> SEQ ID NO 105
<211> LENGTH: 37
<212> TYPE: DNA
<213> ORGANISM: Pediococcus pentosaceus

<400> SEQUENCE: 105
tttcaaaaca gaatgttaaa tcaataagtt taagtac                                   37

<210> SEQ ID NO 106
<211> LENGTH: 38
<212> TYPE: DNA
<213> ORGANISM: Lactobacillus nodensis

<400> SEQUENCE: 106
gttttactgt tactaaattc ttgagaacct actaaaat                                    38

<210> SEQ ID NO 107
<211> LENGTH: 39
<212> TYPE: DNA
<213> ORGANISM: artificial sequence
<220> FEATURE:
<223> OTHER INFORMATION: sequence from Sulfurospirillum sp. SCADC (Sspe)

<400> SEQUENCE: 107
atttcagtgc atcgaacgat acgtgttgta aagtgtcgt                                   39

<210> SEQ ID NO 108
<211> LENGTH: 36
<212> TYPE: DNA
<213> ORGANISM: Bifidobacterium thermophilum

<400> SEQUENCE: 108
gtgtagcgcg atatactaaa aaagctaatt ctcagt                                      36

<210> SEQ ID NO 109
<211> LENGTH: 36
<212> TYPE: DNA
<213> ORGANISM: Loktanella vestfoldensis

<400> SEQUENCE: 109
ttaacggctc gaccgcgaat tttgaacatt tggata                                      36

<210> SEQ ID NO 110
<211> LENGTH: 36
<212> TYPE: DNA
<213> ORGANISM: Sphingomonas sanxanigenens

<400> SEQUENCE: 110
ttaaccgcca gaccacgatc tctgaagtgc tcaggc                                      36

<210> SEQ ID NO 111
<211> LENGTH: 47
<212> TYPE: DNA
<213> ORGANISM: Epilithonimonas tenax

<400> SEQUENCE: 111
attgtgaatt gctttcggat acaaatgtag aaattaatta tttatat                          47

<210> SEQ ID NO 112
<211> LENGTH: 47
<212> TYPE: DNA
<213> ORGANISM: Sporocytophaga myxococcoides

<400> SEQUENCE: 112
attgtgattt gctttcacta gcaaatatat ataaatttaa ttttatt                          47

<210> SEQ ID NO 113
<211> LENGTH: 46
<212> TYPE: DNA
<213> ORGANISM: Psychroflexus torquis

<400> SEQUENCE: 113
attgtgaatt gcttcaaaat tgtgtaccaa atatattaat attata                           46

<210> SEQ ID NO 114

```
<211> LENGTH: 169
<212> TYPE: RNA
<213> ORGANISM: Artificial Sequence
<220> FEATURE:
<223> OTHER INFORMATION: synthesized Lreu Single Guide RNA

<400> SEQUENCE: 114
gggcgcuaaa gaggaagagg acaguuuuag auguacuucg aaagaaguac agaguuaaaa     60
ucaaacaagu gcuucagcac aaguuucuac uuuugaguca guuaucugac caauacauaa    120
aagggaauua aaucguucac augagcguuu uaauucccuu ucucucuuu                169

<210> SEQ ID NO 115
<211> LENGTH: 166
<212> TYPE: RNA
<213> ORGANISM: Artificial Sequence
<220> FEATURE:
<223> OTHER INFORMATION: synthesized  Lros  Single Guide RNA

<400> SEQUENCE: 115
gggcgcuaaa gaggaagagg acaguuuuag auguaugucg aaagacauac agcguuaaaa     60
ucaagcaagg cuucgagcc aaguuuaaau cuuuggguuc gcuauucgga ccguacauag     120
uaaaagggcg ucaucgaguu caaauucgau ggcgcccuuu aguuuu                   166

<210> SEQ ID NO 116
<211> LENGTH: 168
<212> TYPE: RNA
<213> ORGANISM: Artificial Sequence
<220> FEATURE:
<223> OTHER INFORMATION: synthesized  Ppen  Single Guide RN

<400> SEQUENCE: 116
gggcgcuaaa gaggaagagg acaguuucag aagaguguug aaaaacauuc uguuugaaa     60 ucaaacaacg cuuuacgcgg aguuuacaca ucugucccau uauaugggca uuacauaaua   120
aaagagaaau caccuuuaag guugauuccu cuuuucuug cguccuu                  168

<210> SEQ ID NO 117
<211> LENGTH: 114
<212> TYPE: RNA
<213> ORGANISM: Artificial Sequence2
<220> FEATURE:
<223> OTHER INFORMATION: synthesized  Lnod Single Guide RNA

<400> SEQUENCE: 117
gggcgcuaaa gaggaagagg acaguuuuag uacucucaag gaaacuugag aaccuacuaa     60
aauaaggauu uauuccgaau uuaccaccua uuuuuaaua ggugguuuuu uuuu          114

<210> SEQ ID NO 118
<211> LENGTH: 180
<212> TYPE: RNA
<213> ORGANISM: Artificial Sequence
<220> FEATURE:
<223> OTHER INFORMATION: synthesized  Sspe  Single Guide RNA

<400> SEQUENCE: 118
gggcgcuaaa gaggaagagg acaacgacac uuuacaacac gaaagug uug uaaagugucg     60 ugagugaaag uauagcauuu uucucaaaau aucgcacuuu uuuugcaagg aaauaauuug    120
cgaaaaaaag agacaauuuc gauacaagaa agccccauca agucgaugau uuguaaggcu    180

<210> SEQ ID NO 119
<211> LENGTH: 117
```

```
<212> TYPE: RNA
<213> ORGANISM: Artificial Sequence
<220> FEATURE:
<223> OTHER INFORMATION: synthesized  Sspe Single Guide RNA (tracrRNA
      Antisense-crRNA Antisens

<400> SEQUENCE: 119
gggcgcuaaa gaggaagagg acaguuccag uugcuaagcg aaaguucgau gcacugaaau        60
caucgaaaag auauauagac ccgcccaacu gccuuaggca uggcgggcuu cuuucuu         117

<210> SEQ ID NO 120
<211> LENGTH: 254
<212> TYPE: RNA
<213> ORGANISM: Artificial Sequence
<220> FEATURE:
<223> OTHER INFORMATION: synthesized  Bthe  Single Guide RNA

<400> SEQUENCE: 120
gggcgcuaaa gaggaagagg acagcugaga auuagcaucg aaaaaagcua auucucagua        60
aguacagcaa uuuauagcug uaucugaaug cuaagcgguu agccgcaggg gagagcuucg       120
gcucuccccg uucuuuucua gucgcacgug acacgccaua gguagauugc cugugagcaa       180
cucgagaaua guaguauucu ucucuguaaa acgagacauc guugcugaug acuccauuga       240
caaagaaggg aauu                                                        254

<210> SEQ ID NO 121
<211> LENGTH: 200
<212> TYPE: RNA
<213> ORGANISM: Artificial Sequence
<220> FEATURE:
<223> OTHER INFORMATION: synthesized Lves  Single Guide RNA

<400> SEQUENCE: 121
gggcgcuaaa gaggaagagg acaguugcgg cuggaccgcg aaagcggucg agccguuaac        60
aagcauucga uugcaccaca uugaaacgca ggcuacggcc ugcguuuucu uauuuccggu       120
augguucguc uugucaaagu gucucagaga ugcccgcuuu cuaaaugugg auugucgagg       180
uucgcacccg uagcguuuuu                                                  200

<210> SEQ ID NO 122
<211> LENGTH: 195
<212> TYPE: RNA
<213> ORGANISM: Artificial Sequence
<220> FEATURE:
<223> OTHER INFORMATION: synthesized  Ssan  Single Guide RNA

<400> SEQUENCE: 122
gggcgcuaaa gaggaagagg acaguugccg cuggaccgcg aaagugguct ggcgguuaac        60
aagcagccag ucugcaccag auaagggcgg cgcuccggcg ccgccuuuuu uguuugcccg       120
gaauguugag acaggcgcca aaccauccc ccuccccucg gggcgugcgg caaucgcugc       180
uuucagcuca cucca                                                       195

<210> SEQ ID NO 123
<211> LENGTH: 155
<212> TYPE: RNA
<213> ORGANISM: Artificial Sequence
<220> FEATURE:
<223> OTHER INFORMATION: synthesized  Eten Single Guide RNA

<400> SEQUENCE: 123
gggcgcuaaa gaggaagagg acaguuguga auugcuuucg aaagaaagca auucacaaua        60
```
aggauuauuc cguugugaaa acauuuagca ccucgccuau cugcggggua uuuuuuauuu    120
aauacauuca aacaaugaag ucgauugcau uuauu    155

<210> SEQ ID NO 124
<211> LENGTH: 149
<212> TYPE: RNA
<213> ORGANISM: Artificial Sequences
<220> FEATURE:
<223> OTHER INFORMATION: synthesized  Smyx Single Guide RNA

<400> SEQUENCE: 124
gggcgcuaaa gaggaagagg acaguuguga uuugcuuucg aaaaaagcaa aucacaauaa    60
ggauuauucc guugugaaaa cauauaagcc gccucgucuu acaauacggg gcuuuuuua    120 uuccccauuc acauauggcc auccauuuu    149

<210> SEQ ID NO 125
<211> LENGTH: 155
<212> TYPE: RNA
<213> ORGANISM: Artificial Sequence
<220> FEATURE:
<223> OTHER INFORMATION: synthesized  Ptor Single Guide RNA

<400> SEQUENCE: 125
gggcgcuaaa gaggaagagg acaguuguga auugcuuuca gaaaugaagc aauucacaau    60
aaggauuauu ccguugugaa aacauuuaaa gcggccuuua cgggucgcuu ucuuuuuua    120 aagaacuuaa acuuaauaaa uucuuuacaa acuca    155

<210> SEQ ID NO 126
<211> LENGTH: 57
<212> TYPE: DNA
<213> ORGANISM: Artificial sequence
<220> FEATURE:
<223> OTHER INFORMATION: synthesized  GG-939

<400> SEQUENCE: 126 gactagaccct gcaggggatc ccgtcgacaa attctaaacg ctaaagagga agaggac    57

<210> SEQ ID NO 127
<211> LENGTH: 174
<212> TYPE: RNA
<213> ORGANISM: Artificial sequence
<220> FEATURE:
<223> OTHER INFORMATION: synthesized single guide RNA
<220> FEATURE:
<221> NAME/KEY: misc_feature
<222> LOCATION: (1)..(20)
<223> OTHER INFORMATION: n is a, c, g, or u

<400> SEQUENCE: 127
nnnnnnnnnn nnnnnnnnnn gcuauaguuc cuuacugaaa gguaaguugc uauaguaagg    60
gcaacagacc cgaggcguug gggaucgccu agcccguuuu uacgggcucu ccccauauuc    120
aaaauaauga cagacgagca ccuuggagca uuuauuuccg aggugcuuuu uuuu    174

<210> SEQ ID NO 128
<211> LENGTH: 166
<212> TYPE: RNA
<213> ORGANISM: Artificial Sequence
<220> FEATURE:
<223> OTHER INFORMATION: synthesized Lreu Single Guide RNA
<220> FEATURE:
<221> NAME/KEY: misc_feature
<222> LOCATION: (1)..(20)

<223> OTHER INFORMATION: n is a, c, g, or u

<400> SEQUENCE: 128
nnnnnnnnnn nnnnnnnnnn guuuuagaug uacuucgaaa gaaguacaga guuaaaauca    60
aacaagugcu ucagcacaag uuucuacuuu ugagucaguu aucugaccaa uacauaaaag   120
ggaauuaaau cguucacaug agcguuuuaa uucccuuucu cucuuu                  166

<210> SEQ ID NO 129
<211> LENGTH: 163
<212> TYPE: RNA
<213> ORGANISM: Artificial Sequence
<220> FEATURE:
<223> OTHER INFORMATION: synthesized Lros Single Guide RNA
<220> FEATURE:
<221> NAME/KEY: misc_feature
<222> LOCATION: (1)..(20)
<223> OTHER INFORMATION: n is a, c, g, or u

<400> SEQUENCE: 129
nnnnnnnnnn nnnnnnnnnn guuuuagaug uaugucgaaa gacauacagc guuaaaauca    60
agcaaggcuu ucgagccaag uuuaaaucuu ugg guucgcu auucgaccg uacauaguaa   120 aagggcguca ucgaguucaa auucgauggc gcccuuuagu uuu                     163

<210> SEQ ID NO 130
<211> LENGTH: 165
<212> TYPE: RNA
<213> ORGANISM: Artificial Sequence
<220> FEATURE:
<223> OTHER INFORMATION: synthesized Ppen Single Guide RNA
<220> FEATURE:
<221> NAME/KEY: misc_feature
<222> LOCATION: (1)..(20)
<223> OTHER INFORMATION: n is a, c, g, or u

<400> SEQUENCE: 130
nnnnnnnnnn nnnnnnnnnn guuucagaag aguguugaaa aacauucugu uuugaaauca    60
aacaacgcuu uacgcggagu uuacacaucu gucccauuau augggcauua cauaauaaaa   120
gagaaaucac cuuuaagguu gauuccucuu uuucuugcgu uccuu                   165

<210> SEQ ID NO 131
<211> LENGTH: 111
<212> TYPE: RNA
<213> ORGANISM: Artificial Sequence
<220> FEATURE:
<223> OTHER INFORMATION: synthesized Lnod Single Guide RNA
<220> FEATURE:
<221> NAME/KEY: misc_feature
<222> LOCATION: (1)..(20)
<223> OTHER INFORMATION: n is a, c, g, or u

<400> SEQUENCE: 131
nnnnnnnnnn nnnnnnnnnn guuuuaguac ucucaaggaa acuugagaac cuacuaaaau    60
aaggauuuau uccgaauuua ccaccuauuu uuuaauaggu gguuuuuuu u             111

<210> SEQ ID NO 132
<211> LENGTH: 177
<212> TYPE: RNA
<213> ORGANISM: Artificial Sequence
<220> FEATURE:
<223> OTHER INFORMATION: synthesized Sspe Single Guide RNA
<220> FEATURE:
<221> NAME/KEY: misc_feature
<222> LOCATION: (1)..(20)
<223> OTHER INFORMATION: n is a, c, g, or u

```
<400> SEQUENCE: 132
nnnnnnnnnn nnnnnnnnnn acgacacuuu acaacacgaa aguguuguaa agugucguga      60
gugaaaguau agcauuuuuc ucaaaauauc gcacuuuuuu ugcaaggaaa uaauuugcga     120
aaaaaagaga caauuucgau acaagaaagc cccaucaagu cgaugauuug uaaggcu       177

<210> SEQ ID NO 133
<211> LENGTH: 114
<212> TYPE: RNA
<213> ORGANISM: Artificial Sequence
<220> FEATURE:
<223> OTHER INFORMATION: synthesized  Sspe Single Guide RNA (tracrRNA
      Antisense-crRNA Antisense
<220> FEATURE:
<221> NAME/KEY: misc_feature
<222> LOCATION: (1)..(20)
<223> OTHER INFORMATION: n is a, c, g, or u

<400> SEQUENCE: 133
nnnnnnnnnn nnnnnnnnnn guuccaguug cuaagcgaaa guucgaugca cugaaaucau      60
cgaaaagaua uauagacccg cccaacugcc uuaggcaugg cgggcuucuu ucuu           114

<210> SEQ ID NO 134
<211> LENGTH: 251
<212> TYPE: RNA
<213> ORGANISM: Artificial Sequence
<220> FEATURE:
<223> OTHER INFORMATION: synthesized  Bthe  Single Guide RNA
<220> FEATURE:
<221> NAME/KEY: misc_feature
<222> LOCATION: (1)..(20)
<223> OTHER INFORMATION: n is a, c, g, or u

<400> SEQUENCE: 134
nnnnnnnnnn nnnnnnnnnn gcugagaauu agcaucgaaa aaagcuaauu cucaguaagu      60
acagcaauuu auagcuguau cugaaugcua agcgguuagc cgcaggggag agcuucggcu    120
cuccccguuc uuuucuaguc gcacgugaca cgccauaggu agauugccug ugagcaacuc    180
gagaauagua guauucuucu cuguaaaacg agacaucguu gcugaugacu ccauugacaa    240
agaagggaau u                                                         251

<210> SEQ ID NO 135
<211> LENGTH: 197
<212> TYPE: RNA
<213> ORGANISM: Artificial Sequence
<220> FEATURE:
<223> OTHER INFORMATION: synthesized  Lves  Single Guide RNA
<220> FEATURE:
<221> NAME/KEY: misc_feature
<222> LOCATION: (1)..(20)
<223> OTHER INFORMATION: n is a, c, g, or u

<400> SEQUENCE: 135
nnnnnnnnnn nnnnnnnnnn guugcggcug gaccgcgaaa gcggucgagc cguuaacaag      60
cauucgauug caccacauug aaacgcaggc uacgccugc guuucuuau uuccgguaug      120 guucgucuug ucaaagguguc ucagagaugc ccgcuuucua aauguggauu gucgagguuc    180
gcacccguag cguuuuu                                                    197

<210> SEQ ID NO 136
<211> LENGTH: 192
<212> TYPE: RNA
<213> ORGANISM: Artificial Sequence
```

```
<220> FEATURE:
<223> OTHER INFORMATION: synthesized  Ssan Single Guide RNA
<220> FEATURE:
<221> NAME/KEY: misc_feature
<222> LOCATION: (1)..(20)
<223> OTHER INFORMATION: n is a, c, g, or u

<400> SEQUENCE: 136
nnnnnnnnnn nnnnnnnnnn guugccgcug gaccgcgaaa guggucuggc gguuaacaag    60
cagccagucu gcaccagaua agggcggcgc uccggcgccg ccuuuuugu uugcccggaa    120 uguugagaca ggcgccaaac cauccccccu ccccucgggg cgugcggcaa ucgcugcuuu   180
cagcucacuc ca                                                       192

<210> SEQ ID NO 137
<211> LENGTH: 152
<212> TYPE: RNA
<213> ORGANISM: Artificial Sequence
<220> FEATURE:
<223> OTHER INFORMATION: synthesized  Eten  Single Guide RNA
<220> FEATURE:
<221> NAME/KEY: misc_feature
<222> LOCATION: (1)..(20)
<223> OTHER INFORMATION: n is a, c, g, or u

<400> SEQUENCE: 137
nnnnnnnnnn nnnnnnnnnn guugugaauu gcuucgaaa gaaagcaauu cacaauaagg    60
auuauuccgu ugugaaaaca uuuagcaccu cgccuaucug cggggauuuu uuuauuuaau   120
acauucaaac aaugaagucg auugcauuua uu                                 152

<210> SEQ ID NO 138
<211> LENGTH: 146
<212> TYPE: RNA
<213> ORGANISM: Artificial Sequence
<220> FEATURE:
<223> OTHER INFORMATION: synthesized  Smyx  Single Guide RNA
<220> FEATURE:
<221> NAME/KEY: misc_feature
<222> LOCATION: (1)..(20)
<223> OTHER INFORMATION: n is a, c, g, or u

<400> SEQUENCE: 138
nnnnnnnnnn nnnnnnnnnn guugugauuu gcuuucgaaa aaagcaaauc acaauaagga    60
uuauuccguu gugaaaacau auaagccgcc ucgucuuaca auacgggcu uuuuuauuc    120 cccauucaca uauggccauc cauuuu                                        146

<210> SEQ ID NO 139
<211> LENGTH: 152
<212> TYPE: RNA
<213> ORGANISM: Artificial Sequence
<220> FEATURE:
<223> OTHER INFORMATION: synthesized Ptor  Single Guide RNA
<220> FEATURE:
<221> NAME/KEY: misc_feature
<222> LOCATION: (1)..(20)
<223> OTHER INFORMATION: n is a, c, g, or u

<400> SEQUENCE: 139
nnnnnnnnnn nnnnnnnnnn guugugaauu gcuucagaa augaagcaau ucacaauaag    60
gauuauuccg uugugaaaac auuuaaagcg gccuuuacgg gucgcuuucu uuuuuaaag    120 aacuuaaacu uaauaaauuc uuuacaaacu ca                                 152

<210> SEQ ID NO 140
```

```
<211> LENGTH: 1092
<212> TYPE: PRT
<213> ORGANISM: Brevibacillus laterosporus

<400> SEQUENCE: 140

Met Ala Tyr Thr Met Gly Ile Asp Val Gly Ile Ala Ser Cys Gly Trp
1               5                   10                  15

Ala Ile Val Asp Leu Glu Arg Gln Arg Ile Ile Asp Ile Gly Val Arg
            20                  25                  30

Thr Phe Glu Lys Ala Glu Asn Pro Lys Asn Gly Glu Ala Leu Ala Val
        35                  40                  45

Pro Arg Arg Glu Ala Arg Ser Ser Arg Arg Leu Arg Arg Lys Lys
    50                  55                  60

His Arg Ile Glu Arg Leu Lys His Met Phe Val Arg Asn Gly Leu Ala
65                  70                  75                  80

Val Asp Ile Gln His Leu Glu Gln Thr Leu Arg Ser Gln Asn Glu Ile
                85                  90                  95

Asp Val Trp Gln Leu Arg Val Asp Gly Leu Asp Arg Met Leu Thr Gln
            100                 105                 110

Lys Glu Trp Leu Arg Val Leu Ile His Leu Ala Gln Arg Arg Gly Phe
        115                 120                 125

Gln Ser Asn Arg Lys Thr Asp Gly Ser Ser Glu Asp Gly Gln Val Leu
    130                 135                 140

Val Asn Val Thr Glu Asn Asp Arg Leu Met Glu Lys Asp Tyr Arg
145                 150                 155                 160

Thr Val Ala Glu Met Met Val Lys Asp Glu Lys Phe Ser Asp His Lys
                165                 170                 175

Arg Asn Lys Asn Gly Asn Tyr His Gly Val Val Ser Arg Ser Ser Leu
            180                 185                 190

Leu Val Glu Ile His Thr Leu Phe Glu Thr Gln Arg Gln His His Asn
        195                 200                 205

Ser Leu Ala Ser Lys Asp Phe Glu Leu Glu Tyr Val Asn Ile Trp Ser
    210                 215                 220

Ala Gln Arg Pro Val Ala Thr Lys Asp Gln Ile Glu Lys Met Ile Gly
225                 230                 235                 240

Thr Cys Thr Phe Leu Pro Lys Glu Lys Arg Ala Pro Lys Ala Ser Trp
                245                 250                 255

His Phe Gln Tyr Phe Met Leu Leu Gln Thr Ile Asn His Ile Arg Ile
            260                 265                 270

Thr Asn Val Gln Gly Thr Arg Ser Leu Asn Lys Glu Glu Ile Glu Gln
        275                 280                 285

Val Val Asn Met Ala Leu Thr Lys Ser Lys Val Ser Tyr His Asp Thr
    290                 295                 300

Arg Lys Ile Leu Asp Leu Ser Glu Glu Tyr Gln Phe Val Gly Leu Asp
305                 310                 315                 320

Tyr Gly Lys Glu Asp Lys Lys Val Glu Ser Lys Glu Thr Ile
                325                 330                 335

Ile Lys Leu Asp Asp Tyr His Lys Leu Asn Lys Ile Phe Asn Glu Val
            340                 345                 350

Glu Leu Ala Lys Gly Glu Thr Trp Glu Ala Asp Tyr Asp Thr Val
        355                 360                 365

Ala Tyr Ala Leu Thr Phe Phe Lys Asp Glu Asp Ile Arg Asp Tyr
    370                 375                 380

Leu Gln Asn Lys Tyr Lys Asp Ser Lys Asn Arg Leu Val Lys Asn Leu
```

-continued

```
            385                 390                 395                 400
        Ala Asn Lys Glu Tyr Thr Asn Glu Leu Ile Gly Lys Val Ser Thr Leu
                        405                 410                 415

Ser Phe Arg Lys Val Gly His Leu Ser Leu Lys Ala Leu Arg Lys Ile
                        420                 425                 430

Ile Pro Phe Leu Glu Gln Gly Met Thr Tyr Asp Lys Ala Cys Gln Ala
                        435                 440                 445

Ala Gly Phe Asp Phe Gln Gly Ile Ser Lys Lys Arg Ser Val Val
                        450                 455                 460

Leu Pro Val Ile Asp Gln Ile Ser Asn Pro Val Val Asn Arg Ala Leu
        465                 470                 475                 480

Thr Gln Thr Arg Lys Val Ile Asn Ala Leu Ile Lys Lys Tyr Gly Ser
                        485                 490                 495

Pro Glu Thr Ile His Ile Glu Thr Ala Arg Glu Leu Ser Lys Thr Phe
                        500                 505                 510

Asp Glu Arg Lys Asn Ile Thr Lys Asp Tyr Lys Glu Asn Arg Asp Lys
                        515                 520                 525

Asn Glu His Ala Lys Lys His Leu Ser Glu Leu Gly Ile Ile Asn Pro
        530                 535                 540

Thr Gly Leu Asp Ile Val Lys Tyr Lys Leu Trp Cys Glu Gln Gln Gly
        545                 550                 555                 560

Arg Cys Met Tyr Ser Asn Gln Pro Ile Ser Phe Glu Arg Leu Lys Glu
                        565                 570                 575

Ser Gly Tyr Thr Glu Val Asp His Ile Ile Pro Tyr Ser Arg Ser Met
                        580                 585                 590

Asn Asp Ser Tyr Asn Asn Arg Val Leu Val Met Thr Arg Glu Asn Arg
                        595                 600                 605

Glu Lys Gly Asn Gln Thr Pro Phe Glu Tyr Met Gly Asn Asp Thr Gln
                        610                 615                 620

Arg Trp Tyr Glu Phe Glu Gln Arg Val Thr Thr Asn Pro Gln Ile Lys
        625                 630                 635                 640

Lys Glu Lys Arg Gln Asn Leu Leu Lys Gly Phe Thr Asn Arg Arg
                        645                 650                 655

Glu Leu Glu Met Leu Glu Arg Asn Leu Asn Asp Thr Arg Tyr Ile Thr
                        660                 665                 670

Lys Tyr Leu Ser His Phe Ile Ser Thr Asn Leu Glu Phe Ser Pro Ser
                        675                 680                 685

Asp Lys Lys Lys Lys Val Val Asn Thr Ser Gly Arg Ile Thr Ser His
                        690                 695                 700

Leu Arg Ser Arg Trp Gly Leu Glu Lys Asn Arg Gly Gln Asn Asp Leu
        705                 710                 715                 720

His His Ala Met Asp Ala Ile Val Ile Ala Val Thr Ser Asp Ser Phe
                        725                 730                 735

Ile Gln Gln Val Thr Asn Tyr Tyr Lys Arg Lys Glu Arg Arg Glu Leu
                        740                 745                 750

Asn Gly Asp Asp Lys Phe Pro Leu Pro Trp Lys Phe Phe Arg Glu Glu
                        755                 760                 765

Val Ile Ala Arg Leu Ser Pro Asn Pro Lys Glu Gln Ile Glu Ala Leu
                        770                 775                 780

Pro Asn His Phe Tyr Ser Glu Asp Glu Leu Ala Asp Leu Gln Pro Ile
        785                 790                 795                 800

Phe Val Ser Arg Met Pro Lys Arg Ser Ile Thr Gly Glu Ala His Gln
                        805                 810                 815
```

-continued

```
Ala Gln Phe Arg Arg Val Val Gly Lys Thr Lys Glu Gly Lys Asn Ile
            820                 825                 830

Thr Ala Lys Lys Thr Ala Leu Val Asp Ile Ser Tyr Asp Lys Asn Gly
            835                 840                 845

Asp Phe Asn Met Tyr Gly Arg Glu Thr Asp Pro Ala Thr Tyr Glu Ala
850                 855                 860

Ile Lys Glu Arg Tyr Leu Glu Phe Gly Asn Val Lys Lys Ala Phe
865                 870                 875                 880

Ser Thr Asp Leu His Lys Pro Lys Asp Gly Thr Lys Gly Pro Leu
                885                 890                 895

Ile Lys Ser Val Arg Ile Met Glu Asn Lys Thr Leu Val His Pro Val
            900                 905                 910

Asn Lys Gly Lys Gly Val Val Tyr Asn Ser Ser Ile Val Arg Thr Asp
            915                 920                 925

Val Phe Gln Arg Lys Glu Lys Tyr Tyr Leu Leu Pro Val Tyr Val Thr
930                 935                 940

Asp Val Thr Lys Gly Lys Leu Pro Asn Lys Val Ile Val Ala Lys Lys
945                 950                 955                 960

Gly Tyr His Asp Trp Ile Glu Val Asp Asp Ser Phe Thr Phe Leu Phe
                965                 970                 975

Ser Leu Tyr Pro Asn Asp Leu Ile Phe Ile Arg Gln Asn Pro Lys Lys
            980                 985                 990

Lys Ile Ser Leu Lys Lys Arg Ile Glu Ser His Ser Ile Ser Asp Ser
            995                 1000                1005

Lys Glu Val Gln Glu Ile His Ala Tyr Tyr Lys Gly Val Asp Ser
    1010                1015                1020

Ser Thr Ala Ala Ile Glu Phe Ile Ile His Asp Gly Ser Tyr Tyr
    1025                1030                1035

Ala Lys Gly Val Gly Val Gln Asn Leu Asp Cys Phe Glu Lys Tyr
    1040                1045                1050

Gln Val Asp Ile Leu Gly Asn Tyr Phe Lys Val Lys Gly Glu Lys
    1055                1060                1065

Arg Leu Glu Leu Glu Thr Ser Asp Ser Asn His Lys Gly Lys Asp
    1070                1075                1080

Val Asn Ser Ile Lys Ser Thr Ser Arg
    1085                1090

<210> SEQ ID NO 141
<211> LENGTH: 20
<212> TYPE: RNA
<213> ORGANISM: Artificial Sequence
<220> FEATURE:
<223> OTHER INFORMATION: synthesized  Variable Targeting domain T1

<400> SEQUENCE: 141
cgcuaaagag gaagaggaca                                                    20

<210> SEQ ID NO 142
<211> LENGTH: 20
<212> TYPE: RNA
<213> ORGANISM: Artificial Sequence
<220> FEATURE:
<223> OTHER INFORMATION: synthesized  Variable Targeting domain T2-5

<400> SEQUENCE: 142
ucuagauaga uuacgaauuc                                                    20
```

<210> SEQ ID NO 143
<211> LENGTH: 20
<212> TYPE: RNA
<213> ORGANISM: Artificial Sequence
<220> FEATURE:
<223> OTHER INFORMATION: synthesized  Variable Targeting domain T2-7

<400> SEQUENCE: 143
ccggcgacgu ugggucaacu                                            20

<210> SEQ ID NO 144
<211> LENGTH: 105
<212> TYPE: RNA
<213> ORGANISM: Artificial Sequence
<220> FEATURE:
<223> OTHER INFORMATION: synthesized  Spy sgRNA T2

<400> SEQUENCE: 144
gggucuagau agauuacgaa uucguuuuag agcuagaaau agcaaguuaa aauaaggcua     60
guccguuauc aacugaaaaa aguggcaccg agucggugcu uuuuu                   105

<210> SEQ ID NO 145
<211> LENGTH: 123
<212> TYPE: RNA
<213> ORGANISM: Artificial Sequence
<220> FEATURE:
<223> OTHER INFORMATION: synthesized  Sth3 sgRNA T2

<400> SEQUENCE: 145
gggucuagau agauuacgaa uucguuuuag agcuguguug uuucgguuaa acaacacag     60 cgaguuaaaa uaaggcuuag uccguacuca acuugaaaag guggcaccga uucgguguuu   120
uuu                                                               123

<210> SEQ ID NO 146
<211> LENGTH: 122
<212> TYPE: RNA
<213> ORGANISM: Artificial Sequence
<220> FEATURE:
<223> OTHER INFORMATION: synthesized  Sth1 sgRNA T1

<400> SEQUENCE: 146
gggcgcuaaa gaggaagagg acaguuuuug uacucucaag auucaauaau cuugcagaag    60
cuacaaagau aaggcuucau gccgaaauca acacccuguc auuuuauggc aggguguuuu   120
cg                                                                 122

<210> SEQ ID NO 147
<211> LENGTH: 122
<212> TYPE: RNA
<213> ORGANISM: Artificial Sequence
<220> FEATURE:
<223> OTHER INFORMATION: synthesized  Sth1 sgRNA T2

<400> SEQUENCE: 147
gggccggcga cguuggguca acuguuuuug uacucucaag auucaauaau cuugcagaag    60
cuacaaagau aaggcuucau gccgaaauca acacccuguc auuuuauggc aggguguuuu   120
cg                                                                 122

<210> SEQ ID NO 148
<211> LENGTH: 20
<212> TYPE: RNA
<213> ORGANISM: Artificial Sequence

```
<220> FEATURE:
<223> OTHER INFORMATION: synthesized  shifted T1 variable targeting
      domain, T1-3

<400> SEQUENCE: 148
aaacgcuaaa gaggaagagg                                                   20

<210> SEQ ID NO 149
<211> LENGTH: 177
<212> TYPE: RNA
<213> ORGANISM: Artificial Sequence
<220> FEATURE:
<223> OTHER INFORMATION: synthesized  Blat sgRNA (T1)-3

<400> SEQUENCE: 149
gggaaacgcu aaagaggaag agggcuauag uuccuuacug aaagguaagu ugcuauagua       60
agggcaacag acccgaggcg uuggggaucg ccuagcccgu uuuuacgggc ucuccccaua      120
uucaaaauaa ugacagacga gcaccuugga gcauuauuu ccgaggugcu uuuuuu          177

<210> SEQ ID NO 150
<211> LENGTH: 9
<212> TYPE: PRT
<213> ORGANISM: Simian virus

<400> SEQUENCE: 150

Met Ala Pro Lys Lys Lys Arg Lys Val
1               5

<210> SEQ ID NO 151
<211> LENGTH: 18
<212> TYPE: PRT
<213> ORGANISM: Agrobacterium tumefaciens

<400> SEQUENCE: 151

Lys Arg Pro Arg Asp Arg His Asp Gly Glu Leu Gly Gly Arg Lys Arg
1               5                   10                  15

Ala Arg

<210> SEQ ID NO 152
<211> LENGTH: 147
<212> TYPE: RNA
<213> ORGANISM: Brevibacillus laterosporus

<400> SEQUENCE: 152
gcuauaguuc cuuacugaaa gguaaguugc uauaguaagg gcaacagacc cgaggcguug       60
gggaucgccu agcccguuuu uacgggcucu ccccauauuc aaaauaauga cagacgagca      120
ccuuggagca uuuauuuccg aggugcu                                          147

<210> SEQ ID NO 153
<211> LENGTH: 147
<212> TYPE: RNA
<213> ORGANISM: Brevibacillus laterosporus

<400> SEQUENCE: 153
gcuauaguuc cuuacugaaa gguaaguugc uauaguaagg gcaacagacc cgaggcguug       60
gggaucgccu agcccguguu uacgggcucu ccccauauuc aaaauaauga cagacgagca      120
ccuuggagca uuuaucuccg aggugcu                                          147

<210> SEQ ID NO 154
<211> LENGTH: 73
```

```
<212> TYPE: DNA
<213> ORGANISM: Zea mays

<400> SEQUENCE: 154
ccttgaccag gataatgagg tactggctgg aaggcccaag agcgggcgag gtagaggtgt      60
tcgcgaacct gcc                                                        73

<210> SEQ ID NO 155
<211> LENGTH: 73
<212> TYPE: DNA
<213> ORGANISM: Zea mays

<400> SEQUENCE: 155
cttgaccagg ataatgaggt actggcttgg aaggcccaag agcgggcgag gtagaggtgt      60
tcgcgaacct gcc                                                        73

<210> SEQ ID NO 156
<211> LENGTH: 73
<212> TYPE: DNA
<213> ORGANISM: Zea mays

<400> SEQUENCE: 156
cttgaccagg ataatgaggt actggctagg aaggcccaag agcgggcgag gtagaggtgt      60
tcgcgaacct gcc                                                        73

<210> SEQ ID NO 157
<211> LENGTH: 73
<212> TYPE: DNA
<213> ORGANISM: Zea mays

<400> SEQUENCE: 157
cttgaccagg ataatgaggt actggctggg aaggcccaag agcgggcgag gtagaggtgt      60
tcgcgaacct gcc                                                        73

<210> SEQ ID NO 158
<211> LENGTH: 73
<212> TYPE: DNA
<213> ORGANISM: Zea mays

<400> SEQUENCE: 158
cttgaccagg ataatgaggt actggctcgg aaggcccaag agcgggcgag gtagaggtgt      60
tcgcgaacct gcc                                                        73

<210> SEQ ID NO 159
<211> LENGTH: 72
<212> TYPE: DNA
<213> ORGANISM: Zea mays

<400> SEQUENCE: 159
ccttgaccag gataatgagg tactggcgga aggcccaaga gcgggcgagg tagaggtgtt      60
cgcgaacctg cc                                                         72

<210> SEQ ID NO 160
<211> LENGTH: 73
<212> TYPE: DNA
<213> ORGANISM: Zea mays

<400> SEQUENCE: 160
ttgaccagga taatgaggta ctggctttgg aaggcccaag agcgggcgag gtagaggtgt      60
```

```
tcgcgaacct gcc                                                          73

<210> SEQ ID NO 161
<211> LENGTH: 73
<212> TYPE: DNA
<213> ORGANISM: Zea mays

<400> SEQUENCE: 161
cttgaccagg ataatgaggt actggcgtgg aaggcccaag agcgggcgag gtagaggtgt      60
tcgcgaacct gcc                                                          73

<210> SEQ ID NO 162
<211> LENGTH: 71
<212> TYPE: DNA
<213> ORGANISM: Zea mays

<400> SEQUENCE: 162
ccttgaccag gataatgagg tactggctaa ggcccaagag cgggcgaggt agaggtgttc      60
gcgaacctgc c                                                            71

<210> SEQ ID NO 163
<211> LENGTH: 42
<212> TYPE: DNA
<213> ORGANISM: Zea mays

<400> SEQUENCE: 163
ccttgaccag gataatgagg tagaggtgtt cgcgaacctg cc                          42

<210> SEQ ID NO 164
<211> LENGTH: 65
<212> TYPE: DNA
<213> ORGANISM: Zea mays

<400> SEQUENCE: 164
ccttgaccag gataatgagg tactggccca agagcgggcg aggtagaggt gttcgcgaac      60
ctgcc                                                                   65

<210> SEQ ID NO 165
<211> LENGTH: 73
<212> TYPE: DNA
<213> ORGANISM: Zea mays

<400> SEQUENCE: 165
cttgaccagg ataatgaggt actggcttgg aaggcccaag agcgggcgag gtagaggtgt      60
tcgcgaacct gcc                                                          73

<210> SEQ ID NO 166
<211> LENGTH: 72
<212> TYPE: DNA
<213> ORGANISM: Zea mays

<400> SEQUENCE: 166
ccttgaccag gataatgagg tactggcgga aggcccaaga gcgggcgagg tagaggtgtt      60
cgcgaacctg cc                                                           72

<210> SEQ ID NO 167
<211> LENGTH: 69
<212> TYPE: DNA
<213> ORGANISM: Zea mays

<400> SEQUENCE: 167
```

```
ccttgaccag gataatgagg tactggaagg cccaagagcg ggcgaggtag aggtgttcgc    60
gaacctgcc                                                            69
```

<210> SEQ ID NO 168
<211> LENGTH: 72
<212> TYPE: DNA
<213> ORGANISM: Zea mays

<400> SEQUENCE: 168

```
ccttgaccag gataatgagg tactggtgga aggcccaaga gcgggcgagg tagaggtgtt    60
cgcgaacctg cc                                                        72
```

<210> SEQ ID NO 169
<211> LENGTH: 73
<212> TYPE: DNA
<213> ORGANISM: Zea mays

<400> SEQUENCE: 169

```
cttgaccagg ataatgaggt actggcgtgg aaggcccaag agcgggcgag gtagaggtgt    60
tcgcgaacct gcc                                                       73
```

<210> SEQ ID NO 170
<211> LENGTH: 53
<212> TYPE: DNA
<213> ORGANISM: Zea mays

<400> SEQUENCE: 170

```
ccttgaccag gataatgagg tactggcgag gtagaggtgt tcgcgaacct gcc           53
```

<210> SEQ ID NO 171
<211> LENGTH: 42
<212> TYPE: DNA
<213> ORGANISM: Zea mays

<400> SEQUENCE: 171

```
ccttgaccag gataatgagg tagaggtgtt cgcgaacctg cc                       42
```

<210> SEQ ID NO 172
<211> LENGTH: 68
<212> TYPE: DNA
<213> ORGANISM: Zea mays

<400> SEQUENCE: 172

```
ccttgaccag gataatgagg tacggaaggc ccaagagcgg gcgaggtaga ggtgttcgcg    60
aacctgcc                                                             68
```

<210> SEQ ID NO 173
<211> LENGTH: 73
<212> TYPE: DNA
<213> ORGANISM: Zea mays

<400> SEQUENCE: 173

```
cttgaccagg ataatgaggt actggctagg aaggcccaag agcgggcgag gtagaggtgt    60
tcgcgaacct gcc                                                       73
```

<210> SEQ ID NO 174
<211> LENGTH: 67
<212> TYPE: DNA
<213> ORGANISM: Zea mays

<400> SEQUENCE: 174
ccttgaccag gataatgagg taggaaggcc caagagcggg cgaggtagag gtgttcgcga    60
acctgcc                                                              67

<210> SEQ ID NO 175
<211> LENGTH: 28
<212> TYPE: DNA
<213> ORGANISM: Artificial Sequence
<220> FEATURE:
<223> OTHER INFORMATION: synthesized sequence TK-113

<400> SEQUENCE: 175
gaaattctaa acgctaaaga ggaagagg                                        28

<210> SEQ ID NO 176
<211> LENGTH: 60
<212> TYPE: DNA
<213> ORGANISM: Artificial Sequence
<220> FEATURE:
<223> OTHER INFORMATION: synthesized sequence JKYS921.1

<400> SEQUENCE: 176
ctacactctt tccctacacg acgctcttcc gatctggaat aaacgctaaa gaggaagagg    60

<210> SEQ ID NO 177
<211> LENGTH: 43
<212> TYPE: DNA
<213> ORGANISM: Artificial Sequence
<220> FEATURE:
<223> OTHER INFORMATION: synthesized sequence JKY557

<400> SEQUENCE: 177
aatgatacgg cgaccaccga gatctacact ctttccctac acg                      43

<210> SEQ ID NO 178
<211> LENGTH: 18
<212> TYPE: DNA
<213> ORGANISM: Artificial Sequence
<220> FEATURE:
<223> OTHER INFORMATION: synthesized sequence  JKY558

<400> SEQUENCE: 178
caagcagaag acggcata                                                   18

<210> SEQ ID NO 179
<211> LENGTH: 21
<212> TYPE: DNA
<213> ORGANISM: Artificial Sequence
<220> FEATURE:
<223> OTHER INFORMATION: synthesized sequence pUC-EheD

<400> SEQUENCE: 179
ccgcatcagg cgccattcgc c                                               21

<210> SEQ ID NO 180
<211> LENGTH: 22
<212> TYPE: DNA
<213> ORGANISM: Artificial Sequence
<220> FEATURE:
<223> OTHER INFORMATION: synthesized sequence pUC-LguR

<400> SEQUENCE: 180
gcgaggaagc ggaagagcgc cc                                              22

```
<210> SEQ ID NO 181
<211> LENGTH: 58
<212> TYPE: DNA
<213> ORGANISM: Artificial Sequence
<220> FEATURE:
<223> OTHER INFORMATION: synthesized sequence JKYX1.1

<400> SEQUENCE: 181
ctacactctt tccctacacg acgctcttcc gatctaaggg gcgctggccc tcctagtc      58

<210> SEQ ID NO 182
<211> LENGTH: 54
<212> TYPE: DNA
<213> ORGANISM: Artificial Sequence
<220> FEATURE:
<223> OTHER INFORMATION: synthesized sequence JKYS178Rd

<400> SEQUENCE: 182
caagcagaag acggcatacg agctcttccg atctgccggc tggcattgtc tctg          54

<210> SEQ ID NO 183
<211> LENGTH: 58
<212> TYPE: DNA
<213> ORGANISM: Artificial Sequence
<220> FEATURE:
<223> OTHER INFORMATION: synthesized sequence JKYS1083.1

<400> SEQUENCE: 183
ctacactctt tccctacacg acgctcttcc gatctggaag gcaggttcgc gaacacct      58

<210> SEQ ID NO 184
<211> LENGTH: 57
<212> TYPE: DNA
<213> ORGANISM: Artificial Sequence
<220> FEATURE:
<223> OTHER INFORMATION: synthesized sequence JKYS1084

<400> SEQUENCE: 184
caagcagaag acggcatacg agctcttccg atctctccga gacaacaaac tgcaggt       57

<210> SEQ ID NO 185
<211> LENGTH: 55
<212> TYPE: DNA
<213> ORGANISM: Artificial Sequence
<220> FEATURE:
<223> OTHER INFORMATION: synthesized sequence  JKYX2.1

<400> SEQUENCE: 185
ctacactctt tccctacacg acgctcttcc gatctaaggg gccggacgcg gtgtt         55

<210> SEQ ID NO 186
<211> LENGTH: 58
<212> TYPE: DNA
<213> ORGANISM: Artificial Sequence
<220> FEATURE:
<223> OTHER INFORMATION: synthesized sequence JKYX3

<400> SEQUENCE: 186
caagcagaag acggcatacg agctcttccg atcttacatg cgcaggtgca aagtctac      58

<210> SEQ ID NO 187
<211> LENGTH: 22
<212> TYPE: DNA
<213> ORGANISM: Artificial Sequence
<220> FEATURE:
<223> OTHER INFORMATION: synthesized sequence in Figure 40
```

-continued

<400> SEQUENCE: 187
agaggaagag gacagtcccg aa                                          22

<210> SEQ ID NO 188
<211> LENGTH: 12
<212> TYPE: DNA
<213> ORGANISM: Artificial Sequence
<220> FEATURE:
<223> OTHER INFORMATION: synthesized sequence in Figure 40
<220> FEATURE:
<221> NAME/KEY: misc_feature
<222> LOCATION: (1)..(1)
<223> OTHER INFORMATION: n is a, c, g, or t

<400> SEQUENCE: 188
ntgtcagggc tt                                                     12

<210> SEQ ID NO 189
<211> LENGTH: 22
<212> TYPE: DNA
<213> ORGANISM: Artificial Sequence
<220> FEATURE:
<223> OTHER INFORMATION: synthesized sequence in Figure 40

<400> SEQUENCE: 189
tctccttctc ctgtcagggc tt                                          22

<210> SEQ ID NO 190
<211> LENGTH: 12
<212> TYPE: DNA
<213> ORGANISM: Artificial Sequence
<220> FEATURE:
<223> OTHER INFORMATION: synthesized sequence in Figure 40
<220> FEATURE:
<221> NAME/KEY: misc_feature
<222> LOCATION: (12)..(12)
<223> OTHER INFORMATION: n is a, c, g, or t

<400> SEQUENCE: 190
agaggaagag gn                                                     12

<210> SEQ ID NO 191
<211> LENGTH: 28
<212> TYPE: DNA
<213> ORGANISM: Artificial Sequence
<220> FEATURE:
<223> OTHER INFORMATION: synthesized sequence in Figure 40

<400> SEQUENCE: 191
cgctaaagag gaagaggaca gtcccgaa                                    28

<210> SEQ ID NO 192
<211> LENGTH: 28
<212> TYPE: DNA
<213> ORGANISM: Artificial Sequence
<220> FEATURE:
<223> OTHER INFORMATION: synthesized sequence in Figure 40

<400> SEQUENCE: 192
gcgatttctc cttctcctgt cagggctt                                    28

<210> SEQ ID NO 193
<211> LENGTH: 20
<212> TYPE: RNA
<213> ORGANISM: Artificial sequence
<220> FEATURE:
<223> OTHER INFORMATION: synthesized Variable Targeting domain-direct

<400> SEQUENCE: 193
cgcuaaagag gaagaggaca                                          20

<210> SEQ ID NO 194
<211> LENGTH: 20
<212> TYPE: RNA
<213> ORGANISM: Artificial sequence
<220> FEATURE:
<223> OTHER INFORMATION: symthesized Variable Targeting domain-reverse

<400> SEQUENCE: 194
cgcuaaagag gaagaggaca                                          20

<210> SEQ ID NO 195
<211> LENGTH: 16
<212> TYPE: RNA
<213> ORGANISM: Brevibacillus laterosporus

<400> SEQUENCE: 195
gcuauaguuc cuuacu                                              16

<210> SEQ ID NO 196
<211> LENGTH: 16
<212> TYPE: RNA
<213> ORGANISM: Brevibacillus laterosporus

<400> SEQUENCE: 196
aucauaucau aucgag                                              16

<210> SEQ ID NO 197
<211> LENGTH: 16
<212> TYPE: RNA
<213> ORGANISM: Brevibacillus laterosporus

<400> SEQUENCE: 197
gguaaguugc uauagu                                              16

<210> SEQ ID NO 198
<211> LENGTH: 16
<212> TYPE: RNA
<213> ORGANISM: Brevibacillus laterosporus

<400> SEQUENCE: 198
cuugauauga uaugau                                              16

<210> SEQ ID NO 199
<211> LENGTH: 118
<212> TYPE: RNA
<213> ORGANISM: Brevibacillus laterosporus

<400> SEQUENCE: 199
aagggcaaca gacccgaggc guugggauc gccuagcccg uuuuuacggg cucucccau    60 auucaaaaua augacagacg agcaccuugg agcauuuauu uccgaggugc uuuuuuu     118

<210> SEQ ID NO 200
<211> LENGTH: 59
<212> TYPE: RNA
<213> ORGANISM: Brevibacillus laterosporus

<400> SEQUENCE: 200
acuuucauuu uauauccaua uaucaucgaa gucaaucuca uuuaucuguc uauuuuaug   59

<210> SEQ ID NO 201
<211> LENGTH: 16
<212> TYPE: RNA
<213> ORGANISM: Lactobacillus reuteri

<400> SEQUENCE: 201
guuuuagaug uacuuc                                                          16

<210> SEQ ID NO 202
<211> LENGTH: 16
<212> TYPE: RNA
<213> ORGANISM: Lactobacillus rossiae

<400> SEQUENCE: 202
guuuuagaug uauguc                                                          16

<210> SEQ ID NO 203
<211> LENGTH: 16
<212> TYPE: RNA
<213> ORGANISM: Pediococcus pentosaceus

<400> SEQUENCE: 203
guuucagaag aguguu                                                          16

<210> SEQ ID NO 204
<211> LENGTH: 17
<212> TYPE: RNA
<213> ORGANISM: Lactobacillus nodensis

<400> SEQUENCE: 204
guuuuaguac ucucaag                                                         17

<210> SEQ ID NO 205
<211> LENGTH: 17
<212> TYPE: RNA
<213> ORGANISM: Artificial Sequence
<220> FEATURE:
<223> OTHER INFORMATION: sequence from Sulfurospirillum species SCADC
      (Sspe)

<400> SEQUENCE: 205
acgacacuuu acaacac                                                         17

<210> SEQ ID NO 206
<211> LENGTH: 16
<212> TYPE: RNA
<213> ORGANISM: Artificial Sequence
<220> FEATURE:
<223> OTHER INFORMATION: sequence from Sulfurospirillum species SCADC
      (Sspe)

<400> SEQUENCE: 206
guuccaguug cuaagc                                                          16

<210> SEQ ID NO 207
<211> LENGTH: 16
<212> TYPE: RNA
<213> ORGANISM: Bifidobacterium thermophilum

<400> SEQUENCE: 207
gcugagaauu agcauc                                                          16

<210> SEQ ID NO 208
<211> LENGTH: 16

```
<212> TYPE: RNA
<213> ORGANISM: Loktanella vestfoldensis

<400> SEQUENCE: 208
guugcggcug gaccgc                                                     16

<210> SEQ ID NO 209
<211> LENGTH: 16
<212> TYPE: RNA
<213> ORGANISM: Sphingomonas sanxanigenens

<400> SEQUENCE: 209
guugccgcug gaccgc                                                     16

<210> SEQ ID NO 210
<211> LENGTH: 16
<212> TYPE: RNA
<213> ORGANISM: Epilithonimonas tenax

<400> SEQUENCE: 210
guugugaauu gcuuuc                                                     16

<210> SEQ ID NO 211
<211> LENGTH: 16
<212> TYPE: RNA
<213> ORGANISM: Sporocytophaga myxococcoides

<400> SEQUENCE: 211
guugugauuu gcuuuc                                                     16

<210> SEQ ID NO 212
<211> LENGTH: 17
<212> TYPE: RNA
<213> ORGANISM: Psychroflexus torquis

<400> SEQUENCE: 212
guugugaauu gcuuuca                                                    17

<210> SEQ ID NO 213
<211> LENGTH: 18
<212> TYPE: RNA
<213> ORGANISM: Lactobacillus reuteri

<400> SEQUENCE: 213
gaaguacaga guuaaaau                                                   18

<210> SEQ ID NO 214
<211> LENGTH: 18
<212> TYPE: RNA
<213> ORGANISM: Lactobacillus rossiae

<400> SEQUENCE: 214
gacauacagc guuaaaau                                                   18

<210> SEQ ID NO 215
<211> LENGTH: 18
<212> TYPE: RNA
<213> ORGANISM: Pediococcus pentosaceus

<400> SEQUENCE: 215
aacauucugu uuugaaau                                                   18

<210> SEQ ID NO 216
```

```
<211> LENGTH: 19
<212> TYPE: RNA
<213> ORGANISM: Lactobacillus nodensis

<400> SEQUENCE: 216
cuugagaacc uacuaaaau                                                    19

<210> SEQ ID NO 217
<211> LENGTH: 17
<212> TYPE: RNA
<213> ORGANISM: Artificial Sequence
<220> FEATURE:
<223> OTHER INFORMATION: sequence from Sulfurospirillum species SCADC
      (Sspe)

<400> SEQUENCE: 217
guguuguaaa gugucgu                                                      17

<210> SEQ ID NO 218
<211> LENGTH: 13
<212> TYPE: RNA
<213> ORGANISM: Artificial Sequence
<220> FEATURE:
<223> OTHER INFORMATION: sequence from Sulfurospirillum species SCADC
      (Sspe)

<400> SEQUENCE: 218
guucgaugca cug                                                          13

<210> SEQ ID NO 219
<211> LENGTH: 16
<212> TYPE: RNA
<213> ORGANISM: Bifidobacterium thermophilum

<400> SEQUENCE: 219
aaagcuaauu cucagu                                                       16

<210> SEQ ID NO 220
<211> LENGTH: 17
<212> TYPE: RNA
<213> ORGANISM: Loktanella vestfoldensis

<400> SEQUENCE: 220
gcggucgagc cguuaac                                                      17

<210> SEQ ID NO 221
<211> LENGTH: 17
<212> TYPE: RNA
<213> ORGANISM: Sphingomonas sanxanigenens

<400> SEQUENCE: 221
guggucuggc gguuaac                                                      17

<210> SEQ ID NO 222
<211> LENGTH: 16
<212> TYPE: RNA
<213> ORGANISM: Epilithonimonas tenax

<400> SEQUENCE: 222
gaaagcaauu cacaau                                                       16

<210> SEQ ID NO 223
<211> LENGTH: 15
<212> TYPE: RNA
<213> ORGANISM: Sporocytophaga myxococcoides
```

<400> SEQUENCE: 223
aaagcaaauc acaau                                                    15

<210> SEQ ID NO 224
<211> LENGTH: 16
<212> TYPE: RNA
<213> ORGANISM: Psychroflexus torquis

<400> SEQUENCE: 224
ugaagcaauu cacaau                                                   16

<210> SEQ ID NO 225
<211> LENGTH: 108
<212> TYPE: RNA
<213> ORGANISM: Lactobacillus reuteri

<400> SEQUENCE: 225
caaacaagug cuucagcaca aguuucuacu uuugagucag uuaucugacc aauacauaaa    60
agggaauuaa aucguucaca ugagcguuuu aauucccuuu cucucuuu                108

<210> SEQ ID NO 226
<211> LENGTH: 105
<212> TYPE: RNA
<213> ORGANISM: Lactobacillus rossiae

<400> SEQUENCE: 226
caagcaaggc uuucgagcca aguuuaaauc uuuggguucg cuauucggac cguacauagu    60 aaagggcgu caucgaguuc aaauucgaug gcgcccuuua guuuu                    105

<210> SEQ ID NO 227
<211> LENGTH: 107
<212> TYPE: RNA
<213> ORGANISM: Pediococcus pentosaceus

<400> SEQUENCE: 227
caaacaacgc uuuacgcgga guuuacacau cugucccauu auaugggcau uacauaauaa    60
aagagaaauc accuuuaagg uugauuccuc uuuuucuugc guuccuu                 107

<210> SEQ ID NO 228
<211> LENGTH: 51
<212> TYPE: RNA
<213> ORGANISM: Lactobacillus nodensis

<400> SEQUENCE: 228
aaggauuuau uccgaauuua ccaccuauuu uuuaauaggu gguuuuuuuu u             51

<210> SEQ ID NO 229
<211> LENGTH: 119
<212> TYPE: RNA
<213> ORGANISM: Artificial Sequence
<220> FEATURE:
<223> OTHER INFORMATION: sequence from Sulfurospirillum species SCADC
      (Sspe)

<400> SEQUENCE: 229
gagugaaagu auagcauuuu ucucaaaaua ucgcacuuuu uuugcaagga aauaauuugc    60 gaaaaaaga gacaauuucg auacaagaaa gccccaucaa gucgaugauu uguaaggcu     119

<210> SEQ ID NO 230
<211> LENGTH: 61

```
<212> TYPE: RNA
<213> ORGANISM: Artificial Sequence
<220> FEATURE:
<223> OTHER INFORMATION: sequence from Sulfurospirillum species SCADC
      (Sspe)

<400> SEQUENCE: 230
aaaucaucga aaagauauau agacccgccc aacugccuua ggcauggcgg gcuucuuucu    60
u                                                                   61

<210> SEQ ID NO 231
<211> LENGTH: 195
<212> TYPE: RNA
<213> ORGANISM: Bifidobacterium thermophilum

<400> SEQUENCE: 231
aaguacagca auuuauagcu guaucugaau gcuaagcggu uagccgcagg ggagagcuuc    60
ggcucucccc guucuuuucu agucgcacgu gacacgccau agguagauug ccgugagca   120 acucgagaau aguaguauuc uucucuguaa acgagacau cguugcugau gacuccauug    180
acaaagaagg gaauu                                                   195

<210> SEQ ID NO 232
<211> LENGTH: 140
<212> TYPE: RNA
<213> ORGANISM: Loktanella vestfoldensis

<400> SEQUENCE: 232
aagcauucga uugcaccaca uugaaacgca ggcuacggcc ugcguuuucu uauuuccggu    60
augguucguc uugucaaagu gucucagaga ugcccgcuuu cuaaaugugg auugucgagg   120
uucgcacccg uagcguuuuu                                              140

<210> SEQ ID NO 233
<211> LENGTH: 135
<212> TYPE: RNA
<213> ORGANISM: Sphingomonas sanxanigenens

<400> SEQUENCE: 233
aagcagccag ucugcaccag auaagggcgg cgcuccggcg ccgccuuuuu uguuugcccg    60
gaauguugag acaggcgcca aaccauccc cucccccucg gggcgugcgg caaucgcugc   120
uuucagcuca cucca                                                   135

<210> SEQ ID NO 234
<211> LENGTH: 96
<212> TYPE: RNA
<213> ORGANISM: Epilithonimonas tenax

<400> SEQUENCE: 234
aaggauuauu ccguugugaa acauuuagc accucgccua ucugcggggu auuuuuauu    60 uaauacauuc aaacaaugaa gucgauugca uuuauu                            96

<210> SEQ ID NO 235
<211> LENGTH: 91
<212> TYPE: RNA
<213> ORGANISM: Sporocytophaga myxococcoides

<400> SEQUENCE: 235
aaggauuauu ccguugugaa acauauaag ccgccucguc uuacaauacg ggcuuuuuu    60 uauucccau ucacauaugg ccauccauuu u                                  91
```

```
<210> SEQ ID NO 236
<211> LENGTH: 95
<212> TYPE: RNA
<213> ORGANISM: Psychroflexus torquis

<400> SEQUENCE: 236
aaggauuauu ccguugugaa aacauuuaaa gcggccuuua cgggucgcuu ucuuuuuuua      60
aagaacuuaa acuuaauaaa uucuuuacaa acuca                                95
```

RAPID CHARACTERIZATION OF CAS ENDONUCLEASE SYSTEMS, PAM SEQUENCES AND GUIDE RNA ELEMENTS

CROSS-REFERENCE TO RELATED APPLICATIONS

This application is a 371 National Stage entry of PCT/US16/32028 filed 12 May 2016, which claims the benefit of U.S. Provisional Application No. 62/162,353, filed May 15, 2015, U.S. Provisional Application No. 62/162,377, filed May 15, 2015, and U.S. Provisional Application No. 62/196,535, filed Jul. 24, 2015, each of which is incorporated herein in their entirety by reference.

FIELD

The disclosure relates to the field of plant molecular biology, in particular, to methods for characterization of Cas endonuclease systems and methods for altering the genome of a cell.

REFERENCE TO SEQUENCE LISTING SUBMITTED ELECTRONICALLY

The official copy of the sequence listing is submitted electronically via EFS-Web as an ASCII formatted sequence listing with a file named 20160502_BB2475PCT_SequenceListing.txt created on May 2, 2016 and having a size of 252,527 bytes and is filed concurrently with the specification. The sequence listing contained in this ASCII formatted document is part of the specification and is herein incorporated by reference in its entirety.

BACKGROUND

Recombinant DNA technology has made it possible to insert DNA sequences at targeted genomic locations and/or modify (edit) specific endogenous chromosomal sequences, thus altering the organism's phenotype. Site-specific integration techniques, which employ site-specific recombination systems, as well as other types of recombination technologies, have been used to generate targeted insertions of genes of interest in a variety of organism. Genome-editing techniques such as designer zinc finger nucleases (ZFNs) or transcription activator-like effector nucleases (TALENs), or homing meganucleases, are available for producing targeted genome perturbations, but these systems tends to have a low specificity and employ designed nucleases that need to be redesigned for each target site, which renders them costly and time-consuming to prepare.

Although several approaches have been developed to target a specific site for modification in the genome of an organism, there still remains a need for new genome engineering technologies that are affordable, easy to set up, scalable, and amenable to targeting multiple positions within the genome of an organism

BRIEF SUMMARY

Compositions and methods are provided for rapid characterization of Cas endonuclease systems and the elements comprising such a systems, including, but not limiting to, rapid characterization of PAM sequences, guide RNA elements and CAS endonucleases.

In one embodiment of the disclosure, the method comprises a method for producing a plasmid DNA library containing a randomized Protospacer-Adjacent-w Motif (PAM) sequence, the method comprising: a) providing a first single stranded oligonucleotide comprising a target sequence that can be recognized by a guide RNA/Cas endonuclease complex; b) providing a second single stranded oligonucleotide comprising a randomized PAM sequence adjacent to a nucleotide sequence capable of hybridizing with the target sequence of (a); c) producing an oligoduplex comprising said randomized PAM sequence by combining the first single stranded oligonucleotide of (a) and the second single stranded oligonucleotide of (b); d) producing a ligation product by ligating the oligoduplex from (c) with a linearized plasmid; and, e) transforming host cells with the ligation product of (e) and recovering multiple host cell colonies representing the plasmid library.

Host cells include, but are not limited to, human, non-human, animal, bacterial, fungal, insect, yeast, non-conventional yeast, and plant cells.

In another embodiment of the disclosure, the method comprises a method for producing a ligation product containing a randomized Protospacer-Adjacent-Motif (PAM) sequence, the method comprising: a) providing a first single stranded oligonucleotide comprising restriction endonuclease recognition site located upstream of a target sequence that can be recognized by a guide RNA/Cas endonuclease complex; b) providing a second single stranded oligonucleotide comprising a randomized PAM sequence adjacent a nucleotide sequence capable of hybridizing with the target sequence of (a); c) producing an oligoduplex comprising said randomized PAM sequence by combining the first single stranded oligonucleotide of (a) and the second single stranded oligonucleotide of (b); and, d) producing a ligation product by ligating the oligoduplex from (c) with a linearized plasmid.

In another embodiment of the disclosure, the method comprises a method for identification of a Protospacer-Adjacent-Motif (PAM) sequence, the method comprising: a) providing a library of plasmid DNAs, wherein each one of said plasmid DNAs comprises a randomized Protospacer-Adjacent-Motif sequence integrated adjacent to a target sequence that can be recognized by a guide RNA/Cas endonuclease complex; b) providing to said library of plasmids a guide RNA and a Cas endonuclease protein, wherein said guide RNA and Cas endonuclease protein can form a complex that is capable of introducing a double strand break into the said target sequence, thereby creating a library of cleaved targets; c) ligating adaptors to the library of cleaved targets of (b) allowing for the library of cleaved targets to be amplified; d) amplifying the library of cleaved targets such that cleaved products containing the randomized PAM sequence are enriched, thereby producing a library of enriched PAM-sided targets; e) sequencing the library of (a) and the library of enriched PAM-sided targets of (d) and identifying the nucleotide sequence adjacent to the cleaved targets of (b) on either strand of the plasmid DNA, wherein said nucleotide sequence represents a putative Protospacer-Adjacent-Motif sequences; and, f) determining the fold enrichment of each nucleotide within the putative Protospacer-Adjacent-Motif sequence relative to the plasmid DNA library of (a).

In another embodiment of the disclosure, the method comprises a method for identification of a tracrRNA of an organism, the method comprising: a) identifying a CRISPR array repeat sequence in a genomic locus of said organism; b) aligning the CRISPR array repeat sequence of (a) with the sequence of the genomic locus of (a) and identifying an antirepeat sequence that encodes a tracrRNA; and, c) determining the transcriptional direction of the tracrRNA.

In another embodiment of the disclosure, the method comprises a method for designing a single guide RNA, the method comprising: a) aligning a tracrRNA sequence with a CRISPR array repeat sequence from a genomic locus of an organism, wherein said CRISPR array repeat sequence comprises a crRNA sequence; b) deducing the transcriptional direction of the CRISPR array, thereby also deducing the crRNA sequence; and, c) designing a single guide RNA comprising said tracrRNA and crRNA sequences.

In another embodiment of the disclosure, the method comprises a method for producing target sequences, the method comprising: a) identifying a polynucleotides of interest; b) introducing a Protospacer-Adjacent-Motif (PAM) sequence adjacent to said polynucleotide of interest, wherein said PAM sequence comprises the nucleotide sequence NNNNCND, thereby creating a thereby creating a target site for a guide RNA/Cas9 endonuclease complex; and, c) identifying a polynucleotides of interest.

Also provided are guide RNAs capable of forming a guide RNA/Cas endonuclease complex, wherein said guide RNA/Cas endonuclease complex can recognize, bind to, and optionally nick or cleave a target sequence, wherein said guide RNA is a duplex molecule comprising a chimeric non-naturally occurring crRNA and a tracrRNA, wherein said guide RNA/Cas endonuclease complex can recognize, bind to, and optionally nick or cleave a target sequence wherein said chimeric non-naturally occurring crRNA comprises a variable targeting domain capable of hybridizing to said target sequence, wherein said tracrRNA is originated from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755.

In another embodiment of the disclosure, the guide RNA is a guide RNA capable of forming a guide RNA/Cas endonuclease complex, wherein said guide RNA/Cas endonuclease complex can recognize, bind to, and optionally nick or cleave a target sequence, wherein said guide RNA is a single molecule comprising a chimeric non-naturally occurring crRNA linked to a tracrRNA originating from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755, wherein said chimeric non-naturally occurring crRNA comprises a variable targeting domain capable of hybridizing to said target sequence.

In another embodiment of the disclosure, the guide RNA is a guide RNA capable of forming a guide RNA/Cas endonuclease complex, wherein said guide RNA/Cas endonuclease complex can recognize, bind to, and optionally nick or cleave a target sequence, wherein said guide RNA is a duplex molecule comprising a chimeric non-naturally occurring crRNA and a tracrRNA, wherein said chimeric non-naturally occurring crRNA comprises at least a fragment of a crRNA originating from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755, wherein said chimeric non-naturally occurring crRNA comprises a variable targeting domain capable of hybridizing to said target sequence.

In another embodiment of the disclosure, the guide RNA is a guide RNA capable of forming a guide RNA/Cas endonuclease complex, wherein said guide RNA/Cas endonuclease complex can recognize, bind to, and optionally nick or cleave a target sequence, wherein said guide RNA is a single molecule comprising a tracrRNA linked to a chimeric non-naturally occurring crRNA comprising at least a fragment of a crRNA originating from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755, wherein said chimeric non-naturally occurring crRNA comprises a variable targeting domain capable of hybridizing to said target sequence.

Also provided are nucleic acid constructs, plants, plant cells, explants, seeds and grain having an altered target site or altered polynucleotide of interest produced by the methods described herein. Additional embodiments of the methods and compositions of the present disclosure are shown herein.

BRIEF DESCRIPTION OF THE DRAWINGS AND THE SEQUENCE LISTING

The disclosure can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§ 1.821-1.825. The sequence descriptions contain the three letter codes for amino acids as defined in 37 C.F.R. §§ 1.821-1.825, which are incorporated herein by reference.

FIGURES

Figure 10:
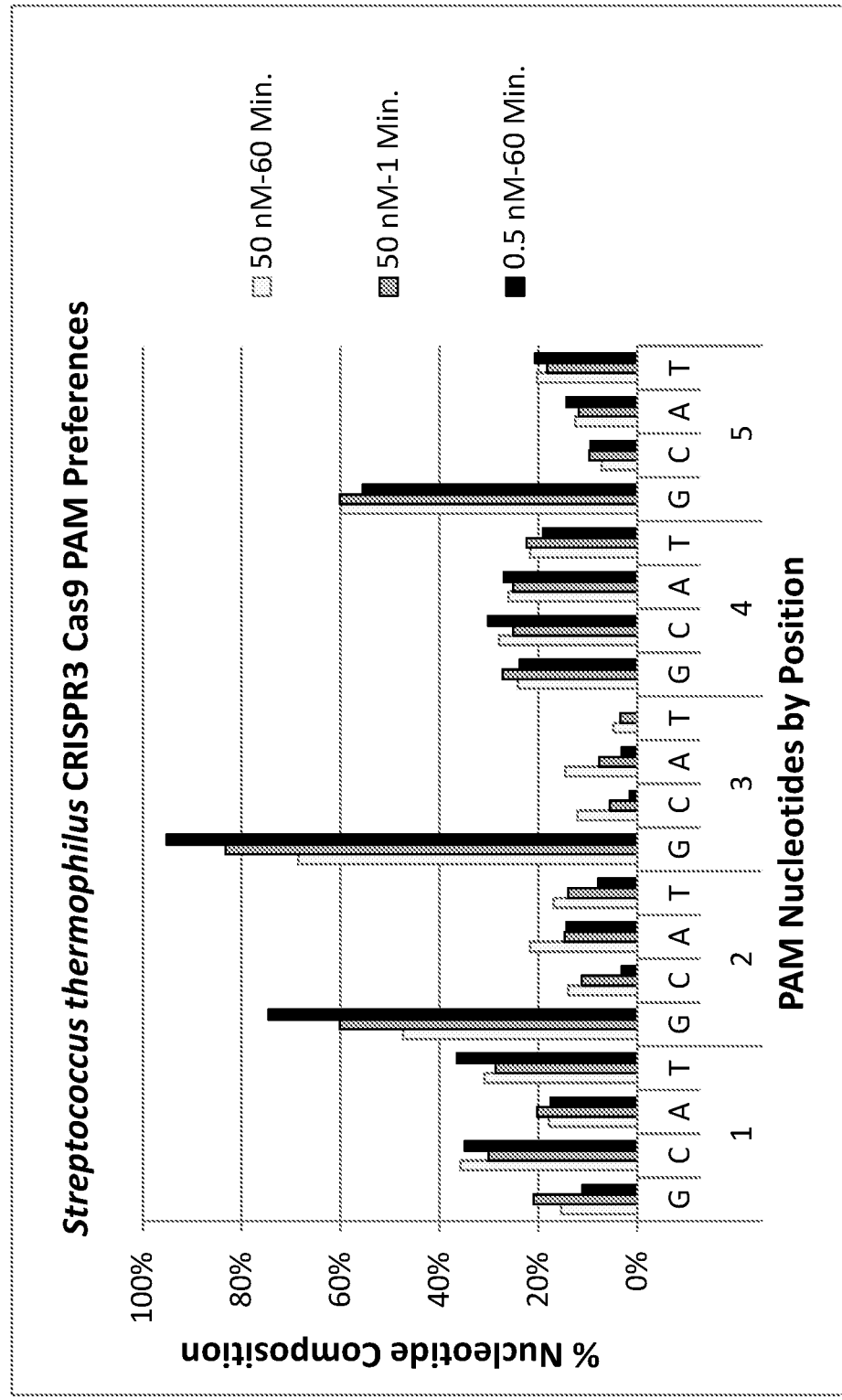

FIG. 10 shown the PAM preferences (NGGNG) observed in the minimally *Streptococcus thermophilus* Sth3 digested libraries (0.5 nM-60 min and 50 nM-1 min) compared to that exhibited by the respective 50 nM-60 minute positive control.

Figure 11:
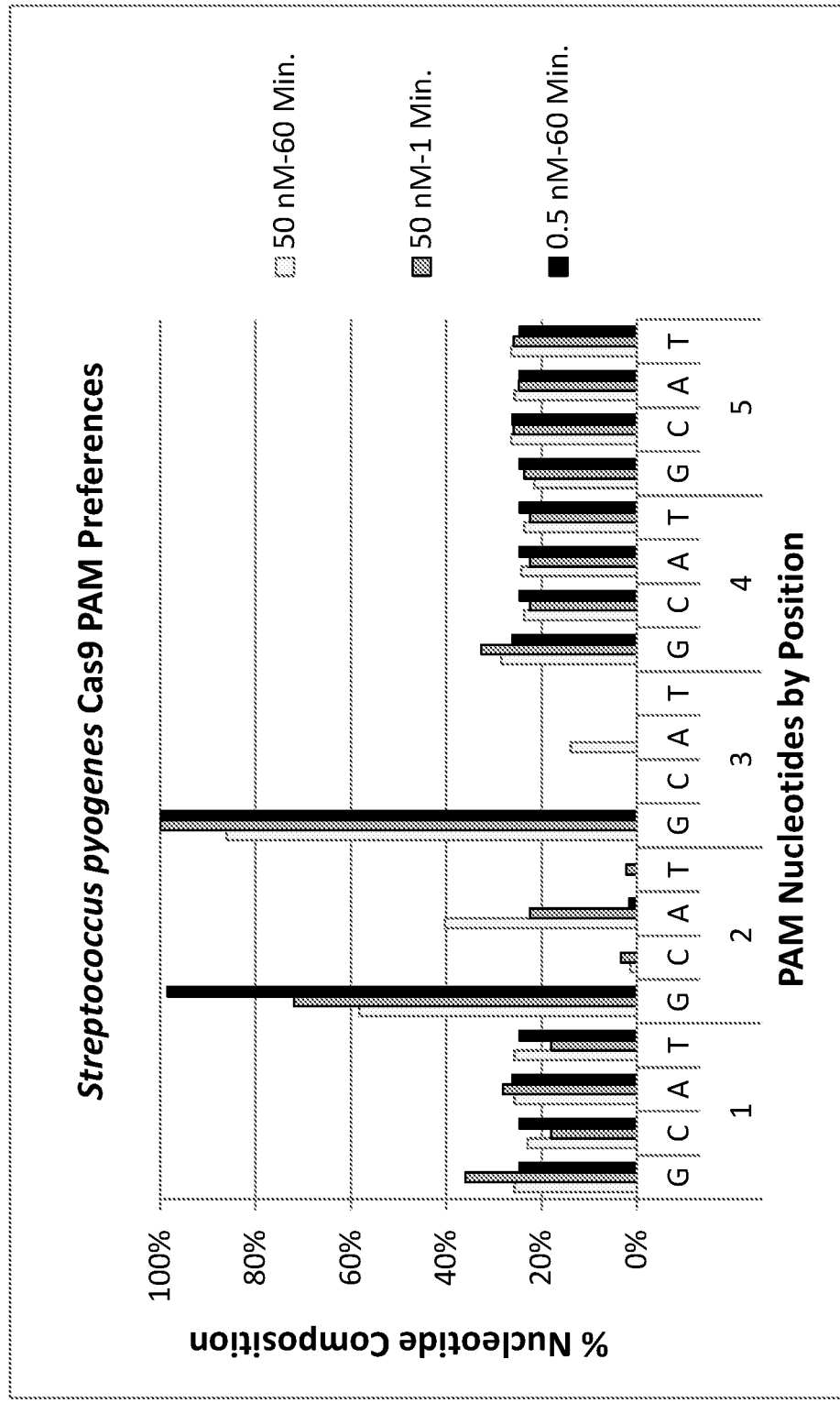

FIG. 11 shown the PAM preferences (NGGNG) observed in the minimally *Streptococcus pyogenes* Spy digested libraries (0.5 nM-60 min and 50 nM-1 min) compared to that exhibited by the respective 50 nM-60 minute positive control.

Figure 12:
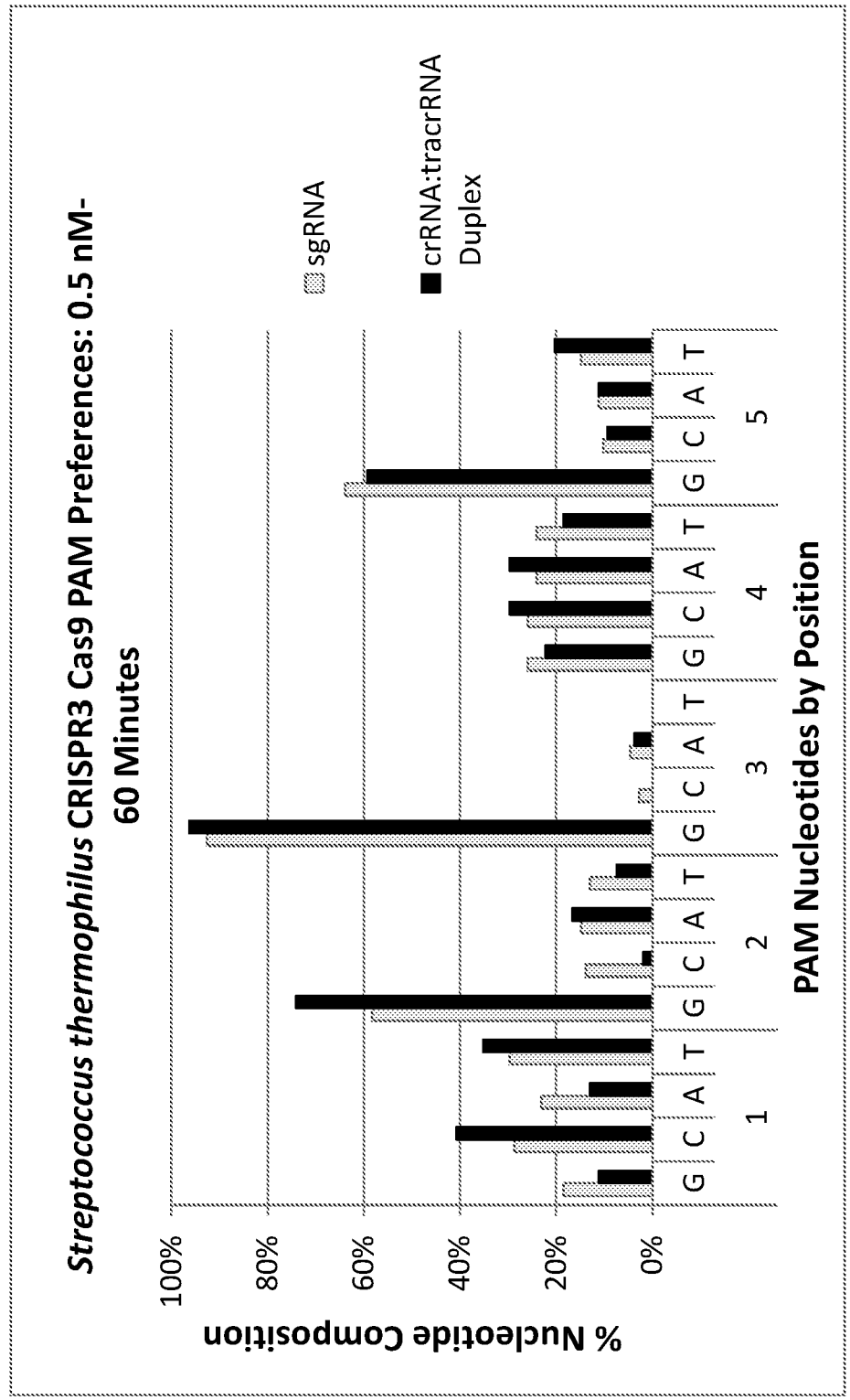
Figure 13:
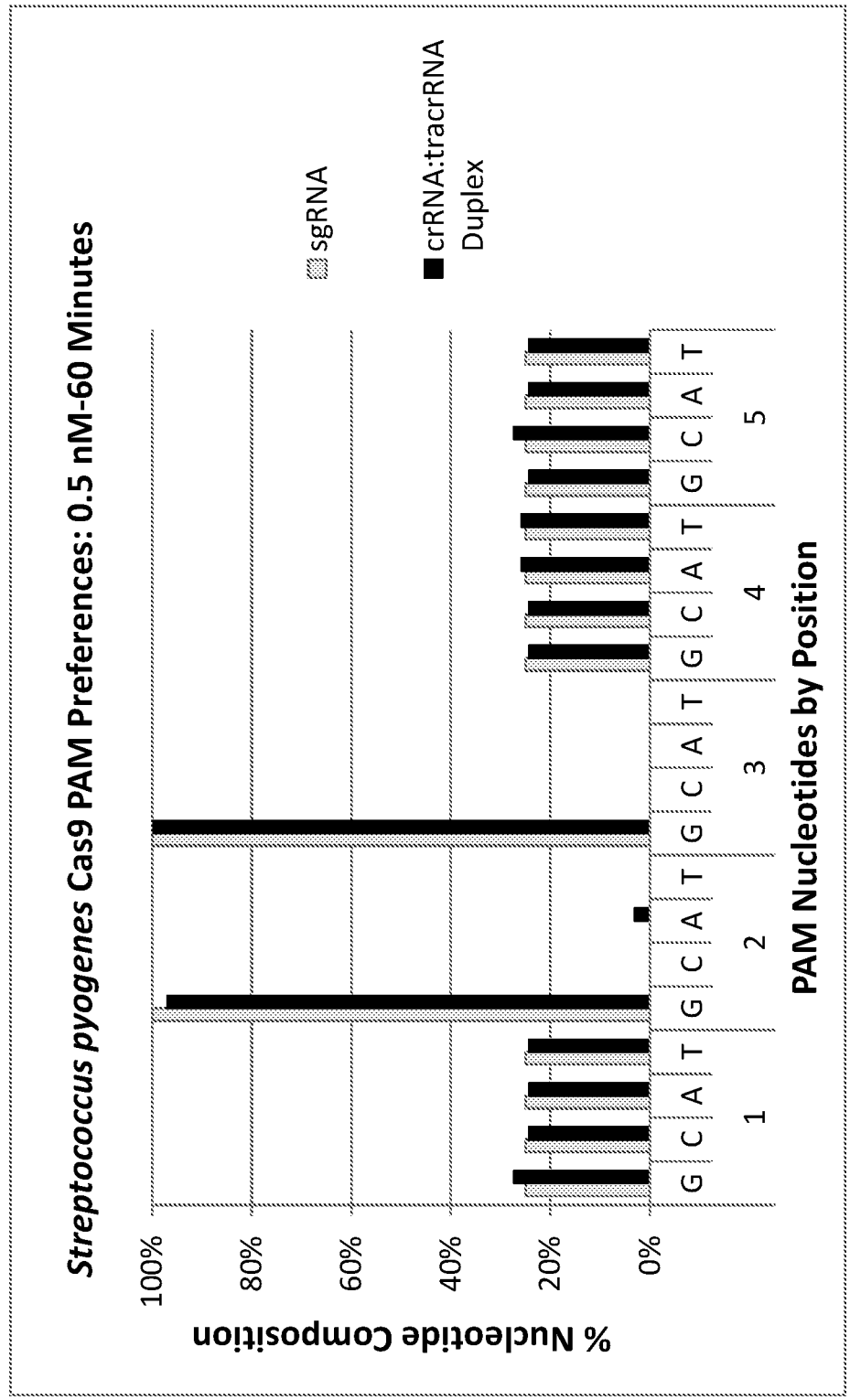
Figure 14:
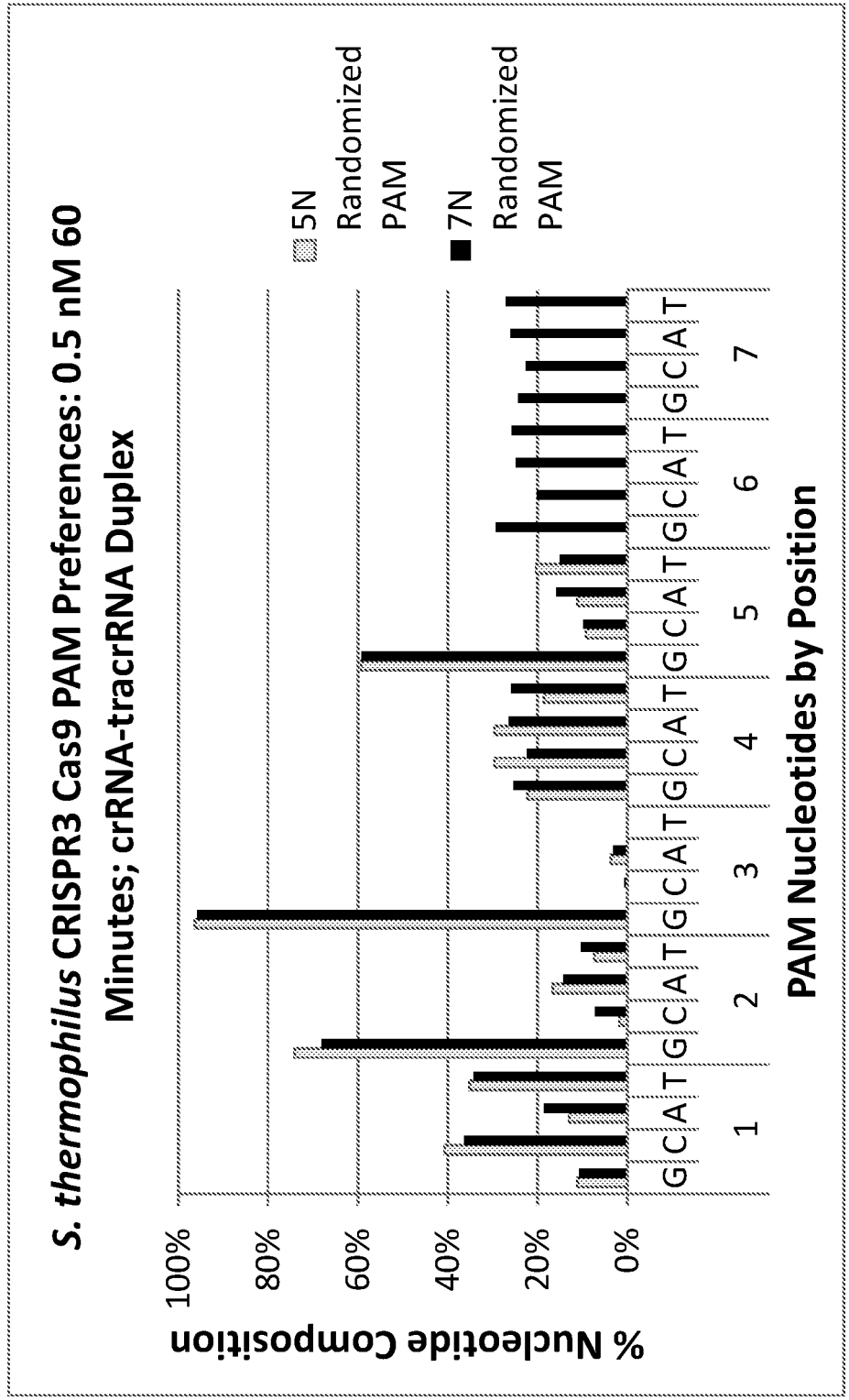

FIG. 12 shows the PAM preferences for *Streptococcus pyogenes* (Spy) Cas9 endonuclease guided by a single guide RNA (sgRNA) or guided by a crRNA:tracrRNA duplex. The NGGNG PAM preference is nearly identical regardless of the type of guide RNA used FIG. 13 shows the PAM preferences (NGG) for *Streptococcus pyogenes* (Spy) Cas9 endonuclease guided by a single guide RNA (sgRNA) or guided by a crRNA:tracrRNA duplex. The NGG PAM preference is nearly identical regardless of the type of guide RNA used FIG. 14 shows the PAM preferences for *Streptococcus thermophilus* CRISPR3 (Sth3) Cas9 endonuclease positive controls for comparing of a 5N randomized PAM plasmid DNA library and a 7N randomized PAM plasmid DNA library.

Figure 15:
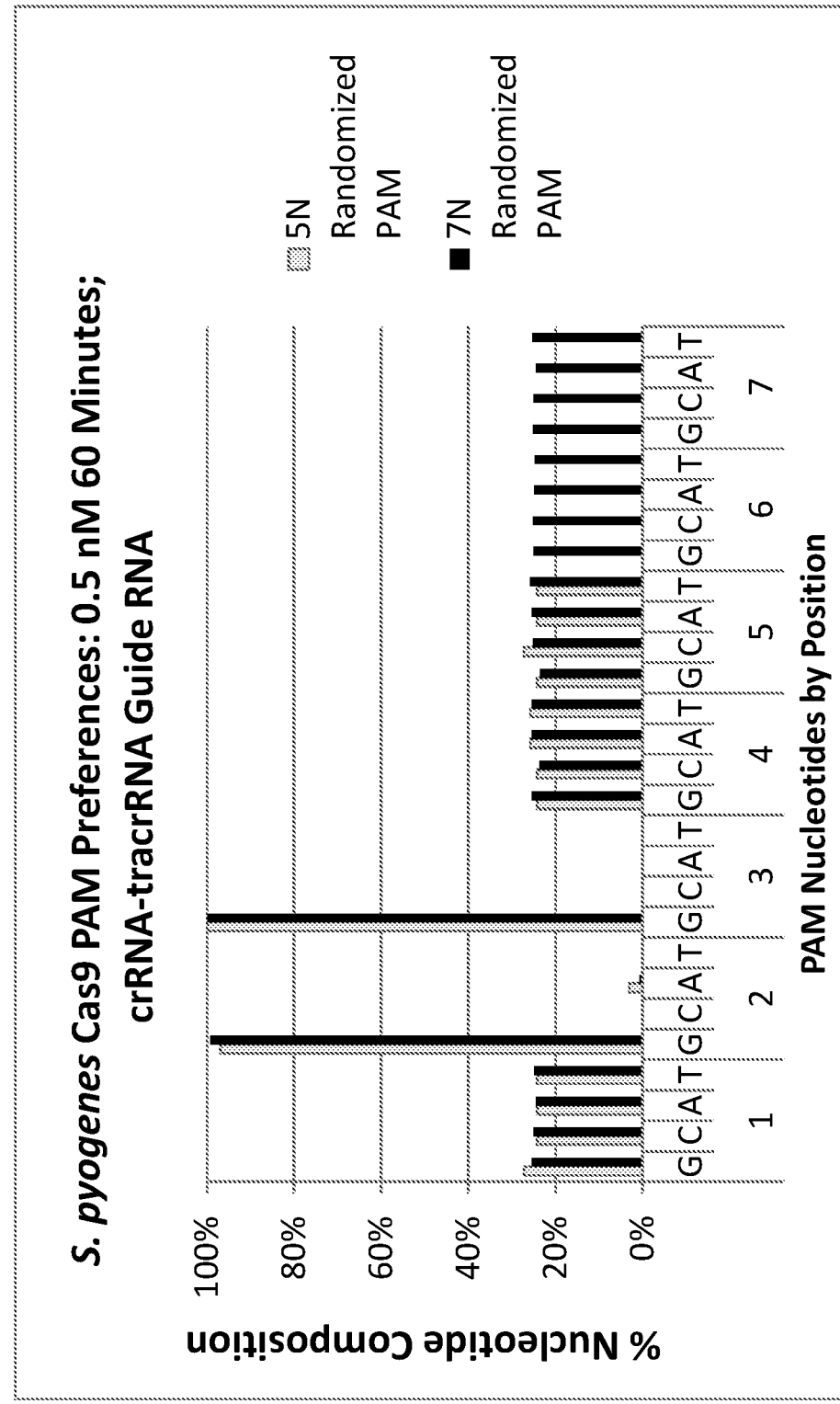

FIG. 15 shows the PAM preferences (NGG) for *Streptococcus pyogenes* (Spy) Cas9 endonuclease positive controls for comparing of a 5N randomized PAM plasmid DNA library and a 7N randomized PAM plasmid DNA library.

Figure 16:
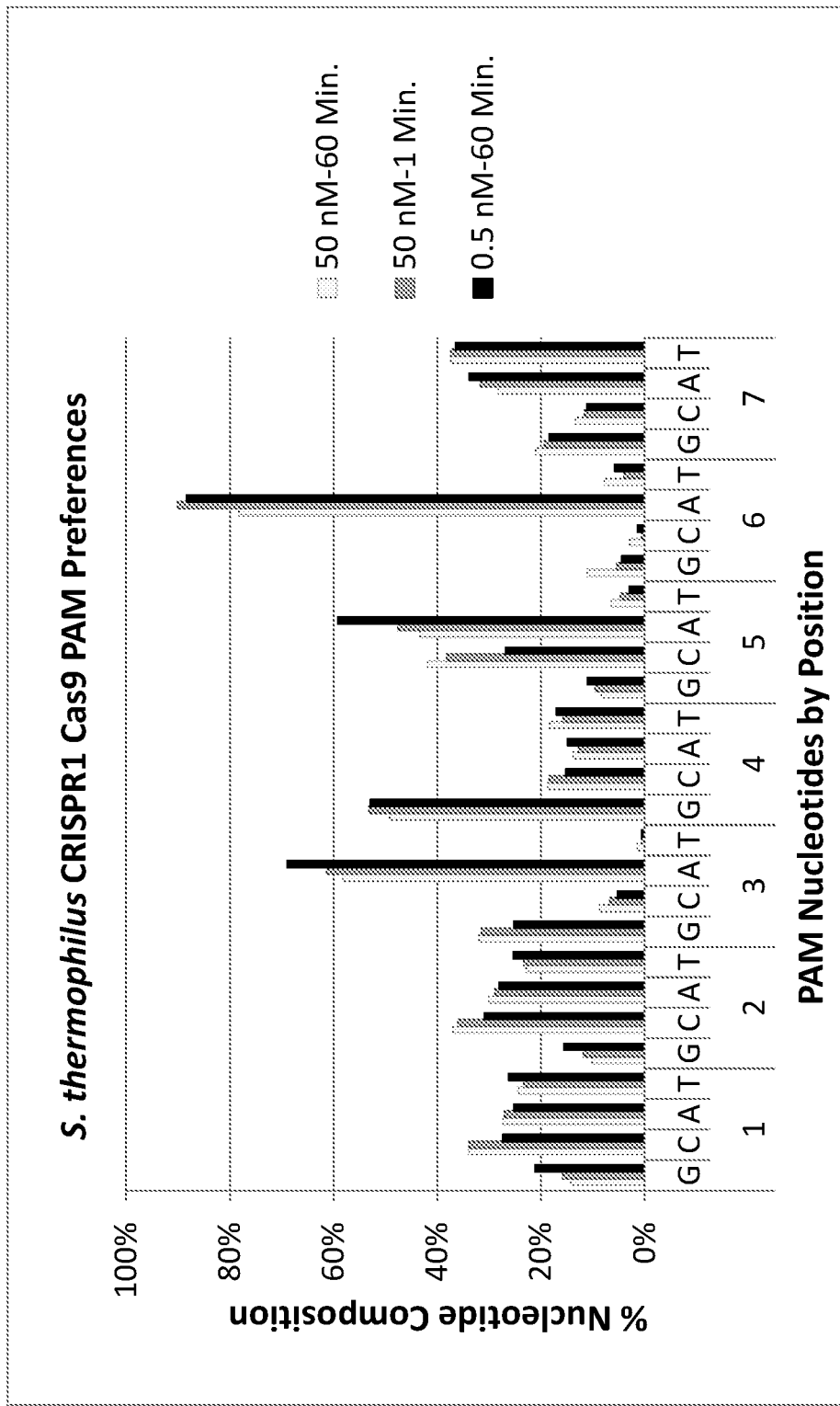

FIG. 16 shows the PAM preferences (NNAGAAW) for *Streptococcus thermophilus* CRISPR1 (Sth1) Cas9 endonuclease in both 50 nM and 0.5 nM nM digests.

FIG. 17-A shows a genomic DNA region from, *Brevibacillus laterosporus* representing the Type II CRISPR-Cas system described herein. FIG. 17-B list 8 repeat sequences (SEQ ID NOs: 37-44) of the genomic DNA region from the *Brevibacillus laterosporus*.

Figure 18:
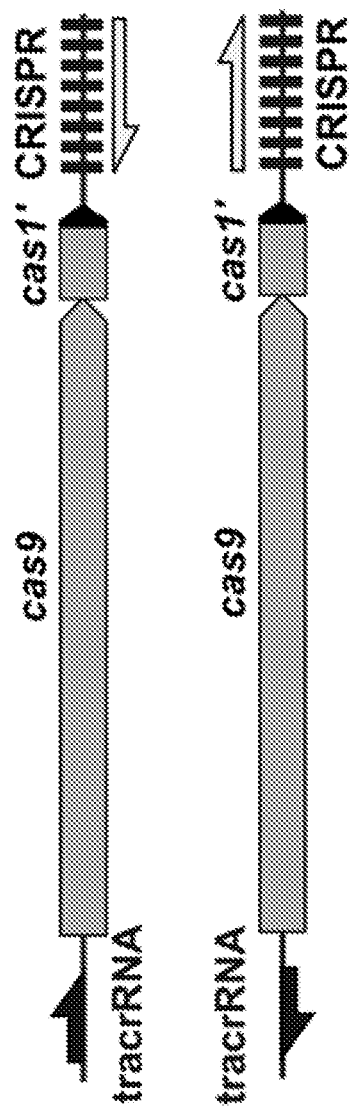

FIG. 18 shows a diagram of the "direct" scenario and the "reverse" scenario of the tracrRNA and CRISPR array to determine a guide RNA for the Cas9 protein identified from the *Brevibacillus laterosporus* (Blat).

Figure 19:
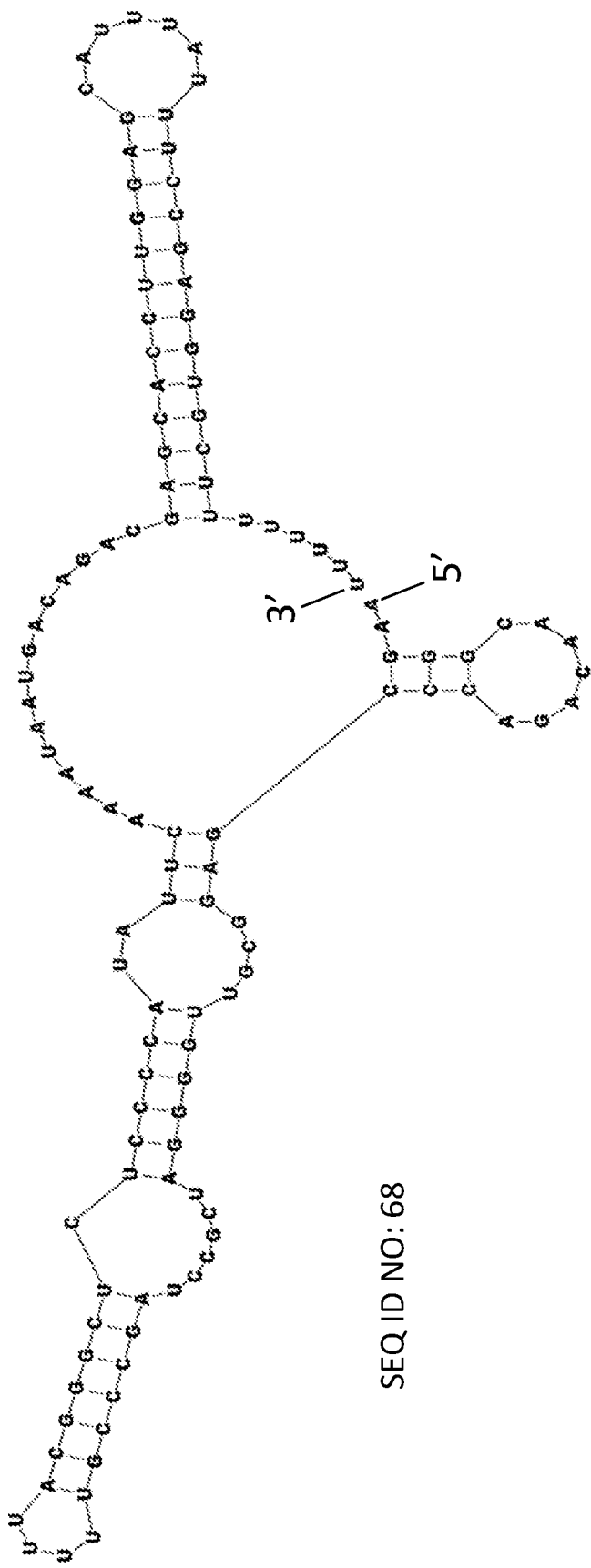

FIG. 19 shows the secondary structure of the "direct" tracrRNA region downstream of the anti-repeat (SEQ ID NO: 68) from, *Brevibacillus laterosporus*.

Figure 20:
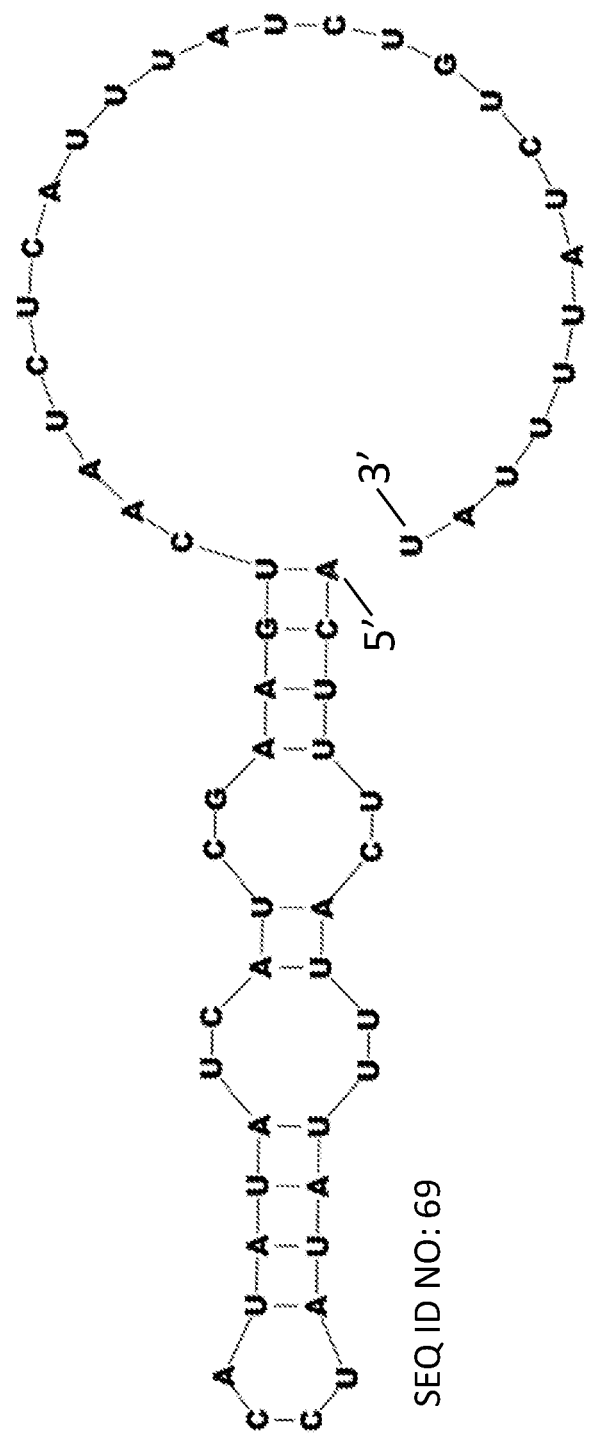

FIG. 20 shows the secondary structure of the "reverse" tracrRNA region downstream of the anti-repeat (SEQ ID NO: 69) from, *Brevibacillus laterosporus*.

Figure 21:
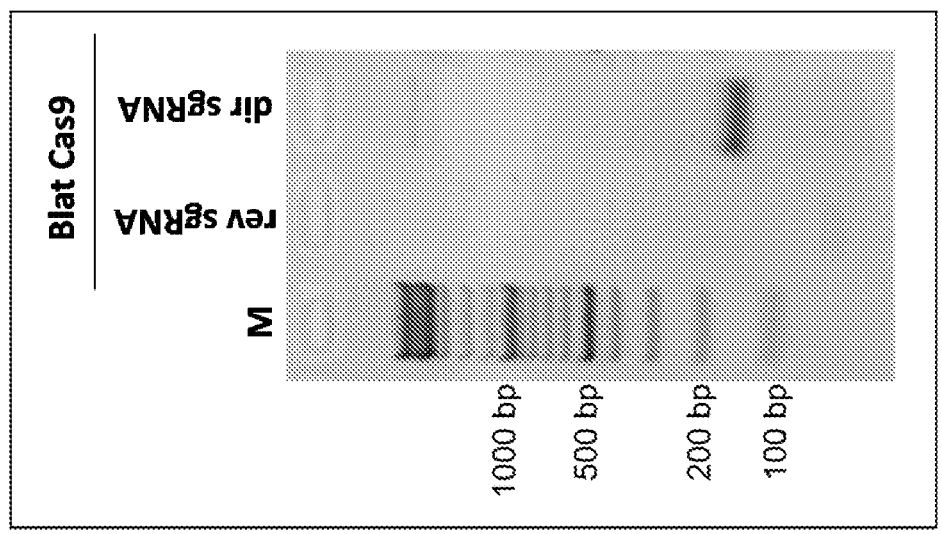

FIG. 21 shown an agarose gel with reaction products, indicating that only the "direct" sgRNA (dirsgRNA), but not the "reverse" sgRNA (revsgRNA) supported plasmid library cleavage in combination with a Cas9 endonuclease originating from *Brevibacillus laterosporus*. (BlatCas9).

Figure 22:
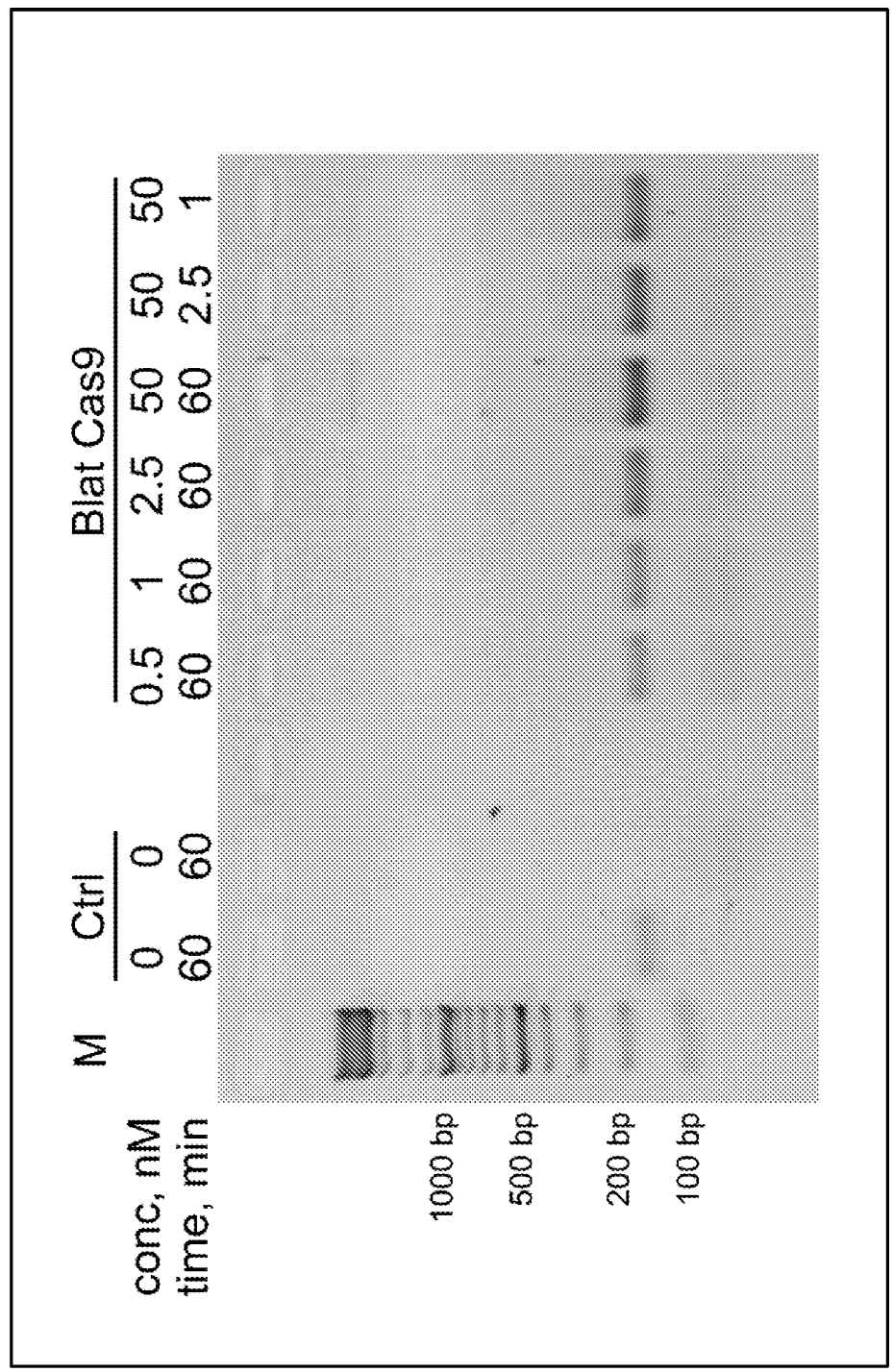

FIG. 22 shows the effect of decreasing BlatCas9 concentration and digestion time to determine the minimal Blast Cas9 concentration and shortest digestion time where PCR amplified cleavage products may still be obtained from the randomized PAM plasmid library.

Figure 23:
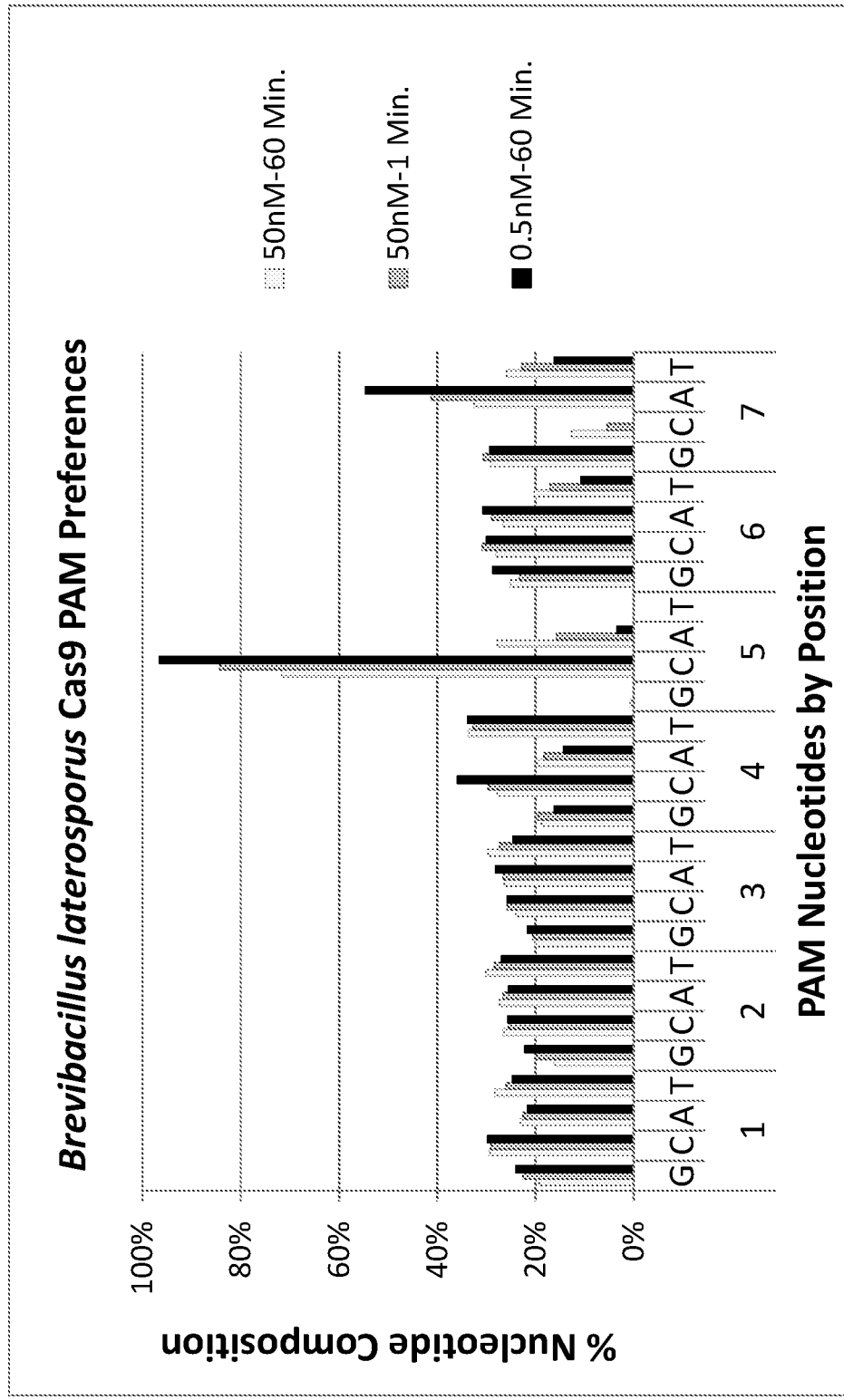

FIG. 23 shows the PAM preferences (NNNNCND) for *Brevibacillus laterosporus* (Blat) Cas9 endonuclease in both 50 nM and 0.5 nM digests.

Figure 24:
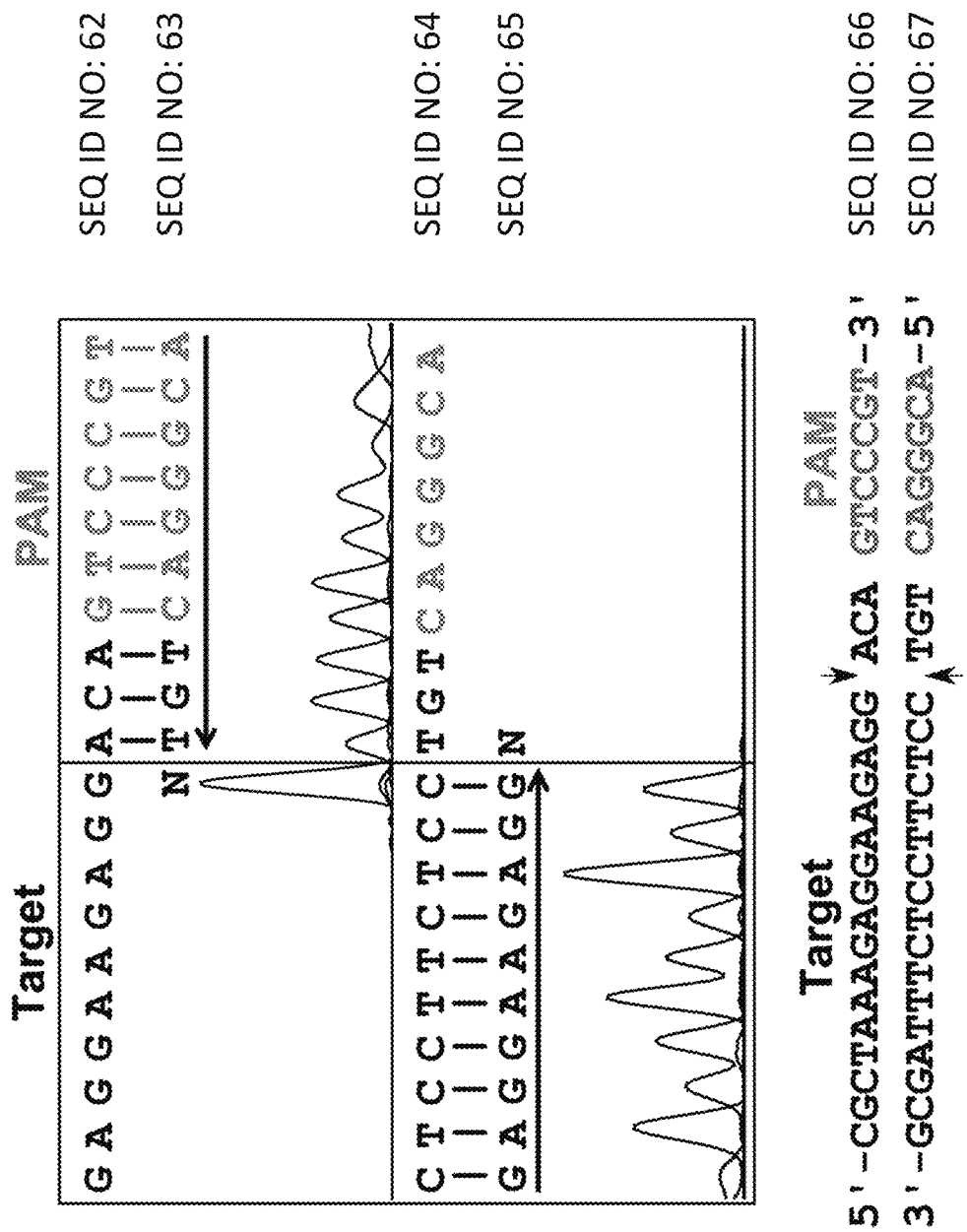

FIG. 24 Depiction of run-off sequencing results illustrating that plasmid DNA cleavage occurred in the protospacer between the 3rd and 4th bp upstream from the PAM sequence.

Figure 25:
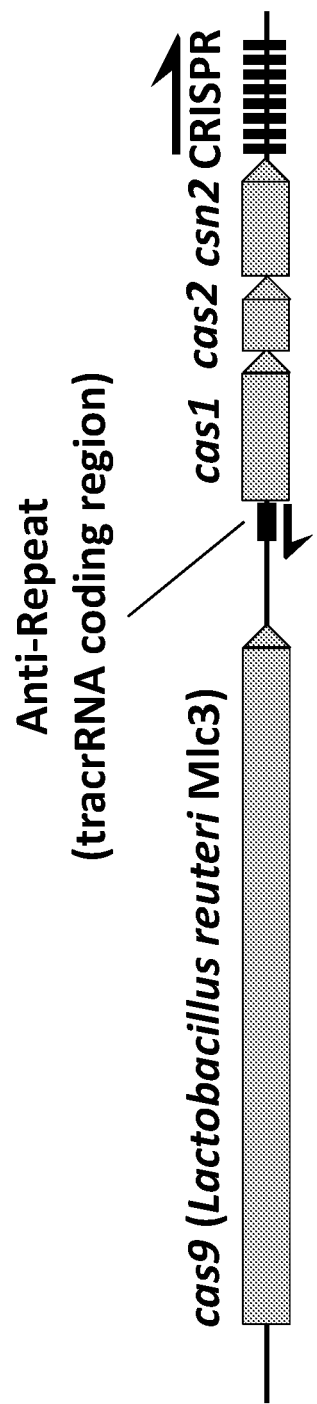

FIG. 25 shows a genomic DNA region from *Lactobacillus reuteri* Mlc3 representing an example of a Type II CRISPR-Cas system described herein.

Figure 26:
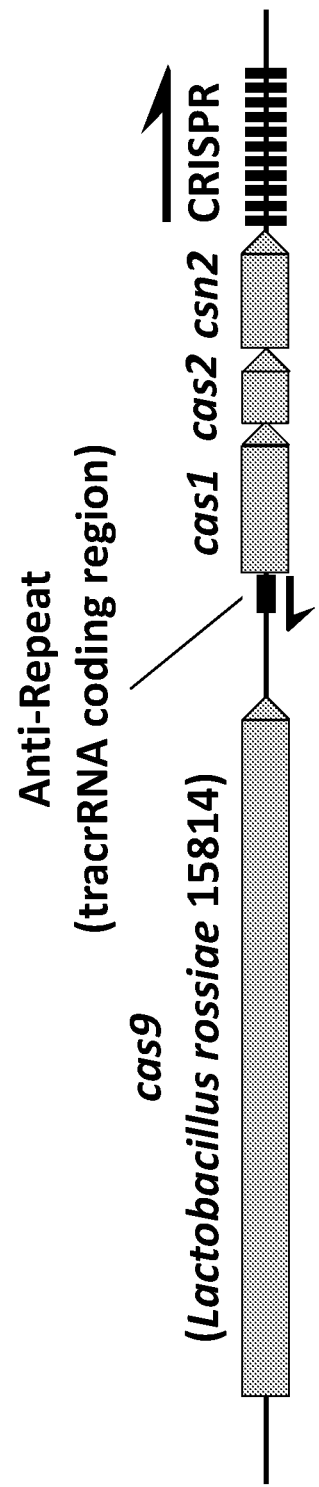

FIG. 26 shows a genomic DNA region from *Lactobacillus rossiae* DSM 15814 representing an example of a Type II CRISPR-Cas system described herein.

Figure 27:
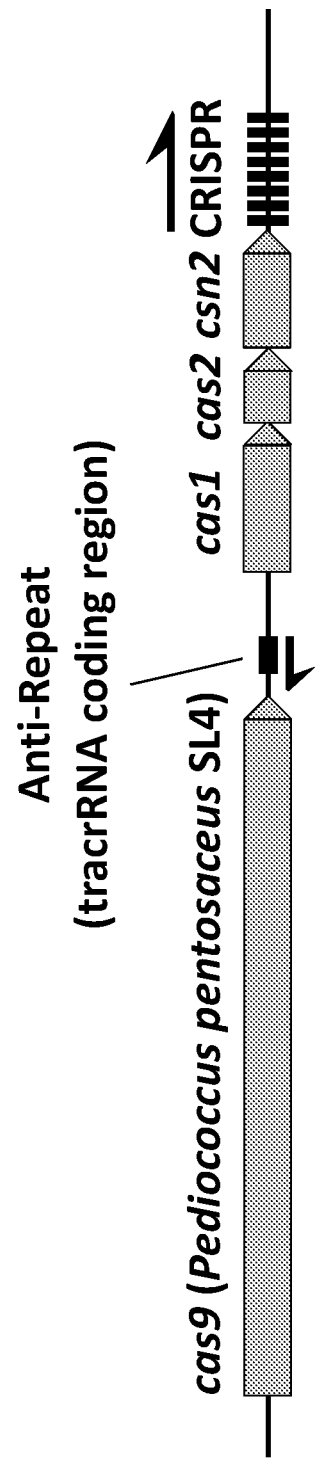

FIG. 27 shows a genomic DNA region from *Pediococcus pentosaceus* SL4 representing an example of a Type II CRISPR-Cas system described herein.

Figure 28:
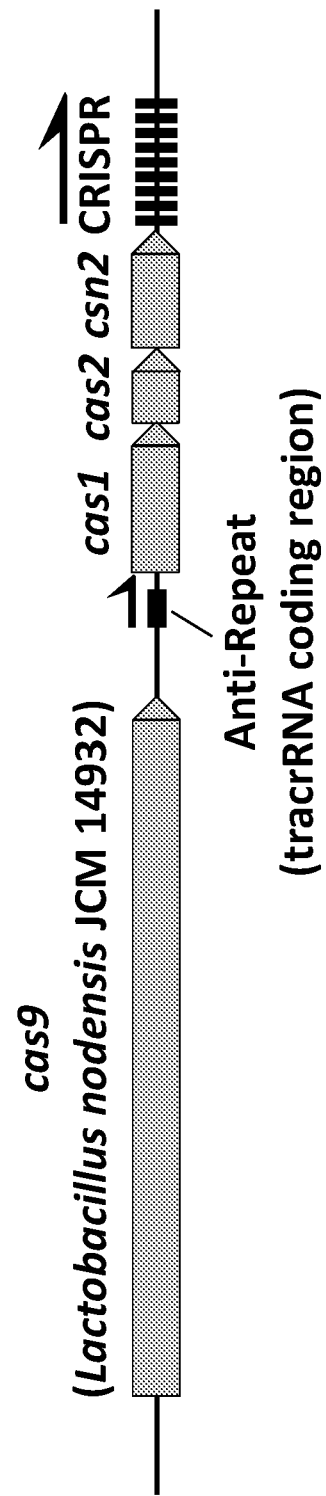

FIG. 28 shows a genomic DNA region from *Lactobacillus nodensis* JCM 14932 representing an example of a Type II CRISPR-Cas system described herein.

Figure 29:
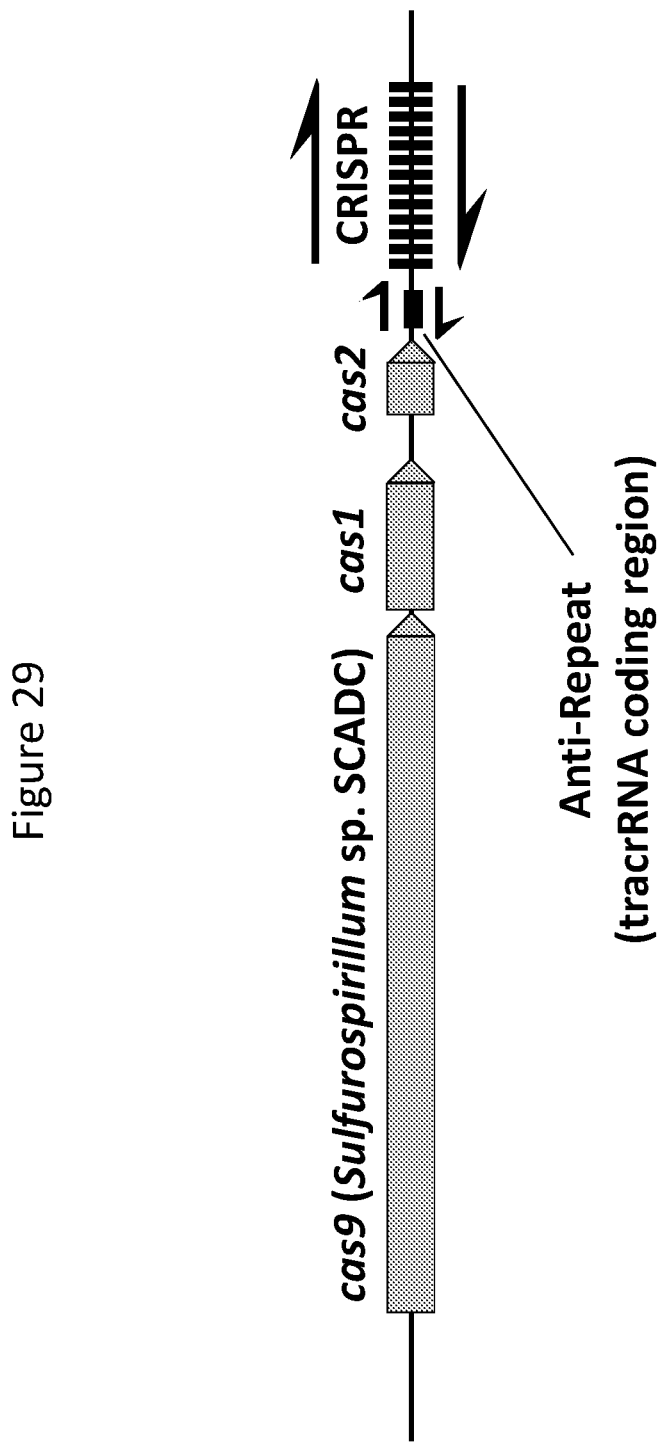

FIG. 29 shows a genomic DNA region from *Sulfurospirillum* sp. SCADC representing an example of a Type II CRISPR-Cas system described herein.

Figure 30:
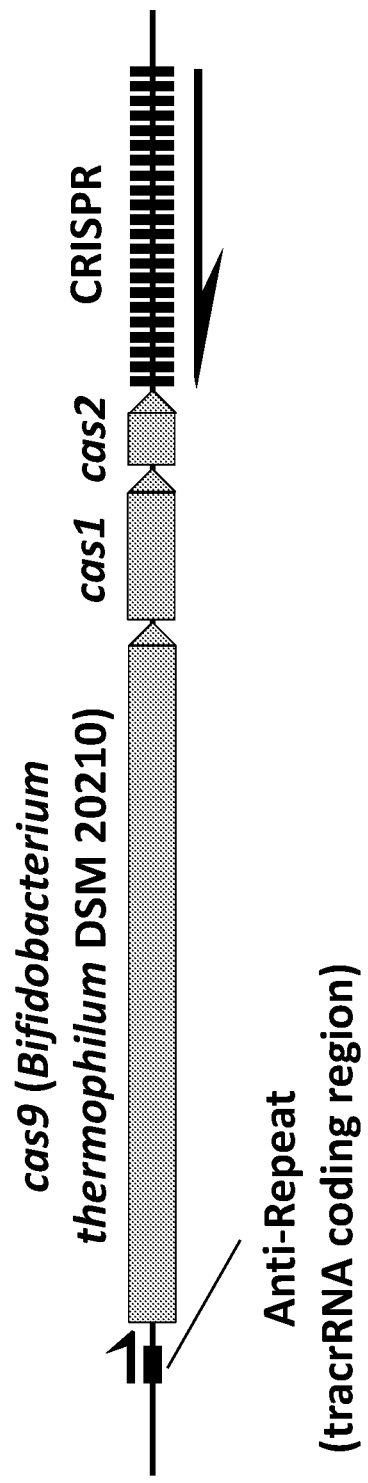

FIG. 30 shows a genomic DNA region from *Bifidobacterium thermophilum* DSM 20210 representing an example of a Type II CRISPR-Cas system described herein.

Figure 31:
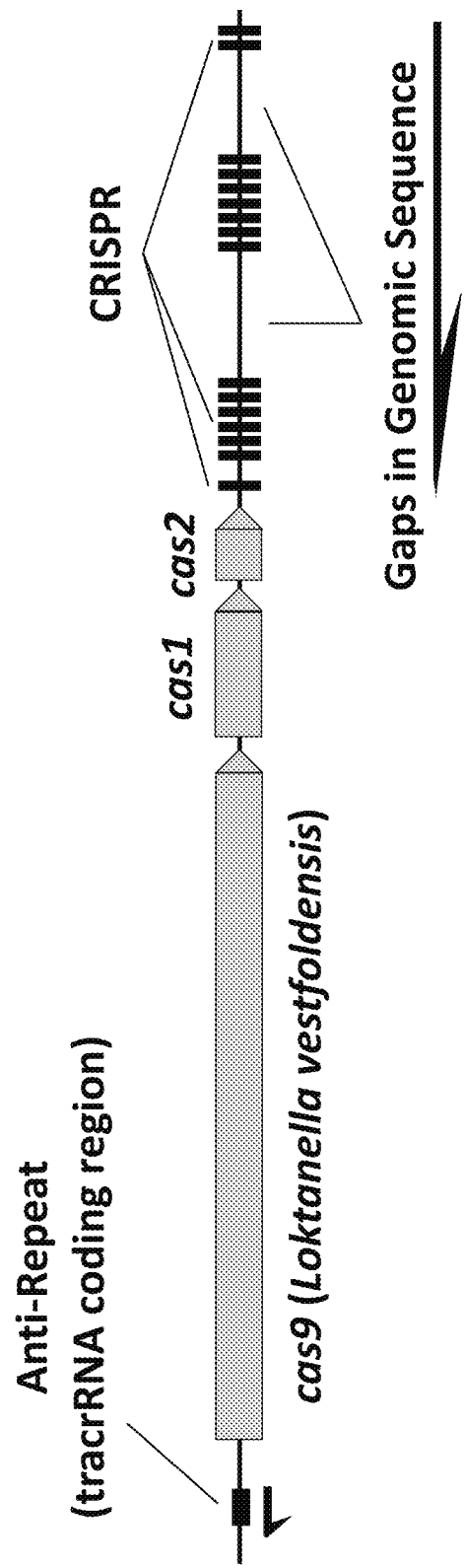

FIG. 31 shows a genomic DNA region from *Loktanella vestfoldensis* representing an example of a Type II CRISPR-Cas system described herein.

Figure 32:
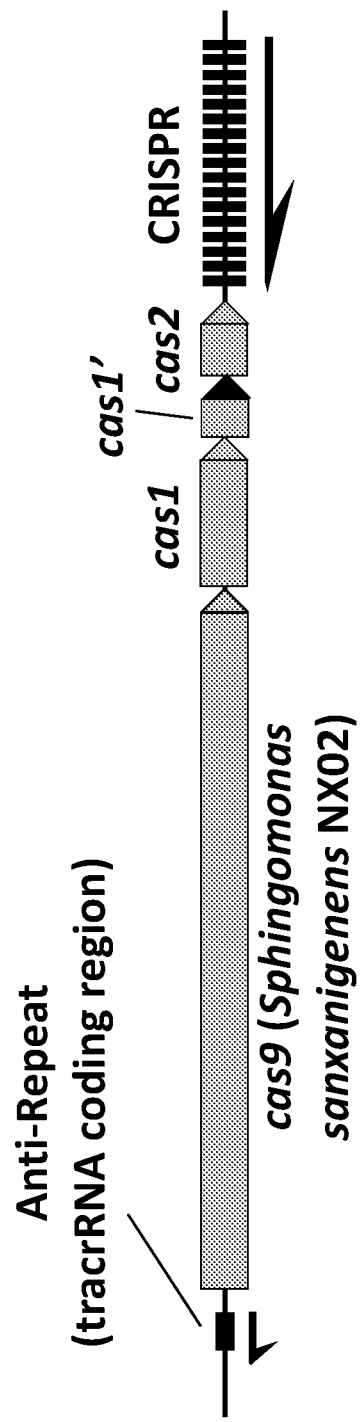

FIG. 32 shows a genomic DNA region from *Sphingomonas sanxanigenens* NX02 representing an example of a Type II CRISPR-Cas system described herein.

Figure 33:
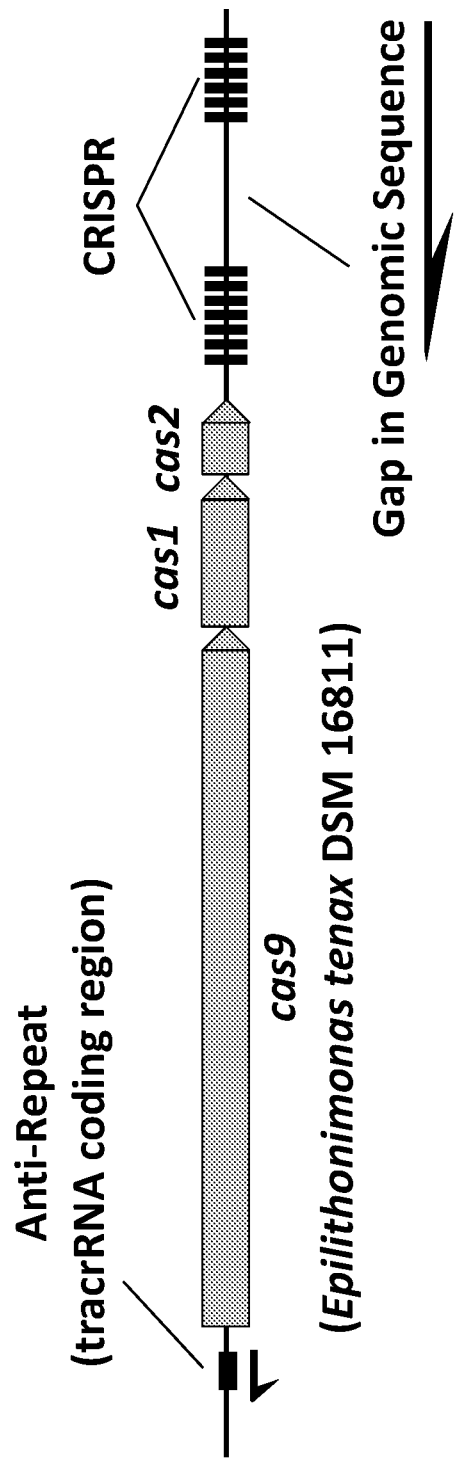

FIG. 33 shows a genomic DNA region from *Epilithonimonas tenax* DSM 16811 representing an example of a Type II CRISPR-Cas system described herein.

Figure 34:
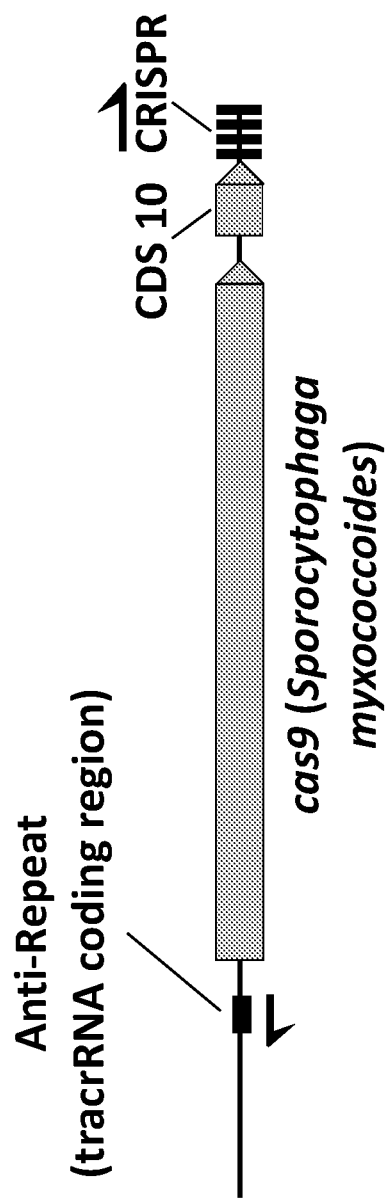

FIG. 34 shows a genomic DNA region from *Sporocytophaga myxococcoides* representing an example of a Type II CRISPR-Cas system described herein.

Figure 35:
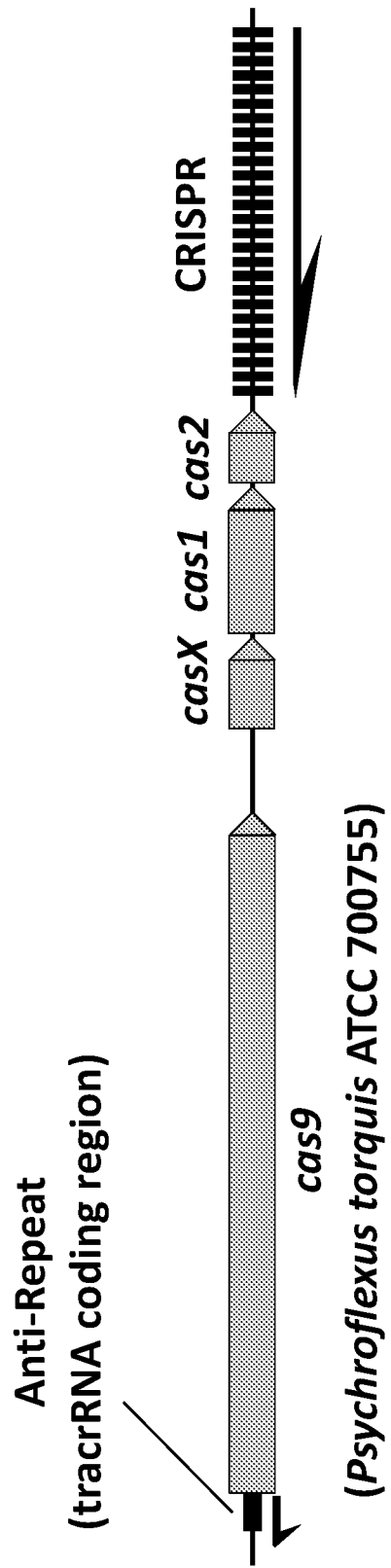

FIG. 35 shows a genomic DNA region from *Psychroflexus torquis* ATCC 700755 representing an example of a Type II CRISPR-Cas system described herein.

Figure 36:
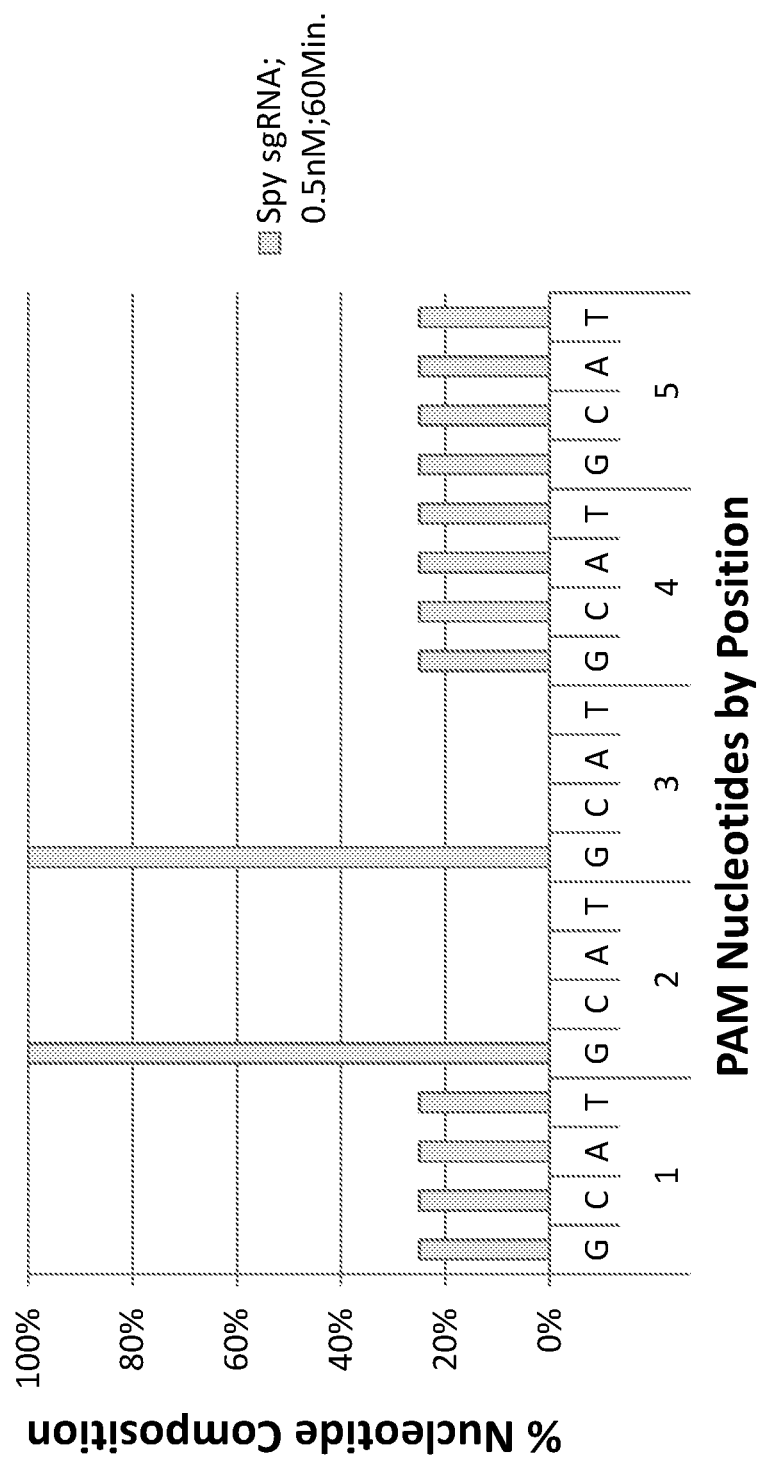
Figure 36:
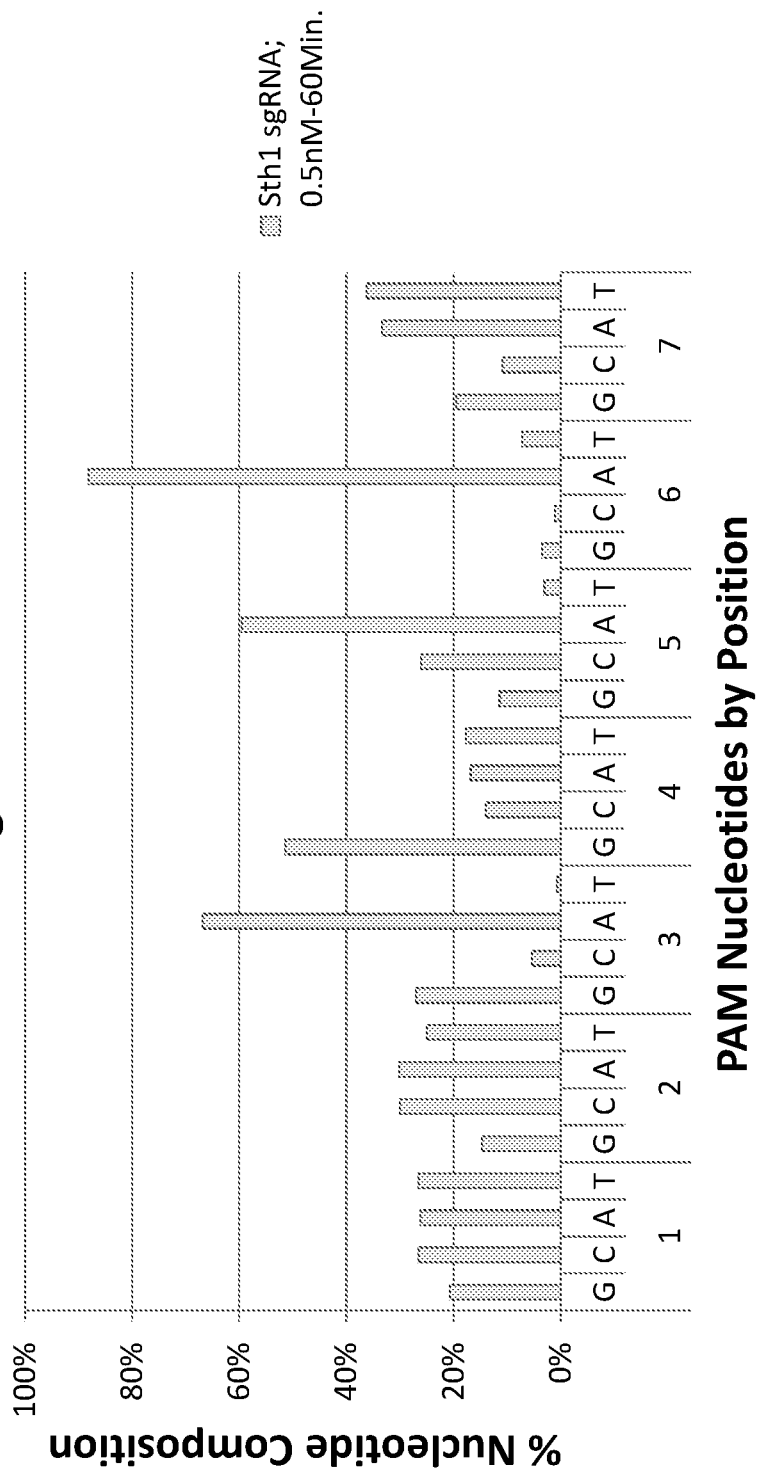

FIG. 36 A shows the PAM preferences for *Streptococcus pyogenes* (Spy) Cas9 with a single guide RNA (sgRNA). FIG. 36 B shows PAM preferences for *Streptococcus thermophilus* CRISPR3 (Sth3) Cas9 with a sgRNA. FIG. 36 C shows PAM preferences for *Streptococcus thermophilus* CRISPR1 (Sth1) Cas9 with a sgRNA.

Figure 37:
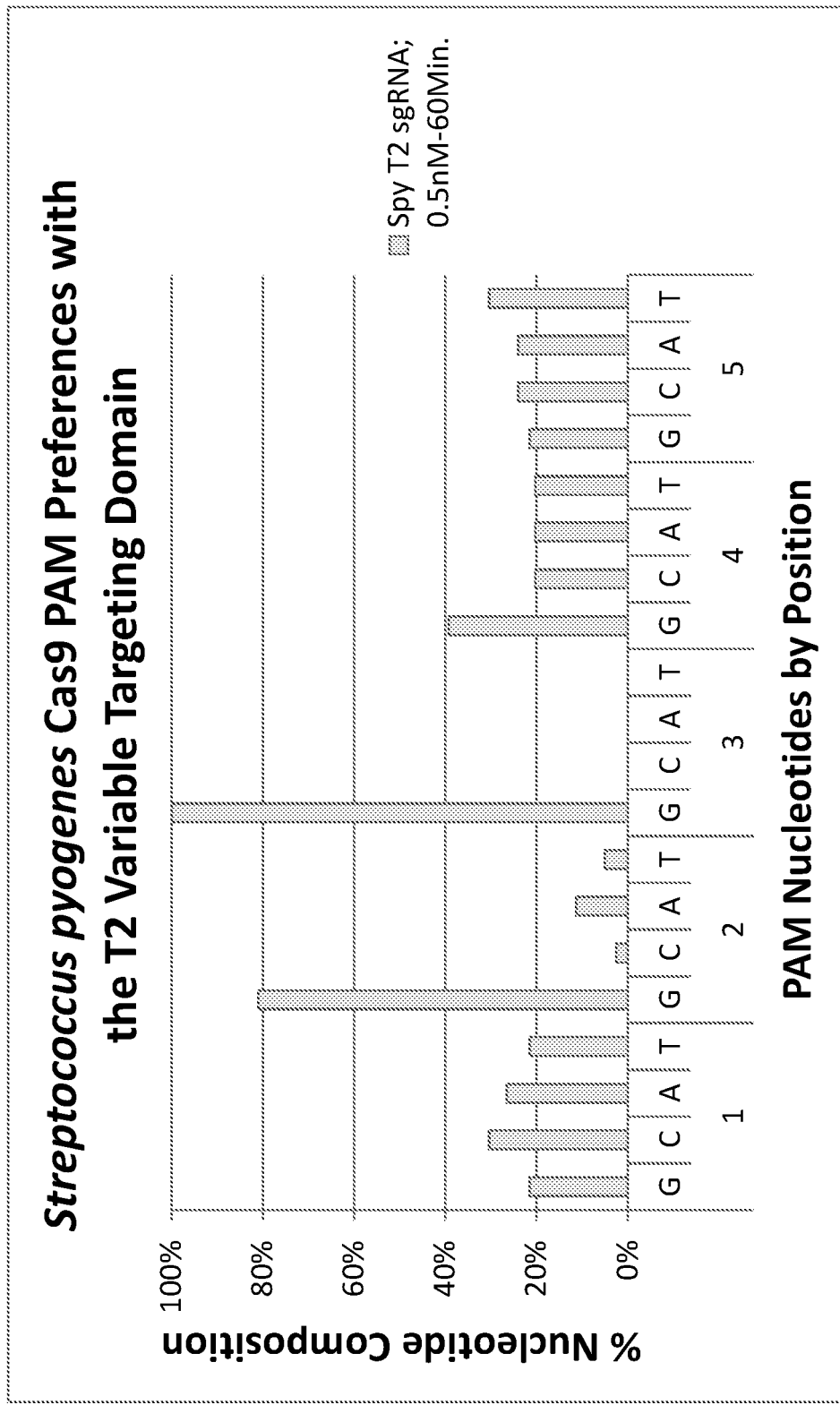
Figure 37:
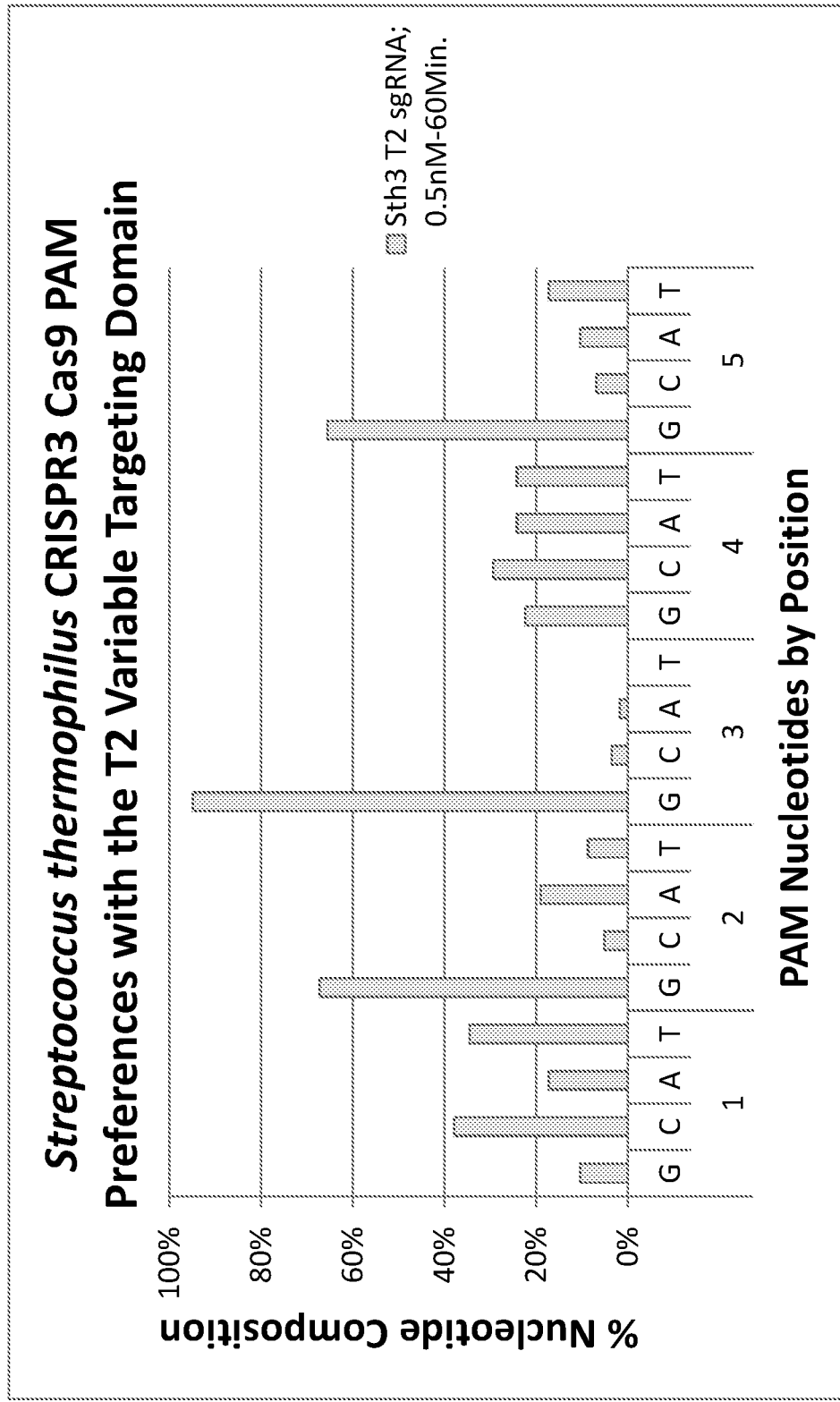

FIG. 37 A shows the PAM preferences for *Streptococcus pyogenes* (Spy) Cas9 with a sgRNA having a different variable targeting domain (VT, T2. FIG. 37 B shows the PAM preferences for *Streptococcus thermophilus* CRISPR3 (Sth3) Cas9 with a sgRNA having a different variable targeting domain, T2. FIG. 37 C shows the PAM preferences for *Streptococcus thermophilus* CRISPR1 (Sth1) Cas9 with a sgRNA having a different variable targeting domain, T2.

Figure 38:
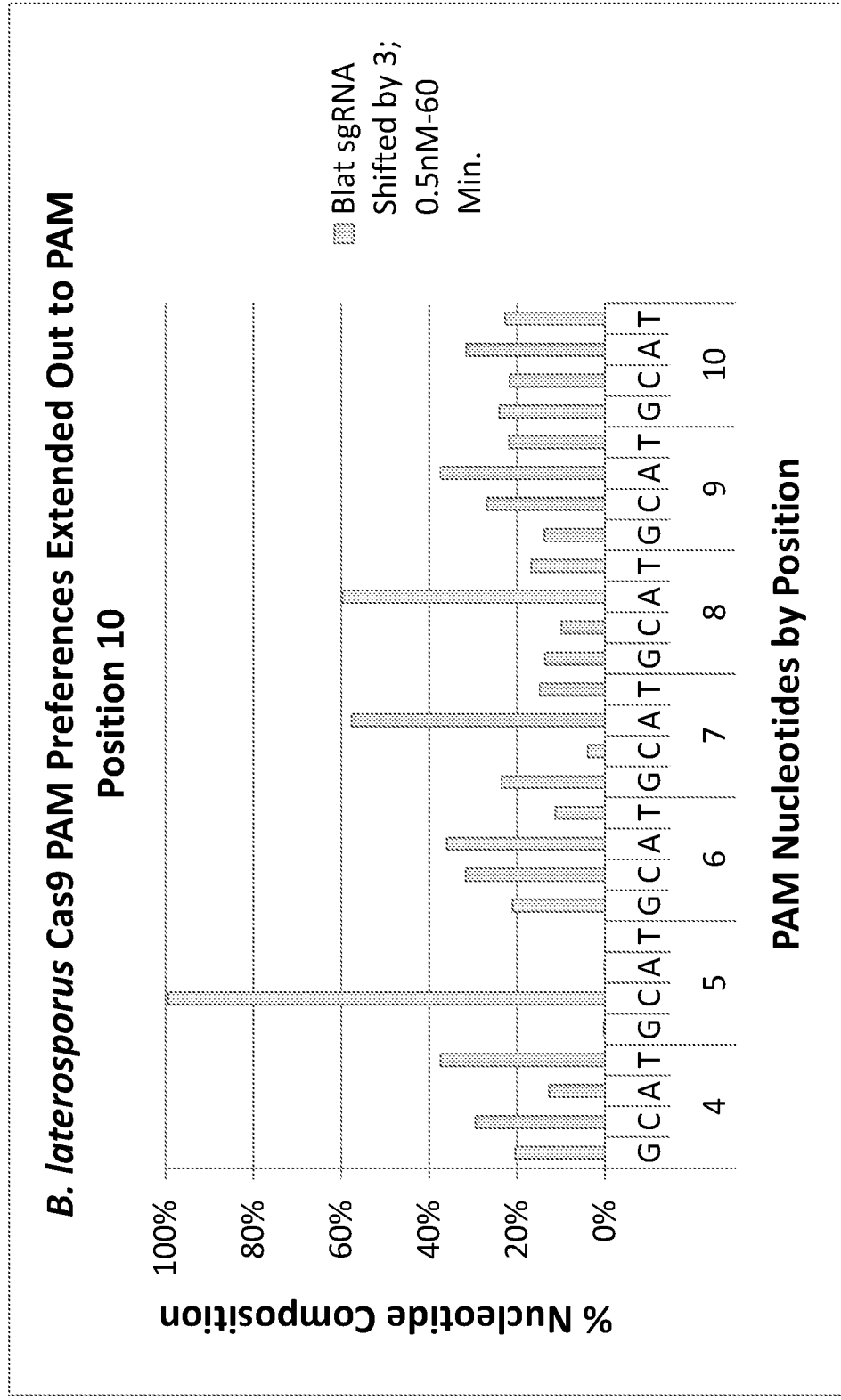

FIG. 38 shows the PAM preferences for *Brevibacillus laterosporus* (Blat) Cas9 extended out to PAM position 10. PAM specificity for Blat extends out to position 8 where there is a moderate preference for an A residue.

Figure 39:
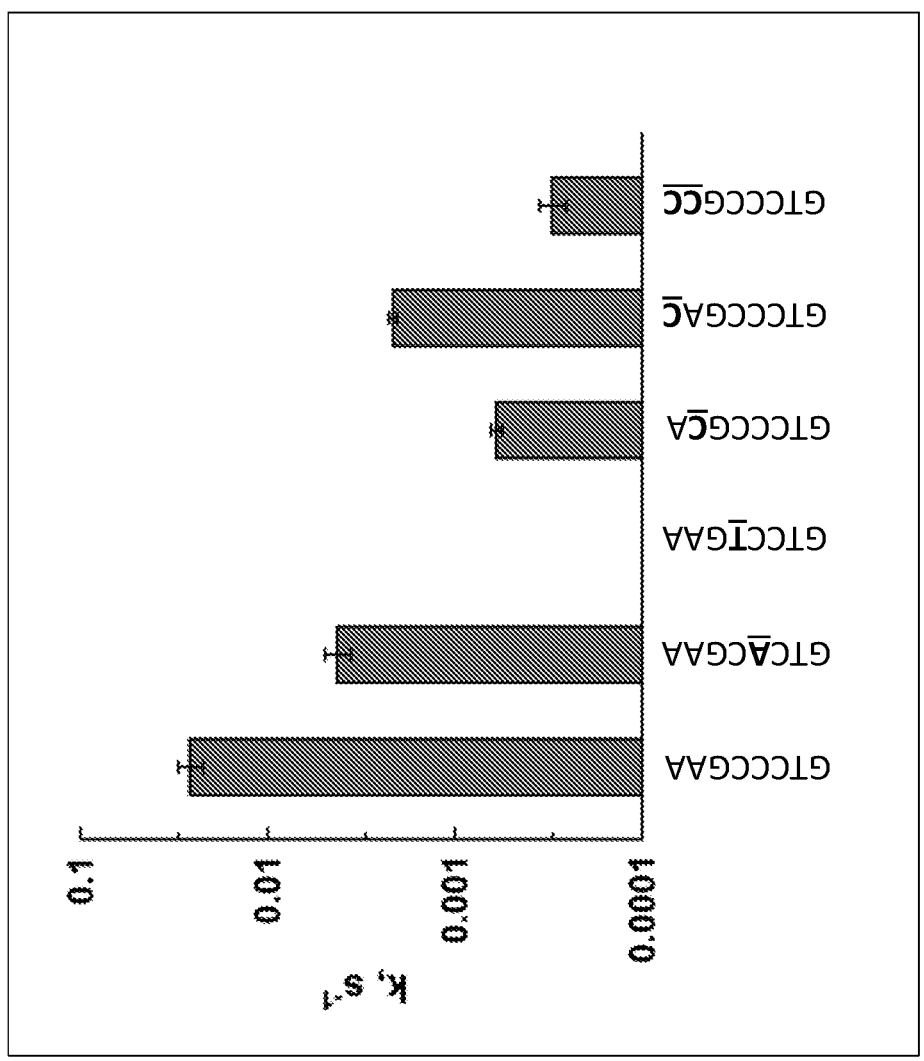

FIG. 39 Validation of PAM preferences for *Brevibacillus laterosporus* (Blat) Cas9. Cleavage rates of supercoiled plasmid DNA substrates containing mutations (shown mutations in bold underlined; GTCCCGAA (reference), GTCACGAA, GTCCTGAA, GTCCCGCA, GTCCCGAC, GTCCCGCC) in GTCCCGAA PAM sequence. All data points are mean values from independent experiments. Error bars are given as S.D.

Figure 40:
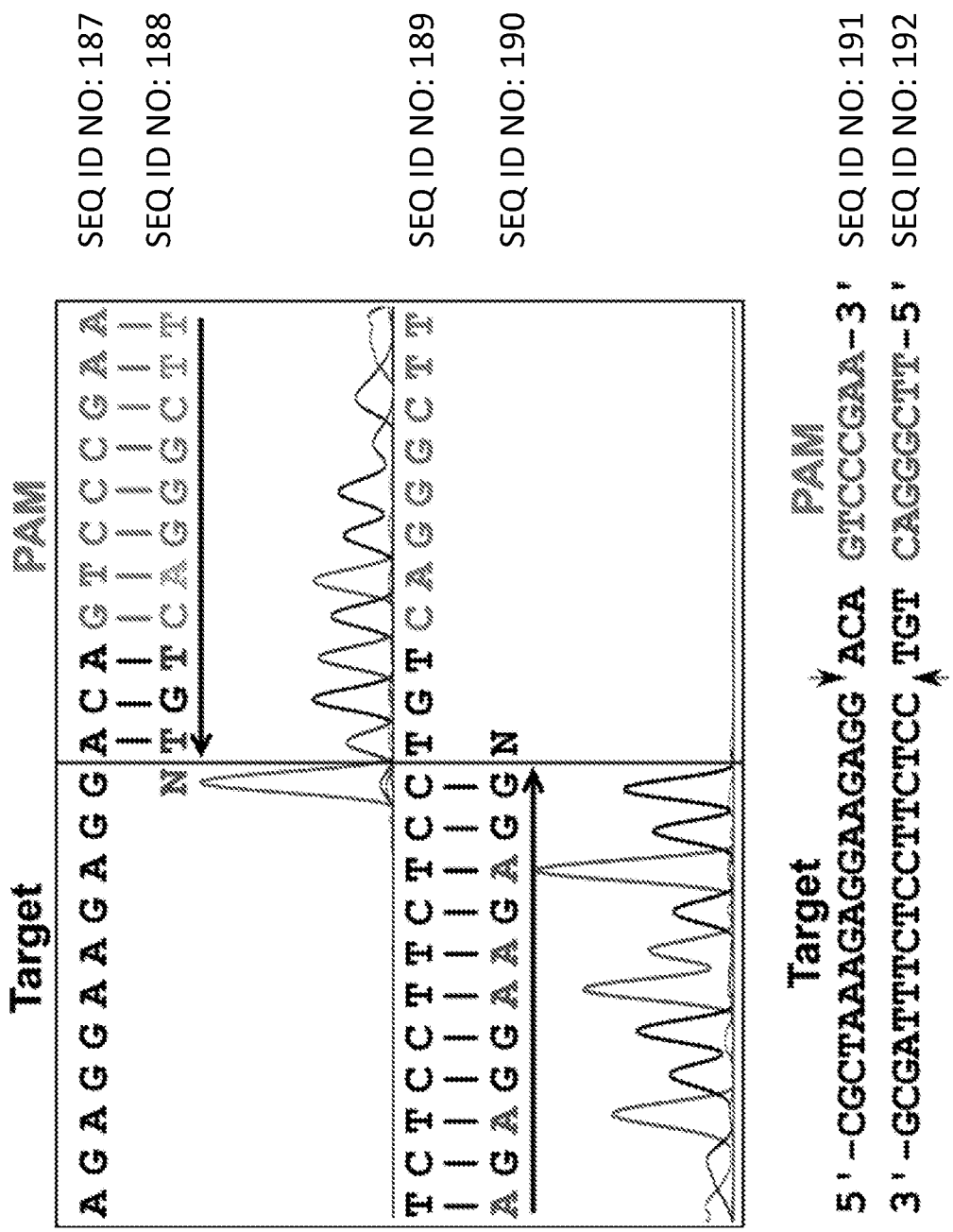

FIG. 40 Depiction of run-off sequencing results illustrating that plasmid DNA cleavage occurred in the protospacer between the 3rd and 4th bp upstream from the PAM sequence.

Figure 41:
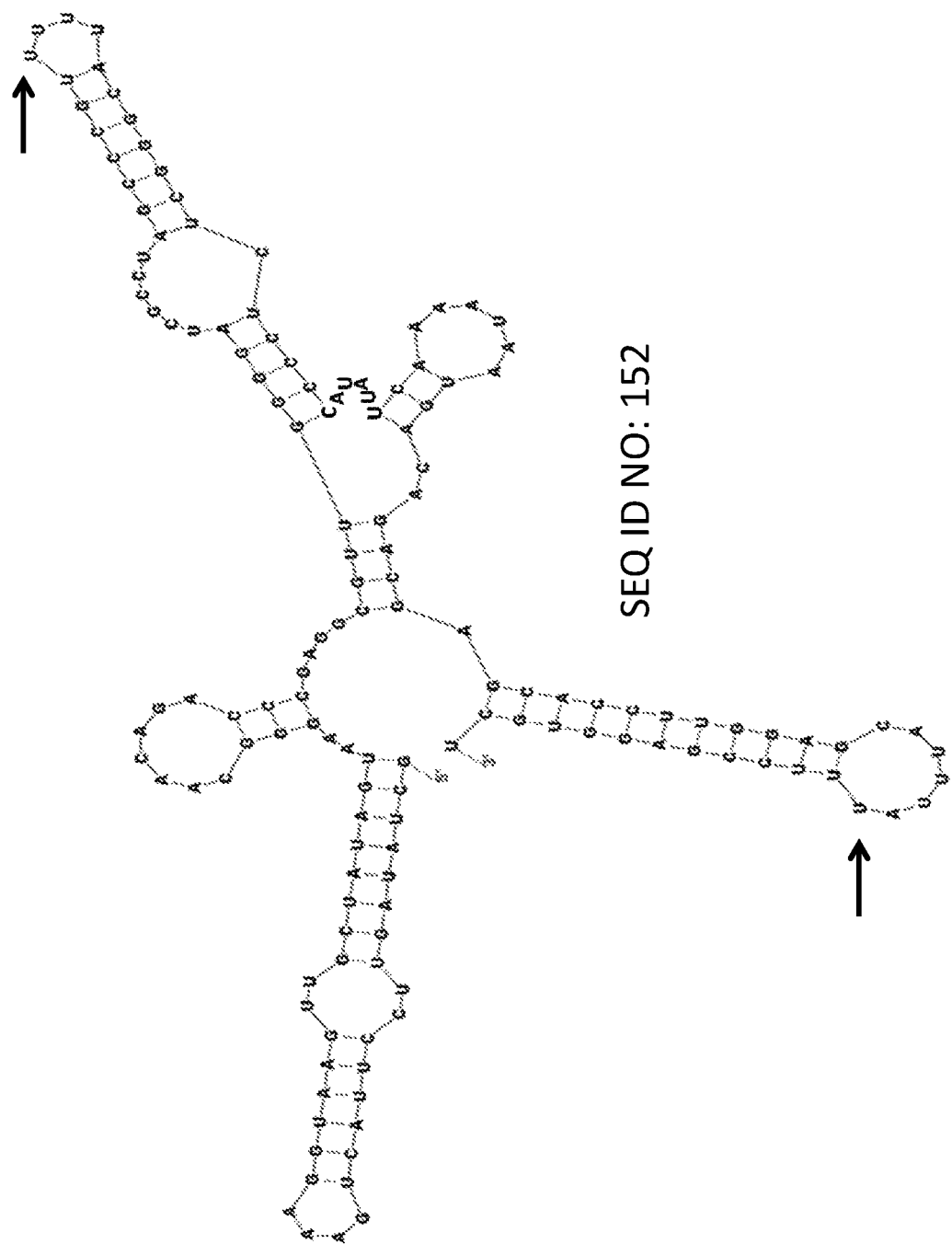

FIG. 41 Secondary structure for *Brevibacillus laterosporus* Cas9 (Blat) sgRNA (without variable targeting domain) used in the in vitro studies (SEQ ID NO: 152). Arrows indicate positions that were altered to disrupt potential U6 polymerase III termination signals.

Figure 42:
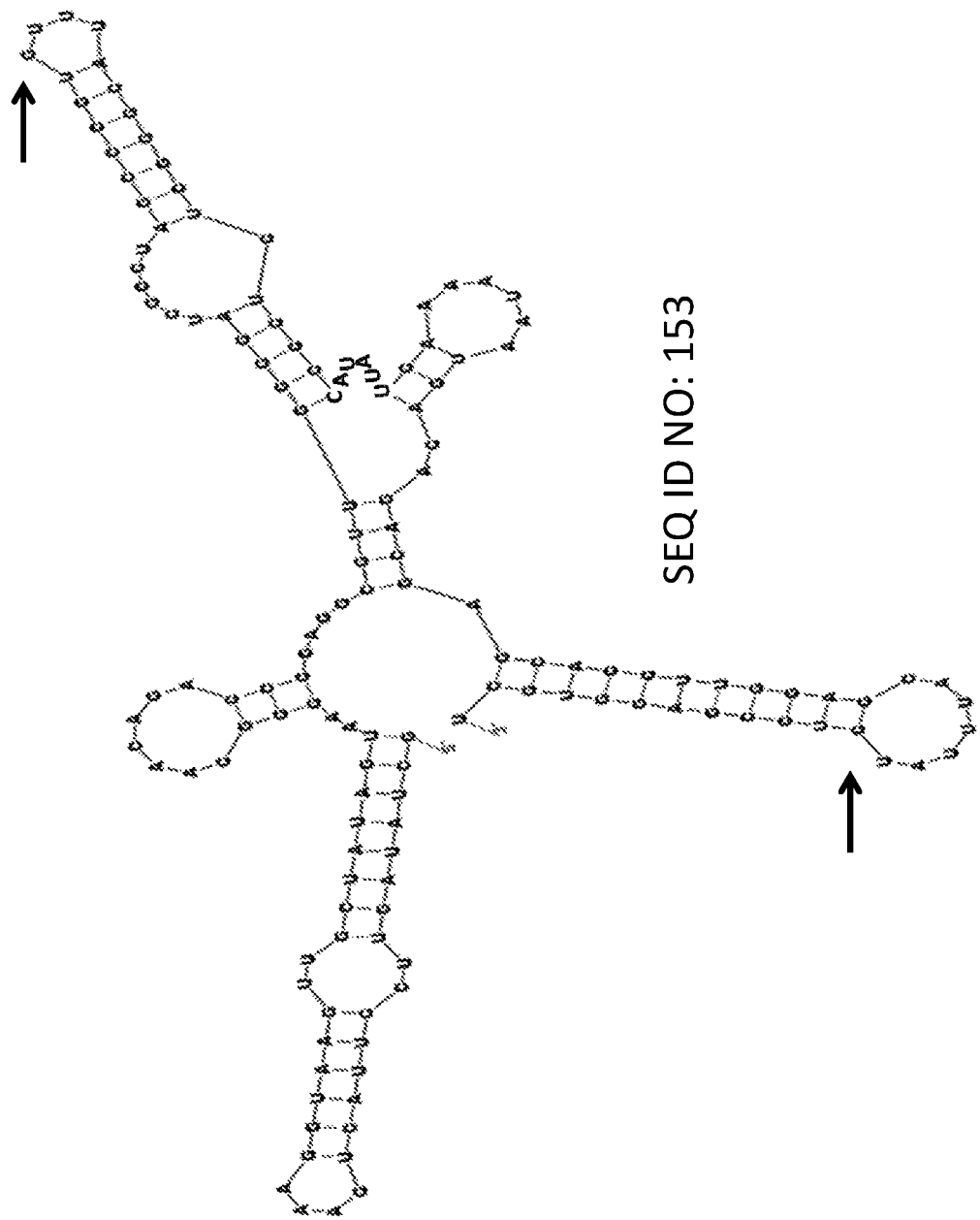

FIG. 42 Secondary structure for *B. laterosporus* Cas9 (Blat) sgRNA (without variable targeting domain) used in the in vivo studies (SEQ ID NO: 153). Arrows indicate positions that were altered to disrupt potential U6 polymerase III termination signals.

FIG. 43 Top 10 most prevalent types of NHEJ mutations detected with *Brevibacillus laterosporus* (Blat) Cas9 in exon 4 of the Ms45 gene. Lower case font indicates an insertion; "-" indicates a deletion. Reference target sequence is shown in SEQ ID NO: 154 and mutated sequences are shown in SEQ ID NOs: 155-164.

FIG. 44 Top 10 most prevalent types of NHEJ mutations detected with *Streptococcus pyogenes* (Spy) Cas9 in exon 4 of the Ms45 gene. Lower case font indicates an insertion; "-" indicates a deletion. Reference target sequence is shown in SEQ ID NO: 154 and mutated sequences are shown in SEQ ID NOs: 165-174.

Figure 45:
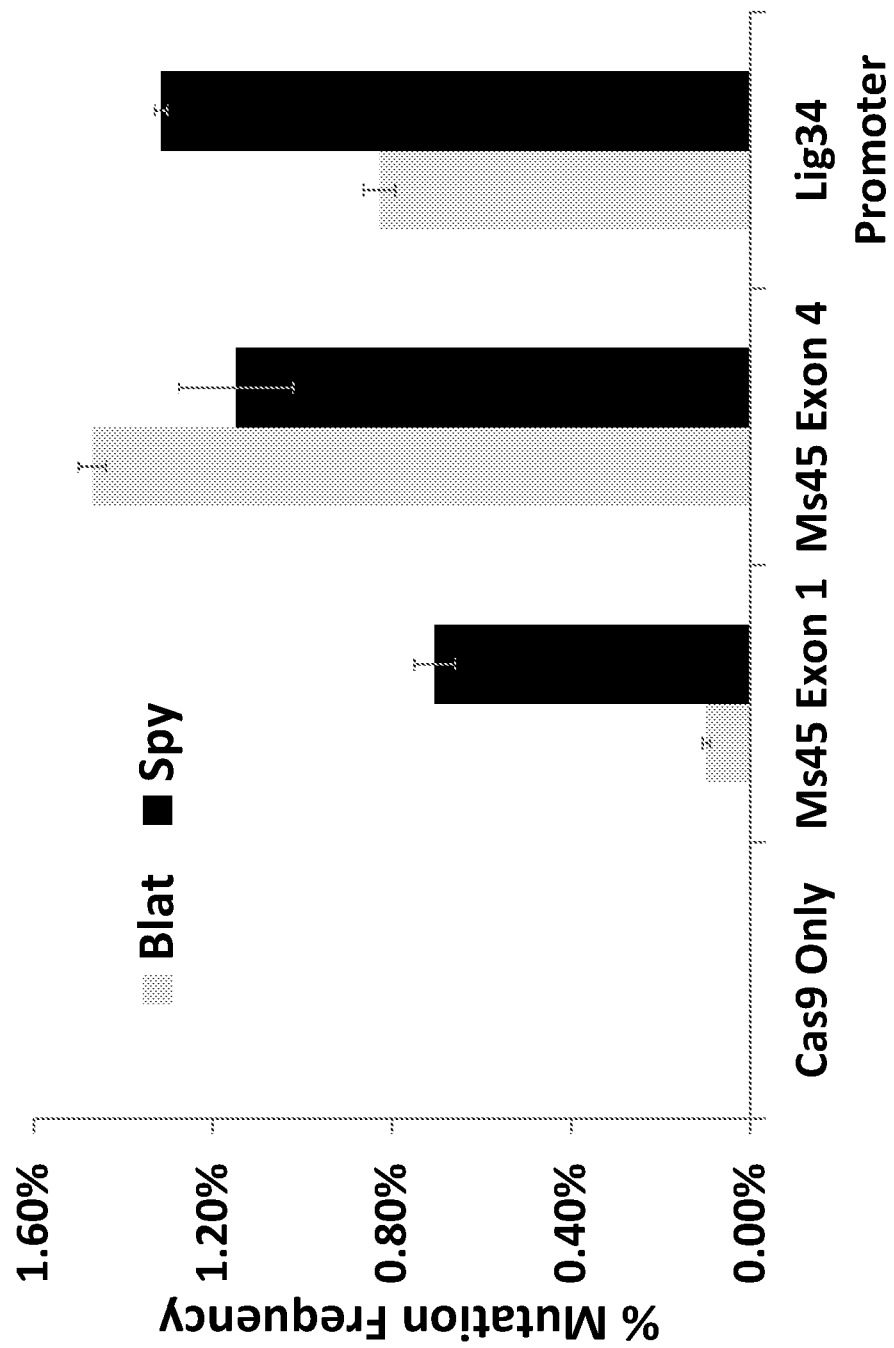

FIG. 45 Comparison of Spy and Blat Cas9 NHEJ mutation frequencies at 3 proto-spacer identical target sites in maize (MS45 Exon 1, MS45 Exon 4 and LIG34). NHEJ mutations were detected by deep sequencing 3 days after transformation. Error bars represent standard error of the mean (s.e.m.), n=3 particle gun transformations.

Figure 46:
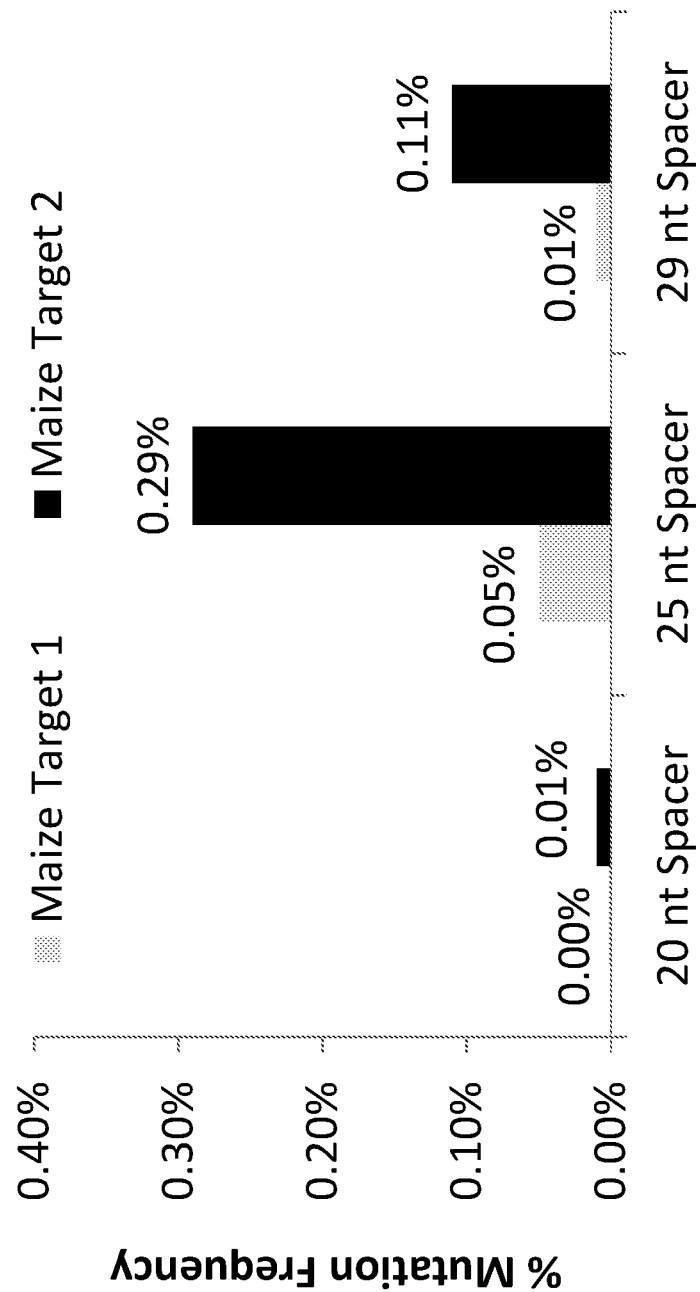

FIG. 46 *Bifidobacterium thermophilum* (Bthe) Cas9 non-homologous end-joining (NHEJ) mutation frequencies with different single guide RNA (sgRNA) variable targeting domain (spacer) lengths (20 nt, 25 nt and 29 nt) at 2 maize target sites. NHEJ mutations were detected by deep sequencing 2 days after transformation.

SEQUENCES

TABLE 1

Summary of Nucleic Acid and Protein SEQ ID Numbers

| Description | Nucleic acid SEQ ID NO. | Protein SEQ ID NO. |
| --- | --- | --- |
| Target sequence T1 | 1 (80 bases) | |
| Single oligonucleotide GG-821N | 2 (47 bases) | |
| Oligonucleotide GG-820 | 3 (44 bases) | |
| TK-119 primer | 4 (22 bases) | |
| pUC-dir primer | 5 (22 bases) | |
| JKYS800.1 forward primer | 6 (59 bases) | |
| JKYS803 reverse primer | 7 (53 bases) | |
| Universal Forward primer | 8 (43 bases) | |
| Universal Reverse primer | 9 (18 bases) | |
| Sth1-dir primer | 10 (34 bases) | |
| Sth1-rev primer | 11 (27 bases) | |
| Sth3-dir primer | 12 (26 bases) | |
| Sth3-rev primer | 13 (30 bases) | |
| Spy-dir primer | 14 (38 bases) | |
| Spy-rev primer | 15 (32 bases) | |
| *Streptococcus thermophilus* (Sth3) crRNA | 16 (42 bases) | |
| *Streptococcus thermophilus* (Sth3) tracrRNA | 17 (78 bases) | |
| *Streptococcus pyogenes* (Spy) crRNA | 18 (42 bases) | |
| *Streptococcus pyogenes* (Spy) tracrRNA | 19 (78 bases) | |
| TK-117 | 20 (31 bases) | |
| TK-111 | 21 (30 bases) | |
| JKYS807.1 primer | 22 (56 bases) | |
| JKYS807.2 primer | 23 (56 bases) | |
| JKYS807.3 primer | 24 (56 bases) | |
| JKYS807.4 primer | 25 (56 bases) | |
| Sth3 sgRNA | 26 (123 bases) | |
| Spy sgRNA | 27 (105 bases) | |
| GG-940-G oligonucleotide | 28 (59 bases) | |
| GG-940-C oligonucleotide | 29 (59 bases) | |
| GG-940-A oligonucleotide | 30 (59 bases) | |
| GG-940-T oligonucleotide | 31 (59 bases) | |
| JKYS812 | 32 (49 bases) | |
| *Streptococcus thermophilus* CRISPR1 (Sth1) crRNA | 33 (42 bases) | |
| *Streptococcus thermophilus* CRISPR1 Sth1 tracrRNA | 34 (80 bases) | |
| *Streptococcus thermophilus* CRISPR3 (Sth3) Cas9 | | 35 (1388 aa) |
| Cas9 single long open-reading-frame from the *Brevibacillus laterosporus* bacterial strain SSP360D4 | 36 (3279 bases) | |
| Repeat 1, *Brevibacillus laterosporus* SSP360D4 | 37 (36 bases) | |
| Repeat 2, *Brevibacillus laterosporus* SSP360D4 | 38 (36 bases) | |

TABLE 1-continued

Summary of Nucleic Acid and Protein SEQ ID Numbers

| Description | Nucleic acid SEQ ID NO. | Protein SEQ ID NO. |
|---|---|---|
| Repeat 3, *Brevibacillus laterosporus* SSP360D4 | 39 (36 bases) | |
| Repeat 4, *Brevibacillus laterosporus* SSP360D4 | 40 (36 bases) | |
| Repeat 5, *Brevibacillus laterosporus* SSP360D4 | 41 (36 bases) | |
| Repeat 6, *Brevibacillus laterosporus* SSP360D4 | 42 (36 bases) | |
| Repeat 7, *Brevibacillus laterosporus* SSP360D4 | 43 (36 bases) | |
| Repeat 8, *Brevibacillus laterosporus* SSP360D4 | 44 (36 bases) | |
| Blat-Cas9-dir | 45 (29 bases) | |
| Blat-Cas9-rev | 46 35 bases) | |
| Blat sgRNA Direct | 47 (177 bases) | |
| Blat sgRNA Reverse | 48 (118 bases) | |
| GG-969 oligonucleotide | 49 (68 bases) | |
| GG-839 oligonucleotide | 50 (62 bases) | |
| TK-149 | 51 55 bases) | |
| TK-150 | 52 (62 bases) | |
| GG-840 | 53 (71 bases) | |
| GG-841 | 54 (75 bases) | |
| TK-124 | 55 (37 bases) | |
| TK-151 | 56 (26 bases) | |
| TK-126; | 57 (32 bases) | |
| GG-935 | 58 (37 bases) | |
| GG-936 | 59 (45 bases) | |
| pUC-EheD primer | 60 (21 bases) | |
| pUC-LguR primer | 61 (22 bases) | |
| Sense DNA Strand of Cleaved Sequencing Template | 62 (21 bases) | |
| Anti-Sense DNA Strand Sequencing Read | 63 (11 bases) | |
| Anti-Sense DNA Strand of Cleaved Sequencing Template | 64 (21 bases) | |
| Sense DNA Strand of DNA Sequencing Read | 65 (11 bases) | |
| Sense DNA Strand of Target and PAM | 66 (27 bases) | |
| Anti-Sense DNA Strand of Target and PAM | 67 (27 bases) | |
| "Direct" tracrRNA region downstream of the anti-repeat *Brevibacillus laterosporus* SSP360D4 | 68 (118 bases) | |
| "Reverse" tracrRNA region downstream of the anti-repeat *Brevibacillus laterosporus* SSP360D4 | 69 (58 bases) | |
| *Lactobacillus reuteri* MIc3 (Lreu) Cas9 Open Reading Frame | 70 (4107 bases) | |
| *Lactobacillus rossiae* DSM 15814 (Lros) Cas9 Open Reading Frame | 71 (4110 bases) | |
| *Pediococcus pentosaceus* SL4 (Ppen) Cas9 Open Reading Frame | 72 (4041 bases) | |
| *Lactobacillus nodensis* JCM 14932 (Lnod) Cas9 Open Reading Frame | 73 (3393 bases) | |
| *Sulfurospirillum* sp. SCADC (Sspe) Cas9 Open Reading Frame | 74 (4086 bases) | |
| *Bifidobacterium thermophilum* DSM 20210 (Bthe) Cas9 Open Reading Frame | 75 (3444 bases) | |
| *Loktanella vestfoldensis* (Lves) Cas9 Open Reading Frame | 76 (3216 bases) | |
| *Sphingomonas sanxanigenens* NX02 (Ssan) Cas9 Open Reading Frame | 77 (3318 bases) | |
| *Epilithonimonas tenax* DSM 16811 (Eten) Cas9 Open Reading Frame | 78 (4200 bases) | |
| *Sporocytophaga myxococcoides* (Smyx) Cas9 Open Reading Frame | 79 (4362 bases) | |
| *Psychroflexus torquis* ATCC 700755 (Ptor) Cas9 Open Reading Frame | 80 (4530 bases) | |
| Lreu Cas9 Endonuclease | | 81 (1368 aa) |
| Lros Cas9 Endonuclease | | 82 (1369 aa) |
| Ppen Cas9 Endonuclease | | 83 (1346 aa) |
| Lnod Cas9 Endonuclease | | 84 (1130 aa) |
| Sspe Cas9 Endonuclease | | 85 (1361 aa) |
| Bthe Cas9 Endonuclease | | 86 (1147 aa) |
| Lves Cas9 Endonuclease | | 87 (1071 aa) |
| Ssan Cas9 Endonuclease | | 88 (1105 aa) |
| Eten Cas9 Endonuclease | | 89 (1399 aa) |
| Smyx Cas9 Endonuclease | | 90 (1453 aa) |
| Ptor Cas9 Endonuclease | | 91 (1509 aa) |
| Lreu CRISPR Repeat Consensus | 92 (36 bases) | |
| Lros CRISPR Repeat Consensus | 93 (36 bases) | |
| Ppen CRISPR Repeat Consensus | 94 (36 bases) | |
| Lnod CRISPR Repeat Consensus | 95 (36 bases) | |
| Sspe CRISPR Repeat Consensus | 96 (36 bases) | |

TABLE 1-continued

Summary of Nucleic Acid and Protein SEQ ID Numbers

| Description | Nucleic acid SEQ ID NO. | Protein SEQ ID NO. |
|---|---|---|
| Bthe CRISPR Repeat Consensus | 97 (36 bases) | |
| Lves CRISPR Repeat Consensus | 98 (36 bases) | |
| Ssan CRISPR Repeat Consensus | 99 (36 bases) | |
| Eten CRISPR Repeat Consensus | 100 (47 bases) | |
| Smyx CRISPR Repeat Consensus | 101 (47 bases) | |
| Ptor CRISPR Repeat Consensus | 102 (46 bases) | |
| Lreu Anti-Repeat | 103 (36 bases) | |
| Lros Anti-Repeat | 104 (37 bases) | |
| Ppen Anti-Repeat | 105 (37 bases) | |
| Lnod Anti-Repeat | 106 (38 bases) | |
| Sspe Anti-Repeat | 107 (39 bases) | |
| Bthe Anti-Repeat | 108 (36 bases) | |
| Lves Anti-Repeat | 109 (36 bases) | |
| Ssan Anti-Repeat | 110 (36 bases) | |
| Eten Anti-Repeat | 111 (47 bases) | |
| Smyx Anti-Repeat | 112 (47 bases) | |
| Ptor Anti-Repeat | 113 (46 bases) | |
| Lreu Single guide RNA | 114 (169 bases) | |
| Lros Single guide RNA | 115 (166 bases) | |
| Ppen Single guide RNA | 116 (168 bases) | |
| Lnod Single guide RNA | 117 (114 bases) | |
| Sspe Single guide RNA | 118 (180 bases) | |
| Sspe Single guide RNA | 119 (117 bases) | |
| Bthe Single guide RNA | 120 (254 bases) | |
| Lves Single guide RNA | 121 (200 bases) | |
| Ssan Single guide RNA | 122 (195 bases) | |
| Eten Single guide RNA | 123 (155 bases) | |
| Smyx Single guide RNA | 124 (149 bases) | |
| Ptor Single guide RNA | 125 (155 bases) | |
| GG-939 | 126 (57 bases) | |
| Single guide RNA | 127 (174 bases) | |
| Lreu Single guide RNA | 128 (166 bases) | |
| Lros Single guide RNA | 129 (163 bases) | |
| Ppen Single guide RNA | 130 (165 bases) | |
| Lnod Single guide RNA | 131 (111 bases) | |
| Sspe Single guide RNA | 132 (177 bases) | |
| Sspe Single guide RNA | 133 (114 bases) | |
| Bthe Single guide RNA | 134 (251 bases) | |
| Lves Single guide RNA | 135 (197 bases) | |
| Ssan Single guide RNA | 136 (192 bases) | |
| Eten Single guide RNA | 137 (152 bases) | |
| Smyx Single guide RNA | 138 (146 bases) | |
| Ptor Single guide RNA | 139 (152 bases) | |
| Cas9 endonuclease *Brevibacillus laterosporus* bacterial strain SSP360D4 | | 140 (1092 aa) |
| Variable Targeting domain T1 (RNA) | 141 (20 bases) | |
| Variable Targeting domain T2-5 (RNA) | 142 (20 bases) | |
| Variable Targeting domain T2-7 (RNA) | 143 (20 bases) | |
| Spy sgRNA T2 | 144 (105 bases) | |
| Sth3 sgRNA T2 | 145 (123 bases) | |
| Sth1 sgRNA T1 | 146 (122 bases) | |
| Sth1 sgRNA T2 | 147 (122 bases) | |
| shifted T1 variable targeting domain, T1-3 | 148 (20 bases) | |
| Blat sgRNA (T1)-3 | 149 (177 bases) | |
| Simian virus 40 (SV40) monopartite NLS | | 150 (9 aa) |
| *Agrobacterium tumefaciens* bipartite VirD2 T-DNA border NLS | | 151 (18 aa) |
| Sequence of FIG. 41 | 152 (147 bases) | |
| Sequence of FIG. 42 | 153 (147 bases) | |
| Reference sequence of FIG. 43 and FIG. 44 | 154 (73 bases) | |
| Mutations 1-10 of FIG. 43 | 155-164 | |
| Mutations 1-10 of FIG. 44 | 165-174 | |
| TK-113 | 175 (28 bases) | |
| JKYS921.1 | 176 (60 bases) | |
| JKY557 | 177 (43 bases) | |
| JKY558 | 178 (18 bases) | |
| pUC-EheD | 179 (21 bases) | |
| pUC-LguR | 180 (22 bases) | |
| JKYX1.1 | 181 (58 bases) | |
| JKYS178Rd | 182 (54 bases) | |
| JKYS1083.1 | 183 (58 bases) | |
| JKYS1084 | 184 (57 bases) | |
| JKYX2.1 | 185 (28 bases) | |
| JKYX3 | 186 (58 bases) | |
| FIG. 40 sequences | 187-192 | |

TABLE 1-continued

Summary of Nucleic Acid and Protein SEQ ID Numbers

| Description | Nucleic acid SEQ ID NO. | Protein SEQ ID NO. |
|---|---|---|
| Variable Targeting domain-direct | 193 | |
| Variable Targeting domain-reverse | 194 | |
| 16 nt loop of the repeat-direct | 195 | |
| 16 nt loop of the repeat-reverse | 196 | |
| anti-repeat region-direct | 197 | |
| anti-repeat region-reverse | 198 | |
| Putative 3' tracrRNA Sequence - direct | 199 | |
| Putative 3' tracrRNA Sequence - reverse | 200 | |
| *Lactobacillus reuteri* MIc3 (Lreu) crRNA repeat region | 201 | |
| *Lactobacillus rossiae* DSM 15814 (Lros) crRNA repeat region | 202 | |
| *Pediococcus pentosaceus* SL4 (Ppen) crRNA repeat region | 203 | |
| *Lactobacillus nodensis* JCM 14932 (Lnod) crRNA repeat region | 204 | |
| *Sulfurospirillum* sp. SCADC (Sspe) crRNA repeat region | 205-206 | |
| *Bifidobacterium thermophilum* DSM 20210 (Bthe) crRNA repeat region | 207 | |
| *Loktanella vestfoldensis* (Lves) crRNA repeat region | 208 | |
| *Sphingomonas sanxanigenens* NX02 (Ssan) crRNA repeat region | 209 | |
| *Epilithonimonas tenax* DSM 16811 (Eten) crRNA repeat region | 210 | |
| *Sporocytophaga myxococcoides* (Smyx) crRNA repeat region | 211 | |
| *Psychroflexus torquis* ATCC 700755 (Ptor) crRNA repeat region | 212 | |
| *Lactobacillus reuteri* MIc3 (Lreu) tracrRNA anti-repeat | 213 | |
| *Lactobacillus rossiae* DSM 15814 (Lros) tracrRNA anti-repeat | 214 | |
| *Pediococcus pentosaceus* SL4 (Ppen) tracrRNA anti-repeat | 215 | |
| *Lactobacillus nodensis* JCM 14932 (Lnod) tracrRNA anti-repeat | 216 | |
| *Sulfurospirillum* sp. SCADC (Sspe) tracrRNA anti-repeat | 217-218 | |
| *Bifidobacterium thermophilum* DSM 20210 (Bthe) tracrRNA anti-repeat | 219 | |
| *Loktanella vestfoldensis* (Lves) tracrRNA anti-repeat | 220 | |
| *Sphingomonas sanxanigenens* NX02 (Ssan) tracrRNA anti-repeat | 221 | |
| *Epilithonimonas tenax* DSM 16811 (Eten) tracrRNA anti-repeat | 222 | |
| *Sporocytophaga myxococcoides* (Smyx) tracrRNA anti-repeat | 223 | |
| *Psychroflexus torquis* ATCC 700755 (Ptor) tracrRNA anti-repeat | 224 | |
| *Lactobacillus reuteri* MIc3 (Lreu) 3' tracrRNA | 225 | |
| *Lactobacillus rossiae* DSM 15814 (Lros) 3' tracrRNA | 226 | |
| *Pediococcus pentosaceus* SL4 (Ppen) 3' tracrRNA | 227 | |
| *Lactobacillus nodensis* JCM 14932 (Lnod) 3' tracrRNA | 228 | |
| *Sulfurospirillum* sp. SCADC (Sspe) 3' tracrRNA | 229-230 | |
| *Bifidobacterium thermophilum* DSM 20210 (Bthe) 3' tracrRNA | 231 | |
| *Loktanella vestfoldensis* (Lves) 3' tracrRNA | 232 | |
| *Sphingomonas sanxanigenens* NX02 (Ssan) 3' tracrRNA | 233 | |
| *Epilithonimonas tenax* DSM 16811 (Eten) 3' tracrRNA | 234 | |
| *Sporocytophaga myxococcoides* (Smyx) 3' tracrRNA | 235 | |
| *Psychroflexus torquis* ATCC 700755 (Ptor) 3' tracrRNA | 236 | |

DETAILED DESCRIPTION

Compositions and methods are provided for rapid characterization of Cas endonuclease systems and the elements comprising such a systems, including, but not limited to, rapid characterization of PAM sequences, guide RNA elements and Cas endonucleases. Cas9 endonuclease systems originating from *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* are described herein.

Methods are disclosed herein that can be used to simultaneously examine the guide RNA and PAM requirements for novel Cas9 proteins. Unlike other approaches that rely on indirect measurements to deduce PAM specificity or unquantified in vivo expression of Cas9, our methods directly and precisely examines PAM specificity and guide RNA requirements in vitro as a function of Cas9-guide RNA complex concentration. Using the methods proposed here, we were able to accurately recapitulate the canonical PAM preferences for *Streptococcus pyogenes* (Spy), *Streptococcus thermophilus* CRISPR3 (Sth3) and *Streptococcus thermophilus* CRISPR1 (Sth1) and provide PAM and single guide RNA solutions for novel Cas9 proteins that support functional activity in vitro and in plants. The methods disclosed herein allow for precise and rapid characterization of novel Cas9 variants for genome editing applications.

The present disclosure also describes methods for genome modification of a target sequence in the genome of a cell, for gene editing, and for inserting a polynucleotide of interest into the genome of a cell.

CRISPR (clustered regularly interspaced short palindromic repeats) loci refers to certain genetic loci encoding factors of DNA cleavage systems, for example, used by bacterial and archaeal cells to destroy foreign DNA (Horvath and Barrangou, 2010, Science 327:167-170). A CRISPR locus can consist of a CRISPR array, comprising short direct repeats separated by short variable DNA sequences (called 'spacers'), which can be flanked by diverse Cas (CRISPR-associated) genes. Multiple CRISPR-Cas systems have been described including Class 1 systems, with multisubunit effector complexes, and Class 2 systems, with single protein effectors (such as but not limiting to Cas9, Cpf1, C2c1, C2c2, C2c3). (Zetsche et al., 2015, Cell 163, 1-13; Shmakov et al., 2015, Molecular Cell 60, 1-13; Makarova et al. 2015, Nature Reviews Microbiology Vol. 13:1-15).

The type II CRISPR/Cas system from bacteria employs a crRNA (CRISPR RNA) and tracrRNA (trans-activating CRISPR RNA) to guide a Cas9 endonuclease to its DNA target. The crRNA contains a region complementary to one strand of the double strand DNA target and a region that base pairs with the tracrRNA (trans-activating CRISPR RNA) forming a RNA duplex that directs the Cas9 endonuclease to cleave the DNA target. CRISPR systems belong to different classes, with different repeat patterns, sets of genes, and species ranges. The number of CRISPR-associated genes at a given CRISPR locus can vary between species (Haft et al., 2005, Computational Biology, PLoS Comput Biol 1(6): e60. doi:10.1371/journal.pcbi.0010060; Makarova et al. 2015, Nature Reviews Microbiology Vol. 13:1-15).

The term "Cas gene" herein refers to a gene that is generally coupled, associated or close to, or in the vicinity of flanking CRISPR loci. The terms "Cas gene", "CRISPR-associated (Cas) gene" are used interchangeably herein.

The term "Cas endonuclease" herein refers to a protein encoded by a Cas gene. A Cas endonuclease herein, when in complex with a suitable polynucleotide component, is capable of recognizing, binding to, and optionally nicking or cleaving all or part of a specific DNA target sequence. A Cas endonuclease described herein comprises one or more nuclease domains. Cas endonucleases of the disclosure include those having a HNH or HNH-like nuclease domain and/or a RuvC or RuvC-like nuclease domain. A Cas endonuclease of the disclosure includes a Cas9 protein, a Cpf1 protein, a C2c1 protein, a C2c2 protein, a C2c3 protein, Cas3, Cas 5, Cas7, Cas8, Cas10, or complexes of these.

As used herein, the terms "guide polynucleotide/Cas endonuclease complex", "guide polynucleotide/Cas endonuclease system", "guide polynucleotide/Cas complex", "guide polynucleotide/Cas system" are used interchangeably herein and refer to at least one guide polynucleotide and at least one Cas endonuclease that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double strand break) into the DNA target site. A guide polynucleotide/Cas endonuclease complex herein can comprise Cas protein(s) and suitable polynucleotide component(s) of any of the four known CRISPR systems (Horvath and Barrangou, Science 327:167-170) such as a type I, II, or III CRISPR system. A Cas endonuclease unwinds the DNA duplex at the target sequence and optionally cleaves at least one DNA strand, as mediated by recognition of the target sequence by a polynucleotide (such as, but not limited to, a crRNA or guide RNA) that is in complex with the Cas protein. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. (See also U.S. Patent Application US 2015-0082478 A1, published on Mar. 19, 2015 and US 2015-0059010 A1, published on Feb. 26, 2015, both are hereby incorporated in its entirety by reference).

A guide polynucleotide/Cas endonuclease complex can cleave one or both strands of a DNA target sequence. A guide polynucleotide/Cas endonuclease complex that can cleave both strands of a DNA target sequence typically comprises a Cas protein that has all of its endonuclease domains in a functional state (e.g., wild type endonuclease domains or variants thereof retaining some or all activity in each endonuclease domain). Thus, a wild type Cas protein (e.g., a Cas9 protein disclosed herein), or a variant thereof retaining some or all activity in each endonuclease domain of the Cas protein, is a suitable example of a Cas endonuclease that can cleave both strands of a DNA target sequence. A Cas9 protein comprising functional RuvC and HNH nuclease domains is an example of a Cas protein that can cleave both strands of a DNA target sequence. A guide polynucleotide/Cas endonuclease complex that can cleave one strand of a DNA target sequence can be characterized herein as having nickase activity (e.g., partial cleaving capability). A Cas nickase typically comprises one functional endonuclease domain that allows the Cas to cleave only one strand (i.e., make a nick) of a DNA target sequence. For example, a Cas9 nickase may comprise (i) a mutant, dysfunctional RuvC domain and (ii) a functional HNH domain (e.g., wild type HNH domain). As another example, a Cas9 nickase may comprise (i) a functional RuvC domain (e.g., wild type RuvC domain) and (ii) a mutant, dysfunctional HNH domain. Non-limiting examples of Cas9 nickases suitable for use herein are disclosed by Gasiunas et al. (Proc. Natl. Acad. Sci. U.S.A. 109:E2579-E2586), Jinek et al. (Science 337:816-821), Sapranauskas et al. (Nucleic Acids Res. 39:9275-9282) and in U.S. Patent Appl. Publ. No. 2014/0189896, which are incorporated herein by reference.

A pair of Cas9 nickases can be used to increase the specificity of DNA targeting. In general, this can be done by providing two Cas9 nickases that, by virtue of being associated with RNA components with different guide sequences, target and nick nearby DNA sequences on opposite strands in the region for desired targeting. Such nearby cleavage of each DNA strand creates a double strand break (i.e., a DSB with single-stranded overhangs), which is then recognized as a substrate for non-homologous-end-joining, NHEJ (leading to indel formation) or homologous recombination, HR. Each nick in these embodiments can be at least about 5, 10, 15, 20, 30, 40, 50, 60, 70, 80, 90, or 100 (or any integer between 5 and 100) bases apart from each other, for example. One or two Cas9 nickase proteins herein can be used in a Cas9 nickase pair. For example, a Cas9 nickase with a mutant RuvC domain, but functioning HNH domain (i.e., Cas9 HNH+/RuvC−), could be used (e.g., *Streptococcus pyogenes* Cas9 HNH+/RuvC−). Each Cas9 nickase (e.g., Cas9 HNH+/RuvC−) would be directed to specific DNA sites nearby each other (up to 100 base pairs apart) by using suitable RNA components herein with guide RNA sequences targeting each nickase to each specific DNA site.

A Cas protein can be part of a fusion protein comprising one or more heterologous protein domains (e.g., 1, 2, 3, or more domains in addition to the Cas protein). Such a fusion protein may comprise any additional protein sequence, and optionally a linker sequence between any two domains, such as between Cas and a first heterologous domain. Examples of protein domains that may be fused to a Cas protein herein include, without limitation, epitope tags (e.g., histidine [His], V5, FLAG, influenza hemagglutinin [HA], myc, VSV-G, thioredoxin [Trx]), reporters (e.g., glutathione-5-transferase [GST], horseradish peroxidase [HRP], chloramphenicol acetyltransferase [CAT], beta-galactosidase, beta-glucuronidase [GUS], luciferase, green fluorescent protein [GFP], HcRed, DsRed, cyan fluorescent protein [CFP], yellow fluorescent protein [YFP], blue fluorescent protein [BFP]), and domains having one or more of the following activities: methylase activity, demethylase activity, transcription activation activity (e.g., VP16 or VP64), transcription repression activity, transcription release factor activity, histone modification activity, RNA cleavage activity and nucleic acid binding activity. A Cas protein can also be in fusion with a protein that binds DNA molecules or other molecules, such as maltose binding protein (MBP), S-tag, Lex A DNA binding domain (DBD), GAL4 A DNA binding domain, and herpes simplex virus (HSV) VP16.

A guide polynucleotide/Cas endonuclease complex in certain embodiments can bind to a DNA target site sequence, but does not cleave any strand at the target site sequence. Such a complex may comprise a Cas protein in which all of its nuclease domains are mutant, dysfunctional. For example, a Cas9 protein herein that can bind to a DNA target site sequence, but does not cleave any strand at the target site sequence, may comprise both a mutant, dysfunctional RuvC domain and a mutant, dysfunctional HNH domain. A Cas protein herein that binds, but does not cleave, a target DNA sequence can be used to modulate gene expression, for example, in which case the Cas protein could be fused with a transcription factor (or portion thereof) (e.g., a repressor or activator, such as any of those disclosed herein).

In one embodiment, the Cas endonuclease gene is a Type II Cas9 endonuclease, such as but not limited to, Cas9 genes listed in SEQ ID NOs: 462, 474, 489, 494, 499, 505, and 518 of WO2007/025097 published Mar. 1, 2007, and incorporated herein by reference. In another embodiment, the Cas endonuclease gene is a plant, maize or soybean optimized Cas9 endonuclease gene. The Cas endonuclease gene can be operably linked to a SV40 nuclear targeting signal upstream of the Cas codon region and a bipartite VirD2 nuclear localization signal (Tinland et al. (1992) Proc. Natl. Acad. Sci. USA 89:7442-6) downstream of the Cas codon region.

In one embodiment of the disclosure, the guide RNA/Cas endonuclease complex is a guide RNA/Cas endonuclease complex comprising a Cas9 endonuclease of SEQ ID NO: 140, or a functional fragment thereof, and a guide RNA, wherein said guide RNA/Cas9 endonuclease complex is capable of recognizing, binding to, and optionally nicking or cleaving all or part of a target sequence.

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence. A Cas9 protein comprises a RuvC nuclease domain and an HNH (H-N-H) nuclease domain, each of which can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al, Cell 157:1262-1278).

Cas9 endonucleases are typically derived from a type II CRISPR system, which includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA In one embodiment of the disclosure, the composition comprises at least one Cas9 endonuclease of SEQ ID NO: 140, or a functional fragment thereof.

Recombinant DNA expressing the Cas9 endonucleases described herein (including functional fragments thereof, plant or microbe codon optimized Cas9 endonuclease) can be stably integrated into the genome of an organism. For example, plants can be produced that comprise a cas9 gene stably integrated in the plant's genome. Plants expressing a stably integrated Cas endonuclease can be exposed to at least one guide RNA and/or a polynucleotide modification templates and/or donor DNAs to enable genome modifications such as gene knockout, gene editing or DNA insertions.

A variant of a Cas9 protein sequence may be used, but should have specific binding activity, and optionally endonucleolytic activity, toward DNA when associated with an RNA component herein. Such a variant may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of the reference Cas9. Alternatively, a Cas9 protein may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%), or 99% identical to any of the foregoing amino acid sequences, for example. Such a variant Cas9 protein should have specific binding activity, and optionally cleavage or nicking activity, toward DNA when associated with an RNA component herein.

The Cas endonuclease can comprise a modified form of the Cas9 polypeptide. The modified form of the Cas9 polypeptide can include an amino acid change (e.g., deletion, insertion, or substitution) that reduces the naturally-occurring nuclease activity of the Cas9 protein. For example, in some instances, the modified form of the Cas9 protein has less than 50%, less than 40%, less than 30%, less than 20%, less than 10%, less than 5%, or less than 1% of the nuclease activity of the corresponding wild-type Cas9 polypeptide (US patent application US20140068797 A1, published on Mar. 6, 2014). In some cases, the modified form of the Cas9 polypeptide has no substantial nuclease activity and is referred to as catalytically "inactivated Cas9" or "deactivated cas9 (dCas9)." Catalytically inactivated Cas9 variants include Cas9 variants that contain mutations in the HNH and RuvC nuclease domains. These catalytically inactivated Cas9 variants are capable of interacting with sgRNA and binding to the target site in vivo but cannot cleave either strand of the target DNA.

A catalytically inactive Cas9 can be fused to a heterologous sequence (US patent application US20140068797 A1, published on Mar. 6, 2014). Suitable fusion partners include, but are not limited to, a polypeptide that provides an activity that indirectly increases transcription by acting directly on the target DNA or on a polypeptide (e.g., a histone or other DNA-binding protein) associated with the target DNA. Additional suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity. Further suitable fusion partners include, but are not limited to, a polypeptide that directly provides for increased transcription of the target nucleic acid (e.g., a transcription activator or a fragment thereof, a protein or fragment thereof that recruits a transcription activator, a small molecule/drug-responsive transcription regulator, etc.). A catalytically inactive Cas9 can also be fused to a FokI nuclease to generate double strand breaks (Guilinger et al. Nature biotechnology, volume 32, number 6, June 2014).

A Cas protein herein such as a Cas9 endonuclease protein can comprise a heterologous nuclear localization sequence (NLS). A heterologous NLS amino acid sequence herein may be of sufficient strength to drive accumulation of a Cas protein in a detectable amount in the nucleus of a yeast cell herein, for example. An NLS may comprise one (monopartite) or more (e.g., bipartite) short sequences (e.g., 2 to 20 residues) of basic, positively charged residues (e.g., lysine and/or arginine), and can be located anywhere in a Cas amino acid sequence but such that it is exposed on the protein surface. An NLS may be operably linked to the N-terminus or C-terminus of a Cas protein herein, for example. Two or more NLS sequences can be linked to a Cas protein, for example, such as on both the N- and C-termini of a Cas protein. The Cas endonuclease gene can be operably linked to a SV40 nuclear targeting signal upstream of the Cas codon region and a bipartite VirD2 nuclear localization signal (Tinland et al. (1992) Proc. Natl. Acad. Sci. USA 89:7442-6) downstream of the Cas codon region. Non-limiting examples of suitable NLS sequences herein include those disclosed in U.S. Pat. No. 7,309,576, which is incorporated herein by reference.

The terms "functional fragment", "fragment that is functionally equivalent" and "functionally equivalent fragment" of a Cas endonuclease are used interchangeably herein, and refer to a portion or subsequence of the Cas endonuclease sequence of the present disclosure in which the ability to recognize, bind to, and optionally nick or cleave (introduce a single or double strand break in) the target site is retained.

The terms "functional variant", "Variant that is functionally equivalent" and "functionally equivalent variant" of a Cas endonuclease are used interchangeably herein, and refer to a variant of the Cas endonuclease of the present disclosure in which the ability to recognize, bind to, and optionally nick or cleave (introduce a single or double strand break in) the target site is retained. Fragments and variants can be obtained via methods such as site-directed mutagenesis and synthetic construction.

In one embodiment, the Cas endonuclease gene is a plant codon optimized *Streptococcus pyogenes* Cas9 gene that can recognize any genomic sequence of the form N(12-30)NGG can in principle be targeted.

In one embodiment, the Cas endonuclease is a Cas9 endonuclease originated from organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755, wherein said Cas9 endonuclease can form a guide RNA/Cas endonuclease complex capable of recognizing, binding to, and optionally nicking or cleaving all or part of a DNA target sequence.

The Cas endonuclease can be introduced directly into a cell by any method known in the art, for example, but not limited to transient introduction methods, transfection and/or topical application.

The guide polynucleotides and guide polynucleotide/Cas endonuclease systems described herein include guide polynucleotides comprising a crRNA (comprising a variable targeting (VT) domain linked to tracr-mate sequence that can hybridized to the tracr nucleotide) wherein said guide polynucleotide directs sequence-specific binding of the guide polynucleotide/Cas endonuclease complex to a target sequence in a eukaryotic cell. In an aspect, the guide polynucleotide targets a target sequence in a non-human eukaryotic organism preferably a multicellular eukaryotic organism, comprising a eukaryotic host cell. In one aspect, the guide polynucleotide is a non-naturally occurring guide polynucleotide or a guide polynucleotide targeting a target sequence that is not natural to bacteria. The disclosed guide polynucleotides can be reprogrammed to target nucleotide sequences in non-bacterial cells such as, but not limiting to changing the VT domain to target non-bacterial target sequences and sequences not naturally acquired by the system from which the crRNA was obtained. Alternatively, the VT domain can be programmed to guide the crRNA to a target sequence in a eukaryotic genome. Any sequence in a eukaryotic genome can be targeted using the disclosed guide polynucleotides, such as, mammalian (e.g. human, mouse, etc.), yeast, insect, animal, and plant sequences. In other embodiments, the VT domain can be programmed to guide the crRNA to a target sequence in a prokaryotic genome or bacterial plasmid sequence that is not naturally targeted by the native system.

In some embodiments, the guide polynucleotide/Cas endonuclease complex comprises one or more nuclear localization sequences of sufficient strength to drive accumulation of said complex in a detectable amount in the nucleus of a eukaryotic cell. For example, nuclear localization signals can be added to the N- or C- or both the N- and C-terminus of the Cas protein. In other embodiments, one or more cellular localization signals can be included in the complex to provide for accumulation of the complex in a detectable amount in cellular organelles in which a desired target sequence is contained. For example, chloroplast targeting sequences can be added to the Cas protein to provide accumulation in a chloroplast organelle in a plant cell where the desired target sequence is found in the plant chloroplast genome.

The guide polynucleotide/Cas endonuclease system described herein can be provided to eukaryotic cells and reprogrammed to facilitate cleavage of endogenous eukaryotic target polynucleotides.

Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex. Endonucleases also include meganucleases, also known as homing endonucleases (HEases), which like restriction endonucleases, bind and cut at a specific recognition site, however the recognition sites for meganucleases are typically longer, about 18 bp or more (patent application WO-PCT PCT/US12/30061 filed on Mar. 22, 2012). Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. This cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families.

TAL effector nucleases are a new class of sequence-specific nucleases that can be used to make double-strand breaks at specific target sequences in the genome of a plant or other organism. (Miller et al. (2011) *Nature Biotechnology* 29:143-148). Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

As used herein, the term "guide polynucleotide", relates to a polynucleotide sequence that can form a complex with a Cas endonuclease and enables the Cas endonuclease to recognize, bind to, and optionally cleave a DNA target site. The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization (Hendel et al. 2015 Nature Biotechnology Vol. 33 pg 985-991). A guide polynucleotide that solely comprises ribonucleic acids is also referred to as a "guide RNA" or "g RNA" (See also U.S. Patent Application US 2015-0082478 A1, published on Mar. 19, 2015 and US 2015-0059010 A1, published on Feb. 26, 2015, both are hereby incorporated in its entirety by reference).

In one embodiment of the disclosure, the guide polynucleotide is a single guide RNA capable of forming a guide RNA/Cas9 endonuclease complex, wherein said guide RNA/Cas9 endonuclease complex can recognize, bind to, and optionally nick or cleave a target sequence, wherein said single guide RNA comprises a chimeric non-naturally occurring crRNA linked to a tracrRNA, wherein said tracrRNA comprises a nucleotide sequence selected from the group consisting of SEQ ID NOs: 173, 174, 175, 176, 177, 178, 179, 180, 181, 182, 183 and 184, wherein said chimeric non-naturally occurring crRNA comprises a nucleotide sequence selected from the group consisting of SEQ ID NOs: 149, 150, 151, 152, 153, 154, 155, 156, 157, 158, 159 and 160.

In one embodiment of the disclosure, the guide polynucleotide is a guide RNA capable of forming a guide RNA/Cas9 endonuclease complex, wherein said guide RNA/Cas9 endonuclease complex can recognize, bind to, and optionally nick or cleave a target sequence, wherein said guide RNA is a duplex molecule comprising a chimeric non-naturally occurring crRNA and a tracrRNA, wherein said tracrRNA comprises a nucleotide sequence selected from the group consisting of SEQ ID NOs: 173, 174, 175, 176, 177, 178, 179, 180, 181, 182, 183 and 184, wherein said chimeric non-naturally occurring crRNA comprises a nucleotide sequence selected from the group consisting of SEQ ID NOs: 149, 150, 151, 152, 153, 154, 155, 156, 157, 158, 159 and 160, wherein said chimeric non-naturally occurring crRNA comprises a variable targeting domain capable of hybridizing to said target sequence.

The guide polynucleotide can be a double molecule (also referred to as duplex guide polynucleotide) comprising a crNucleotide sequence and a tracrNucleotide sequence. The crNucleotide includes a first nucleotide sequence domain (referred to as Variable Targeting domain or VT domain) that can hybridize to a nucleotide sequence in a target DNA and a second nucleotide sequence (also referred to as a tracr mate sequence) that is part of a Cas endonuclease recognition (CER) domain. The tracr mate sequence can hybridized to a tracrNucleotide along a region of complementarity and together form the Cas endonuclease recognition domain or CER domain. The CER domain is capable of interacting with a Cas endonuclease polypeptide. The crNucleotide and the tracrNucleotide of the duplex guide polynucleotide can be RNA, DNA, and/or RNA-DNA-combination sequences. In some embodiments, the crNucleotide molecule of the duplex guide polynucleotide is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the crRNA naturally occurring in Bacteria and Archaea. The size of the fragment of the crRNA naturally occurring in Bacteria and Archaea that can be present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the tracrNucleotide is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides. In one embodiment, the RNA that guides the RNA/Cas9 endonuclease complex is a duplexed RNA comprising a duplex crRNA-tracrRNA. The tracrRNA (trans-activating CRISPR RNA) contains, in the 5'-to-3' direction, (i) a sequence that anneals with the repeat region of CRISPR type II crRNA and (ii) a stem loop-containing portion (Deltcheva et al., Nature 471:602-607). The duplex guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) into the target site. (See also U.S. Patent Application US 2015-0082478 A1, published on Mar. 19, 2015 and US 2015-0059010 A1, published on Feb. 26, 2015, both are hereby incorporated in its entirety by reference.)

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) the target site. (See also U.S. Patent Application US 2015-0082478 A1, published on Mar. 19, 2015 and US 2015-0059010 A1, published on Feb. 26, 2015, both are hereby incorporated in its entirety by reference.)

The term "variable targeting domain" or "VT domain" is used interchangeably herein and includes a nucleotide sequence that can hybridize (is complementary) to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" (of a guide polynucleotide) is used interchangeably herein and includes a nucleotide sequence that interacts with a Cas endonuclease polypeptide. A CER domain comprises a tracrNucleotide mate sequence followed by a tracrNucleotide sequence. The CER domain can be composed of a DNA sequence, a RNA sequence, a modified DNA sequence, a modified RNA sequence (see for example US 2015-0059010 A1, published on Feb. 26, 2015, incorporated in its entirety by reference herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

The terms "a polynucleotide originating from organism", "a polynucleotide derived from organism" are used interchangeably herein and refer to a polynucleotide (such as but not limited to crRNA and tracrRNA) that is naturally occurring in said organism (native to said organism) or is isolated from said organism, or is a synthetic oligonucleotide that is identical to the polynucleotide isolated from said organism). For example, a tracrRNA originating from *Brevibacillus laterosporus* refers to a tracrRNA that occurs in *Brevibacillus laterosporus*, or is isolated from *Brevibacillus laterosporus*, or is a synthetic oligonucleotide that is identical to the tracrRNA isolated from *Brevibacillus laterosporus*.

The terms "functional fragment", "fragment that is functionally equivalent" and "functionally equivalent fragment" of a guide RNA, crRNA or tracrRNA are used interchangeably herein, and refer to a portion or subsequence of the guide RNA, crRNA or tracrRNA, respectively, of the present disclosure in which the ability to function as a guide RNA, crRNA or tracrRNA, respectively, is retained.

The terms "functional variant", "Variant that is functionally equivalent" and "functionally equivalent variant" of a guide RNA, crRNA or tracrRNA (respectively) are used interchangeably herein, and refer to a variant of the guide RNA, crRNA or tracrRNA, respectively, of the present disclosure in which the ability to function as a guide RNA, crRNA or tracrRNA, respectively, is retained.

As used herein, the terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a genomic target site, enabling the Cas endonuclease to t recognize, bind to, and optionally nick or cleave (introduce a single or double strand break) into a genomic target site.

The components of the single or dual guide polynucleotides described herein (such as but no limiting to the crRNA, tracrRNA, variable targeting domain, crRNA repeat, tracr-mate domain, loop, tracrRNA anti-repeat, 3'tracrRNA sequence) can be modified to create functional variants of these components such that these functional variants can be combined to create a functional single or dual guide polynucleotide. Examples of guide polynucleotide component modifications are described herein and include nucleotide extensions at the 3' end, 5' end, or both end of any of components of the guide polynucleotide, and/or nucleotide sequence modifications (substitutions, insertions, deletions), and/or chemical modifications, and/or linkage modifications, or any combinations thereof.

Extensions at 3' end, 5' end, or both ends of any of components of the guide polynucleotide can be can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length.

Nucleotide sequence modification of the guide polynucleotide components include a 5' cap, a 3' polyadenylated tail, a riboswitch sequence, a stability control sequence, a sequence that forms a dsRNA duplex, a modification or sequence that targets the guide polynucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof.

In one aspect, the functional variant single or dual guide polynucleotide has a similar activity than the guide polynucleotides of SEQ ID NOs: 127-139. In another aspect, the functional variant single or dual guide polynucleotide has an increased activity when compared to the guide polynucleotides of SEQ ID NOs: 127-139. The guide activity includes guide polynucleotide/Cas endonuclease ability to recognize, bind to and cleave a double strand break and/or RGEN mutation frequency.

The terms "guide RNA/Cas endonuclease complex", "guide RNA/Cas endonuclease system", "guide RNA/Cas complex", "guide RNA/Cas system", "gRNA/Cas complex", "g RNA/Cas system", "RNA-guided endonuclease", "RGEN" are used interchangeably herein and refer to at least one RNA component and at least one Cas endonuclease that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site. A guide RNA/Cas endonuclease complex herein can comprise Cas protein(s) and suitable RNA component(s) of any of the four known CRISPR systems (Horvath and Barrangou, Science 327:167-170) such as a type I, II, or III CRISPR system. A guide RNA/Cas endonuclease complex can comprise a Type II Cas9 endonuclease and at least one RNA component (e.g., a crRNA and tracrRNA, or a gRNA). (See also U.S. Patent Application US 2015-0082478 A1, published on Mar. 19, 2015 and US 2015-0059010 A1, published on Feb. 26, 2015, both are hereby incorporated in its entirety by reference).

The guide polynucleotide can be introduced into a cell transiently, as single stranded polynucleotide or a double stranded polynucleotide, using any method known in the art such as, but not limited to, particle bombardment, *Agrobacterium* transformation or topical applications. The guide polynucleotide can also be introduced indirectly into a cell by introducing a recombinant DNA molecule (via methods such as, but not limited to, particle bombardment or *Agrobacterium* transformation) comprising a heterologous nucleic acid fragment encoding a guide polynucleotide, operably linked to a specific promoter that is capable of transcribing the guide RNA in said cell. The specific promoter can be, but is not limited to, a RNA polymerase III promoter, which allow for transcription of RNA with precisely defined, unmodified, 5'- and 3'-ends (DiCarlo et al., Nucleic Acids Res. 41: 4336-4343; Ma et al., Mol. Ther. Nucleic Acids 3:e161).

The terms "target site", "target sequence", "target site sequence, "target DNA", "target locus", "genomic target site", "genomic target sequence", "genomic target locus" and "protospacer", are used interchangeably herein and refer to a polynucleotide sequence such as, but not limited to, a nucleotide sequence on a chromosome, episome, or any other DNA molecule in the genome (including chromosomal, choroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. Cells include, but are not limited to, human, non-human, animal, bacterial, fungal, insect, yeast, non-conventional yeast, and plant cells as well as plants and seeds produced by the methods described herein. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

The length of the target DNA sequence (target site) can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs. Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by an Cas endonuclease.

Assays to measure the single or double-strand break of a target site by an endonuclease are known in the art and generally measure the overall activity and specificity of the agent on DNA substrates containing recognition sites.

A "protospacer adjacent motif" (PAM) herein refers to a short nucleotide sequence adjacent to a target sequence (protospacer) that is recognized (targeted) by a guide polynucleotide/Cas endonuclease system described herein. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

A "randomized PAM" and "randomized protospacer adjacent motif" are used interchangeably herein, and refer to a random DNA sequence adjacent to a target sequence (protospacer) that is recognized (targeted) by a guide polynucleotide/Cas endonuclease system described herein. The randomized PAM sequence can be of any length but is typically 1, 2, 3, 4, 5, 6, 7, 8, 9, 10, 11, 12, 13, 14, 15, 16, 17, 18, 19 or 20 nucleotides long. A randomized nucleotide includes anyone of the nucleotides A, C, G or T.

The PAM sequence plays a key role in target recognition by licensing crRNA-guided base pairing to the protospacer sequence (Szczelkun et al, 2014, Proc. Natl. Acad. Sci. U.S.A. 111: 9798-803). A strict PAM requirement constrains DNA target selection and poses a limit to Cas9 genome editing applications. Target site selection may be further confined if unique genomic sites are required especially in large complex plant genomes like maize (Xie et al, 2014, Mol. Plant 7: 923-6). These constraints imposed by the PAM and the specificity of the Spy Cas9 can be overcome by systematically redesigning the PAM specificity of a single Cas9 protein (Kleinstiver et al, 2015, Nature 523, 481-485. Described herein is a different method to overcome constraints imposed by the PAM and the specificity of the Cas9, namely by exploring the natural diversity of Cas9 proteins. The method described herein can also be combined with the method of systematically redesigning the PAM specificity to overcome constraints imposed by the PAM and the specificity of the Cas endonucleases.

Cas9 proteins from different bacteria recognize different PAM sequences (Horvath et al, 2008, J. Bacteriol. 190: 1401-12; Jinek et al, 2012, Science 337: 816-21; Gasiunas et al, 2012, Cell 154: 442-451; Zhang et al, 2013, Cell 50: 488-503; Fonfara et al, 2014, Nucleic Acids Res. 42: 2577-2590). Typically, the PAM sequences of new Cas9 proteins are identified by computational analysis of sequences immediately flanking putative protospacers in bacteriophage genomes (Shah et al, 2013, RNA Biol. 10: 1-9). Currently, with >1000 Cas9 protein orthologues available (Chylinski et al, 2014 Nucleic Acids Res. 42: 6091-6105; Hsu et al, 2014, Cell 157: 1262-1278), most spacers in Type II CRISPR arrays show only a few if any matches to the phage sequences present in databases, indicating that the vast majority of the phage universe is still unexplored. This constrains computational PAM identification methods and hinders the exploration of Cas9 protein diversity for genome editing applications.

As described herein, to address this problem a method was developed to empirically examine the PAM sequence requirements for any Cas9 protein. The method is based on the analysis of the in vitro cleavage products of a plasmid DNA library which contains a fixed protospacer target sequence and a stretch of 5 or 7 randomized base pairs in the putative PAM region. Based on the methods described herein, the a stretch of randomized base pairs in the putative PAM region can be at least 1, 2, 3, 4, 5, 6, 7, 8, 9, 10, 11, 12, 13, 14, 15, 16, 17, 18, 19, or 20 base pairs.

Using the method described herein, the canonical PAM preferences for Cas9 proteins of *S. pyogenes* and *S. thermophilus* CRISPR1 and CRISPR3 systems were first confirmed. Next, the method described herein was applied to identify the PAM and guide RNA requirements for a novel Cas9 protein from the Type II CRISPR-Cas system of *B. laterosporus* SPP360D4. In the Type II system of *B. laterosporus*, the transcriptional direction of the tracrRNA and CRISPR region could not be reliably predicted by computational approaches. Therefore, two single guide RNA (sgRNA) variants for both possible sense and anti-sense expression scenarios of the tracrRNA and CRISPR array (Examples 5-8, 10-12 described herein) were synthesized and only one of the designed sgRNAs supported cleavage of the randomized PAM plasmid library by *B. laterosporus* Cas9. Deep sequencing analysis of the cleavage products revealed a novel PAM requirement for the *B. laterosporus* Cas9. One that requires a strong preference for a C residue at position 5 of the PAM sequence followed by moderate preferences for A residues at positions 7 and 8 with an overall PAM consensus of NNNNCNDD (N=G, C, A or T; D=A, G or T). With a strong preference for just a single nucleotide, *B. laterosporus* Cas9 provides a useful addition to the Cas9 genome editing toolbox.

To examine the genome editing potential of a novel Cas9 and sgRNA characterized with the method described herein, the *B. laterosporus* SPP360D4 Cas9 and sgRNA were tested in maize (Examples 5-8, 10-12, described herein). As a result of cleavage, imperfect DNA repair resulted in INDEL mutations at all 3 chromosomal sites tested with robust INDEL frequencies observed at 2 of the 3 sites. Interestingly, at one of the sites, a ~30% enhancement in the recovery of INDEL mutations was observed for the *B. laterosporus* Cas9 over the *S. pyogenes* Cas9 (Example 12).

In one embodiment described herein it is shown that cleavage of permissive PAMs is dependent on Cas9 concentration. For all Cas9 proteins analyzed, PAM sequences licensing plasmid DNA cleavage at higher (50 nM) Cas9 concentrations were more relaxed than PAM sequences identified at low (0.5 nM) Cas9 concentrations. This finding corroborates previous studies which demonstrated that lowering Cas9 concentration and shortening cleavage time prevents off-target cleavage by *S. pyogenes* Cas9 (Pattanayak et al, 2013, Nat. Biotechnol.: 1-7; Lin et al, 2014, Elife 3: e04766. doi: 10.7554/eLife.04766.). Since most other PAM determination methods have been performed in cells or cell extracts by expressing Cas9 at undefined concentrations (Ran et al, 2015, 2015 Apr. 9; 520(7546):186-91. doi: 10.1038/nature14299; Jiang et al, 2013, Nat. Biotechnol. 31: 233-9; Esvelt et al, 2013, November; 10(11):1116-21. doi: 10.1038/nmeth.2681; Kleinstiver et al, 2015), our method further refines PAM specificity assessments by the dose-dependent control of recombinant Cas9 protein in vitro. This allows the careful detailed examination of Cas9 PAM specificity as a function of Cas9 guide RNA complex concentration.

In one embodiment, the method describes herein further refines Cas9 PAM discovery efforts by the use of recombinant Cas9 protein and reframes PAM specificity as being non-static and dependent on Cas9-guide RNA complex concentration.

Described herein are novel Cas endonucleases derived from diverse organisms capable or forming guide polynucleotide/Cas endonuclease complexes with guide polynucleotides comprising crRNA and tracrRNA sequences fragments derived from their respective organisms. In one example, a Cas endonuclease derived from *Brevibacillus laterosporus* (SEQ ID NO: 140) was able to from a RGEN complex with a guide polynucleotide comprising a crRNA and a tracrRNA fragment derived from *Brevibacillus laterosporus* (such as SEQ ID NO: 47 or 127).

The Cas endonucleases described herein can also be used in complexes with guide polynucleotides derived from other Cas systems. In one example, the crRNA and/or tracrRNA domains of a guide polynucleotide capable of forming a complex with a Cas endonuclease from organism 1 (such that said RGEN complex is capable of recognizing, binding to, and optionally nicking or cleaving all or part of a specific DNA target sequence), can be exchanged with a crRNA and/or tracrRNA domain, or fragment thereof, derived from a different organism (organism 2), thereby forming a chimeric guide, and still be able to form a functional complex with the Cas endonuclease derived from organism 1.

Similarities in guide RNA s between different Cas systems can be determined based on sequence composition and secondary structures of the guide RNAs. In one example, the secondary structure and sequence similarity of the sgRNAs from *Lactobacillus reuteri* Mlc3 (Lreu) (SEQ ID NO: 114), *Lactobacillus rossiae* DSM 15814 (Lros) SEQ ID NO: 115) and *Pediococcus pentosaceus* SL4 (Ppen) SEQ ID NO: 116) was determined and revealed that these three sgRNAs have very similar secondary structures. It is anticipated that fragments from Lreu, Lros and PPen guide RNAs, such as but not limited to repeat structures or anti-repeat structures or any-one guide RNA domain, can be exchanged and/or mixed with one another to create chimeric guides capable of forming a RGEN with any one of the Lrue, Lros or Ppen Cas endonuclease (SEQ ID NOs: 81. 82 and 93, respectively). In another example, the secondary structure and sequence similarity of the sgRNAs from *Lactobacillus nodensis* JCM 14932 (Lnod) (SEQ ID NO:117), *Loktanella vestfoldensis* (Lves) (SEQ ID NO:121) and *Sphingomonas sanxanigenens* NX02 (Ssan) (SEQ ID NO: 122) was determined to be very similar, indicating that fragments from Lnod, Lves and Ssan guide RNAs, such as but not limited to repeat structures or anti-repeat structures or any-one guide RNA domain, can be exchanged and/or mixed with one another to create chimeric guides capable of forming a RGEN with any one of the Lnod, Lves or Ssan Cas endonuclease SEQ ID NOs: 84, 87 and 88, respectively).

In another example, the secondary structure and sequence similarity of the sgRNAs from *Epilithonimonas tenax* DSM 16811 (Eten) (SEQ ID NO:123), *Sporocytophaga myxococcoides* (Smyx) (SEQ ID NO:138) and *Psychroflexus torquis* ATCC 700755 (Ptor) (SEQ ID NO: 139) was determined to be very similar, indicating that fragments from Eten, Smyx and Ptor guide RNAs, such as but not limited to repeat structures or anti-repeat structures or any-one guide RNA domain, can be exchanged and/or mixed with one another to create chimeric guides capable of forming a RGEN with any one of the Eten, Smyx or Ptor Cas endonuclease SEQ ID NOs: 89, 90 and 91, respectively).

In one aspect, the Cas endonuclease and the crRNA and/or tracrRNA (or sg RNA) capable of forming a functional complex are derived or obtained from phylogenetically related groups. (See, for example, Fonfara et al Nucleic acid research 2014 Vol 42, No 4 pg. 2577-2590). It is understood that, based on the components of the novel Cas endonuclease systems described herein (crRNAs, tracrRNAs, Cas endonucleases, PAM sequences) one skilled in the art can exchange and/or mix any one component derived from one organism with any one component derived from another organism to make a functional guide polynucleotide/Cas endonuclease complex.

Guide polynucleotides can be modified to contain different sequence or structure, yet be functionally equivalent or possess superior activity (binding, cutting, specificity). In one aspect, the chimeric guide polynucleotide can comprise at least one nucleotide, phosphodiester bond or linkage modification, or chemical modification such as, but not limited, to Locked Nucleic Acid (LNA), 5-methyl dC, 2,6-Diaminopurine, 2'-Fluoro A, 2'-Fluoro U, 2'-O-Methyl RNA, 2'-O-Methyl (M) modification, 2'-O-Methyl 3'phosphorothioate (MS) modification, 2'-O-Methyl 3'thioPACE (MSP) modification, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization (Hendel et al. 2015 Nature Biotechnology Vol. 33 pg. 985-991). Chimeric guide polynucleotides can be generated chemically, with or without sugar or backbone modifications. Chimeric guide polynucleotides can also be generated by in vitro transcription or delivered by DNA molecules containing promoters for expression The PAM interacting domain, HNH or HNH-like nuclease domain, and/or RuvC or RuvC-like nuclease domains from the Cas endonuclease proteins described herein find use in creating Cas scaffolds (US2016/0102324 entitled "New compact scaffold of Cas9 in the type II CRISPR system, published Apr. 14, 2016 and incorporated herein by reference). The boundaries of the PAM interacting domain, RuvC and HNH domains of the Cas endonuclease described herein can be determined and new shorter Cas endonucleases derived from the Cas endonucleases described herein (or any one functional combination/fusion protein thereof) can be designed, The terms "targeting", "gene targeting" and "DNA targeting" are used interchangeably herein. DNA targeting herein may be the specific introduction of a knock-out, edit, or knock-in at a particular DNA sequence, such as in a chromosome or plasmid of a cell. In general, DNA targeting can be performed herein by cleaving one or both strands at a specific DNA sequence in a cell with a Cas protein associated with a suitable polynucleotide component. Such DNA cleavage, if a double-strand break (DSB), can prompt NHEJ or HDR processes which can lead to modifications at the target site.

The terms "knock-out", "gene knock-out" and "genetic knock-out" are used interchangeably herein. A knock-out represents a DNA sequence of a cell that has been rendered partially or completely inoperative by targeting with a Cas protein; such a DNA sequence prior to knock-out could have encoded an amino acid sequence, or could have had a regulatory function (e.g., promoter), for example. A knock-out may be produced by an indel (insertion or deletion of nucleotide bases in a target DNA sequence through NHEJ), or by specific removal of sequence that reduces or completely destroys the function of sequence at or near the targeting site.

In one embodiment of the disclosure, the method comprises a method for modifying a target site in the genome of a cell, the method comprising providing to said cell at least one Cas9 endonuclease originating from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755, and at least one guide RNA, wherein said guide RNA and Cas endonuclease can form a complex that is capable of recognizing, binding to, and optionally nicking or cleaving all or part of said target site. The embodiment can further comprise identifying at least one cell that has a modification at said target, wherein the modification at said target site is selected from the group consisting of (i) a replacement of at least one nucleotide, (ii) a deletion of at least one nucleotide, (iii) an insertion of at least one nucleotide, and (iv) any combination of (i)-(iii).

The guide polynucleotide/Cas endonuclease system can be used in combination with a co-delivered polynucleotide modification template to allow for editing (modification) of a genomic nucleotide sequence of interest. (See also U.S. Patent Application US 2015-0082478 A1, published on Mar. 19, 2015 and WO2015/026886 A1, published on Feb. 26, 2015, both are hereby incorporated in its entirety by reference.)

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

In one embodiment, the disclosure describes a method for editing a nucleotide sequence in the genome of a cell, the method comprising providing a guide polynucleotide, a polynucleotide modification template, and at least one Cas endonuclease to a cell, wherein the Cas endonuclease is capable of introducing a single or double-strand break at a target sequence in the genome of said cell, wherein said polynucleotide modification template includes at least one nucleotide modification of said nucleotide sequence. Cells include, but are not limited to, human, non-human, animal, bacterial, fungal, insect, yeast, and plant cells as well as plants and seeds produced by the methods described herein. Plant cells include cells selected from the group consisting of maize, rice, sorghum, rye, barley, wheat, millet, oats, sugarcane, turfgrass, or switchgrass, soybean, canola, alfalfa, sunflower, cotton, tobacco, peanut, potato, tobacco, *Arabidopsis*, and safflower cells. The nucleotide to be edited can be located within or outside a target site recognized and cleaved by a Cas endonuclease. In one embodiment, the at least one nucleotide modification is not a modification at a target site recognized and cleaved by a Cas endonuclease. In another embodiment, there are at least 1, 2, 3, 4, 5, 6, 7, 8, 9, 10, 11, 12, 13, 14, 15, 16, 17, 18, 19, 20, 21, 22, 23, 24, 25, 26, 27, 30, 40, 50, 100, 200, 300, 400, 500, 600, 700, 900 or 1000 nucleotides between the at least one nucleotide to be edited and the genomic target site.

In one embodiment of the disclosure, the method comprises a method for editing a nucleotide sequence in the genome of a cell, the method comprising providing to said cell at least one Cas9 endonuclease originating from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755, a polynucleotide modification template, and at least one guide RNA, wherein said polynucleotide modification template comprises at least one nucleotide modification of said nucleotide sequence, wherein said guide RNA and Cas endonuclease can form a complex that is capable of recognizing, binding to, and optionally nicking or cleaving all or part of said target site. Cells include, but are not limited to, human, non-human, animal, bacterial, fungal, insect, yeast, and plant cells as well as plants and seeds produced by the methods described herein.

Genome editing can be accomplished using any method of gene editing available. For example, gene editing can be accomplished through the introduction into a host cell of a polynucleotide modification template (sometimes also referred to as a gene repair oligonucleotide) containing a targeted modification to a gene within the genome of the host cell. The polynucleotide modification template for use in such methods can be either single-stranded or double-stranded. Examples of such methods are generally described, for example, in US Publication No. 2013/0019349.

In some embodiments, gene editing may be facilitated through the induction of a double-stranded break (DSB) in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), and the like. In some embodiments, the introduction of a DSB can be combined with the introduction of a polynucleotide modification template.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB. Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, U.S. application 62/023,246, filed on Jul. 7, 2014, and U.S. application 62/036,652, filed on Aug. 13, 2014, all of which are incorporated by reference herein.

The terms "knock-in", "gene knock-in, "gene insertion" and "genetic knock-in" are used interchangeably herein. A knock-in represents the replacement or insertion of a DNA sequence at a specific DNA sequence in cell by targeting with a Cas protein (by HR, wherein a suitable donor DNA polynucleotide is also used). Examples of knock-ins are a specific insertion of a heterologous amino acid coding sequence in a coding region of a gene, or a specific insertion of a transcriptional regulatory element in a genetic locus.

Various methods and compositions can be employed to obtain a cell or organism having a polynucleotide of interest inserted in a target site for a Cas endonuclease. Such methods can employ homologous recombination to provide integration of the polynucleotide of Interest at the target site. In one method provided, a polynucleotide of interest is provided to the organism cell in a donor DNA construct. As used herein, "donor DNA" is a DNA construct that comprises a polynucleotide of Interest to be inserted into the target site of a Cas endonuclease. The donor DNA construct further comprises a first and a second region of homology that flank the polynucleotide of Interest. The first and second regions of homology of the donor DNA share homology to a first and a second genomic region, respectively, present in or flanking the target site of the cell or organism genome. By "homology" is meant DNA sequences that are similar. For example, a "region of homology to a genomic region" that is found on the donor DNA is a region of DNA that has a similar sequence to a given "genomic region" in the cell or organism genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bps. The amount of homology can also described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al, (1989) *Molecular Cloning: A Laboratory Manual,* (Cold Spring Harbor Laboratory Press, NY); *Current Protocols in Molecular Biology,* Ausubel et al, Eds (1994) Current Protocols, (Greene Publishing Associates, Inc. and John Wiley & Sons, Inc.); and, Tijssen (1993) *Laboratory Techniques in Biochemistry and Molecular Biology—Hybridization with Nucleic Acid Probes,* (Elsevier, New York).

In one embodiment of the disclosure, the method comprises a method for modifying a target site in the genome of a cell, the method comprising providing to said cell at least one guide RNA, at least one donor DNA, and at least one Cas9 endonuclease originating from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755, wherein said at least one guide RNA and at least one Cas endonuclease can form a complex that is capable of recognizing, binding to, and optionally nicking or cleaving all or part of said target site, wherein said donor DNA comprises a polynucleotide of interest. Cells include, but are not limited to, human, non-human, animal, bacterial, fungal, insect, yeast, and plant cells as well as plants and seeds produced by the methods described herein. The embodiment can further comprise, identifying at least one cell that said polynucleotide of interest integrated in or near said target site.

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

Polynucleotides of interest and/or traits can be stacked together in a complex trait locus as described in US-2013-0263324-A1, published 3 Oct. 2013 and in PCT/US13/22891, published Jan. 24, 2013, both applications are hereby incorporated by reference. The guide polynucleotide/Cas9 endonuclease system described herein provides for an efficient system to generate double strand breaks and allows for traits to be stacked in a complex trait locus.

The guide polynucleotide/Cas endonuclease system can be used for introducing one or more polynucleotides of interest or one or more traits of interest into one or more target sites by providing one or more guide polynucleotides, one Cas endonuclease, and optionally one or more donor DNAs to a plant cell. ((as described in U.S. patent application Ser. No. 14/463,687, file Aug. 20, 2014, incorporated by reference herein). A fertile plant can be produced from that plant cell that comprises an alteration at said one or more target sites, wherein the alteration is selected from the group consisting of (i) replacement of at least one nucleotide, (ii) a deletion of at least one nucleotide, (iii) an insertion of at least one nucleotide, and (iv) any combination of (i)-(iii). Plants comprising these altered target sites can be crossed with plants comprising at least one gene or trait of interest in the same complex trait locus, thereby further stacking traits in said complex trait locus. (see also US-2013-0263324-A1, published 3 Oct. 2013 and in PCT/US13/22891, published Jan. 24, 2013).

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the organism genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

As used herein, "homologous recombination" includes the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events: the longer the region of homology, the greater the frequency. The length of the homology region needed to observe homologous recombination is also species-variable. In many cases, at least 5 kb of homology has been utilized, but homologous recombination has been observed with as little as 25-50 bp of homology. See, for example, Singer et al., (1982) Cell 31:25-33; Shen and Huang, (1986) Genetics 112:441-57; Watt et al., (1985) Proc. Natl. Acad. Sci. USA 82:4768-72, Sugawara and Haber, (1992) Mol Cell Biol 12:563-75, Rubnitz and Subramani, (1984) Mol Cell Biol 4:2253-8; Ayares et al., (1986) Proc. Natl. Acad. Sci. USA 83:5199-203; Liskay et al., (1987) Genetics 115:161-7.

Homology-directed repair (HDR) is a mechanism in cells to repair double-stranded and single stranded DNA breaks. Homology-directed repair includes homologous recombination (HR) and single-strand annealing (SSA) (Lieber. 2010 Annu. Rev. Biochem. 79:181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks (Davis and Maizels. PNAS (0027-8424), 111 (10), p. E924-E932.

Alteration of the genome of a plant cell, for example, through homologous recombination (HR), is a powerful tool for genetic engineering. Despite the low frequency of homologous recombination in higher plants, there are a few examples of successful homologous recombination of plant endogenous genes. The parameters for homologous recombination in plants have primarily been investigated by rescuing introduced truncated selectable marker genes. In these experiments, the homologous DNA fragments were typically between 0.3 kb to 2 kb. Observed frequencies for homologous recombination were on the order of $10^{-4}$ to $10^{-5}$. See, for example, Halfter et al., (1992) Mol Gen Genet 231:186-93; Offringa et al., (1990) EMBO J 9:3077-84; Offringa et al., (1993) Proc. Natl. Acad. Sci. USA 90:7346-50; Paszkowski et al., (1988) EMBO J 7:4021-6; Hourda and Paszkowski, (1994) Mol Gen Genet 243:106-11; and Risseeuw et al., (1995) Plant J 7:109-19.

Homologous recombination has been demonstrated in insects. In *Drosophila*, Dray and Gloor found that as little as 3 kb of total template:target homology sufficed to copy a large non-homologous segment of DNA into the target with reasonable efficiency (Dray and Gloor, (1997) Genetics 147:689-99). Using FLP-mediated DNA integration at a target FRT in *Drosophila*, Golic et al., showed integration was approximately 10-fold more efficient when the donor and target shared 4.1 kb of homology as compared to 1.1 kb of homology (Golic et al., (1997) Nucleic Acids Res 25:3665). Data from *Drosophila* indicates that 2-4 kb of homology is sufficient for efficient targeting, but there is some evidence that much less homology may suffice, on the order of about 30 bp to about 100 bp (Nassif and Engels, (1993) Proc. Natl. Acad. Sci. USA 90:1262-6; Keeler and Gloor, (1997) Mol Cell Biol 17:627-34).

Homologous recombination has also been accomplished in other organisms. For example, at least 150-200 bp of homology was required for homologous recombination in the parasitic protozoan *Leishmania* (Papadopoulou and Dumas, (1997) Nucleic Acids Res 25:4278-86). In the filamentous fungus *Aspergillus nidulans*, gene replacement has been accomplished with as little as 50 bp flanking homology (Chaveroche et al., (2000) Nucleic Acids Res 28:e97). Targeted gene replacement has also been demonstrated in the ciliate Tetrahymena *thermophila* (Gaertig et al., (1994) Nucleic Acids Res 22:5391-8). In mammals, homologous recombination has been most successful in the mouse using pluripotent embryonic stem cell lines (ES) that can be grown in culture, transformed, selected and introduced into a mouse embryo. Embryos bearing inserted transgenic ES cells develop as genetically offspring. By interbreeding siblings, homozygous mice carrying the selected genes can be obtained. An overview of the process is provided in Watson et al., (1992) Recombinant DNA, 2nd Ed., (Scientific American Books distributed by WH Freeman & Co.); Capecchi, (1989) Trends Genet 5:70-6; and Bronson, (1994) J Biol Chem 269:27155-8. Homologous recombination in mammals other than mouse has been limited by the lack of stem cells capable of being transplanted to oocytes or developing embryos. However, McCreath et al., Nature 405:1066-9 (2000) reported successful homologous recombination in sheep by transformation and selection in primary embryo fibroblast cells.

Error-prone DNA repair mechanisms can produce mutations at double-strand break sites. The Non-Homologous-End-Joining (NHEJ) pathways are the most common repair mechanism to bring the broken ends together (Bleuyard et al., (2006) DNA Repair 5:1-12). The structural integrity of chromosomes is typically preserved by the repair, but deletions, insertions, or other rearrangements are possible. The two ends of one double-strand break are the most prevalent substrates of NHEJ (Kirik et al., (2000) EMBO J 19:5562-6), however if two different double-strand breaks occur, the free ends from different breaks can be ligated and result in chromosomal deletions (Siebert and Puchta, (2002) Plant Cell 14:1121-31), or chromosomal translocations between different chromosomes (Pacher et al., (2007) Genetics 175: 21-9).

Episomal DNA molecules can also be ligated into the double-strand break, for example, integration of T-DNAs into chromosomal double-strand breaks (Chilton and Que, (2003) Plant Physiol 133:956-65; Salomon and Puchta, (1998) EMBO J 17:6086-95). Once the sequence around the double-strand breaks is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) Plant Cell 16:342-52). Ectopic and/or epigenic DNA sequences may also serve as a DNA repair template for homologous recombination (Puchta, (1999) Genetics 152: 1173-81).

Once a double-strand break is induced in the DNA, the cell's DNA repair mechanism is activated to repair the break. Error-prone DNA repair mechanisms can produce mutations at double-strand break sites. The most common repair mechanism to bring the broken ends together is the nonhomologous end-joining (NHEJ) pathway (Bleuyard et al., (2006) DNA Repair 5:1-12). The structural integrity of chromosomes is typically preserved by the repair, but deletions, insertions, or other rearrangements are possible (Siebert and Puchta, (2002) Plant Cell 14:1121-31; Pacher et al., (2007) Genetics 175:21-9).

Alternatively, the double-strand break can be repaired by homologous recombination between homologous DNA sequences. Once the sequence around the double-strand break is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) Plant Cell 16:342-52). Ectopic and/or epigenic DNA sequences may also serve as a DNA repair template for homologous recombination (Puchta, (1999) Genetics 152:1173-81).

DNA double-strand breaks appear to be an effective factor to stimulate homologous recombination pathways (Puchta et al., (1995) Plant Mol Biol 28:281-92; Tzfira and White, (2005) Trends Biotechnol 23:567-9; Puchta, (2005) J Exp Bot 56:1-14). Using DNA-breaking agents, a two- to nine-fold increase of homologous recombination was observed between artificially constructed homologous DNA repeats in plants (Puchta et al., (1995) Plant Mol Biol 28:281-92). In maize protoplasts, experiments with linear DNA molecules demonstrated enhanced homologous recombination between plasmids (Lyznik et al., (1991) Mol Gen Genet 230:209-18).

The donor DNA may be introduced by any means known in the art. For example, a plant having a target site is provided. The donor DNA may be provided by any transformation method known in the art including, for example, *Agrobacterium*-mediated transformation or biolistic particle bombardment. The donor DNA may be present transiently in the cell or it could be introduced via a viral replicon. In the presence of the Cas endonuclease and the target site, the donor DNA is inserted into the transformed plant's genome.

Further uses for guide RNA/Cas endonuclease systems have been described (See U.S. Patent Application US 2015-0082478 A1, published on Mar. 19, 2015, WO2015/026886 A1, published on Feb. 26, 2015, US 2015-0059010 A1, published on Feb. 26, 2015, U.S. application 62/023,246, filed on Jul. 7, 2014, and U.S. application 62/036,652, filed on Aug. 13, 2014, all of which are incorporated by reference herein) and include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

Given the diversity of Type II CRISPR-Cas systems (Fonfara et al. (2014) Nucleic Acids Res. 42:2577-2590), it is plausible that many of the Cas9 endonucleases and cognate guide RNAs may have unique sequence recognition and enzymatic properties different from those previously described or characterized. For example, cleavage activity and specificity may be enhanced or proto-spacer adjacent motif (PAM) sequence may be different leading to increased genomic target site density. To tap into this vast unexplored diversity and expand the repertoire of Cas9 endonucleases and cognate guide RNAs available for genome targeting, two components of target site recognition need to be cooperatively characterized for each new system, the PAM sequence and the guide RNA (either duplexed CRISPR RNA (crRNA) and trans-activating CRISPR RNA (tracrRNA) or chimeric fusion of crRNA and tracrRNA (single guide RNA (sgRNA. Rapid in vitro methods described herein have been developed to concertedly characterize both the guide RNA and PAM sequence of Type II Cas9 proteins.

Figure 3:
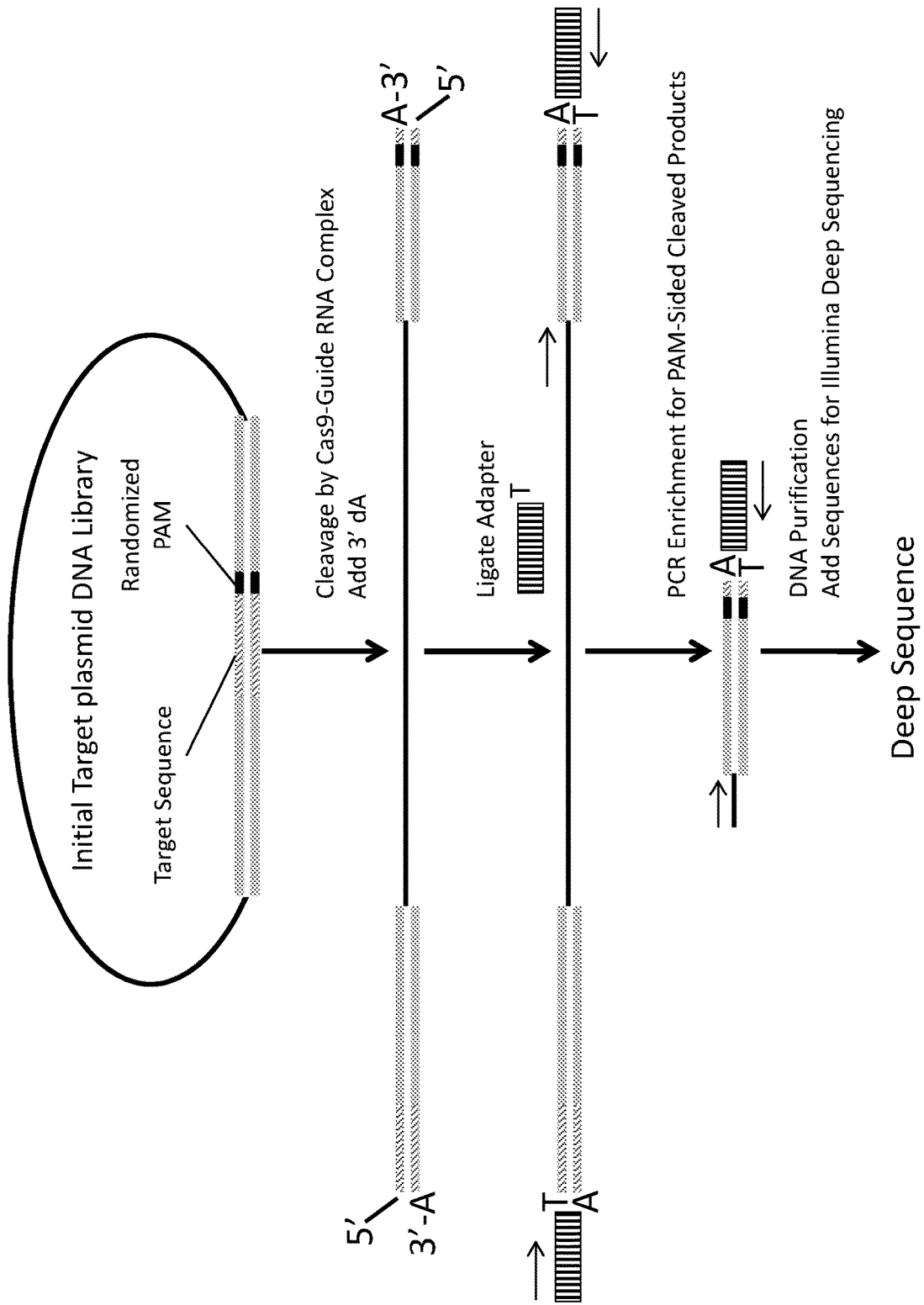
FIG. 3 shows a diagram of the production of enriched PAM sided products for deep sequencing and identification of PAM preferences.

Methods for assaying Cas9 PAM preferences have been described herein (see Example 3, Example 4 and Example 7). In one embodiment, the Cas9 endonuclease PAM preferences was assayed in a dose dependent manner by subjecting the randomized PAM libraries described herein to in vitro digestion with different concentrations of recombinant Cas9 protein preloaded with guide RNA. After digestion with Cas9-guide RNA ribonucleoprotein (RNP) complexes, PAM sequence combinations from the randomized PAM library that supported cleavage were captured by ligating adapters to the free-ends of the plasmid DNA molecules cleaved by the Cas9-guide RNA complex (FIG. 3). To promote efficient ligation and capture of the cleaved ends, the typically blunt-ended double-stranded DNA cut generated by Cas9 endonucleases was modified to contain a 3' dA overhang and adapters were modified to contain a complementary 3'dT overhang. To generate sufficient quantities of DNA for sequencing, DNA fragments harboring the PAM sequence supporting cleavage were PCR amplified using a primer in the adapter and another directly adjacent to the PAM region. The resulting PCR amplified Cas9 PAM libraries were converted into ampli-seq templates and single-read deep sequenced from the adapter-side of the amplicon. To ensure adequate coverage, the Cas9 PAM libraries were sequenced to a depth at least 5 times greater than the diversity in the initial randomized PAM library (5,120 and 81,920 reads for the 5 and 7 bp PAM randomized libraries, respectively). PAM sequences were identified from the resulting sequence data by only selecting those reads containing a 12 nt sequence match flanking either side of the 5 or 7 nt PAM sequence (depending on the randomized PAM library used); capturing only those PAM sequences resulting from perfect Cas9-guide RNA target site recognition and cleavage. To compensate for the inherent bias in the initial randomized PAM libraries, the frequency of each PAM sequence was normalized to its frequency in the starting library. The composition of the resulting PAM sequences can then be examined using a position frequency matrix (PFM) (Stormo, 2013 Quant. Biol. 1: 115-130)

As described herein, to validate the randomness of the PAM library disclosed herein (PAM library validation), PCR fragments spanning the 5 bp and 7 bp randomized PAM regions were generated by Phusion High-Fidelity DNA Polymerase (Thermo Fisher Scientific) amplification (15 cycles of a 2-step amplification protocol) using the primer pair combinations TK-119/pUC-dir and TK-113/pUC-dir (SEQ ID NO: 175/SEQ ID NO:5) for the 5 bp and 7 bp libraries, respectively. The resulting 145 bp PCR product was purified using GeneJET PCR Purification Kit (Thermo Fisher Scientific) and the sequences necessary for amplicon-specific barcodes and Illumina sequencing were "tailed" on through two rounds of PCR each consisting of 10 cycles. In some examples, the primer pair combinations in the first round of PCR were JKYS800.1/JKYS803 and JKYS921.1 (SEQ ID NO:176)/JKYS812 (SEQ ID NO: 32) for the 5 bp and 7 bp libraries, respectively. A set of primers, JKYS557 (SEQ ID NO: 177)/JKYS558 (SEQ ID NO: 178), universal to all primary PCR reactions were utilized for the secondary PCR amplification. The resulting PCR amplifications were purified with a Qiagen PCR purification spin column, concentration measured with a Hoechst dye-based fluorometric assay, combined in an equimolar ratio and single read 60-100 nucleotide-length deep sequencing was performed on Illumina's MiSeq Personal Sequencer with a 5-10% (v/v) spike of PhiX control v3 (Illumina, FC-110-3001) to off-set sequence bias. The PAM sequence for only those reads containing a perfect 12 nt sequence match flanking either side of the randomized PAM sequence were captured and used to examine the frequency and diversity of PAM sequences present in the library.

In one embodiment of the disclosure, the method comprises a method for producing a plasmid DNA library containing a randomized Protospacer-Adjacent-Motif (PAM) sequence, the method comprising: a) providing a first single stranded oligonucleotide comprising a target sequence that can be recognized by a guide RNA/Cas endonuclease complex; b) providing a second single stranded oligonucleotide comprising a randomized PAM sequence adjacent to a nucleotide sequence capable of hybridizing with the target sequence of (a); c) producing an oligoduplex comprising said randomized PAM sequence by combining the first single stranded oligonucleotide of (a) and the second single stranded oligonucleotide of (b); d) producing a ligation product by ligating the oligoduplex from (c) with a linearized plasmid; and, e) transforming host cells with the ligation product of (e) and recovering multiple host cell colonies representing the plasmid library.

Host cells include, but are not limited to, human, non-human, animal, bacterial, fungal, insect, yeast, non-conventional yeast, and plant cells. One skilled in the art can ligate the oligoduplex of (c) directly into a linearized vector without restriction enzyme digestion, or can use two restriction enzyme sites, one upstream (5') and one downstream (3') of the target site. The first single stranded oligonucleotide can comprise a restriction endonuclease recognition site located upstream of a target sequence and the ligation product of (d) is produced by first cleaving the oligoduplex with a restriction endonuclease that recognizes the restriction endonuclease recognition site of (a) followed by ligating the cleaved oligoduplex from (d) with a linearized plasmid.

In one embodiment, a method is described that allows the direct-read out of Cas9 endonuclease PAM specificity as a function of Cas9-guide RNA complex concentration in vitro. We confirmed the reported PAM sequences for *Streptococcus pyogenes* (Spy), *Streptococcus thermophilus* CRISPR1 (Sth1) and *Streptococcus thermophilus* CRISPR3 (Sth3) and identified the PAM sequence and guide RNA for a novel Cas9 from *Brevibacillus laterosporus* SPP360D4 (Blat), and provided experimental evidence for Blat Cas9 functional activity both in vitro and in plants.

In one embodiment of the disclosure, the method comprises a method for producing a plasmid DNA library containing a randomized Protospacer-Adjacent-Motif (PAM) sequence, the method comprising transforming at least one host cell with a ligation product and recovering multiple host cell colonies representing the plasmid library, wherein said ligation product was generated by contacting a library of linear oligoduplexes with a linearized plasmid, wherein each oligoduplex member of said library of oligoduplexes comprises a first single stranded oligonucleotide comprising a-target sequence, and a second single stranded oligonucleotide comprising a randomized PAM sequence adjacent to a nucleotide sequence capable of hybridizing with said target sequence. One skilled in the art can ligate the oligoduplex of (c) directly into a linearized vector without restriction enzyme digestion, or can use two restriction enzyme sites, one upstream (5') and one downstream (3') of the target site.

In one embodiment of the disclosure, the method comprises a method for producing a ligation product containing a randomized Protospacer-Adjacent-Motif (PAM) sequence, the method comprising: a) providing a first single stranded oligonucleotide comprising restriction endonuclease recognition site located upstream of a target sequence that can be recognized by a guide RNA/Cas endonuclease complex; b) providing a second single stranded oligonucleotide comprising a randomized PAM sequence adjacent a nucleotide sequence capable of hybridizing with the target sequence of (a); c) producing an oligoduplex comprising said randomized PAM sequence by combining the first single stranded oligonucleotide of (a) and the second single stranded oligonucleotide of (b); and, d) producing a ligation product by ligating the oligoduplex from (c) with a linearized plasmid.

In one embodiment of the disclosure, the method comprises a method for identification of a Protospacer-Adjacent-Motif (PAM) sequence, the method comprising: a) providing a library of plasmid DNAs, wherein each one of said plasmid DNAs comprises a randomized Protospacer-Adjacent-Motif sequence integrated adjacent to a target sequence that can be recognized by a guide RNA/Cas endonuclease complex; b) providing to said library of plasmids a guide RNA and a Cas endonuclease protein, wherein said guide RNA and Cas endonuclease protein can form a complex that is capable of introducing a double strand break into the said target sequence, thereby creating a library of cleaved targets; c) ligating adaptors to the library of cleaved targets of (b) allowing for the library of cleaved targets to be amplified; d) amplifying the library of cleaved targets such that cleaved products containing the randomized PAM sequence are enriched, thereby producing a library of enriched PAM-sided targets; e) sequencing the library of (a) and the library of enriched PAM-sided targets of (d) and identifying the nucleotide sequence adjacent to the cleaved targets of (b) on either strand of the plasmid DNA, wherein said nucleotide sequence represents a putative Protospacer-Adjacent-Motif sequences; and, f) determining the fold enrichment of each nucleotide within the putative Protospacer-Adjacent-Motif sequence relative to the plasmid DNA library of (a).

The randomized PAM libraries described herein can also be used in combination with immunoprecipitation then sequencing approach using dCAS9 for further PAM discovery. The randomized PAM libraries can also be put on a microchip followed by cleaving the chip-array library. The randomized PAM libraries described herein can also be used in combination with Phage-display as a method to identify PAMs. (Isalan, M., Klug, A. and Choo, Y. (2001) A rapid, generally applicable method to engineer zinc fingers illustrated by targeting the HIV-1 120 promoter. Nat. Biotechnol., 19, 656-660.; Dreier, B., Fuller, R. P., Segal, D. J., Lund, C., Blancafort, P., Huber, A., Koksch, B. and Barbas, C. F., III (2005) Development of zinc finger domains for recognition of the 50-CNN-30 family DNA sequences and their use in the construction of artificial transcription factors. J. Biol. 125 Chem., 280, 35588-35597).

In one embodiment of the disclosure, the method comprises a method for identification of a tracrRNA of an organism, the method comprising: a) providing a first single guide RNA candidate comprising a chimeric non-naturally occurring crRNA comprising a variable targeting domain capable of hybridizing to a target sequence in the genome of a cell, linked to a first nucleotide sequence representing the sense expression of a candidate tracrRNA naturally occurring in said organism; b) providing a second single guide RNA candidate comprising a chimeric non-naturally occurring crRNA comprising a variable targeting domain capable of hybridizing to a target sequence in the genome of said cell, linked to a second nucleotide sequence representing the sense expression of a candidate tracrRNA naturally occurring in said organism; c) providing to the first and second single guide RNA candidates a Cas endonuclease protein, wherein said Cas endonuclease protein can form a complex with either the first single guide RNA candidate or the second single guide RNA candidate, wherein said complex is capable of introducing a double strand break into said target sequence; and d) identification of the first or second guide RNA candidate and its tracrRNA component that complexes to the Cas endonuclease of (c) and results in cleavage of the target sequence in the genome of said cell.

In one embodiment of the disclosure, the method comprises a method for identification of a tracrRNA of an organism, the method comprising: a) identifying a CRISPR array repeat sequence in a genomic locus of said organism; b) aligning the CRISPR array repeat sequence of (a) with the sequence of the genomic locus of (a) and identifying an antirepeat sequence that encodes a tracrRNA; and, c) determining the transcriptional direction of the tracrRNA.

In one embodiment of the disclosure, the method comprises a method for designing a single guide RNA, the method comprising: a) aligning a tracrRNA sequence with a CRISPR array repeat sequence from a genomic locus of an organism, wherein said CRISPR array repeat sequence comprises a crRNA sequence; b) deducing the transcriptional direction of the CRISPR array, thereby also deducing the crRNA sequence; and, c) designing a single guide RNA comprising said tracrRNA and crRNA sequences.

In one embodiment of the disclosure, the method comprises a method for producing target sequences, the method comprising: a) identifying a polynucleotides of interest; b) introducing a Protospacer-Adjacent-Motif (PAM) sequence adjacent to said polynucleotide of interest, wherein said PAM sequence comprises the nucleotide sequence NNNNCND, thereby creating a thereby creating a target site for a guide RNA/Cas9 endonuclease complex; and, c) identifying a polynucleotides of interest.

Polynucleotides of interest are further described herein and include polynucleotides reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for genetic engineering will change accordingly.

Further provided are methods for identifying at least one plant cell, comprising in its genome, a polynucleotide of interest integrated at the target site. A variety of methods are available for identifying those plant cells with insertion into the genome at or near to the target site without using a screenable marker phenotype. Such methods can be viewed as directly analyzing a target sequence to detect any change in the target sequence, including but not limited to PCR methods, sequencing methods, nuclease digestion, Southern blots, and any combination thereof. See, for example, U.S. patent application Ser. No. 12/147,834, herein incorporated by reference to the extent necessary for the methods described herein. The method also comprises recovering a plant from the plant cell comprising a polynucleotide of Interest integrated into its genome. The plant may be sterile or fertile. It is recognized that any polynucleotide of interest can be provided, integrated into the plant genome at the target site, and expressed in a plant.

Polynucleotides/polypeptides of interest include, but are not limited to, herbicide-resistance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, fatty acids, and oil content and/or composition. More specific polynucleotides of interest include, but are not limited to, genes that improve crop yield, polypeptides that improve desirability of crops, genes encoding proteins conferring resistance to abiotic stress, such as drought, nitrogen, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, fertility or sterility, grain characteristics, and commercial products. Genes of interest include, generally, those involved in oil, starch, carbohydrate, or nutrient metabolism as well as those affecting kernel size, sucrose loading, and the like that can be stacked or used in combination with other traits, such as but not limited to herbicide resistance, described herein.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference.

Polynucleotide sequences of interest may encode proteins involved in providing disease or pest resistance. By "disease resistance" or "pest resistance" is intended that the plants avoid the harmful symptoms that are the outcome of the plant-pathogen interactions. Pest resistance genes may encode resistance to pests that have great yield drag such as rootworm, cutworm, European Corn Borer, and the like. Disease resistance and insect resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products. Genes encoding disease resistance traits include detoxification genes, such as against fumonisin (U.S. Pat. No. 5,792,931); avirulence (avr) and disease resistance (R) genes (Jones et al. (1994) Science 266:789; Martin et al. (1993) Science 262:1432; and Mindrinos et al. (1994) Cell 78:1089); and the like. Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) Gene 48:109); and the like.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS), in particular the sulfonylurea-type herbicides, genes coding for resistance to herbicides that act to inhibit the action of glutamine synthase, such as phosphinothricin or basta (e.g., the bar gene), glyphosate (e.g., the EPSP synthase gene and the GAT gene), HPPD inhibitors (e.g, the HPPD gene) or other such genes known in the art. See, for example, U.S. Pat. Nos. 7,626,077, 5,310,667, 5,866,775, 6,225,114, 6,248,876, 7,169,970, 6,867,293, and U.S. Provisional Application No. 61/401,456, each of which is herein incorporated by reference. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male fertility genes such as MS26 (see for example U.S. Pat. Nos. 7,098,388, 7,517,975, 7,612,251), MS45 (see for example U.S. Pat. Nos. 5,478,369, 6,265,640) or MSCA1 (see for example U.S. Pat. No. 7,919,676). Maize plants (*Zea mays* L.) can be bred by both self-pollination and cross-pollination techniques. Maize has male flowers, located on the tassel, and female flowers, located on the ear, on the same plant. It can self-pollinate ("selfing") or cross pollinate. Natural pollination occurs in maize when wind blows pollen from the tassels to the silks that protrude from the tops of the incipient ears. Pollination may be readily controlled by techniques known to those of skill in the art. The development of maize hybrids requires the development of homozygous inbred lines, the crossing of these lines, and the evaluation of the crosses. Pedigree breeding and recurrent selections are two of the breeding methods used to develop inbred lines from populations. Breeding programs combine desirable traits from two or more inbred lines or various broad-based sources into breeding pools from which new inbred lines are developed by selfing and selection of desired phenotypes. A hybrid maize variety is the cross of two such inbred lines, each of which may have one or more desirable characteristics lacked by the other or which complement the other. The new inbreds are crossed with other inbred lines and the hybrids from these crosses are evaluated to determine which have commercial potential. The hybrid progeny of the first generation is designated F1. The F1 hybrid is more vigorous than its inbred parents. This hybrid vigor, or heterosis, can be manifested in many ways, including increased vegetative growth and increased yield.

Hybrid maize seed can be produced by a male sterility system incorporating manual detasseling. To produce hybrid seed, the male tassel is removed from the growing female inbred parent, which can be planted in various alternating row patterns with the male inbred parent. Consequently, providing that there is sufficient isolation from sources of foreign maize pollen, the ears of the female inbred will be fertilized only with pollen from the male inbred. The resulting seed is therefore hybrid (F1) and will form hybrid plants.

Field variation impacting plant development can result in plants tasseling after manual detasseling of the female parent is completed. Or, a female inbred plant tassel may not be completely removed during the detasseling process. In any event, the result is that the female plant will successfully shed pollen and some female plants will be self-pollinated. This will result in seed of the female inbred being harvested along with the hybrid seed which is normally produced. Female inbred seed does not exhibit heterosis and therefore is not as productive as F1 seed. In addition, the presence of female inbred seed can represent a germplasm security risk for the company producing the hybrid.

Alternatively, the female inbred can be mechanically detasseled by machine. Mechanical detasseling is approximately as reliable as hand detasseling, but is faster and less costly. However, most detasseling machines produce more damage to the plants than hand detasseling. Thus, no form of detasseling is presently entirely satisfactory, and a need continues to exist for alternatives which further reduce production costs and to eliminate self-pollination of the female parent in the production of hybrid seed.

Mutations that cause male sterility in plants have the potential to be useful in methods for hybrid seed production for crop plants such as maize and can lower production costs by eliminating the need for the labor-intensive removal of male flowers (also known as de-tasseling) from the maternal parent plants used as a hybrid parent. Mutations that cause male sterility in maize have been produced by a variety of methods such as X-rays or UV-irradiations, chemical treatments, or transposable element insertions (ms23, ms25, ms26, ms32) (Chaubal et al. (2000) Am J Bot 87:1193-1201). Conditional regulation of fertility genes through fertility/sterility "molecular switches" could enhance the options for designing new male-sterility systems for crop improvement (Unger et al. (2002) Transgenic Res 11:455-465).

Besides identification of novel genes impacting male fertility, there remains a need to provide a reliable system of producing genetic male sterility.

In U.S. Pat. No. 5,478,369, a method is described by which the Ms45 male fertility gene was tagged and cloned on maize chromosome 9. Previously, there had been described a male fertility gene on chromosome 9, ms2, which had never been cloned and sequenced. It is not allelic to the gene referred to in the '369 patent. See Albertsen, M. and Phillips, R. L., "Developmental Cytology of 13 Genetic Male Sterile Loci in Maize" Canadian Journal of Genetics & Cytology 23:195-208 (January 1981). The only fertility gene cloned before that had been the *Arabidopsis* gene described at Aarts, et al., supra.

Furthermore, it is recognized that the polynucleotide of interest may also comprise antisense sequences complementary to at least a portion of the messenger RNA (mRNA) for a targeted gene sequence of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the polynucleotide of interest may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity. See, U.S. Pat. Nos. 5,283,184 and 5,034,323; herein incorporated by reference.

The polynucleotide of interest can also be a phenotypic marker. A phenotypic marker is screenable or a selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See for example, Yarranton, (1992) Curr Opin Biotech 3:506-11; Christopherson et al., (1992) Proc. Natl. Acad. Sci. USA 89:6314-8; Yao et al., (1992) Cell 71:63-72; Reznikoff, (1992) Mol Microbiol 6:2419-22; Hu et al., (1987) Cell 48:555-66; Brown et al., (1987) Cell 49:603-12; Figge et al., (1988) Cell 52:713-22; Deuschle et al., (1989) Proc. Natl. Acad. Sci. USA 86:5400-4; Fuerst et al., (1989) Proc. Natl. Acad. Sci. USA 86:2549-53; Deuschle et al., (1990) Science 248:480-3; Gossen, (1993) Ph.D. Thesis, University of Heidelberg; Reines et al., (1993) Proc. Natl. Acad. Sci. USA 90:1917-21; Labow et al., (1990) Mol Cell Biol 10:3343-56; Zambretti et al., (1992) Proc. Natl. Acad. Sci. USA 89:3952-6; Baim et al., (1991) Proc. Natl. Acad. Sci. USA 88:5072-6; Wyborski et al., (1991) Nucleic Acids Res 19:4647-53; Hillen and Wissman, (1989) Topics Mol Struc Biol 10:143-62; Degenkolb et al., (1991) Antimicrob Agents Chemother 35:1591-5; Kleinschnidt et al., (1988) Biochemistry 27:1094-104; Bonin, (1993) Ph.D. Thesis, University of Heidelberg; Gossen et al., (1992) Proc. Natl. Acad. Sci. USA 89:5547-51; Oliva et al., (1992) Antimicrob Agents Chemother 36:913-9; Hlavka et al., (1985) Handbook of Experimental Pharmacology, Vol. 78 (Springer-Verlag, Berlin); Gill et al., (1988) Nature 334:721-4. Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) J. Bacteriol. 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The transgenes, recombinant DNA molecules, DNA sequences of interest, and polynucleotides of interest can be comprise one or more DNA sequences for gene silencing. Methods for gene silencing involving the expression of DNA sequences in plant are known in the art include, but are not limited to, cosuppression, antisense suppression, double-stranded RNA (dsRNA) interference, hairpin RNA (hpRNA) interference, intron-containing hairpin RNA (ihpRNA) interference, transcriptional gene silencing, and micro RNA (miRNA) interference As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

"Open reading frame" is abbreviated ORF.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of genes to produce the desired phenotype in a transformed plant. Genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to polypeptide or nucleic acid fragments wherein changes in one or more amino acids or nucleotide bases do not affect the function of the molecule, such as the ability to mediate gene expression or to produce a certain phenotype. These terms also refer to modification(s) of nucleic acid fragments that do not substantially alter the functional properties of the resulting nucleic acid fragment relative to the initial, unmodified fragment. These modifications include deletion, substitution, and/or insertion of one or more nucleotides in the nucleic acid fragment.

Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence in an in vitro hybridization assay. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salt(s)) at pH 7.0 to 8.3, and at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) *CABIOS* 5:151-153; Higgins et al., (1992) *Comput Appl Biosci* 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) *CABIOS* 5:151-153; Higgins et al., (1992) *Comput Appl Biosci* 8:189-191) and found in the MegAlign™ v6.1 program of the LASERGENE bioinformatics computing suite (DNASTAR Inc., Madison, Wis.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) *Proc. Natl. Acad. Sci. USA* 89:10915). GAP uses the algorithm of Needleman and Wunsch, (1970) *J Mol Biol* 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

"BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present disclosure, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Gene" includes a nucleic acid fragment that expresses a functional molecule such as, but not limited to, a specific protein, including regulatory sequences preceding (5' non-coding sequences) and following (3' non-coding sequences) the coding sequence. "Native gene" refers to a gene as found in nature with its own regulatory sequences.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated plant is a plant comprising a mutated gene.

As used herein, a "targeted mutation" is a mutation in a native gene that was made by altering a target sequence within the native gene using a method involving a double-strand-break-inducing agent that is capable of inducing a double-strand break in the DNA of the target sequence as disclosed herein or known in the art.

The guide RNA/Cas endonuclease induced targeted mutation can occur in a nucleotide sequence that is located within or outside a genomic target site that is recognized and cleaved by a Cas endonuclease.

The term "genome" as it applies to a plant cells encompasses not only chromosomal DNA found within the nucleus, but organelle DNA found within subcellular components (e.g., mitochondria, or plastid) of the cell.

A "codon-modified gene" or "codon-preferred gene" or "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, 5' untranslated sequences, 3' untranslated sequences, introns, polyadenylation target sequences, RNA processing sites, effector binding sites, and stem-loop structures.

"A plant-optimized nucleotide sequence" is nucleotide sequence that has been optimized for increased expression in plants, particularly for increased expression in plants or in one or more plants of interest. For example, a plant-optimized nucleotide sequence can be synthesized by modifying a nucleotide sequence encoding a protein such as, for example, double-strand-break-inducing agent (e.g., an endonuclease) as disclosed herein, using one or more plant-preferred codons for improved expression. See, for example, Campbell and Gowri (1990) *Plant Physiol.* 92:1-11 for a discussion of host-preferred codon usage.

Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference. Additional sequence modifications are known to enhance gene expression in a plant host. These include, for example, elimination of: one or more sequences encoding spurious polyadenylation signals, one or more exon-intron splice site signals, one or more transposon-like repeats, and other such well-characterized sequences that may be deleterious to gene expression. The G-C content of the sequence may be adjusted to levels average for a given plant host, as calculated by reference to known genes expressed in the host plant cell. When possible, the sequence is modified to avoid one or more predicted hairpin secondary mRNA structures. Thus, "a plant-optimized nucleotide sequence" of the present disclosure comprises one or more of such sequence modifications.

A promoter is a region of DNA involved in recognition and binding of RNA polymerase and other proteins to initiate transcription. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels. Since patterns of expression of a chimeric gene (or genes) introduced into a plant are controlled using promoters, there is an ongoing interest in the isolation of novel promoters which are capable of controlling the expression of a chimeric gene or (genes) at certain levels in specific tissue types or at specific plant developmental stages.

A plant promoter can include a promoter capable of initiating transcription in a plant cell, for a review of plant promoters, see, Potenza et al., (2004) *In Vitro Cell Dev Biol* 40:1-22. Constitutive promoters include, for example, the core promoter of the Rsyn7 promoter and other constitutive promoters disclosed in WO99/43838 and U.S. Pat. No. 6,072,050; the core CaMV 35S promoter (Odell et al., (1985) *Nature* 313:810-2); rice actin (McElroy et al., (1990)

*Plant Cell* 2:163-71); ubiquitin (Christensen et al., (1989) *Plant Mol Biol* 12:619-32; Christensen et al., (1992) *Plant Mol Biol* 18:675-89); pEMU (Last et al., (1991) *Theor Appl Genet* 81:581-8); MAS (Velten et al., (1984) *EMBO J* 3:2723-30); ALS promoter (U.S. Pat. No. 5,659,026), and the like. Other constitutive promoters are described in, for example, U.S. Pat. Nos. 5,608,149; 5,608,144; 5,604,121; 5,569,597; 5,466,785; 5,399,680; 5,268,463; 5,608,142 and 6,177,611. In some examples an inducible promoter may be used. Pathogen-inducible promoters induced following infection by a pathogen include, but are not limited to those regulating expression of PR proteins, SAR proteins, beta-1, 3-glucanase, chitinase, etc.

Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize ln2-2 promoter, activated by benzene sulfonamide herbicide safeners (De Veylder et al., (1997) *Plant Cell Physiol* 38:568-77), the maize GST promoter (GST-II-27, WO93/01294), activated by hydrophobic electrophilic compounds used as pre-emergent herbicides, and the tobacco PR-1a promoter (Ono et al., (2004) *Biosci Biotechnol Biochem* 68:803-7) activated by salicylic acid. Other chemical-regulated promoters include steroid-responsive promoters (see, for example, the glucocorticoid-inducible promoter (Schena et al., (1991) *Proc. Natl. Acad. Sci. USA* 88:10421-5; McNellis et al., (1998) *Plant J* 14:247-257); tetracycline-inducible and tetracycline-repressible promoters (Gatz et al., (1991) *Mol Gen Genet* 227:229-37; U.S. Pat. Nos. 5,814,618 and 5,789,156).

Tissue-preferred promoters can be utilized to target enhanced expression within a particular plant tissue. Tissue-preferred promoters include, for example, Kawamata et al., (1997) *Plant Cell Physiol* 38:792-803; Hansen et al., (1997) *Mol Gen Genet* 254:337-43; Russell et al., (1997) *Transgenic Res* 6:157-68; Rinehart et al., (1996) *Plant Physiol* 112:1331-41; Van Camp et al., (1996) *Plant Physiol* 112:525-35; Canevascini et al., (1996) *Plant Physiol* 112:513-524; Lam, (1994) *Results Probl Cell Differ* 20:181-96; and Guevara-Garcia et al., (1993) *Plant J* 4:495-505. Leaf-preferred promoters include, for example, Yamamoto et al., (1997) *Plant J* 12:255-65; Kwon et al., (1994) *Plant Physiol* 105:357-67; Yamamoto et al., (1994) *Plant Cell Physiol* 35:773-8; Gotor et al., (1993) *Plant J* 3:509-18; Orozco et al., (1993) *Plant Mol Biol* 23:1129-38; Matsuoka et al., (1993) *Proc. Natl. Acad. Sci. USA* 90:9586-90; Simpson et al., (1958) *EMBO J* 4:2723-9; Timko et al., (1988) *Nature* 318:57-8. Root-preferred promoters include, for example, Hire et al., (1992) *Plant Mol Biol* 20:207-18 (soybean root-specific glutamine synthase gene); Miao et al., (1991) *Plant Cell* 3:11-22 (cytosolic glutamine synthase (GS)); Keller and Baumgartner, (1991) *Plant Cell* 3:1051-61 (root-specific control element in the GRP 1.8 gene of French bean); Sanger et al., (1990) *Plant Mol Biol* 14:433-43 (root-specific promoter of *A. tumefaciens* mannopine synthase (MAS)); Bogusz et al., (1990) *Plant Cell* 2:633-41 (root-specific promoters isolated from *Parasponia andersonii* and *Trema tomentosa*); Leach and Aoyagi, (1991) *Plant Sci* 79:69-76 (*A. rhizogenes* rolC and rolD root-inducing genes); Teeri et al., (1989) *EMBO J* 8:343-50 (*Agrobacterium* wound-induced TR1' and TR2' genes); VfENOD-GRP3 gene promoter (Kuster et al., (1995) *Plant Mol Bic)/29*:759-72); and rolB promoter (Capana et al., (1994) *Plant Mol Biol* 25:681-91; phaseolin gene (Murai et al., (1983) *Science* 23:476-82; Sengopta-Gopalen et al., (1988) *Proc. Natl. Acad. Sci. USA* 82:3320-4). See also, U.S. Pat. Nos. 5,837,876; 5,750,386; 5,633,363; 5,459,252; 5,401,836; 5,110,732 and 5,023,179.

Seed-preferred promoters include both seed-specific promoters active during seed development, as well as seed-germinating promoters active during seed germination. See, Thompson et al., (1989) *BioEssays* 10:108. Seed-preferred promoters include, but are not limited to, Cim1 (cytokinin-induced message); cZ19B1 (maize 19 kDa zein); and milps (myo-inositol-1-phosphate synthase); (WO00/11177; and U.S. Pat. No. 6,225,529). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, and nuc1. See also, WO00/12733, where seed-preferred promoters from END1 and END2 genes are disclosed.

The term "inducible promoter" refers to promoters that selectively express a coding sequence or functional RNA in response to the presence of an endogenous or exogenous stimulus, for example by chemical compounds (chemical inducers) or in response to environmental, hormonal, chemical, and/or developmental signals. Inducible or regulated promoters include, for example, promoters induced or regulated by light, heat, stress, flooding or drought, salt stress, osmotic stress, phytohormones, wounding, or chemicals such as ethanol, abscisic acid (ABA), jasmonate, salicylic acid, or safeners.

An example of a stress-inducible is RD29A promoter (Kasuga et al. (1999) Nature Biotechnol. 17:287-91). One of ordinary skill in the art is familiar with protocols for simulating drought conditions and for evaluating drought tolerance of plants that have been subjected to simulated or naturally-occurring drought conditions. For example, one can simulate drought conditions by giving plants less water than normally required or no water over a period of time, and one can evaluate drought tolerance by looking for differences in physiological and/or physical condition, including (but not limited to) vigor, growth, size, or root length, or in particular, leaf color or leaf area size. Other techniques for evaluating drought tolerance include measuring chlorophyll fluorescence, photosynthetic rates and gas exchange rates. Also, one of ordinary skill in the art is familiar with protocols for simulating stress conditions such as osmotic stress, salt stress and temperature stress and for evaluating stress tolerance of plants that have been subjected to simulated or naturally-occurring stress conditions.

Another example of an inducible promoter useful in plant cells has been described in US patent application, US 2013-0312137A1, published on Nov. 21, 2013, incorporated by reference herein. US patent application US 2013-0312137A1 describes a ZmCAS1 promoter from a CBSU-Anther_Subtraction library (CAS1) gene encoding a mannitol dehydrogenase from maize, and functional fragments thereof. The ZmCAS1 promoter (also referred to as "CAS1 promoter", "mannitol dehydrogenase promoter", "mdh promoter") can be induced by a chemical or stress treatment. The chemical can be a safener such as, but not limited to, N-(aminocarbonyl)-2-chlorobenzenesulfonamide (2-CBSU). The stress treatment can be a heat treatment such as, but not limited to, a heat shock treatment (see also U.S. provisional patent application 62/120,421, filed on Feb. 25, 2015, incorporated by reference herein.

New promoters of various types useful in plant cells are constantly being discovered; numerous examples may be found in the compilation by Okamuro and Goldberg, (1989) In *The Biochemistry of Plants*, Vol. 115, Stumpf and Conn, eds (New York, N.Y.: Academic Press), pp. 1-82.

"Translation leader sequence" refers to a polynucleotide sequence located between the promoter sequence of a gene and the coding sequence. The translation leader sequence is present in the mRNA upstream of the translation start sequence. The translation leader sequence may affect processing of the primary transcript to mRNA, mRNA stability or translation efficiency. Examples of translation leader sequences have been described (e.g., Turner and Foster, (1995) *Mol Biotechnol* 3:225-236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al, (1989) *Plant Cell* 1:671-680.

"RNA transcript" refers to the product resulting from RNA polymerase-catalyzed transcription of a DNA sequence. When the RNA transcript is a perfect complimentary copy of the DNA sequence, it is referred to as the primary transcript or pre-mRNA. A RNA transcript is referred to as the mature RNA or mRNA when it is a RNA sequence derived from post-transcriptional processing of the primary transcript pre mRNAt. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook et al., *Molecular Cloning: A Laboratory Manual; Cold Spring Harbor Laboratory*: Cold Spring Harbor, NY (1989). Transformation methods are well known to those skilled in the art and are described infra.

"PCR" or "polymerase chain reaction" is a technique for the synthesis of specific DNA segments and consists of a series of repetitive denaturation, annealing, and extension cycles. Typically, a double-stranded DNA is heat denatured, and two primers complementary to the 3' boundaries of the target segment are annealed to the DNA at low temperature, and then extended at an intermediate temperature. One set of these three consecutive steps is referred to as a "cycle".

The term "recombinant" refers to an artificial combination of two otherwise separated segments of sequence, e.g., by chemical synthesis, or manipulation of isolated segments of nucleic acids by genetic engineering techniques.

The terms "plasmid", "vector" and "cassette" refer to an extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector containing a gene and having elements in addition to the gene that facilitates transformation of a particular host cell. "Expression cassette" refers to a specific vector containing a gene and having elements in addition to the gene that allow for expression of that gene in a host.

The terms "recombinant DNA molecule", "recombinant construct", "expression construct", "construct", "construct", and "recombinant DNA construct" are used interchangeably herein. A recombinant construct comprises an artificial combination of nucleic acid fragments, e.g., regulatory and coding sequences that are not all found together in nature. For example, a construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) *EMBO J* 4:2411-2418; De Almeida et al., (1989) *Mol Gen Genetics* 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

The term "expression", as used herein, refers to the production of a functional end-product (e.g., an mRNA, guide RNA, or a protein) in either precursor or mature form.

The term "providing" includes providing a nucleic acid (e.g., expression construct) or protein into a cell. Providing includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "providing" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or other DNA-containing organelle, of a host organism resulting in gene expression without integration or stable inheritance. Host organisms containing the transformed nucleic acid fragments are referred to as "transgenic" organisms.

The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different genes of interest.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant. The term "genome" refers to the entire complement of genetic material (genes and non-coding sequences) that is present in each cell of an organism, or virus or organelle; and/or a complete set of chromosomes inherited as a (haploid) unit from one parent. "Progeny" comprises any subsequent generation of a plant.

A transgenic plant includes, for example, a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. A heterologous polynucleotide can include a sequence that originates from a foreign species, or, if from the same species, can be substantially modified from its native form. Transgenic can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of the genome (chromosomal or extra-chromosomal) by conventional plant breeding methods, by the genome editing procedure described herein that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

In certain embodiments of the disclosure, a fertile plant is a plant that produces viable male and female gametes and is self-fertile. Such a self-fertile plant can produce a progeny plant without the contribution from any other plant of a gamete and the genetic material contained therein. Other embodiments of the disclosure can involve the use of a plant that is not self-fertile because the plant does not produce male gametes, or female gametes, or both, that are viable or otherwise capable of fertilization. As used herein, a "male sterile plant" is a plant that does not produce male gametes that are viable or otherwise capable of fertilization. As used herein, a "female sterile plant" is a plant that does not produce female gametes that are viable or otherwise capable of fertilization. It is recognized that male-sterile and female-sterile plants can be female-fertile and male-fertile, respectively. It is further recognized that a male fertile (but female sterile) plant can produce viable progeny when crossed with a female fertile plant and that a female fertile (but male sterile) plant can produce viable progeny when crossed with a male fertile plant.

The term "non-conventional yeast" herein refers to any yeast that is not a *Saccharomyces* (e.g., *S. cerevisiae*) or *Schizosaccharomyces* yeast species. Non-conventional yeast are described in *Non-Conventional Yeasts in Genetics, Biochemistry and Biotechnology: Practical Protocols* (K. Wolf, K. D. Breunig, G. Barth, Eds., Springer-Verlag, Berlin, Germany, 2003), which is incorporated herein by reference. Non-conventional yeast in certain embodiments may additionally (or alternatively) be yeast that favor non-homologous end-joining (NHEJ) DNA repair processes over repair processes mediated by homologous recombination (HR). Definition of a non-conventional yeast along these lines—preference of NHEJ over HR—is further disclosed by Chen et al. (*PLoS ONE* 8:e57952), which is incorporated herein by reference. Preferred non-conventional yeast herein are those of the genus *Yarrowia* (e.g., *Yarrowia lipolytica*). The term "yeast" herein refers to fungal species that predominantly exist in unicellular form. Yeast can alternative be referred to as "yeast cells" herein. (see also U.S. provisional application 62/036,652, filed on Aug. 13, 2014, which is incorporated by reference herein.

A "centimorgan" (cM) or "map unit" is the distance between two linked genes, markers, target sites, loci, or any pair thereof, wherein 1% of the products of meiosis are recombinant. Thus, a centimorgan is equivalent to a distance equal to a 1% average recombination frequency between the two linked genes, markers, target sites, loci, or any pair thereof.

The present disclosure finds use in the breeding of plants comprising one or more transgenic traits. Most commonly, transgenic traits are randomly inserted throughout the plant genome as a consequence of transformation systems based on *Agrobacterium*, biolistics, or other commonly used procedures. More recently, gene targeting protocols have been developed that enable directed transgene insertion. One important technology, site-specific integration (SSI) enables the targeting of a transgene to the same chromosomal location as a previously inserted transgene. Custom-designed meganucleases and custom-designed zinc finger meganucleases allow researchers to design nucleases to target specific chromosomal locations, and these reagents allow the targeting of transgenes at the chromosomal site cleaved by these nucleases.

The currently used systems for precision genetic engineering of eukaryotic genomes, e.g. plant genomes, rely upon homing endonucleases, meganucleases, zinc finger nucleases, and transcription activator-like effector nucleases (TALENs), which require de novo protein engineering for every new target locus. The highly specific, RNA-directed DNA nuclease, guide RNA/Cas9 endonuclease system described herein, is more easily customizable and therefore more useful when modification of many different target sequences is the goal. This disclosure takes further advantage of the two component nature of the guide RNA/Cas system, with its constant protein component, the Cas endonuclease, and its variable and easily reprogrammable targeting component, the guide RNA or the crRNA.

The guide RNA/Cas system described herein is especially useful for genome engineering, especially plant genome engineering, in circumstances where nuclease off-target cutting can be toxic to the targeted cells. In one embodiment of the guide RNA/Cas system described herein, the constant component, in the form of an expression-optimized Cas9 gene, is stably integrated into the target genome, e.g. plant genome. Expression of the Cas9 gene is under control of a promoter, e.g. plant promoter, which can be a constitutive promoter, tissue-specific promoter or inducible promoter, e.g. temperature-inducible, stress-inducible, developmental stage inducible, or chemically inducible promoter. In the absence of the variable component, i.e. the guide RNA or crRNA, the Cas9 protein is not able to cut DNA and therefore its presence in the plant cell should have little or no consequence. Hence a key advantage of the guide RNA/Cas system described herein is the ability to create and maintain a cell line or transgenic organism capable of efficient expression of the Cas9 protein with little or no consequence to cell viability. In order to induce cutting at desired genomic sites to achieve targeted genetic modifications, guide RNAs or crRNAs can be introduced by a variety of methods into cells containing the stably-integrated and expressed cas9 gene. For example, guide RNAs or crRNAs can be chemically or enzymatically synthesized, and introduced into the Cas9 expressing cells via direct delivery methods such a particle bombardment or electroporation.

Alternatively, genes capable of efficiently expressing guide RNAs or crRNAs in the target cells can be synthesized chemically, enzymatically or in a biological system, and these genes can be introduced into the Cas9 expressing cells via direct delivery methods such a particle bombardment, electroporation or biological delivery methods such as *Agrobacterium* mediated DNA delivery.

A guide RNA/Cas system mediating gene targeting can be used in methods for directing transgene insertion and/or for producing complex transgenic trait loci comprising multiple transgenes in a fashion similar as disclosed in WO2013/0198888 (published Aug. 1, 2013) where instead of using a double strand break inducing agent to introduce a gene of interest, a guide RNA/Cas system as disclosed herein is used. In one embodiment, a complex transgenic trait locus is a genomic locus that has multiple transgenes genetically linked to each other. By inserting independent transgenes within 0.1, 0.2, 0.3, 0.4, 0.5, 1.0, 2, or even 5 centimorgans (cM) from each other, the transgenes can be bred as a single genetic locus (see, for example, U.S. patent application Ser. No. 13/427,138) or PCT application PCT/US2012/030061. After selecting a plant comprising a transgene, plants containing (at least) one transgenes can be crossed to form an F1 that contains both transgenes. In progeny from these F1 (F2 or BC1) 1/500 progeny would have the two different transgenes recombined onto the same chromosome. The complex locus can then be bred as single genetic locus with both transgene traits. This process can be repeated to stack as many traits as desired.

Chromosomal intervals that correlate with a phenotype or trait of interest can be identified. A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as a marker for northern leaf blight resistance. In one embodiment, the chromosomal interval comprises at least one QTL, and furthermore, may indeed comprise more than one QTL. Close proximity of multiple QTLs in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifies the same QTL or two different QTL. The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question. An "allele of a QTL" can comprise multiple genes or other genetic factors within a contiguous genomic region or linkage group, such as a haplotype. An allele of a QTL can denote a haplotype within a specified window wherein said window is a contiguous genomic region that can be defined, and tracked, with a set of one or more polymorphic markers. A haplotype can be defined by the unique fingerprint of alleles at each marker within the specified window.

A variety of methods are available to identify those cells having an altered genome at or near a target site without using a screenable marker phenotype. Such methods can be viewed as directly analyzing a target sequence to detect any change in the target sequence, including but not limited to PCR methods, sequencing methods, nuclease digestion, Southern blots, and any combination thereof.

Proteins may be altered in various ways including amino acid substitutions, deletions, truncations, and insertions. Methods for such manipulations are generally known. For example, amino acid sequence variants of the protein(s) can be prepared by mutations in the DNA. Methods for mutagenesis and nucleotide sequence alterations include, for example, Kunkel, (1985) *Proc. Natl. Acad. Sci. USA* 82:488-92; Kunkel et al., (1987) *Meth Enzymol* 154:367-82; U.S. Pat. No. 4,873,192; Walker and Gaastra, eds. (1983) *Techniques in Molecular Biology* (MacMillan Publishing Company, New York) and the references cited therein. Guidance regarding amino acid substitutions not likely to affect biological activity of the protein is found, for example, in the model of Dayhoff et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double-strand-break-inducing activity are known and generally measure the overall activity and specificity of the agent on DNA substrates containing target sites.

A variety of methods are known for the introduction of nucleotide sequences and polypeptides into an organism, including, for example, transformation, sexual crossing, and the introduction of the polypeptide, DNA, or mRNA into the cell.

Methods for contacting, providing, and/or introducing a composition into various organisms are known and include but are not limited to, stable transformation methods, transient transformation methods, virus-mediated methods, and sexual breeding. Stable transformation indicates that the introduced polynucleotide integrates into the genome of the organism and is capable of being inherited by progeny thereof. Transient transformation indicates that the introduced composition is only temporarily expressed or present in the organism.

Protocols for introducing polynucleotides and polypeptides into plants may vary depending on the type of plant or plant cell targeted for transformation, such as monocot or dicot. Suitable methods of introducing polynucleotides and polypeptides into plant cells and subsequent insertion into the plant genome include microinjection (Crossway et al., (1986) *Biotechniques* 4:320-34 and U.S. Pat. No. 6,300,543), meristem transformation (U.S. Pat. No. 5,736,369), electroporation (Riggs et al, (1986) *Proc. Natl. Acad. Sci. USA* 83:5602-6, *Agrobacterium*-mediated transformation (U.S. Pat. Nos. 5,563,055 and 5,981,840), direct gene transfer (Paszkowski et al., (1984) *EMBO J* 3:2717-22), and ballistic particle acceleration (U.S. Pat. Nos. 4,945,050; 5,879,918; 5,886,244; 5,932,782; Tomes et al., (1995) "Direct DNA Transfer into Intact Plant Cells via Microprojectile Bombardment" in *Plant Cell, Tissue, and Organ Culture: Fundamental Methods*, ed. Gamborg & Phillips (Springer-Verlag, Berlin); McCabe et al., (1988) *Biotechnology* 6:923-6; Weissinger et al., (1988) *Ann Rev Genet* 22:421-77; Sanford et al., (1987) *Particulate Science and Technology* 5:27-37 (onion); Christou et al., (1988) *Plant Physiol* 87:671-4 (soybean); Finer and McMullen, (1991) *In Vitro Cell Dev Biol* 27P:175-82 (soybean); Singh et al., (1998) *Theor Appl Genet* 96:319-24 (soybean); Datta et al., (1990) *Biotechnology* 8:736-40 (rice); Klein et al., (1988) *Proc. Natl. Acad. Sci. USA* 85:4305-9 (maize); Klein et al., (1988) *Biotechnology* 6:559-63 (maize); U.S. Pat. Nos. 5,240,855; 5,322,783 and 5,324,646; Klein et al., (1988) *Plant Physiol* 91:440-4 (maize); Fromm et al., (1990) *Biotechnology* 8:833-9 (maize); Hooykaas-Van Slogteren et al., (1984) *Nature* 311:763-4; U.S. Pat. No. 5,736,369 (cereals); Bytebier et al., (1987) *Proc. Natl. Acad. Sci. USA* 84:5345-9 (Liliaceae); De Wet et al., (1985) in *The Experimental Manipulation of Ovule Tissues*, ed. Chapman et al., (Longman, New York), pp. 197-209 (pollen); Kaeppler et al., (1990) *Plant Cell Rep* 9:415-8) and Kaeppler et al., (1992) *Theor Appl Genet* 84:560-6 (whisker-mediated transformation); D'Halluin et al., (1992) *Plant Cell* 4:1495-505 (electroporation); Li et al., (1993) *Plant Cell Rep* 12:250-5; Christou and Ford (1995) *Annals Botany* 75:407-13 (rice) and Osjoda et al., (1996) *Nat Biotechnol* 14:745-50 (maize via *Agrobacterium tumefaciens*).

Alternatively, polynucleotides may be introduced into plants by contacting plants with a virus or viral nucleic acids. Generally, such methods involve incorporating a polynucleotide within a viral DNA or RNA molecule. In some examples a polypeptide of interest may be initially synthesized as part of a viral polyprotein, which is later processed by proteolysis in vivo or in vitro to produce the desired recombinant protein. Methods for introducing polynucleotides into plants and expressing a protein encoded therein, involving viral DNA or RNA molecules, are known, see, for example, U.S. Pat. Nos. 5,889,191, 5,889,190, 5,866,785, 5,589,367 and 5,316,931. Transient transformation methods include, but are not limited to, the introduction of polypeptides, such as a double-strand break inducing agent, directly into the organism, the introduction of polynucleotides such as DNA and/or RNA polynucleotides, and the introduction of the RNA transcript, such as an mRNA encoding a double-strand break inducing agent, into the organism. Such methods include, for example, microinjection or particle bombardment. See, for example Crossway et al., (1986) *Mol Gen Genet* 202:179-85; Nomura et al., (1986) *Plant Sci* 44:53-8; Hepler et al., (1994) *Proc. Natl. Acad. Sci. USA* 91:2176-80; and, Hush et al., (1994) *J Cell Sci* 107:775-84.

The term "dicot" refers to the subclass of angiosperm plants also knows as "dicotyledoneae" and includes reference to whole plants, plant organs (e.g., leaves, stems, roots, etc.), seeds, plant cells, and progeny of the same. Plant cell, as used herein includes, without limitation, seeds, suspension cultures, embryos, meristematic regions, callus tissue, leaves, roots, shoots, gametophytes, sporophytes, pollen, and microspores.

The term "crossed" or "cross" or "crossing" in the context of this disclosure means the fusion of gametes via pollination to produce progeny (i.e., cells, seeds, or plants). The term encompasses both sexual crosses (the pollination of one plant by another) and selfing (self-pollination, i.e., when the pollen and ovule (or microspores and megaspores) are from the same plant or genetically identical plants).

The term "introgression" refers to the transmission of a desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene, a modified (mutated or edited) native allele, or a selected allele of a marker or QTL.

Standard DNA isolation, purification, molecular cloning, vector construction, and verification/characterization methods are well established, see, for example Sambrook et al., (1989) *Molecular Cloning: A Laboratory Manual*, (Cold Spring Harbor Laboratory Press, NY). Vectors and constructs include circular plasmids, and linear polynucleotides, comprising a polynucleotide of interest and optionally other components including linkers, adapters, regulatory or analysis. In some examples a recognition site and/or target site can be contained within an intron, coding sequence, 5' UTRs, 3' UTRs, and/or regulatory regions.

The present disclosure further provides expression constructs for expressing in a plant, plant cell, or plant part a guide RNA/Cas system that is capable of binding to and creating a double strand break in a target site. In one embodiment, the expression constructs of the disclosure comprise a promoter operably linked to a nucleotide sequence encoding a Cas gene and a promoter operably linked to a guide RNA of the present disclosure. The promoter is capable of driving expression of an operably linked nucleotide sequence in a plant cell.

A phenotypic marker is a screenable or selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as asp-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See for example, Yarranton, (1992) *Curr Opin Biotech* 3:506-11; Christopherson et al., (1992) *Proc. Natl. Acad. Sci. USA* 89:6314-8; Yao et al., (1992) *Cell* 71:63-72; Reznikoff, (1992) *Mol Microbiol* 6:2419-22; Hu et al., (1987) *Cell* 48:555-66; Brown et al., (1987) *Cell* 49:603-12; Figge et al., (1988) *Cell* 52:713-22; Deuschle et al., (1989) *Proc. Natl. Acad. Sci. USA* 86:5400-4; Fuerst et al., (1989) *Proc. Natl. Acad. Sci. USA* 86:2549-53; Deuschle et al., (1990) *Science* 248:480-3; Gossen, (1993) Ph.D. Thesis, University of Heidelberg; Reines et al., (1993) *Proc. Natl. Acad. Sci. USA* 90:1917-21; Labow et al., (1990) *Mol Cell Biol* 10:3343-56; Zambretti et al., (1992) *Proc. Natl. Acad. Sci. USA* 89:3952-6; Baim et al., (1991) *Proc. Natl. Acad. Sci. USA* 88:5072-6; Wyborski et al., (1991) *Nucleic Acids Res* 19:4647-53; Hillen and Wissman, (1989) *Topics Mol Struc Biol* 10:143-62; Degenkolb et al., (1991) *Antimicrob Agents Chemother* 35:1591-5; Kleinschnidt et al., (1988) *Biochemistry* 27:1094-104; Bonin, (1993) Ph.D. Thesis, University of Heidelberg; Gossen et al., (1992) *Proc. Natl. Acad. Sci. USA* 89:5547-51; Oliva et al., (1992) *Antimicrob Agents Chemother* 36:913-9; Hlavka et al., (1985) *Handbook of Experimental Pharmacology*, Vol. 78 (Springer-Verlag, Berlin); Gill et al., (1988) *Nature* 334:721-4.

The cells having the introduced sequence may be grown or regenerated into plants using conventional conditions, see for example, McCormick et al., (1986) *Plant Cell Rep* 5:81-4. These plants may then be grown, and either pollinated with the same transformed strain or with a different transformed or untransformed strain, and the resulting progeny having the desired characteristic and/or comprising the introduced polynucleotide or polypeptide identified. Two or more generations may be grown to ensure that the polynucleotide is stably maintained and inherited, and seeds harvested.

Any plant can be used, including monocot and dicot plants. Examples of monocot plants that can be used include, but are not limited to, corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), wheat (*Triticum aestivum*), sugarcane (*Saccharum* spp.), oats (*Avena*), barley (*Hordeum*), switchgrass (*Panicum virgatum*), pineapple (*Ananas comosus*), banana (*Musa* spp.), palm, ornamentals, turfgrasses, and other grasses. Examples of dicot plants that can be used include, but are not limited to, soybean (*Glycine max*), canola (*Brassica napus* and *B. campestris*), alfalfa (*Medicago sativa*), tobacco (*Nicotiana tabacum*), *Arabidopsis* (*Arabidopsis thaliana*), sunflower (*Helianthus annuus*), cotton (*Gossypium arboreum*), and peanut (*Arachis hypogaea*), tomato (*Solanum lycopersicum*), potato (*Solanum tuberosum*) etc.

The transgenes, recombinant DNA molecules, DNA sequences of interest, and polynucleotides of interest can comprise one or more genes of interest. Such genes of interest can encode, for example, a protein that provides agronomic advantage to the plant.

Also provided are kits for performing any of the above methods described herein. The kits typically contain polynucleotides encoding one or more Cas endonuclease, or Cas endonuclease protein wherein the Cas endonuclease protein is provided as a purified protein, a cell lysate comprising said Cas endonuclease, a dilution of a cell lysate comprising said Cas endonuclease, an in-vitro translation mixture or an dilution of an in-vitro translation mixture, and/or single or dual guide polynucleotides, and/or template polynucleotides for gene editing and/or donor polynucleotides for inserting polynucleotides of interest into a genome of interest, as described herein. The kit can further contain instructions for administering all these components into the cells. The kits can also contain cells, buffers for transformation of cells, culture media for cells, and/or buffers for performing assays. The kits can further contain one or more inhibitors of proteins involved in NHEJ, or components which promote or increase homology-dependent repair (HDR) and instructions for introducing the Cas endonucleases and inhibitors into the cells such that Cas endonuclease-mediated gene disruption and/or targeted integration is enhanced. Optionally, cells containing the target site(s) of the Cas endonuclease may also be included in the kits described herein.

Inhibitors of non-homologous end joining (NHEJ) are known in the art and include molecules, such as but not limited to small molecules that inhibits (decrease) the binding or activity of a DNA-dependent-protein kinase catalytic subunit (DNA-PKcs), a Poly(ADP-ribose) polymerase 1/2 (PARPI/2), a PARPI, Ku70/80, a DNA-PKcs, a XRCC4/XLF, a Ligase IV, a Ligase III, a XRCCI, an Artemis Polynucleotide Kinase (PNK), SCR7, and any one combinations thereof (Sfeir et al. 2015, TIBS Vol 40 (11), pp 701-713; Srivastava, M. et al. An inhibitor of nonhomologous end-joining abrogates double-strand break repair and impedes cancer progression. *Cell* 151, 1474-1487 (2012); US patent application US2014/0242702, published on Aug. 28, 2014, herein incorporated in its entirety by reference). Other molecules that decrease the activity of the non-homologous end joining (NHEJ) DNA repair complex are known in the art and include RNAi-molecules, antisense nucleic acid molecules, ribozymes, compounds inhibiting the formation of a functional DNA Ligase IV (LIG4) complex and compounds enhancing proteolytic degradation of a functional DNA Ligase IV complex (US patent application 2014/0304847, published on Oct. 9, 2014, herein incorporated in its entirety by reference.

Activators of HDR are known in the art and include molecules, such as but not limited to RS1, RAD51 and RAD51B (Song et al. 2016 "RS-1 enhances CRISPR/Cas9- and TALEN-mediated knock-in efficiency" Nature communications 7, Article number:10548; Takaku, M. et of 2009. Recombination activator function of the novel RAD51- and RAD51B-binding protein, human EVL. *J. Biol. Chem.* 284, 14326-14336 (2009).

In certain embodiments, the kits comprise at least one construct with a target gene and a Cas endonuclease described herein capable of cleaving within or in close proximity to the target gene. Such kits are useful for optimization of cleavage conditions in a variety of varying host cell types. In one aspect, the kit is a kit useful for increasing gene disruption, gene editing and/or targeted integration following Cas endonuclease mediated cleavage of a cell's genome.

In one embodiment, the kit includes a Cas endonuclease described herein capable of cleaving within a known target locus within a genome, and may additionally comprise a template DNA for gene editing and/or a donor nucleic acid for introducing a polynucleotide of interest into the cell's genome. Such kits are useful for optimization of conditions for template recognition, donor integration or for the construction of specifically modified cells, cell lines, and transgenic plants and animals containing gene disruptions, gene edits or targeted insertions. These and other aspects will be readily apparent to the skilled artisan in light of disclosure as a whole.

Also provided are kits containing any one or more of the elements disclosed in compositions described herein. In one aspect, the kits comprise a single guide polynucleotide comprising a crRNA, as described herein linked to a tracrRNA, wherein the crRNA comprises a variable targeting domain operably linked to a tracr mate sequence and/or one or more insertion sites for inserting or exchanging the variable targeting domain upstream of the tracr mate sequence, wherein when expressed, the single guide polynucleotide directs sequence-specific binding of a guide polynucleotide/Cas endonuclease complex to a target sequence in a eukaryotic cell. In another aspect, the kits comprise a dual guide polynucleotide comprising a crRNA molecule and a tracrRNA molecule, as described herein, wherein the crRNA molecule comprises a variable targeting domain operably linked to a tracr mate sequence and/or one or more insertion sites for inserting or exchanging the variable targeting domain upstream of the tracr mate sequence, wherein when expressed, the dual guide polynucleotide directs sequence-specific binding of a guide polynucleotide/Cas endonuclease complex to a target sequence in a eukaryotic cell.

The kits can contain one or more vectors encoding the guide polynucleotides, Cas endonucleases and/or template DNAs and/or donor DNAs described herein, and or the kits can contain the elements (guide polynucleotides, DNA templates, DNA donors and/or Cas endonucleases in purified or non-purified forms).

In one aspect, the kit comprises a Cas endonuclease as described herein, and/or a polynucleotide modification template and/or a donor DNA for inserting a polynucleotide of interest as described herein.

Components may be provide individually or in combinations, and may be provided in any suitable container, such as a vial, a bottle, or a tube. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some aspects, the kit includes instructions in one or more languages, for example in more than one language.

The meaning of abbreviations is as follows: "sec" means second(s), "min" means minute(s), "h" means hour(s), "d" means day(s), "A" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kb" means kilobase(s).

Non-limiting examples of compositions and methods disclosed herein are as follows:

1. A method for producing a plasmid DNA library containing a randomized Protospacer-Adjacent-Motif (PAM) sequence, the method comprising:
   a) providing a first single stranded oligonucleotide comprising a target sequence that can be recognized by a guide RNA/Cas endonuclease complex;
   b) providing a second single stranded oligonucleotide comprising a randomized PAM sequence adjacent to a nucleotide sequence capable of hybridizing with the target sequence of (a);
   c) producing an oligoduplex comprising said randomized PAM sequence by combining the first single stranded oligonucleotide of (a) and the second single stranded oligonucleotide of (b);
   d) producing a ligation product by ligating the oligoduplex from (c) with a linearized plasmid; and,
   e) transforming host cells with the ligation product of (e) and recovering multiple host cell colonies representing the plasmid library.

2. A method for producing a ligation product containing a randomized Protospacer-Adjacent-Motif (PAM) sequence, the method comprising:
   a) providing a first single stranded oligonucleotide comprising restriction endonuclease recognition site located upstream of a target sequence that can be recognized by a guide RNA/Cas endonuclease complex;
   b) providing a second single stranded oligonucleotide comprising a randomized PAM sequence adjacent a nucleotide sequence capable of hybridizing with the target sequence of (a);
   c) producing an oligoduplex comprising said randomized PAM sequence by combining the first single stranded oligonucleotide of (a) and the second single stranded oligonucleotide of (b); and,
   d) producing a ligation product by ligating the oligoduplex from (c) with a linearized plasmid;
3. The method of embodiment 1, wherein the host cells of (e) are *E. coli* cells.
4. A ligation product produced by the method of anyone of embodiments 1-2.
5. A library of host cells produced by the method of embodiment 1.
6. The method of anyone of embodiments 1-2, wherein the first single stranded oligonucleotide comprises a restriction endonuclease recognition site located upstream of a target sequence and wherein the ligation product of (d) is produced by first cleaving the oligoduplex with a restriction endonuclease that recognizes the restriction endonuclease recognition site of (a) followed by ligating the cleaved oligoduplex from (d) with a linearized plasmid.
7. The method of anyone of embodiments 1-2, wherein the second single stranded oligonucleotide comprises a randomized PAM of at least 5 randomized nucleotides (5Ns).
8. The method of anyone of embodiments 1-2, wherein the second single stranded oligonucleotide comprises a randomized PAM of at least 7 randomized nucleotides (7Ns).
9. A method for identification of a Protospacer-Adjacent-Motif (PAM) sequence, the method comprising:
   a) providing a library of plasmid DNA, wherein each one of said plasmid DNA comprises a randomized Protospacer-Adjacent-Motif sequence integrated adjacent to a target sequence that can be recognized by a guide RNA/Cas endonuclease complex;
   b) providing to said library of plasmids a guide RNA and a Cas endonuclease protein, wherein said guide RNA and Cas endonuclease protein can form a complex that is capable of introducing a double strand break into the said target sequence, thereby creating a library of cleaved targets;
   c) ligating adaptors to the library of cleaved targets of (b) allowing for the library of cleaved targets to be amplified;
   d) amplifying the library of cleaved targets such that cleaved products containing the randomized PAM sequence are enriched, thereby producing a library of enriched PAM-sided targets;
   e) sequencing the library of (a) and the library of enriched PAM-sided targets of (d) and identifying the nucleotide sequence adjacent to the cleaved targets of (b) on either strand of the plasmid DNA, wherein said nucleotide sequence represents a putative Protospacer-Adjacent-Motif sequences; and,
   f) determining the fold enrichment of each nucleotide within the putative Protospacer-Adjacent-Motif sequence relative to the plasmid DNA library of (a).
10. The method of anyone of embodiments 1-2 and 9, wherein the randomized PAM sequence comprises at least 1, 2, 3, 4, 5, 6, 7, 8, 9, 10, 11, 12, 13, 14, 15, 16, 17, 18, 19 or 20 randomized nucleotides.
11. The method of anyone of anyone of embodiments 1-2 and 9, wherein the target sequence is at least 12, 13, 14, 15, 16, 17, 18, 19, 20, 21, 22, 23, 24, 25, 26, 27, 28, 29 or 30 nucleotides in length.
12. The method of embodiment 9, wherein the Cas endonuclease is a Cas9 endonuclease from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755.
13. The method of embodiment 9, wherein the guide RNA comprises a single molecule of a chimeric non-naturally occurring crRNA linked to a tracrRNA.
14. The method of embodiment 9, wherein the guide RNA comprises a duplex molecule of a chimeric non-naturally occurring crRNA and a tracrRNA.
15. The method of embodiment 9, wherein the chimeric non-naturally occurring crRNA comprises a variable targeting domain capable of hybridizing to a target sequence in the genome of an organism, wherein said crRNA is linked a tracrRNA originating from organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755.
16. The method of embodiment 9, wherein the chimeric non-naturally occurring crRNA comprises a variable targeting domain capable of hybridizing to a target sequence in the genome of an organism, wherein said crRNA can form a duplex with a tracrRNA originating from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755.
17. The method of embodiment 9, wherein the chimeric non-naturally occurring crRNA comprises at least a fragment of a crRNA originating from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755.
18. A recombinant construct comprising at least one of the Protospacer-Adjacent-Motif (PAM) sequence identified by the method of embodiment 9.

19. A method for identification of a tracrRNA of an organism, the method comprising:
   a) providing a first single guide RNA candidate comprising a chimeric non-naturally occurring crRNA comprising a variable targeting domain capable of hybridizing to a target sequence in the genome of a cell, linked to a first nucleotide sequence representing the sense expression of a candidate tracrRNA naturally occurring in said organism;
   b) providing a second single guide RNA candidate comprising a chimeric non-naturally occurring crRNA comprising a variable targeting domain capable of hybridizing to a target sequence in the genome of said cell, linked to a second nucleotide sequence representing the sense expression of a candidate tracrRNA naturally occurring in said organism;
   c) providing to the first and second single guide RNA candidates a Cas endonuclease protein, wherein said Cas endonuclease protein can form a complex with either the first single guide RNA candidate or the second single guide RNA candidate, wherein said complex is capable of introducing a double strand break into said target sequence; and,
   d) identification of the first or second guide RNA candidate and its tracrRNA component that complexes to the Cas endonuclease of (c) and results in cleavage of the target sequence in the genome of said cell.

20. A method for identification of a tracrRNA of an organism, the method comprising:
   a) identifying a CRISPR array repeat sequence in a genomic locus of said organism;
   b) aligning the CRISPR array repeat sequence of (a) with the sequence of the genomic locus of (a) and identifying an antirepeat sequence that encodes a tracrRNA; and,
   c) determining the transcriptional direction of the tracrRNA.

21. A guide RNA capable of forming a guide RNA/Cas endonuclease complex, wherein said guide RNA/Cas endonuclease complex can recognize, bind to, and optionally nick or cleave a target sequence, wherein said guide RNA is a duplex molecule comprising a chimeric non-naturally occurring crRNA and a tracrRNA, wherein said chimeric non-naturally occurring crRNA comprises a variable targeting domain capable of hybridizing to said target sequence, wherein said tracrRNA is originated from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755.

22. A guide RNA capable of forming a guide RNA/Cas endonuclease complex, wherein said guide RNA/Cas endonuclease complex can recognize, bind to, and optionally nick or cleave a target sequence, wherein said guide RNA is a single molecule comprising a chimeric non-naturally occurring crRNA linked to a tracrRNA originating from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755, wherein said chimeric non-naturally occurring crRNA comprises a variable targeting domain capable of hybridizing to said target sequence.

23. A guide RNA capable of forming a guide RNA/Cas endonuclease complex, wherein said guide RNA/Cas endonuclease complex can recognize, bind to, and optionally nick or cleave a target sequence, wherein said guide RNA is a duplex molecule comprising a chimeric non-naturally occurring crRNA and a tracrRNA, wherein said chimeric non-naturally occurring crRNA comprises at least a fragment of a crRNA originating from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755, wherein said chimeric non-naturally occurring crRNA comprises a variable targeting domain capable of hybridizing to said target sequence.

24. A guide RNA capable of forming a guide RNA/Cas endonuclease complex, wherein said guide RNA/Cas endonuclease complex can recognize, bind to, and optionally nick or cleave a target sequence, wherein said guide RNA is a single molecule comprising a tracrRNA linked to a chimeric non-naturally occurring crRNA comprising at least a fragment of a crRNA originating from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755, wherein said chimeric non-naturally occurring crRNA comprises a variable targeting domain capable of hybridizing to said target sequence.

25. A guide RNA/Cas endonuclease complex comprising a Cas9 endonuclease originating from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755, and at least one guide RNA, wherein said guide RNA/Cas9 endonuclease complex is capable of recognizing, binding to, and optionally nicking or cleaving all or part of a target sequence.

26. The guide RNA/Cas endonuclease complex of embodiment 25 comprising at least one guide RNA of any one of embodiments 21-24.

27. The guide RNA/Cas endonuclease complex of embodiment 25, wherein said target sequence is located in the genome of a cell.

28. The guide RNA/Cas endonuclease complex of embodiment 25, wherein said Cas endonuclease is a Cas9 endonuclease selected from the group consisting of SEQ ID NOs: 35 and 81-91, or a functional fragment thereof, wherein said guide RNA/Cas9 endonuclease capable of recognizing, binding to, and optionally nicking or cleaving all or part of a specific DNA target sequence.

29. A method for modifying a target site in the genome of a cell, the method comprising providing to said cell at least one Cas9 endonuclease originating from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755, and at least one guide RNA, wherein said guide RNA and Cas endonuclease can form a complex that is capable of recognizing, binding to, and optionally nicking or cleaving all or part of said target site.

30. The method of embodiment 29, further comprising identifying at least one cell that has a modification at said target, wherein the modification at said target site is selected from the group consisting of (i) a replacement of at least one nucleotide, (ii) a deletion of at least one nucleotide, (iii) an insertion of at least one nucleotide, and (iv) any combination of (i)-(iii).

31. A method for editing a nucleotide sequence in the genome of a cell, the method comprising providing to said cell at least one Cas9 endonuclease originating from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755, a polynucleotide modification template, and at least one guide RNA, wherein said polynucleotide modification template comprises at least one nucleotide modification of said nucleotide sequence, wherein said guide RNA and Cas endonuclease can form a complex that is capable of recognizing, binding to, and optionally nicking or cleaving all or part of said target site.

32. A method for modifying a target site in the genome of a cell, the method comprising providing to said cell at least one guide RNA, at least one donor DNA, and at least one Cas9 endonuclease originating from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755, wherein said at least one guide RNA and at least one Cas endonuclease can form a complex that is capable of recognizing, binding to, and optionally nicking or cleaving all or part of said target site, wherein said donor DNA comprises a polynucleotide of interest.

33. The method of embodiment 32, further comprising identifying at least one cell that said polynucleotide of interest integrated in or near said target site.

34. The method of any one of embodiments 29-33, wherein the cell is selected from the group consisting of a human, non-human, animal, bacterial, fungal, insect, yeast, non-conventional yeast, and plant cell.

35. The method of embodiment 34, wherein the plant cell is selected from the group consisting of a monocot and dicot cell.

36. The method of embodiment 35, wherein the plant cell is selected from the group consisting of maize, rice, sorghum, rye, barley, wheat, millet, oats, sugarcane, turfgrass, or switchgrass, soybean, canola, alfalfa, sunflower, cotton, tobacco, peanut, potato, tobacco, *Arabidopsis*, and safflower cell.

37. A plant comprising a modified target site, wherein said plant originates from a plant cell comprising a modified target site produced by the method of any of embodiments 29-36.

38. A plant comprising an edited nucleotide, wherein said plant originates from a plant cell comprising an edited nucleotide produced by the method of embodiment 31.

39. A method for designing a single guide RNA, the method comprising:
   a) aligning a tracrRNA sequence with a CRISPR array repeat sequence from a genomic locus of an organism, wherein said CRISPR array repeat sequence comprises a crRNA sequence;
   b) deducing the transcriptional direction of the CRISPR array, thereby also deducing the crRNA sequence; and,
   c) designing a single guide RNA comprising said tracrRNA and crRNA sequences 40. A method for producing target sequences, the method comprising:
   a) identifying a polynucleotides of interest;
   b) introducing a Protospacer-Adjacent-Motif (PAM) sequence adjacent to said polynucleotide of interest, wherein said PAM sequence comprises the nucleotide sequence NNNNCND, thereby creating a thereby creating a target site for a guide RNA/Cas9 endonuclease complex
   c) identifying a polynucleotides of interest;

41. The method for embodiment 40, wherein the guide RNA/Cas9 endonuclease complex, comprises at least one Cas9 endonuclease originated from organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755, wherein said guide RNA/Cas9 endonuclease complex is capable of recognizing, binding to, and optionally nicking or cleaving all or part of a target sequence 42. A method for producing a plasmid DNA library containing a randomized Protospacer-Adjacent-Motif (PAM) sequence, the method comprising transforming at least one host cell with a ligation product and recovering multiple host cell colonies representing the plasmid library, wherein said ligation product was generated by contacting a library of linear oligoduplexes with a linearized plasmid, wherein each oligoduplex member of said library of oligoduplexes comprises a first single stranded oligonucleotide comprising a-target sequence, and a second single stranded oligonucleotide comprising a randomized PAM sequence adjacent to a nucleotide sequence capable of hybridizing with said target sequence.

43. A method for identification of a Protospacer-Adjacent-Motif (PAM), the method comprising:
   a) providing a library of plasmids, wherein each one of said plasmids comprise a randomized Protospacer- Adjacent-Motif sequence integrated adjacent to a target sequence that can be recognized by a guide RNA/Cas endonuclease complex;
b) producing a 3 prime (3') or 5 prime (5') overhang into the target sequence of (a) by providing to the plasmids of (a) a 3 prime deoxyadenine, a guide RNA and a Cas endonuclease protein, wherein said guide RNA and Cas endonuclease can form a complex that is capable of introducing a double strand break into said target sequence;
c) ligating adapters to the 3 prime or 5 prime overhang of (c), thereby creating a library of cleaved targets that can be amplified;
d) amplifying the library of cleaved targets such that cleaved products containing the randomized PAM sequence are enriched;
e) sequencing the library of (a) and the library of enriched PAM-sided targets of (d) and identifying the nucleotide sequence adjacent to the cleaved targets of (b) on either strand of the plasmid DNA, wherein said nucleotide sequence represents a putative Protospacer-Adjacent-Motif sequences; and,
f) determining the fold enrichment of each nucleotide within the putative Protospacer-Adjacent-Motif sequence relative to the plasmid DNA library of (a).

44. A single guide RNA selected from the group consisting of SEQ ID NOs: 47, 127, 114-125, and 128-139.

45. The method of embodiment 9, wherein the Cas endonuclease protein is provided as a purified protein, a cell lysate comprising said Cas endonuclease, a dilution of a cell lysate comprising said Cas endonuclease, an in-vitro translation mixture or an dilution of an in-vitro translation mixture.

46. The method of embodiment 9, wherein the Cas endonuclease protein is selected from the group consisting of includes a Cas9 protein, a Cpf1 protein, a C2c1 protein, a C2c2 protein, a C2c3 protein, Cas3, Cas3-HD, Cas 5, Cas7, Cas8, Cas10, or complexes of these.

47. The method of embodiment 9, wherein the Cas endonuclease is a Cas9 endonuclease from an organism selected from the group consisting of SEQ ID NOs: 81, 82, 83, 84, 85, 86, 87, 88, 89, 90, 91 and 140.

48. A recombinant DNA comprising at least one of randomized Protospacer-Adjacent-Motif (PAM) sequence adjacent to a target sequence that can be recognized by a guide RNA/Cas endonuclease complex.

49. A single guide RNA capable of forming a guide RNA/Cas9 endonuclease complex, wherein said guide RNA/Cas9 endonuclease complex can recognize, bind to, and optionally nick or cleave a target sequence, wherein said single guide RNA is selected from the group consisting of SEQ ID NOs: 47 and 127.

50. A guide RNA capable of forming a guide RNA/Cas endonuclease complex, wherein said guide RNA/Cas endonuclease complex can recognize, bind to, and optionally nick or cleave a target sequence, wherein said guide RNA is a duplex molecule comprising a chimeric non-naturally occurring crRNA comprising SEQ ID NO:185 and a tracrRNA comprising SEQ ID NO:199, wherein said chimeric non-naturally occurring crRNA comprises a variable targeting domain capable of hybridizing to said target sequence.

51. A guide RNA/Cas endonuclease complex comprising a Cas9 endonuclease of SEQ ID NO: 140, or a functional fragment thereof, and a guide RNA, wherein said guide RNA/Cas9 endonuclease complex is capable of recognizing, binding to, and optionally nicking or cleaving all or part of a target sequence.

52. The guide RNA/Cas endonuclease complex of embodiment 51 comprising at least one guide RNA of embodiment 49 or embodiment 50.

53. The guide RNA/Cas endonuclease complex of embodiment 51, wherein said target sequence is located in the genome of a cell.

54. A method for modifying a target site in the genome of a cell, the method comprising providing to said cell at least one Cas9 endonuclease of SEQ ID NO: 140, or a functional fragment thereof, and at least one guide RNA, wherein said guide RNA and Cas endonuclease can form a complex that is capable of recognizing, binding to, and optionally nicking or cleaving all or part of said target site.

55. The method of embodiment 54, further comprising identifying at least one cell that has a modification at said target, wherein the modification at said target site is selected from the group consisting of (i) a replacement of at least one nucleotide, (ii) a deletion of at least one nucleotide, (iii) an insertion of at least one nucleotide, and (iv) any combination of (i)-(iii).

56. A method for editing a nucleotide sequence in the genome of a cell, the method comprising providing to said cell at least one Cas9 endonuclease of SEQ ID NO: 140, or a functional fragment thereof, a polynucleotide modification template, and at least one guide RNA, wherein said polynucleotide modification template comprises at least one nucleotide modification of said nucleotide sequence, wherein said guide RNA and Cas endonuclease can form a complex that is capable of recognizing, binding to, and optionally nicking or cleaving all or part of said target site.

57. A method for modifying a target site in the genome of a cell, the method comprising providing to said cell at least one guide RNA, at least one donor DNA, and at least one Cas9 endonuclease of SEQ ID NO: 140, or a functional fragment thereof, wherein said at least one guide RNA and at least one Cas endonuclease can form a complex that is capable of recognizing, binding to, and optionally nicking or cleaving all or part of said target site, wherein said donor DNA comprises a polynucleotide of interest.

58. A single guide RNA capable of forming a guide RNA/Cas endonuclease complex, wherein said guide RNA/Cas endonuclease complex can recognize, bind to, and optionally nick or cleave a target sequence, wherein said guide RNA is a single molecule comprising a chimeric non-naturally occurring crRNA linked to a tracrRNA comprising SEQ ID NO:199.

59. A guide RNA capable of forming a guide RNA/Cas endonuclease complex, wherein said guide RNA/Cas endonuclease complex can recognize, bind to, and optionally nick or cleave a target sequence, wherein said guide RNA is a duplex molecule comprising a chimeric non-naturally occurring crRNA and a tracrRNA, wherein said chimeric non-naturally occurring crRNA comprises at least a fragment of a crRNA comprising SEQ ID NO:195, wherein said chimeric non-naturally occurring crRNA comprises a variable targeting domain capable of hybridizing to said target sequence.

60. A kit for binding, cleaving or nicking a target sequence in eukaryotic cells or organisms comprising a guide RNA specific for said target DNA, and a Cas endonuclease protein of SEQ ID NO:140.

61. A kit for cleaving a target sequence in eukaryotic cells or organisms comprising a guide RNA specific for said target DNA, and a Cas endonuclease protein, wherein said guide RNA is capable of forming a guide RNA/Cas9 endonuclease complex, wherein said guide RNA/Cas9 endonuclease complex can recognize, bind to, and optionally nick or cleave said target sequence, wherein said guide RNA is selected from the group consisting of SEQ ID NOs: 47 and 127.

62. A kit for targeted mutagenesis in eukaryotic cells or organisms comprising a guide RNA specific for said target DNA, a polynucleotide modification template, and a Cas endonuclease protein of SEQ ID NO:140, wherein said guide RNA is capable of forming a guide RNA/Cas9 endonuclease complex, wherein said guide RNA/Cas9 endonuclease complex can recognize, bind to, and optionally nick or cleave said target sequence, wherein said guide RNA is selected from the group consisting of SEQ ID NOs: 47 and 127.

63. The kit of any one of embodiments 60-61, further comprising a molecule selected from the group consisting of an inhibitors of NHEJ, an activator of HDR or MMEJ repair pathways, an exogenous sequence, a homologous recombination DNA, a donor DNA, and any one combination thereof.

EXAMPLES

In the following Examples, unless otherwise stated, parts and percentages are by weight and degrees are Celsius. It should be understood that these Examples, while indicating embodiments of the disclosure, are given by way of illustration only. From the above discussion and these Examples, one skilled in the art can make various changes and modifications of the disclosure to adapt it to various usages and conditions. Such modifications are also intended to fall within the scope of the appended claims.

Example 1

Figure 1:
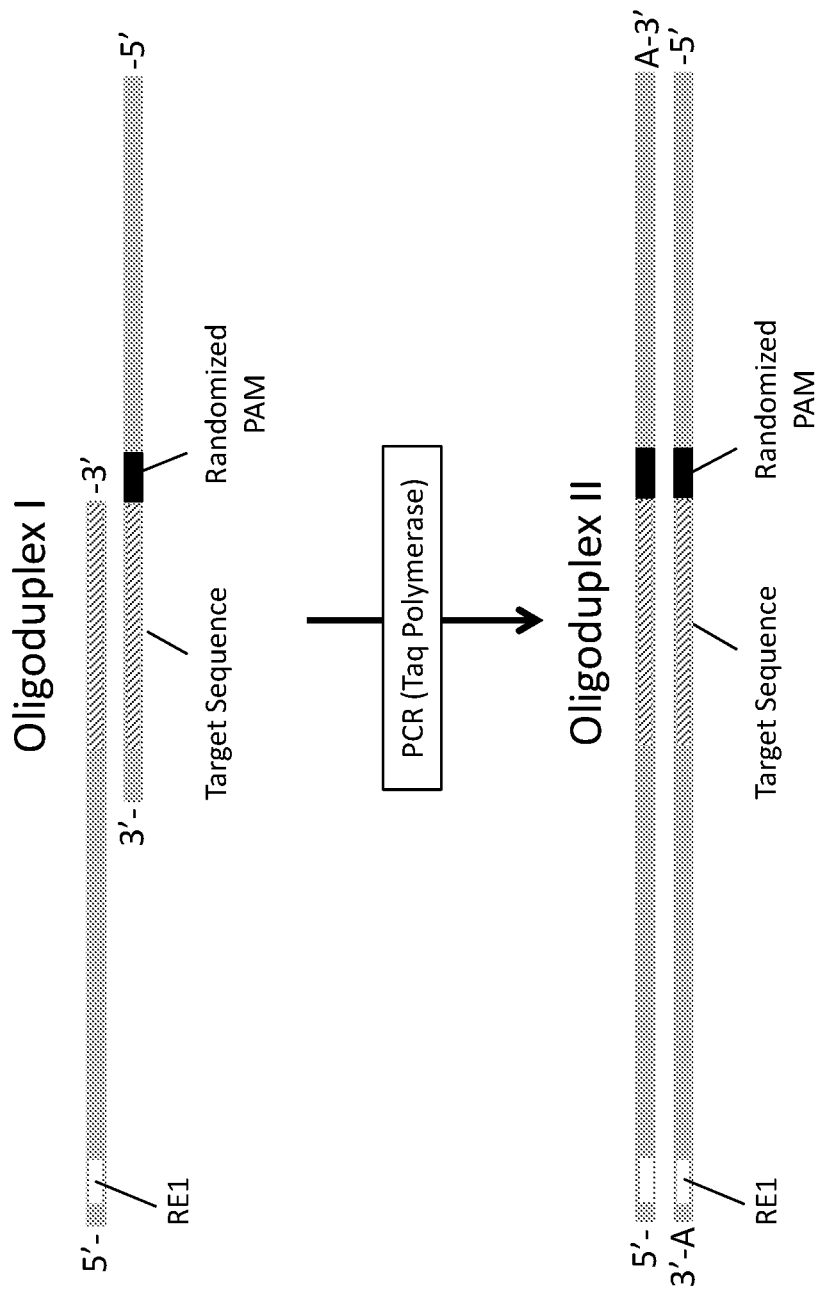
FIG. 1 shows a diagram of the formation of a full Oligoduplex II comprising a restriction enzyme recognition site (RE1), a target sequence and a randomized Protospacer-Adjacent-Motif (PAM) sequence.
Figure 2:
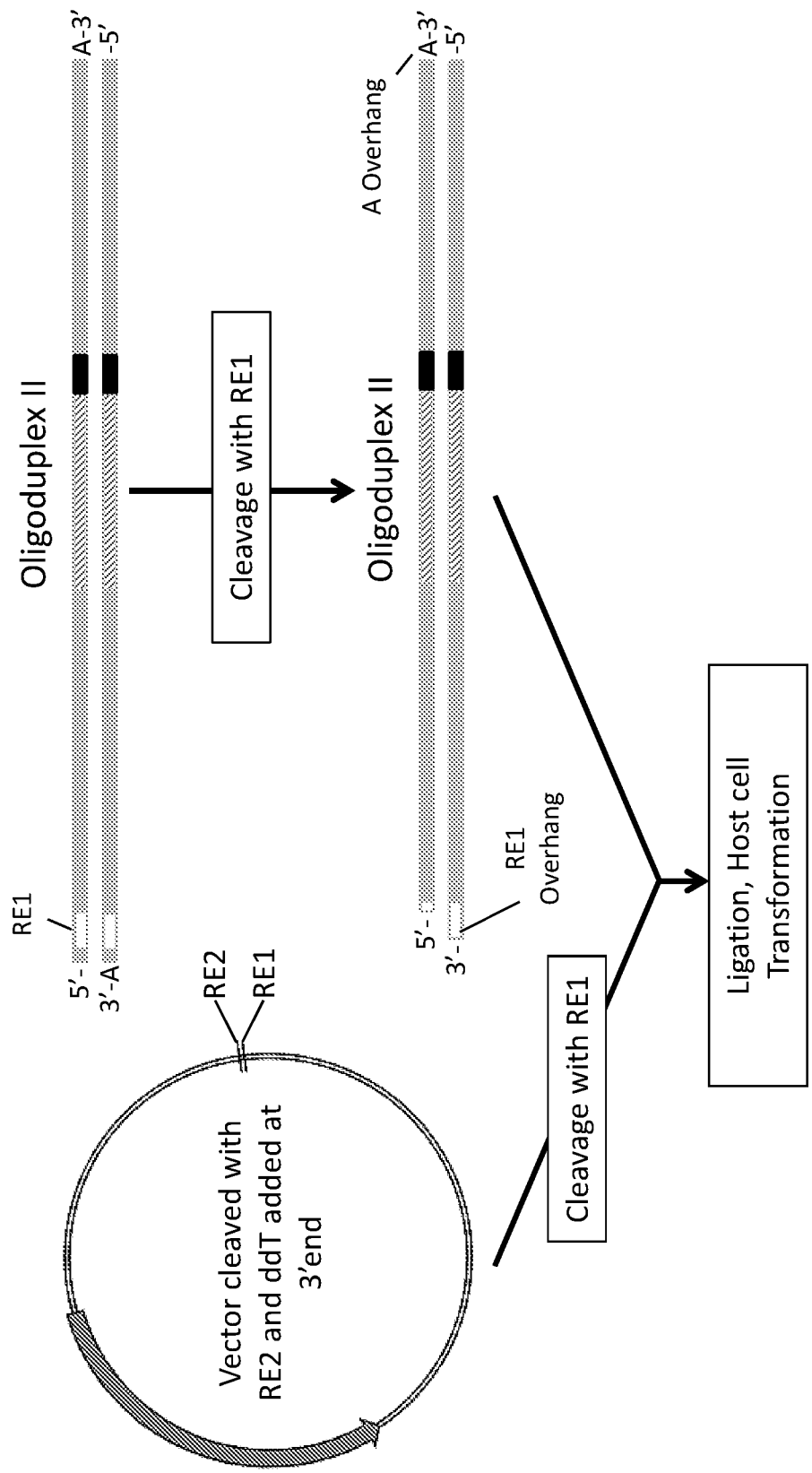
FIG. 2 show a diagram of the design and construction of a 5 nucleotide (5N) randomized Protospacer-Adjacent-Motif (PAM) plasmid library and host cell library. RE1=restriction endonuclease 1, RE2=restriction endonuclease 2.

Design and Construction of 5N Randomized Protospacer-Adjacent-Motif (PAM) Library for Assaying Cas9 PAM Preferences To characterize the Protospacer-Adjacent-Motif (PAM) specificity of Cas9 proteins from Type II CRISPR (clustered, regularly interspaced, short palindromic repeats)-Cas (CRISPR-associated) nucleic acid-based adaptive immune systems found in most archaea and some bacteria, a plasmid DNA library containing a section of 5 random base pairs immediately adjacent to a 20 base pair target sequence, T1 (CGCTAAAGAGGAAGAGGACA (SEQ ID NO: 1), was developed. Randomization of the PAM sequence was generated through the synthesis of a single oligonucleotide, GG-821N (TGACCATGATTACGAATTCNNNNNT-GTCCTCTTCCTCTTTAGCGAGC (SEQ ID NO: 2), with hand-mixing used to create a random incorporation of nucleotides across the 5 random residues (represented as N in the sequence of GG-821N). To convert the single stranded template of GG-821N into a double-stranded DNA template for cloning into the plasmid vector, a second oligonucleotide, GG-820 (AAGGATCCCCGGGTACCGAGCTG-CTCGCTAAAGAGGAAGAGGAC (SEQ ID NO: 3), was synthesized with complementation to the 3' end of GG-821N to form a partial oligonucleotide duplex (oligoduplex I) as depicted in FIG. 1. The partial duplex was then extended by PCR using DreamTaq polymerase (Thermo Fisher Scientific) to generate a full duplex containing the target sequence, 5 NNNNN randomized base pairs downstream of the target sequence and cleavage site for the BamHI restriction enzyme (oligoduplex II in FIG. 1). To generate the plasmid library, the oligoduplex, purified using GeneJET PCR Purification Kit (Thermo Fisher Scientific), was digested with BamHI and ligated into pTZ57R/T vector (Thermo Fisher Scientific) pre-cleaved with BamHI. Linear pTZ57R/T vector contains protruding ddT nucleotide at the 3' ends, whereas PCR fragments generated with DreamTaq polymerase contains dA at the 3' ends. Therefore one end of the PCR fragment is ligated into the vector through BamHI sticky ends, while another through A/T ends (FIG. 2). The $E.$ $coli$ DH5α strain was transformed ($Ca^{2+}$ transformation) with the ligated plasmid library and plated onto Luria Broth (LB) containing agar. The transformation efficiency was estimated from plated dilutions. Overall, 12,000 colonies were recovered. The colonies were harvested from the plate by gently resuspending them in liquid LB media and plasmid DNA was purified using GeneJET Plasmid Miniprep kit (Thermo Fisher Scientific).

Figure 4:
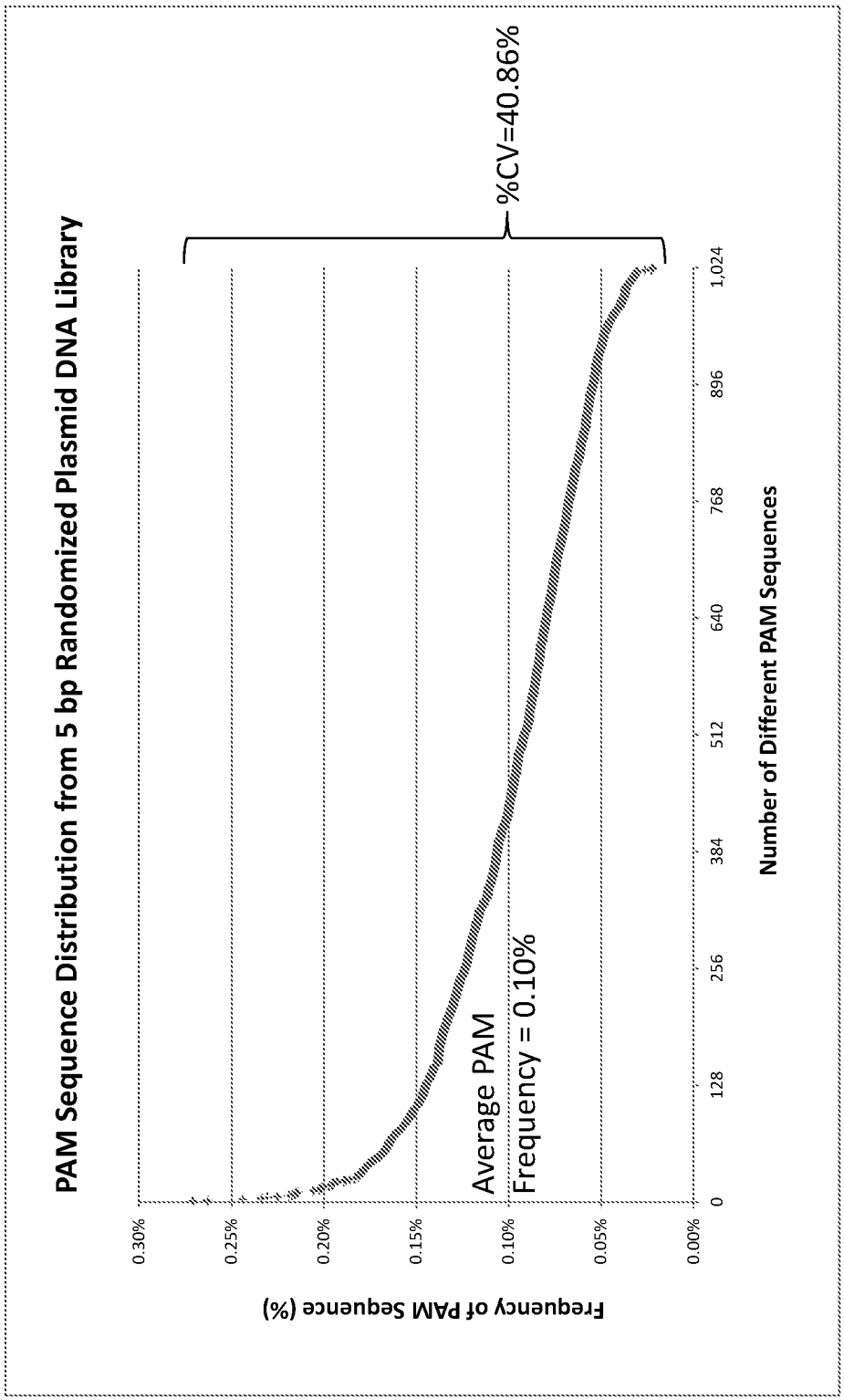
FIG. 4 depicts the PAM sequence distribution from a 5 nucleotide (5N) randomized Protospacer-Adjacent-Motif (PAM) plasmid library.

To validate the randomness of the resulting PAM library, PCR fragments spanning the 5 bp randomized PAM region were generated by Phusion High-Fidelity DNA Polymerase (Thermo Fisher Scientific) amplification (15 cycles of a 2-step amplification protocol) using a TK-119 (GAGCTCGCTAAAGAGGAAGAGG (SEQ ID NO: 4) and pUC-dir (GCCAGGGTTTTCCCAGTCACGA (SEQ ID NO: 5) primer pair and 50 ng of plasmid DNA library as template. The resulting 122 bp PCR product was purified using GeneJET PCR Purification Kit (Thermo Fisher Scientific). 40 ng of the resulting PCR product was then amplified with Phusion® High Fidelity PCR Master Mix (New England Biolabs, M0531 L) adding on the sequences necessary for amplicon-specific barcodes and Illumnia sequencing using "tailed" primers through two rounds of PCR each consisting of 10 cycles. The primers used in the primary PCR reaction are shown in Table 2 and a set of primers (AATGATACGGCGACCACCGAGATCTA-CACTCTTTCCCTACACG (Universal Forward, SEQ ID NO: 8) and CAAGCAGAAGACGGCATA (Universal Reverse, SEQ ID NO: 9) universal to all primary PCR reactions were utilized for the secondary PCR amplification. The resulting PCR amplifications were purified with a Qiagen PCR purification spin column, concentration measured with a Hoechst dye-based fluorometric assay, combined in an equimolar ratio, and single read 60-100 nucleotide-length deep sequencing was performed on Illumina's MiSeq Personal Sequencer with a 5-10% (v/v) spike of PhiX control v3 (Illumina, FC-110-3001) to off-set sequence bias. The PAM sequence for only those reads containing a perfect 12 nt sequence match flanking either side of the 5 nucleotide randomized PAM sequence were captured and used to examine the frequency and diversity of PAM sequences present in the library. The frequency of each PAM sequence was calculated by dividing the number of reads with a given PAM by the total number of reads. The PAM sequence distribution was visualized by ordering the frequency of each PAM from greatest to least and displaying them graphically and by calculating the standard deviation of the resulting PAM frequencies relative to the average. As shown in FIG. 4, all 1,024 possible PAM sequences were present at an average frequency of 0.10% with a coefficient of variation of 40.86%.

TABLE 2

Primary PCR primer sequences for tailing on the sequences needed for Illumina deep sequencing of initial uncut 5 bp randomized PAM pTZ57R/T library.

| Primer Name | Primer Orientation | Primary PCR Primer Sequence | SEQ ID NO. |
|---|---|---|---|
| JKYS800.1 | Forward | CTACACTCTTTCCCTACACGACGCTCTT CCGATCTAAGTGAGCTCGCTAAAGAGGA AGA | 6 |
| JKYS803 | Reverse | CAAGCAGAAGACGGCATACGAGCTCTTC CGATCTGAATTCGAGCTCGGTACCT | 7 |

Example 2

Protein Expression and Purification of *Streptococcus pyogenes*, *Streptococcus thermophilus* CRISPR1 and *Streptococcus thermophilus* CRISPR3 Cas9 Proteins To examine the PAM specificity of the Cas9 proteins from the *Streptococcus pyogenes* (Spy) (Jinek et al. (2012) *Science* 337:816-21), *Streptococcus thermophilus* CRISPR1 (Sth1) (Horvath et al. (2008) *Journal of Bacteriology* 190: 1401-12) and *Streptococcus thermophilus* CRISPR3 (Sth3) (Horvath et al. (2008) *Journal of Bacteriology* 190:1401-12) Type II CRISPR-Cas systems, Spy, Sth1 and Sth3 Cas9 proteins were *E. coli* expressed and purified. Briefly, the cas9 genes of the CRISPR1-Cas and CRISPR3-Cas systems of *Streptococcus thermophilus* (Sth1 and Sth3) were amplified from a genomic DNA sample, while the cas9 gene of *Streptococcus pyogenes* (Spy) was amplified from a plasmid, pMJ806 (Addgene plasmid #39312)). DNA fragments encoding Sth1, Sth3 and Spy Cas9 were PCR amplified using Sth1-dir/Sth1-rev (ACGTCTCACATGACTAAGCCATACTCAATTGGAC (SEQ ID NO: 10); ACTCGAGACCCTCTCCTAGTTTGGCAA (SEQ ID NO: 11), Sth3-dir/Sth3-rev (GGGGGGTCTCACATGAGTGACTTAGT (SEQ ID NO: 12); AATTACTCGAGAAAATCTAGCTTAGGCTTA (SEQ ID NO: 13) and Spy-dir/Spy-rev (AAGGTCTCCCATGGATAAGAAATACTCAATAGGCTTAG (SEQ ID NO: 14); TTCTCGAGGTCACCTCCTAGCTGACTCAAATC (SEQ ID NO: 15) primer pairs, accordingly, and ligated into a pBAD24-CHis expression vector digested over NcoI and XhoI sites.

Sth3 and Spy Cas9 proteins were expressed in *E. coli* DH10HB strain grown in LB broth supplemented with ampicillin (100 mg/ml). Cells were grown at 37° C. to an OD 600 of 0.5 at which time the growth temperature was decreased to 16° C. and expression induced with 0.2% (w/v) arabinose for 20 h. Cells were pelleted and resuspended in loading buffer (20 mM $KH_2PO_4$ pH7.0, 0.5 M NaCl, 10 mM imidazole, 5% glycerol) and disrupted by sonication. Cell debris was removed by centrifugation. The supernatant was loaded onto the $Ni^{2+}$-charged 5 ml HiTrap chelating HP column (GE Healthcare) and eluted with a linear gradient of increasing imidazole concentration. The fractions containing Cas9 were pooled and subsequently loaded onto HiTrap heparin HP column (GE Healthcare) for elution using a linear gradient of increasing NaCl concentration (from 0.5 to 1 M NaCl). The fractions containing Cas9 were pooled and dialyzed against 10 mM Bis-Tris-HCl pH 7.0, 300 mM KCl, 1 mM EDTA, 1 mM DTT, 50% (v/v) glycerol and stored at −20° C.

Example 3

Identification of PAM Preferences for *Streptococcus pyogenes* and *Streptococcus thermophilus* CRISPR3 Cas9 Proteins To empirically examine the PAM preferences for *Streptococcus pyogenes* (Spy) and *Streptococcus thermophilus* CRISPR3 (Sth3) Cas9 proteins, the randomized PAM library described in Example 1 was subject to digestion with purified Sth3 and Spy Cas9 proteins and guide RNA containing a variable targeting domain that hybridizes with, i.e., is complementary to, a sequence in the target DNA molecule (referred herein as target sequence), T1 (SEQ ID NO: 1). Sth3 and Spy Cas9-crRNA-tracrRNA complexes were assembled by mixing Cas9 protein with pre-annealed crRNA and tracrRNA duplex (Table 3) at 1:1 molar ratio followed by incubation in a complex assembly buffer (10 mM Tris-HCl pH 7.5 at 37° C., 100 mM NaCl, 1 mM EDTA, 1 mM DTT) at 37° C. for 1 h. 1 µg of plasmid DNA library with randomized 5 bp NNNNN PAM was cleaved with 50 nM and 100 nM of Cas9 complex in a reaction buffer (10 mM Tris-HCl pH 7.5 at 37° C., 100 mM NaCl, 10 mM $MgCl_2$, 1 mM DTT) for 60 min. at 37° C. in a 100 µl reaction volume (FIG. 3).

TABLE 3

RNA molecules used for Sth3 and Spy Cas9-crRNA-tracrRNA complex assembly.

| Name | Sequence (5'-3') | Origin | SEQ ID NO. |
|---|---|---|---|
| Sth3 crRNA | CGCUAAAGAGGAAGAGGACAGU UUUAGAGCUGUGUUGUUUCG | Synthetic oligonucleotide | 16 |
| Sth3 tracrRNA | GGGCGAAACAACACAGCGAGUU AAAAUAAGGCUUAGUCCGUACUC AACUUGAAAAGGUGGCACCGAU UCGGUGUUUUU | In vitro transcription | 17 |
| Spy crRNA | CGCUAAAGAGGAAGAGGACAGU UUUAGAGCUAUGCUGUUUUG | Synthetic oligonucleotide | 18 |
| Spy tracrRNA | GGGAAACAGCAUAGCAAGUUAAA AUAAGGCUAGUCCGUUAUCAAC UUGAAAAGUGGCACCGAGUCG GUGCUUUUUUU | In vitro transcription | 19 |

To efficiently capture the blunt-ends of the plasmid library generated by Sth3 or Spy cleavage, a 3' dA was added by incubating the completed digestion reactions with 2.5 U of DreamTaq DNA Polymerase (Thermo Fisher Scientific) and 0.5 µl of 10 mM dATP (or dNTP) for an additional 30 min. at 72° C. (FIG. 3). Reaction products were purified using GeneJET PCR Purification Kit (Thermo Fisher Scientific). Next adapters with a 3' dT overhang were generated by annealing TK-117 (CGGCATTCCTGCTGAACCGCTCTTCCGATCT (SEQ ID NO: 20) and phosphorylated TK-111 (GATCGGAAGAGCGGTTCAGCAGGAATGCCG (SEQ ID NO: 21) oligonucleotides. 100 ng of the resulting adapter was ligated to an equal concentration of the purified 3' dA overhanging cleavage products for 1 hour at 22° C. in a 25 µl reaction volume in ligation buffer (40 mM Tris-HCl pH 7.8 at 25° C., 10 mM $MgCl_2$, 10 mM DTT, 0.5 mM ATP, 5% (w/v) PEG 4000, 0.5 U T4 Ligase; Thermo Fisher Scientific) (FIG. 3). Next, to selectively enrich for cleaved products containing the PAM sequence, PCR amplification was performed with a forward primer, pUC-dir (SEQ ID NO: 5), specific to the PAM-side of the cleaved pTZ57R/T plasmid vector and with a reverse primer, TK-117 (SEQ ID NO: 20), specific to the ligated TK-117/TK-111 adapter sequence (FIG. 3). PCR fragments were generated by Phusion High-Fidelity DNA Polymerase (Thermo Fisher Scientific) amplification (15 cycles of a 2-step amplification protocol) with 10 µl of ligation reaction mixtures as a template (in 100 µl total volume). The resulting 131 bp PCR products amplified from the Cas9 pre-cleaved plasmid libraries were purified with GeneJET PCR Purification Kit (Thermo Fisher Scientific) and prepared for Illumina deep sequencing as described in Example 1 except the barcode containing forward primers used in the primary reaction were specific to the TK-117/TK-111 adapter sequence and are shown in Table 4 (FIG. 3).

TABLE 4

Primary PCR primer sequences for tailing on the sequences needed for Illumina deep sequencing of cleaved and adapter ligated 5 bp randomized PAM pTZ57R/T library.

| Primer Name | Digestion Experiment | Primer Orientation | Primary PCR Primer Sequence | SEQ ID NO. |
|---|---|---|---|---|
| JKYS807.1 | 50 nM Sth3 | Forward | CTACACTCTTTCCCTACACGAC GCTCTTCCGATCTAAGGCGGCA TTCCTGCTGAAC | 22 |
| JKYS807.2 | 100 nM Sth3 | Forward | CTACACTCTTTCCCTACACGAC GCTCTTCCGATCTTTCCCGGCA TTCCTGCTGAAC | 23 |
| JKYS807.3 | 50 nM Spy | Forward | CTACACTCTTTCCCTACACGAC GCTCTTCCGATCTGGAACGGCA TTCCTGCTGAAC | 24 |
| JKYS807.4 | 100 nM Spy | Forward | CTACACTCTTTCCCTACACGAC GCTCTTCCGATCTCCTTCGGCA TTCCTGCTGAAC | 25 |

Figure 5:
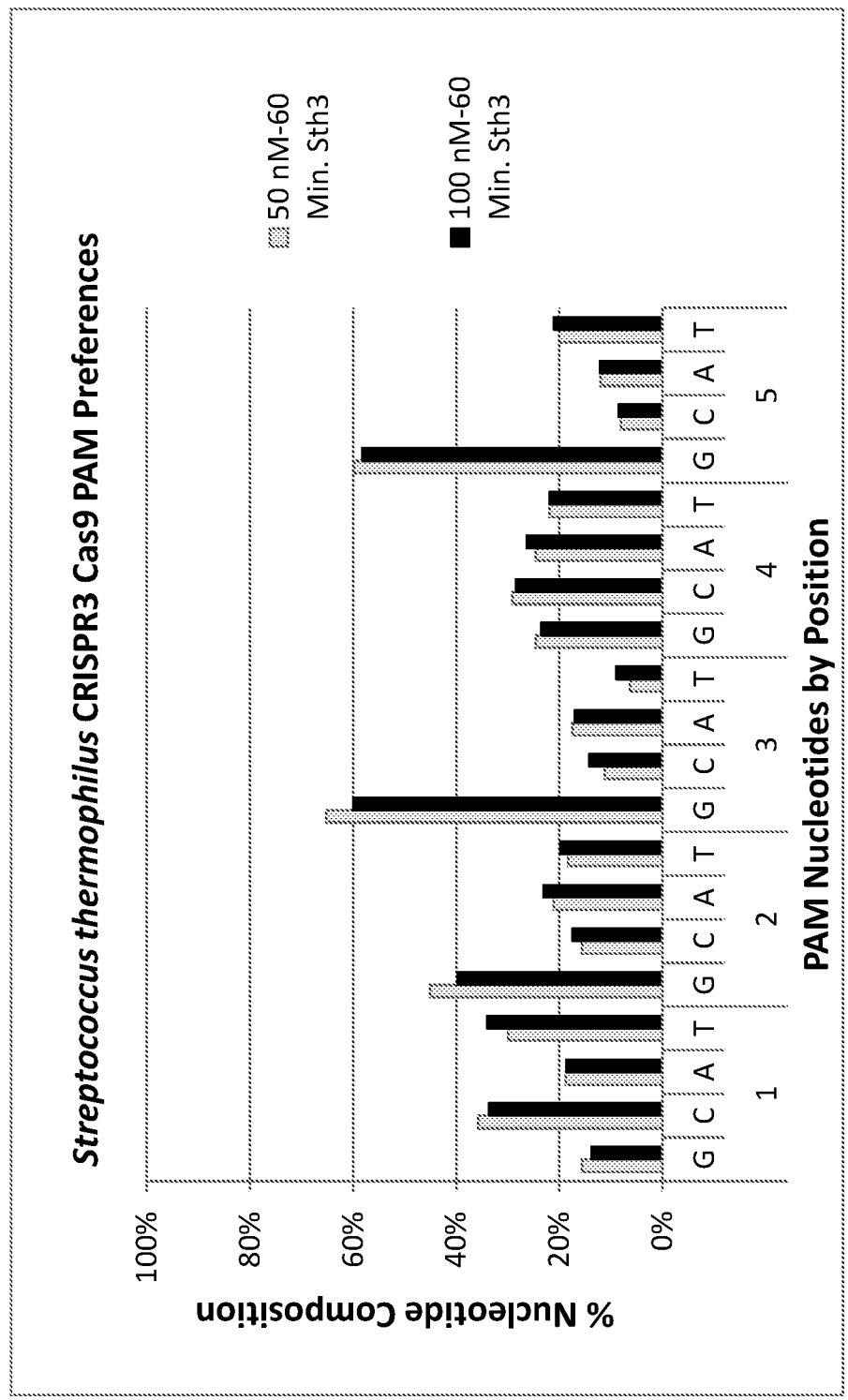
FIG. 5 shows the PAM preferences (NGGNG) for *Streptococcus thermophilus* CRISPR3 (Sth3) Cas9 endonuclease in both 50 nM and 100 nM digests.
Figure 6:
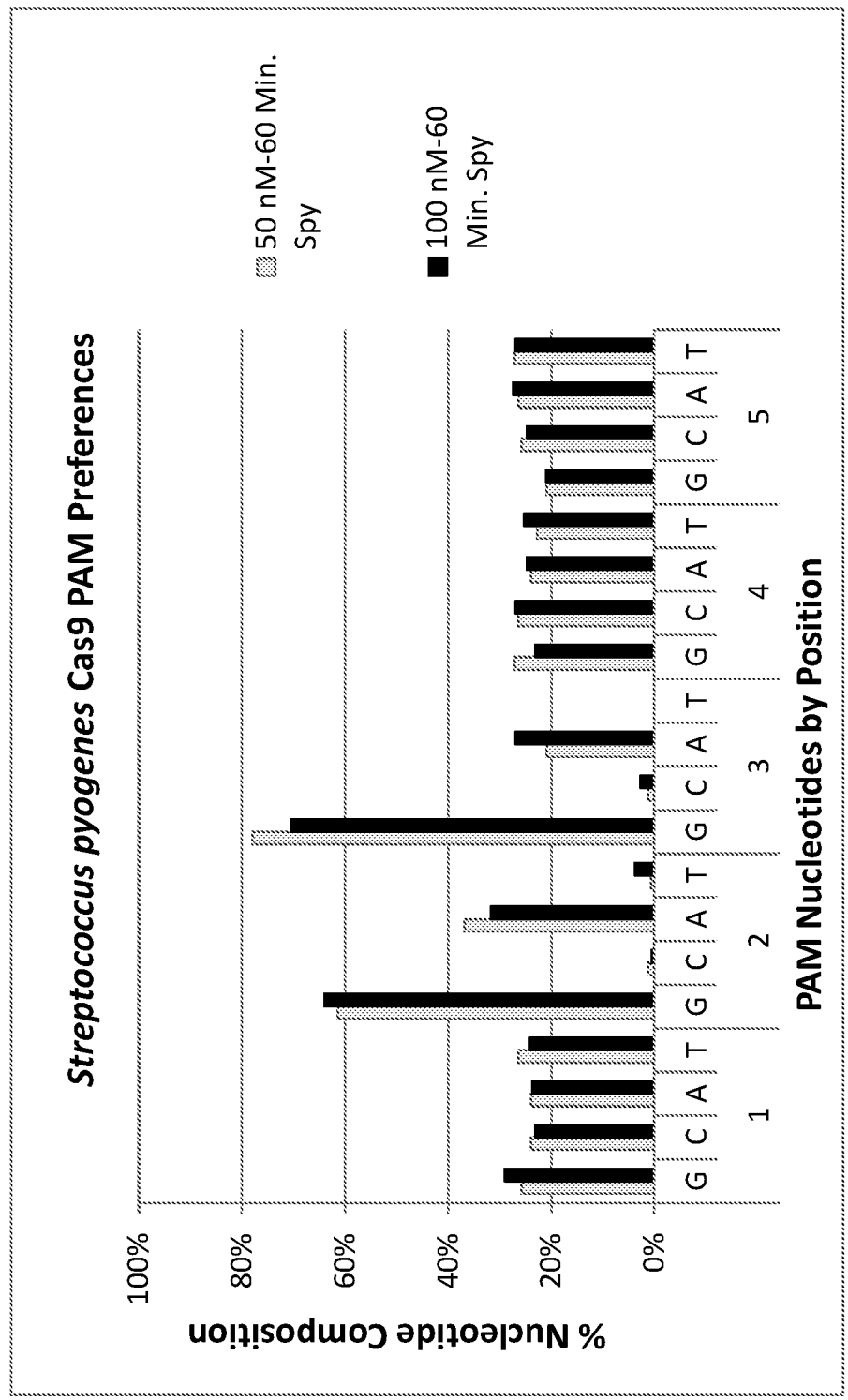
FIG. 6 shows the PAM preferences (NGG) for *Streptococcus pyogenes* (Spy) Cas9 endonuclease in both 50 nM and 100 nM digests.
Figure 7:
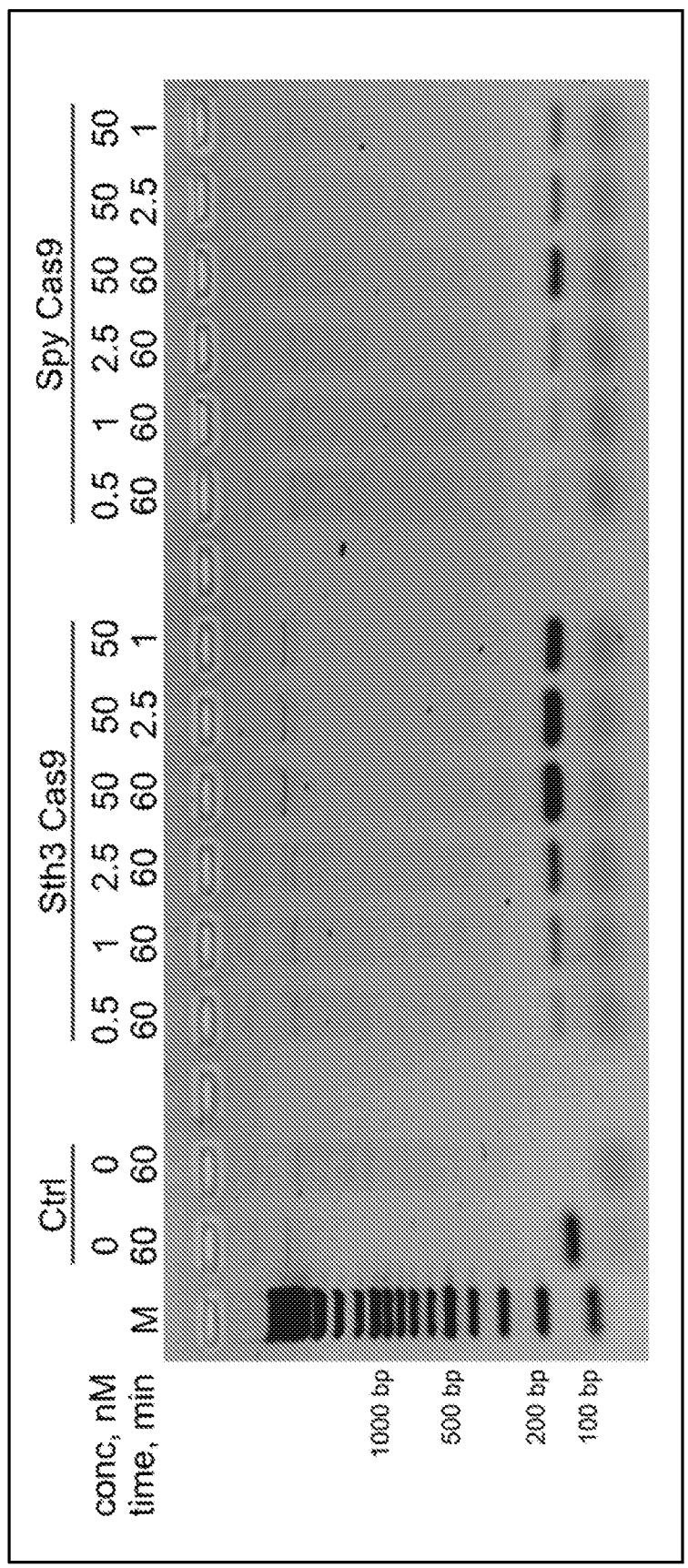
FIG. 7 shows the effect of decreasing Sth3 and Spy Cas9-crRNA-tracrRNA complex concentration and digestion time to determine the minimal Sth3 and Spy Cas9 concentration and shortest digestion time where PCR amplified cleavage products may still be obtained from the randomized PAM plasmid library.

The resulting Illumina compatible libraries were then sequenced as described in Example 1. The PAM sequence for only those reads containing a perfect 12 nt sequence match flanking either side of the 5 nucleotide randomized PAM sequence were captured and used to examine the frequency and diversity of PAM sequences present in the Sth3 and Spy Cas9-guide RNA cleaved libraries. Given the inherent bias in the uncut library observed in FIG. 4 and described in Example 1, PAM preferences were calculated relative to the uncut library by dividing the frequency of a given PAM from the Sth3 or Spy Cas9-guide RNA digested library by the frequency of the same PAM sequence in the uncut library with the resulting value being represented as a fold enrichment correlative to the uncut control. To examine the PAM preferences of Sth3 and Spy Cas9 proteins, the percent nucleotide composition of the PAM sequences with fold enrichment relative to the uncut control were examined. As shown in FIG. 5 and FIG. 6, the canonical PAM preferences for both Sth3 and Spy Cas9 proteins, NGGNG and NGG, respectively, are observed in both the 50 nM and 100 nM digests. For Sth3 Cas9 protein, a slight preference (not previously reported) for a C or T bp at position 1 is also evident. Next, the effect of decreasing Sth3 and Spy Cas9-crRNA-tracrRNA complex concentration and digestion time on PAM preferences was examined. To this end, the minimal Cas9 concentration and shortest time where PCR amplified cleavage products may still be obtained from the randomized PAM plasmid library were determined. First, the reaction time was held constant at 60 minutes while the Cas9-crRNA-tracrRNA complex concentration was varied between 0.5-100 nM. Next, the Cas9-crRNA-tracrRNA complex concentration was fixed at 50 nM and the reaction time was varied between 1-60 minutes. Optimization of the cleavage reaction conditions revealed that the concentration and cleavage time for Sth3 and Spy Cas9 complexes could be reduced to 0.5 nM (at a 60 min. incubation time) or 1 min. (at a 50 nM concentration of Cas9 complex), respectively (FIG. 7).

Figure 8:
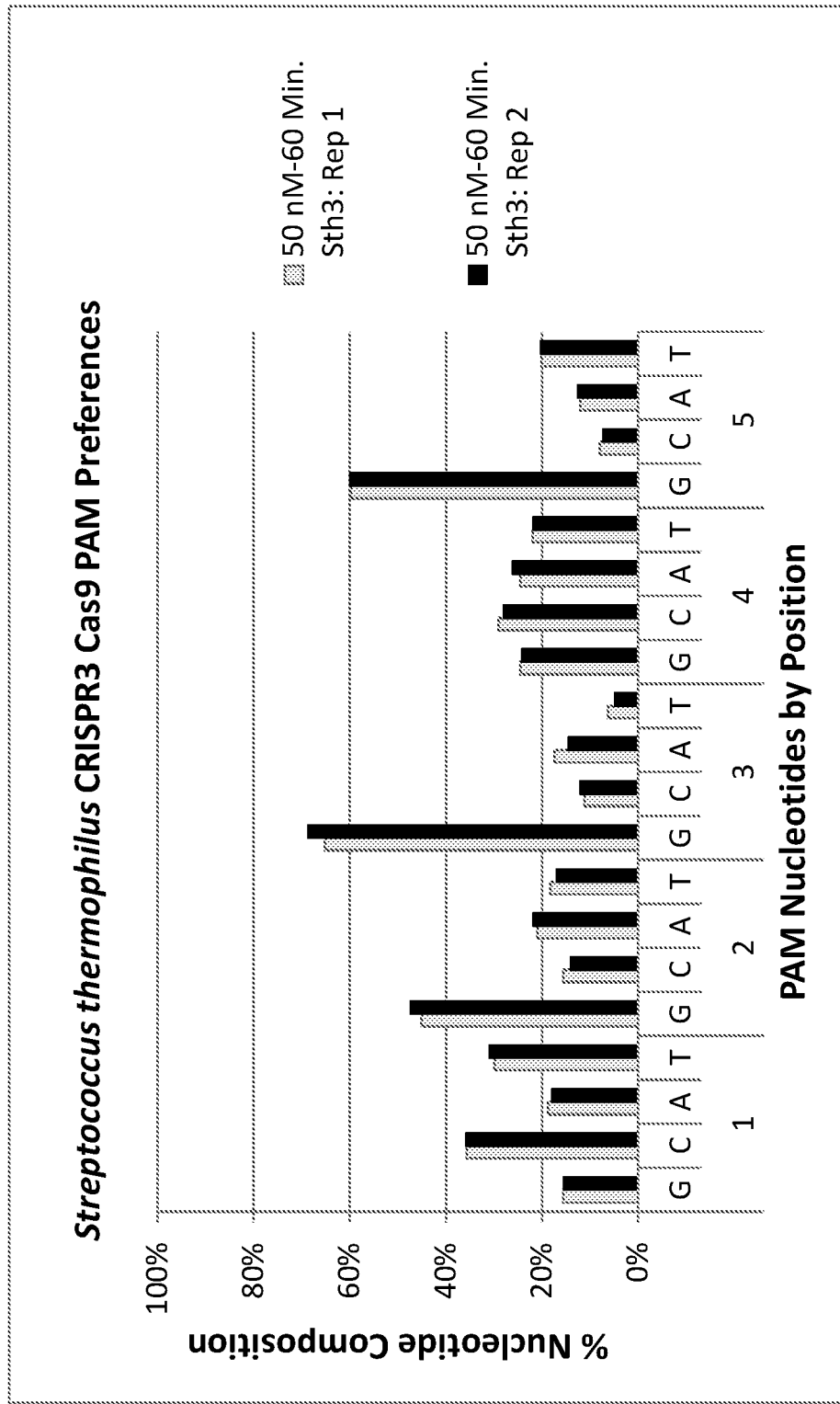
FIG. 8 shows the PAM preferences (NGGNG) for *Streptococcus thermophilus* CRISPR3 (Sth3) Cas9 endonuclease positive controls in both 50 nM and 100 nM digests.
Figure 9:
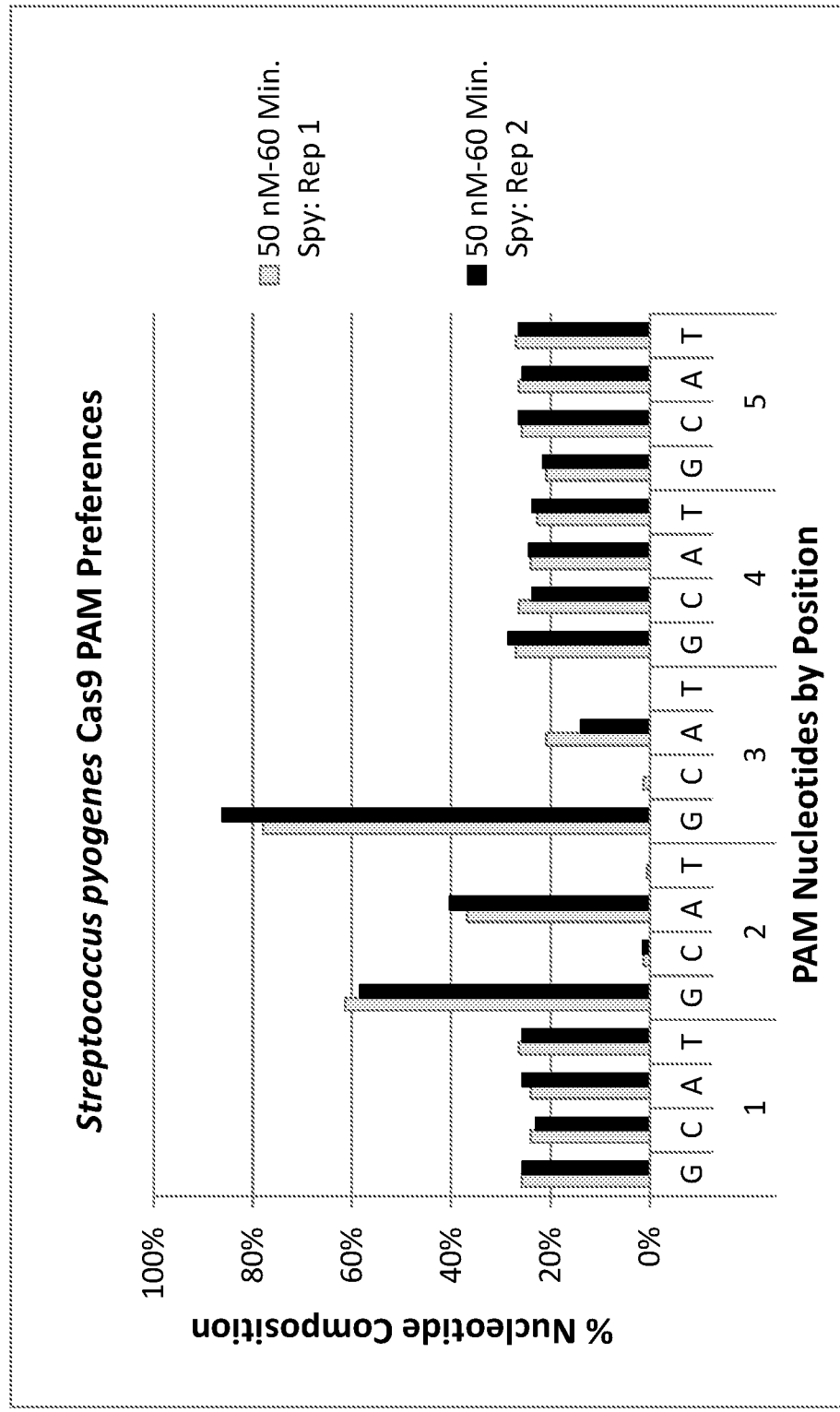
FIG. 9 shows the PAM preferences (NGG) for *Streptococcus pyogenes* (Spy) Cas9 endonuclease positive controls in both 50 nM and 100 nM digests.

To examine the PAM sequences present in the minimally digested Sth3 and Spy Cas9-guide RNA libraries, 0.5 nM-60 minute and 50 nM-1 minute PCR amplified cleavage products were purified with the GeneJET PCR Purification Kit (Thermo Fisher Scientific) and subjected to Illumina deep sequencing as described above for the 50 nM and 100 nM-60 minute Sth3 and Spy digests. As a positive control and to demonstrate the reproducibility of PAM preferences derived from our assay, the 50 nM-60 minute digests for Sth3 and Spy were repeated and Illumina deep sequenced again. PAM preference analysis was carried-out as described above for the Sth3 and Spy (50 nM and 100 nM-60 minute digests) examining the percent nucleotide composition of the PAM sequences with fold enrichment relative to the uncut library. As shown in FIG. 8 and FIG. 9, the positive controls (Sth3 and Spy 50 nM-60 minute digests) demonstrated very similar trends in PAM preferences compared to that observed previously indicating a high degree of assay reproducibility. The PAM preferences observed in the minimally Sth3 and Spy digested libraries compared to that exhibited by the respective 50 nM-60 minute positive control are shown in FIG. 10 and FIG. 11. When the concentration of Sth3 Cas9-crRNA-tracrRNA complex is lowered to 0.5 nM, the percentage of uncanonical PAM residues cleaved by Sth3 decreases; resulting in a tightening of specificity (FIG. 10). This is most evident at positions 2 and 3 where on-nucleotide preferences for a G increase and off-nucleotide preferences decrease. A similar shift in PAM preference towards the reported PAM sequence for Spy (NGG) is observed when the Spy Cas9-crRNA-tracrRNA complex is lowered to 0.5 nM. Here the percentage of PAMs with an uncanonical A residue at position 2 declines from over 20% in the 50 nM-60 minute and 50 nM-1 minute digests to almost zero in the 0.5 nM-60 minute digest (FIG. 11).

Next, the effect of using a chimeric fusion of crRNA and tracrRNA (single guide RNA (sgRNA)) (Jinek et al. (2012) *Science* 337:816-21 and Gasiunas et al. (2012) *Proc. Natl acad. Sci. USA* 109: E2579-E2586) on Sth3 and Spy Cas9 PAM preferences was assayed. Digestion, enrichment, Illumina deep sequencing and PAM preference analysis was carried-out as described above against the randomized 5 bp PAM plasmid DNA library except a sgRNA (Table 5) was used in place of the crRNA-tracrRNA duplex and digests were only performed with 0.5 nM of sgRNA-Cas9 complex for 60 min.

TABLE 5

RNA molecules used for Cas9-sgRNA complex assembly.

| Name | Sequence (5'-3') | Origin | SEQ ID NO. |
|---|---|---|---|
| Sth3 sgRNA | GGGCGCUAAAGAGGAAGAGGACAGU UUUAGAGCUGUGUUGUUUCGGUUAA AACAACACAGCGAGUUAAAAUAAGGC UUAGUCCGUACUCAACUUGAAAAGG UGGCACCGAUUCGGUGUUUUUU | In vitro transcription | 26 |
| Spy sgRNA | GGGCGCUAAAGAGGAAGAGGACAGU UUUAGAGCUAGAAAUAGCAAGUUAAA AUAAGGCUAGUCCGUUAUCAACUUG AAAAAGUGGCACCGAGUCGGUGCUU UUUU | In vitro transcription | 27 |

As shown in FIG. 12 and FIG. 13, the PAM preferences for Sth3 and Spy Cas9 proteins (NGGNG and NGG respectively) are nearly identical regardless of the type of guide RNA used; either a crRNA-tracrRNA duplex or sgRNA.

Example 4

Identification of PAM Preferences for *Streptococcus thermophilus* CRISPR1 Cas9 Protein To empirically examine the PAM preferences for *Streptococcus thermophilus* CRISPR1 (Sth1) Cas9 protein with a reported PAM sequence of 7 nucleotides, NNAGAAW (Horvath et al. (2008) *Journal of Bacteriology* 190:1401-12), a randomized 7 bp PAM plasmid DNA library was generated as described for the 5 bp randomized PAM library in Example 1 with the following modifications. Randomization of the PAM sequence was generated through the synthesis of four oligonucleotides, GG-940-G (GTGCACGCCGGCG-ACGTTGGGTCAACTNNGNNNNTGTCCTCTTCCT-CTTTAG CGTTTAG (SEQ ID NO: 28), GG-940-C (GTGCACGCCGGCGACGTTGGGTCAACTNNCN-NNNTGTCCTCTTCCTCTTTAG CGTTTAG (SEQ ID NO: 29), GG-940-A (GTGCACGCCGGCGACGTTGGGT-CAACTNNANNNNTGTCCTCTTCCTCTTTAG CGTT-TAG (SEQ ID NO: 30) and GG-940-T (GTGCACGCCGGCGACGTTGGGTCAACTNNTNN-NNTGTCCTCTTCCTCTTTAG CGTTTAG (SEQ ID NO: 31), with hand-mixing used to create a random incorporation of nucleotides across the random residues (represented as N). The randomized single stranded oligonucleotides were each separately converted into double-stranded DNA templates for cloning into the plasmid vector using a second oligonucleotide, GG-939 (GACTAGACCTGCAGGG-GATCCCGTCGACAAATTCTAAACGCTAAAGAG-GAAG AGGAC (SEQ ID NO: 126), with complementation to the 3' end of GG-940-G, GG-940-C, GG-940-A and GG-940-T and by PCR extension with DreamTaq polymerase (Thermo Fisher Scientific) (oligoduplexes I & II FIG. 1). To avoid cleavage of some species of the randomized positions, the resulting double-stranded templates were each digested with an 8 bp cutting restriction endonuclease, SdaI, so that overhangs were present at each end; a PstI compatible overhang and a Taq added single 3' A overhang. The resulting overhangs were used to directionally ligate the 4 double-stranded templates into pTZ57R/T (Thermo Fisher Scientific) pre-cleaved with PstI. The ligations were $Ca^{2+}$ transformed into DH5α *E. coli* cells, plasmid DNA was recovered and combined from each of the 4 transformants derived from GG-940-G, GG-940-C, GG-940-A and GG-940-T to generate the randomized 7 bp NNNNNNN PAM plasmid DNA library.

PAM preference experiments with Sth1 Cas9 protein on the resulting 7 bp randomized PAM plasmid DNA library were carried-out similarly to that described in Example 3 for the *Streptococcus thermophilus* CRISPR3 (Sth3) and *Streptococcus pyogenes* (Spy) Cas9 proteins (against the 5 bp randomized PAM library). Briefly, Sth1 Cas9-crRNA-tracrRNA complexes were assembled by mixing Cas9 protein with pre-annealed crRNA and tracrRNA duplex (Table 6) at 1:1 molar ratio followed by incubation in a complex assembly buffer (10 mM Tris-HCl pH 7.5 at 37° C., 100 mM NaCl, 1 mM EDTA, 1 mM DTT) at 37° C. for 1 h. Digests were performed using 1 μg of randomized 7 bp PAM library with 50 nM Sth1 crRNA-tracrRNA-Cas9 complexes at 37° C. for 60 min., 50 nM Sth1 crRNA-tracrRNA-Cas9 complexes at 37° C. for 1 min. and 0.5 nM Sth1 crRNA-tracrRNA-Cas9 complexes at 37° C. for 60 min. (FIG. 3). As a positive control, 1 μg of the randomized 7 bp PAM library was also digested with Sth3 and Spy Cas9-sg RNA complexes (0.5 nM at 37° C. for 60 min.). A 3' dA was added to the blunt-ends of the cleaved fragments (FIG. 3). Next, duplexed adapter TK-117/TK-111 with a 3' dT overhang was ligated to the A overhang (FIG. 3). Then, PCR was assembled using primers pUC-dir (SEQ ID NO: 5) and TK-117 (SEQ ID NO: 20) to enrich for PAM sequences that supported cleavage (FIG. 3). 40 ng of the resulting PCR product was then amplified with Phusion® High Fidelity PCR Master Mix (New England Biolabs, M0531 L) adding on the sequences necessary for amplicon-specific barcodes and Illumina sequencing using "tailed" primers through two rounds of PCR each consisting of 10 cycles (FIG. 3). The sequences of the barcode specific forward primers used in the primary PCR reaction were similar to those listed in Table 3 and the reverse primer, JKYS812 (CAAGCAGAA-GACGGCATACGAGCTCTTCCGATCTCGGCGACG-TTGGGTC (SEQ ID NO: 32)), was paired with each of the forward primers. A set of primers, AATGATACGGCGAC-CACCGAGATCTACACTCTTTCCCTACACG (Universal Forward, SEQ ID NO: 8) and CAAGCAGAAGACGG-CATA (Universal Reverse, SEQ ID NO: 9), universal to all primary PCR reactions were utilized for the secondary PCR amplification.

TABLE 6

RNA molecules used for Sth1 Cas9-crRNA-tracrRNA complex assembly.

| Name | Sequence (5'-3') | Origin | SEQ ID NO. |
|---|---|---|---|
| Sth1 crRNA | CGCUAAAGAGGAAGAGGACAGU UUUUGUACUCUCAAGAUUUA | Synthetic oligonucleotide | 33 |
| Sth1 tracrRNA | GGGUAAAUCUUGCAGAAGCUACA AAGAUAAGGCUUCAUGCCGAAAU CAACACCCUGUCAUUUUAUGGCA GGGUGUUUUCG | In vitro transcription | 34 |

The resulting PCR amplifications were prepared and Illumina deep sequenced as described in Example 1 and PAM preference analysis was carried-out as described in Example 3 for the Sth3 and Spy (50 nM and 100 nM-60 minute digests) examining the percent nucleotide composition of the PAM sequences with fold enrichment relative to the uncut library. As shown in FIG. 14 and FIG. 15, the PAM preferences for the positive controls, Sth3 and Spy Cas9 proteins, are nearly identical regardless of the length of the randomized PAM plasmid DNA library used; either 5 bp or 7 bp. The PAM preferences observed for the Sth1 Cas9 protein are shown in FIG. 16 and match those previously reported (NNAGAAW). Just as observed for Sth3 and Spy Cas9 proteins, the PAM specificity of Sth1 is more relaxed at higher concentrations of guide RNA-Cas9 complex. This is most evident at position 5 where an off-preference for a C nucleotide is less prevalent at the lower 0.5 nM complex concentration.

Since the canonical PAM sequence preferences for Spy, Sth1 and Sth3 Cas9 proteins may be recapitulated with our assay regardless of the type of guide RNA used (either crRNA-tracrRNA or sgRNA) or length of the randomized PAM sequence, suggests that the in vitro PAM library assay described herein or derivations of it may be used to directly interrogate PAM specificity from any Cas9 assuming the guide RNA sequences, either crRNA-tracrRNA or sgRNA, may be successfully deduced. Additionally our assay grants precise control over the amount of Cas9 protein used in the in vitro digestion assays described herein allowing a detailed examination of Cas9 PAM specificity as a function of Cas9-guide RNA complex concentration as evident by the apparent broadening in PAM specificity as Cas9-guide RNA complex concentration was increased.

Example 5

Identification of *Brevibacillus laterosporus* crRNA, tracrRNA and Cas9 Endonuclease To empirically examine the PAM preferences for a Cas9 protein whose PAM was undefined, a cas9 gene from an uncharacterized Type II CRISPR-Cas system was identified by searching internal Pioneer-DuPont databases consisting of microbial genomes with the amino acid sequence of *S. thermophilus* CRISPR3 (Sth3) Cas9 (SEQ ID NO: 35). Amino acid alignment of Sth3 revealed 12.9% identity and 24.4% similarity at the protein level with a protein derived from a single long open-reading-frame of 3279 nucleotides (SEQ ID NO: 36) from the *Brevibacillus laterosporus* bacterial strain SSP360D4. Translation of the open-reading-frame encodes a protein of 1092 amino acids (not including the stop codon). Based on PFAM database searches the protein contained HNH endonuclease and CRISPR-associated domains all hallmarks of a Cas9 protein. The cas9 gene of SSP360D4 was also located upstream of a CRISPR array comprised of 7 repeat-spacer units (FIG. 17A). The repeat and spacer length (36 and 30 bp, accordingly) is similar to other Type II CRISPR-Cas systems. However, 5 of 8 repeats contain 1 or 2 bp mutations (FIG. 17B). Sequences of Repeat1 (SEQ ID NO: 37), Repeat4 (SEQ ID NO: 40) and Repeat5 (SEQ ID NO: 41) are conserved; therefore this sequence was selected as a template for designing single guide RNAs (sgRNAs). A region upstream of the cas9 gene is partially complementary (anti-repeat) to the 5'-terminus of the repeat suggesting a putative tracrRNA (FIG. 17A). The possible transcriptional directions of the putative tracrRNA were considered by examining the secondary structures and possible termination signals present in a RNA version of the sense and anti-sense genomic DNA sequences surrounding the anti-repeat. However, the transcriptional direction of the tracrRNA and CRISPR region could not be reliably determined bioinformatically, so a method described in Example 7 was designed to empirically determine the appropriate directions of transcription. Other genes typically found in a Type II CRISPR-Cas locus were either truncated, as was the case for cas1, or missing (FIG. 17A).

Example 6

Protein Expression and Purification of *Brevibacillus laterosporus* Cas9 Protein To examine the PAM specificity and guide RNA of *Brevibacillus laterosporus* (Blat) Cas9 protein with the in vitro cleavage assays described in Examples 7 & 8, Blat Cas9 protein was *E. coli* expressed and purified. Briefly, a DNA fragment encoding the *Brevibacillus laterosporus* Cas9 protein was PCR amplified directly from the Pioneer-DuPont strain, SSP360D4, using Blat-Cas9-dir (TACCATGGCATA-CACAATGGGAATAGATG (SEQ ID NO: 45) and Blat-Cas9-rev (TTCTCGAGACGACTAGTTGATTTAATC-GAATTGAC (SEQ ID NO: 46) primer pair and cloned into a pBAD24-CHis expression vector pre-cleaved over NcoI and XhoI sites. To establish optimal expression conditions three different *E. coli* strains, BL21 (DE3), DH10B and Rosetta (DE3), were analyzed. Highest expression yield of soluble Blat Cas9 protein was obtained in the BL21 (DE3) strain.

For purification, Blat Cas9 protein was expressed in *E. coli* BL21 (DE3) strain grown in LB broth supplemented with ampicillin (100 mg/ml). Cells were grown at 37° C. to an OD 600 of 0.5 at which time the growth temperature was decreased to 16° C. and expression induced with 0.2% (w/v) arabinose for 20 h. Cells were pelleted and resuspended in loading buffer (20 mM $KH_2PO_4$ pH7.0, 0.5 M NaCl, 10 mM imidazole, 5% glycerol) and disrupted by sonication. Cell debris was removed by centrifugation. The supernatant was loaded onto the $Ni^{2+}$-charged 5 ml HiTrap chelating HP column (GE Healthcare) and eluted with a linear gradient of increasing imidazole concentration. The fractions containing Cas9 were pooled and subsequently loaded onto heparin column for elution using a linear gradient of increasing NaCl concentration (from 0.5 to 1 M NaCl). The fractions containing Cas9 were pooled and dialyzed against 10 mM Bis-Tris-HCl pH 7.0, 300 mM KCl, 1 mM EDTA, 1 mM DTT, 50% (v/v) glycerol and stored at −20° C.

Example 7

Determination of Guide RNAs for the Cas9 of *Brevibacillus laterosporus*

To determine a guide RNA for the Cas9 protein identified in the *Brevibacillus laterosporus* (Blat) Type II CRISPR-Cas system, we designed two single guide RNA (sgRNA) variants to account for both possible expression scenarios of the tracrRNA and CRISPR array (FIG. 18 & Table 7) and used them to probe which expression scenario supported cleavage activity of Blat Cas9 in the 7 bp randomized PAM plasmid DNA library from Example 4.

sgRNAs were designed by first identifying the boundaries of the putative tracrRNA molecules by analyzing regions which were partially complementary to the 22 nt 5' terminus of the repeat (anti-repeat). Next, to determine the 3' end of the tracrRNA, possible secondary structures and terminators were used to predict the region of termination in the downstream fragment (FIGS. 19 and 20) using Mini-fold (Markham et al. (2008) *Methods in Molecular Biology* 453: 3-31). The sgRNAs contained a T7 polymerase transcription initiation recognition signal at the 5' end followed by a 20 nt target recognition sequence, 16 nt of crRNA repeat, 4 nt self-folding hairpin loop and anti-repeat sequence complementary to the repeat region of the crRNA followed by the remaining 3' part of the putative tracrRNA (Table 7). The sgRNA variant which contains a putative tracrRNA transcribed in the same direction as the cas9 gene is termed "direct" sgRNA, while the sgRNA containing the tracrRNA transcribed in the opposite direction a "reverse" sgRNA (FIG. 18).

The "direct" sgRNA encoding gene was obtained in two PCR steps. First two fragments were generated by PCR using GG-969/GG-839 (SEQ ID NO: 49/SEQ ID NO: 50) and TK-149/TK-150 (SEQ ID NO: 51/SEQ ID NO: 52) oligonucleotide primer pairs (Table 8). The fragments were purified with the GeneJET PCR Purification Kit (Thermo Fisher Scientific) and the full length sgRNA gene was assembled from these fragments by overlapping PCR using GG-969/TK-150 primer pairs. The "reverse" sgRNA encoding gene was amplified by PCR using GG-840/GG-841 oligonucleotide primer pairs (Table 8). To generate the sgRNA encoding plasmids pUC-Blat-dir-sgRNA and pUC-Blat-rev-sgRNA, the PCR fragments were cloned into pUC18 vector digested with SacI.

TABLE 7

"Direct" and "reverse" Blat sgRNAs used to deduce transcriptional direction of crRNA and tracrRNA loci.

| Blat sgRNA | T7 Transcription Initiation | Variable Targeting domain (SEQ ID NO:) | 16 nt of the repeat | Loop | Anti-Repeat | Remaining Putative 3' tracrRNA Sequence | SEQ ID NO: |
|---|---|---|---|---|---|---|---|
| Direct | GGG | 193 | 195 | GAAA | 197 | 199 | 47 |
| Reverse | GGG | 194 | 196 | GAAA | 198 | 200 | 48 |

TABLE 8

Oligonucleotides used for Blat sgRNA gene construction and sgRNA production.

| Name | Sequence (5'-3') | SEQ ID NO. |
|---|---|---|
| GG-969 | GGGCGCTAAAGAGGAAGAGGACAGCTATAGTTCCTTACTGAAAGGTAAGTTGCTATAGTAAGGGCAAC | 49 |
| GG-839 | CTAAAAACGGGCTAGGCGATCCCCAACGCCTCGGGTCTGTTGCCCTTACTATAGCAACTTAC | 50 |
| TK-149 | GATCGCCTAGCCCGTTTTTACGGGCTCTCCCCATATTCAAAATAATGACAGACGA | 51 |
| TK-150 | AAAAAAAAGCACCTCGGAAATAAATGCTCCAAGGTGCTCGTCTGTCATTATTTTGAATATGG | 52 |
| GG-840 | GGGCGCTAAAGAGGAAGAGGACAATCATATCATATCGAGGAAACTTGATATGATATGATACTTTCATTTTA | 53 |
| GG-841 | CATAAAATAGACAGATAAATGAGATTGACTTCGATGATATATGGATATAAAATGAAAGTATCATATCATATCAAG | 54 |
| TK-124 | TAATACGACTCACTATAGGGCGCTAAAGAGGAAGAGG | 55 |

TABLE 8-continued

Oligonucleotides used for Blat sgRNA gene construction and sgRNA production.

| Name | Sequence (5'-3') | SEQ ID NO. |
|---|---|---|
| TK-151 | AAAAAAAAGCACCTCGGAAATAAATG | 56 |
| TK-126 | ATAAAATAGACAGATAAATGAGATTGACTTCG | 57 |

"Direct" and "reverse" Blat sgRNAs were obtained by in vitro transcription using TranscriptAid T7 High Yield Transcription Kit (Thermo Fisher Scientific) from the PCR fragments containing a T7 promoter at the proximal end of the RNA coding sequence. The "direct" sgRNA encoding fragment (177 nt) was generated using the TK-124/TK-151primer pair (Table 8) with pUC-Blat-dir-sgRNA plasmid DNA as template, whereas the "reverse" sgRNA encoding fragment (118 nt) was generated using the TK-124/TK-126 primer pair with pUC-Blat-rev-sgRNA plasmid as template (Table 7). The resulting sgRNAs were purified using GeneJET RNA Cleanup and Concentration Micro Kit (Thermo Fisher Scientific) and used for complex assembly. Blat Cas9-sgRNA complexes were assembled by mixing Cas9 protein with sgRNA at 1:1 molar ratio followed by incubation in a complex assembly buffer (10 mM Tris-HCl pH 7.5, 100 mM NaCl, 1 mM EDTA, 1 mM DTT) at 37° C. for 1 h. Blat Cas9 cleavage of the 7 bp randomized PAM plasmid DNA library was performed similarly as described above for Spy and Sth3 Cas9 proteins (Example 3). Briefly, 50 nM of Blat Cas9 complexes, assembled using "direct" or "reverse" sgRNAs, respectively, were incubated with 1 μg plasmid DNA (of the 7 bp randomized library) for 60 min at 37° C. After library digestion and addition of 3' dA overhangs, adapters were ligated and cleavage products were PCR amplified (FIG. 3). Analysis of reaction products by agarose gel electrophoresis revealed that the "direct" sgRNA, but not the "reverse" sgRNA supported plasmid library cleavage (FIG. 21). Single guide RNAs targeting a target site in the genome of an organism can be designed by changing the targeting sequence of SEQ ID NO: 47 with any random nucleotide that can hybridize to any desired target sequence (e.g., guide RNA as shown in SEQ ID NO: 127).

Example 8

Identification of PAM Preferences for *Brevibacillus laterosporus* Cas9 Protein

After determining a guide RNA for *Brevibacillus laterosporus* (Blat) Cas9, PAM identification was performed similarly to that described in Example 3 for the Spy and Sth3 Cas9 proteins. Briefly, 1 μg of 7 bp randomized PAM plasmid library was digested with various concentrations of Blat Cas9-"direct" sgRNA complex, ranging between 0.5-50 nM, and at various reaction times, ranging from 1 to 60 minutes. Next, 3' dA overhangs were added to the cleavage products, adapters ligated and adapter-ligated cleavage products were PCR amplified. PCR reactions were then electrophoresed on a 1% agarose gel and visualized. As shown in FIG. 22 and similarly to that described for Sth3 and Spy Cas9 proteins, the minimal concentration and cleavage time needed to support visualization after PCR amplification were 0.5 nM (at a 60 min. incubation time) or 1 min. (at a 50 nM concentration of Cas9 complex). Next, the amplifications for the 50 nM-60 min., 50 nM-1 min. and 0.5 nM-60 min. digests were purified with the GeneJET PCR Purification Kit (Thermo Fisher Scientific) and Illumina sequencing anchors added by two rounds of PCR as described in Example 3 for the Sth3 and Spy Cas9 proteins when examining their PAM preferences with the 7 bp randomized PAM library. The resulting Illumina compatible libraries were then sequenced as described in Example 1 and PAM preference analysis was carried-out as described in Example 3 for the Sth3 and Spy (50 nM and 100 nM-60 minute digests) examining the percent nucleotide composition of the PAM sequences with fold enrichment relative to the uncut library. When the composition of the PAM sequences with fold enrichment for the 50 nM-60 minute, 50 nM-1 minute and 0.5 nM-60 minute digests were analyzed, the consensus PAM sequence for the Blat Cas9 protein was NNNNCND (N=G, C, A or T; D=A, G or T) with a strong preference for a C at position 5 of the PAM sequence (FIG. 23). A moderate preference for an A was observed at position 7 and slight preferences for a C or T at position 4 and G, C or A over T at position 6 was also noted. Similarly to Sth1, Sth3 and Spy Cas9 proteins, the PAM specificity broadens as the Cas9-sgRNA complex concentration increases. This is most evident at position 5 where a larger proportion of PAM sequences containing an A residue support cleavage at 50 nM compared with 0.5 nM Cas9-sgRNA complexes.

To confirm the cleavage positions for the Blat Cas9 protein, we engineered the pUC18-T1-GTCCCGT-PAM plasmid containing a 20 base pair region matching the spacer T1 (SEQ ID NO: 1) followed by a PAM sequence, GTCCCGT, falling within the PAM consensus for Blat. To generate the plasmid, first the synthetic oligoduplex containing T1 and GTCCCGT PAM sequences was assembled by annealing complementary oligonucleotides GG-935 (CAAATTCTAAACGCTAAAGAGGAAGAGGA-CAGTCCCG (SEQ ID NO: 58) and GG-936 (AAT-TCGGGACTGTCCTCTTCCTCTTTAGCGTTTAGAAT-TTGAGCT (SEQ ID NO: 59) and ligated into pUC18 vector pre-cleaved with ScaI and EcoRI. 2.5 µg of the resulting plasmid was then digested with 100 nM of the Blat Cas9-sgRNA complex in the 500 µl of reaction buffer at 37° C. for 60 min., purified using GeneJET PCR Purification Kit (Thermo Fisher Scientific) and electrophoresed on an agarose gel. Linear digestion products were then purified from the agarose gel using the GeneJET Gel Extraction Kit (Thermo Fisher Scientific). The cleaved region in Blat Cas9 linearized pUC18-T1-GTCCCGT-PAM plasmid was then directly sequenced with the pUC-EheD (CCG-CATCAGGCGCCATTCGCC (SEQ ID NO: 60) and pUC-LguR (GCGAGGAAGCGGAAGAGCGCCC (SEQ ID NO: 61) primers. The sequence results confirmed that plasmid DNA cleavage occurred in the protospacer 3 bp away from the PAM sequence (FIG. 24) similar to that observed for Sth3 and Spy Cas9 proteins.

The NNNNCND PAM sequence identified herein, can be introduced adjacent to any polynucleotide of interest, thereby creating a target site that can be recognized by a guide RNA/Cas9 endonuclease complex described herein, wherein the guide RNA/Cas9 endonuclease system is capable of recognizing, binding to, and optionally nicking or cleaving all or part of the target sequence adjacent to the NNNNCND PAM sequence.

Example 9

Characterization of Cas9 Endonucleases and their PAM Preferences, and Cognate Guide RNAs from Diverse Organisms The rapid in vitro methods described herein (Examples 1-8) can be used to identify and characterize Cas endonucleases from any organism and their related PAM preferences and guide RNAs elements.

Cas9 proteins of Type II-A, II-B and II-C subtypes were identified from the NCBI NR database using the PSI-BLAST program (Altschul S F, et al. (1997) *Nucleic Acids Res.* 25:3389-3402). A phylogenetic relationship of each Cas9 protein was visualized with CLANs software (Frickey T, Lupas A. (2004) *Bioinformatics* 20:3702-3704) and putative Cas9 endonucleases from different groupings were selected. Genomic DNA regions derived from non-pathogenic sources and those containing a clustered-regularly-interspace-short-palindromic repeat (CRISPR) array and a putative trans-activating CRISPR RNA (tracrRNA) coding region (defined by homology to the CRISPR repeat and termed the anti-repeat) in the vicinity of the Cas9 were chosen. In total, 11 diverse genomic DNA regions were selected for further analysis (Table 9).

A schematic of the genomic locus for each system is depicted in FIGS. 25-35. The cas9 gene open-reading-frame (ORF), CRISPR array, anti-repeat (the genomic DNA region demonstrating partial homology to the repeat consensus that indicates the location of the encoded tracrRNA) and other CRISPR-Cas genes are indicated for each system. The genomic DNA sequence and length of each cas9 gene ORF and cas9 gene translation (not including the stop codon) are referenced in Table 10 for each system. Table 10 lists the consensus sequence of the CRISPR array repeats from the genomic DNA locus of each system and the sequences of the anti-repeat for each system (as genomic DNA sequence on the same strand as the cas9 gene ORF).

As was done for the *Brevibacillus laterosporus* (BLAT) Type II CRISPR-Cas system (described in Example 6), the possible transcriptional directions of the putative tracrRNAs for each new system were considered by examining the secondary structures and possible termination signals present in a RNA version of the sense and anti-sense genomic DNA sequences surrounding the anti-repeat. Based on the hairpin-like secondary structures present for each system, the transcriptional direction of the tracrRNA was deduced for 10 of the 11 diverse Type II CRISPR-Cas systems. Because the anti-repeat in the tracrRNA can hybridize to the crRNA derived from the CRISPR array to form a duplexed RNA capable of guiding the Cas9 endonuclease to cleave invading DNA the transcriptional direction of the CRISPR array may also be determined based off the direction of tracrRNA transcription (since double-stranded RNA hybridizes with 5' to 3' directionality). The deduced transcriptional directions of both the tracrRNA and CRISPR array for each system are listed in Table 10 and are depicted in FIGS. 25-35. Based on the likely transcriptional direction of the tracrRNA and CRISPR array, single guide RNAs (sgRNAs) were also designed and are shown in Table 12. For the system, *Sulfurospirillum* sp. SCADC, where the transcriptional direction of the tracrRNA and CRISPR array could not be deduced two sgRNAs were designed (as described in Example 7 for the Blat Type II CRISPR-Cas system); one for each possible direction of tracrRNA transcription (Table 12).

Next the sgRNAs, will be complexed with the respective purified Cas9 protein and assayed for their ability to support cleavage of the 7 bp randomized PAM plasmid DNA library (as described in Example 7 for the Blat Type II CRISPR-Cas system). If the sgRNA does not support cleavage activity, new guide RNA designs (either sgRNA or duplexed crRNA and tracrRNA; in both possible transcriptional directions of the CRISPR array and anti-repeat region) will be tested for their ability to support cleavage.

Once a guide RNA that supports Cas9 cleavage has been established, the PAM specificity of each Cas9 endonuclease can be assayed (as described in Example 7 for the Blat Type II CRISPR-Cas system). After PAM preferences have been determined, the sgRNAs may be further refined for maximal activity or cellular transcription by either increasing or decreasing the tracrRNA 3' end tail length, increasing or decreasing crRNA repeat and tracrRNA anti-repeat length, modifying the 4 nt self-folding loop or altering the sequence composition.

TABLE 9

List of 11 organisms selected for the identification of diverse Type II CRISPR-Cas systems described herein.

| Bacterial Origin | Abbreviation | CRISPR-Cas System Subtype | Isolated from |
| --- | --- | --- | --- |
| *Lactobacillus reuteri* MIc3 | Lreu | II-A | Sourdough |
| *Lactobacillus rossiae* DSM 15814 | Lros | II-A | Sourdough |
| *Pediococcus pentosaceus* SL4 | Ppen | II-A | Meat |
| *Lactobacillus nodensis* JCM 14932 | Lnod | II-A | Dairy |
| *Sulfurospirillum* sp. SCADC | Sspe | II-B | Oil sands tailings pond |
| *Bifidobacterium thermophilum* DSM 20210 | Bthe | II-C | Dairy |
| *Loktanella vestfoldensis* | Lves | II-C | Lakes Ace and Pendant, Vestfold Hills, Antarctica |
| *Sphingomonas sanxanigenens* NX02 | Ssan | II-C | Isolated from soil |
| *Epilithonimonas tenax* DSM 16811 | Eten | II-C | River epilthon |
| *Sporocytophaga myxococcoides* | Smyx | II-C | From soil, cellulose decomposing organism |
| *Psychroflexus torquis* ATCC 700755 | Ptor | II-C | Prydz Bay, Antarctica |

TABLE 10

Sequence and length of the cas9 gene ORF and cas9 gene translation from each Type II CRISPR-Cas system identified by the methods described herein.

| Bacterial Origin | cas9 Gene ORF (SEQ ID NO) | Length of cas9 Gene ORF (bp) | Translation of cas9 Gene ORF (not including the stop codon) (SEQ ID NO) | Length of cas9 Gene Translation (No. of Amino Acids) |
| --- | --- | --- | --- | --- |
| Lreu | 70 | 4107 | 81 | 1368 |
| Lros | 71 | 4110 | 82 | 1369 |
| Ppen | 72 | 4041 | 83 | 1346 |
| Lnod | 73 | 3393 | 84 | 1130 |
| Sspe | 74 | 4086 | 85 | 1361 |
| Bthe | 75 | 3444 | 86 | 1147 |
| Lves | 76 | 3216 | 87 | 1071 |
| Ssan | 77 | 3318 | 88 | 1105 |
| Eten | 78 | 4200 | 89 | 1399 |
| Smyx | 79 | 4362 | 90 | 1453 |
| Ptor | 80 | 4530 | 91 | 1509 |

TABLE 11

CRISPR repeat consensus, anti-repeat (putative tracrRNA coding region) and deduced transcriptional directions of tracrRNA and CRISPR array relative to the cas9 gene ORF for 11 diverse Type II CRISPR-Cas systems.

| Bacterial Origin | CRISPR Repeat Consensus (SEQ ID NO) | Anti-Repeat (SEQ ID NO) | tracrRNA Transcriptional Direction (Relative to the cas9 Gene ORF) | CRISPR Array Transcriptional Direction (Relative to the cas9 Gene ORF) |
| --- | --- | --- | --- | --- |
| Lreu | 92 | 103 | Antisense | Sense |
| Lros | 93 | 104 | Antisense | Sense |
| Ppen | 94 | 105 | Antisense | Sense |
| Lnod | 95 | 106 | Sense | Sense |
| Sspe | 96 | 107 | Sense/Antisense | Sense/Antisense |
| Bthe | 97 | 108 | Sense | Antisense |
| Lves | 98 | 109 | Antisense | Antisense |
| Ssan | 99 | 110 | Antisense | Antisense |
| Eten | 100 | 111 | Antisense | Antisense |
| Smyx | 101 | 112 | Antisense | Sense |
| Ptor | 102 | 113 | Antisense | Antisense |

TABLE 12

Examples of sgRNAs components for each new diverse Type II CRISPR-Cas system described herein.

| Bacterial Origin | T7 Transcription Initiation | Variable Targeting domain (VT) | crRNA Repeat (SEQ ID NO::) | Loop | tracrRNA Anti-Repeat | Remaining Putative 3' tracrRNA Sequence | SEQ ID NO: |
|---|---|---|---|---|---|---|---|
| Lreu | GGG | $N_{20\,(*)}$ | 201 | $N_{4\,(**)}$ | 213 | 225 | 128 |
| Lros | GGG | $N_{20\,(*)}$ | 202 | $N_{4\,(**)}$ | 214 | 226 | 129 |
| Ppen | GGG | $N_{20\,(*)}$ | 203 | $N_{4\,(**)}$ | 215 | 227 | 130 |
| Lnod | GGG | $N_{20\,(*)}$ | 204 | $N_{4\,(**)}$ | 216 | 228 | 131 |
| Sspe (tracrRNA Sense-crRNA Sense) | GGG | $N_{20\,(*)}$ | 205 | $N_{4\,(**)}$ | 217 | 229 | 132 |
| Sspe (tracrRNA Antisense-crRNA Antisense) | GGG | $N_{20\,(*)}$ | 206 | $N_{4\,(**)}$ | 218 | 230 | 133 |
| Bthe | GGG | $N_{20\,(*)}$ | 207 | $N_{4\,(**)}$ | 219 | 231 | 134 |
| Lves | GGG | $N_{20\,(*)}$ | 208 | $N_{4\,(**)}$ | 220 | 232 | 135 |
| Ssan | GGG | $N_{20\,(*)}$ | 209 | $N_{4\,(**)}$ | 221 | 233 | 136 |
| Eten | GGG | $N_{20\,(*)}$ | 210 | $N_{4\,(**)}$ | 222 | 234 | 137 |
| Smyx | GGG | $N_{20\,(*)}$ | 211 | $N_{4\,(**)}$ | 223 | 235 | 138 |
| Ptor | GGG | $N_{20\,(*)}$ | 212 | $N_{4\,(**)}$ | 224 | 236 | 139 |

$N_{20\,(*)}$ indicates a series of 20 nucleotides as one example of a sgRNA variable targeting domain. As described herein, the variable targeting domain of a sgRNA can vary for example, but not limiting from at least 12 to 30 nucleotides. $N_{4\,(**)}$ indicates a loop of 4 nucleotides such as but not limiting to GAAA. As described herein, the length of the loop can vary from at least 3 nucleotides to 100 nucleotides.

Single guide RNAs targeting a target site in the genome of an organism can be designed by changing the targeting sequence of any one of SEQ ID NOs: 114-125 with any random nucleotide that can hybridize to any desired target sequence (such as, but not limiting to, the guide RNAs shown in SEQ ID NO: 127-139).

Example 10

PAM Specificity is not Greatly Influenced by the Type or Composition of the Guide RNA As described in Example 3 and 4, to empirically examine the PAM preferences for *Streptococcus pyogenes* (Spy), *Streptococcus thermophilus* CRISPR3 (Sth3) and *Streptococcus thermophilus* CRISPR1 Cas9 proteins, two randomized PAM libraries (described in Example 1 and 4) were generated. The two libraries increased in size and complexity from 5 randomized base pairs (1,024 potential PAM combinations) to 7 randomized base pairs (16,384 potential PAM combinations). These randomized libraries were subject to digestion with purified Sth3 and Spy Cas9 proteins (5N library, Example 3) and Sth1 (Example 4, 7N library) and guide RNA containing a variable targeting domain T1 (CGCUAAAGAG GAAGAGGACA; SEQ ID NO: 141) that hybridizes with, i.e., is complementary to, a sequence in the target DNA molecule (referred herein as target sequence), T1 (SEQ ID NO: 1).

To confirm that PAM specificity is independent of the type of guide RNA, duplexed crRNA: tracrRNA or single guide RNA (sgRNA), Spy, Sth3 and Sth1 Cas9 PAM preferences were examined using Cas9 sgRNA RNP complexes instead of Cas9 and crRNA:tracrRNA RNP complexes (FIG. 36 A-C). Digestion was carried-out at a single RNP complex concentration of 0.5 nM and PAM preference analysis was performed as described herein. As shown in FIG. 36 A-C, PAM preferences were nearly identical regardless of the type of guide RNA used; either a crRNA:tracrRNA duplex or sgRNA.

To confirm that PAM specificity is not greatly influenced by the composition of the target DNA or spacer sequence, the sequence on the opposite side of the 5 or 7 bp randomized library was targeted for cleavage with a different variable targeting domain, T2-5 (UCUAGAUA-GAUUACGAAUUC; SEQ ID NO: 142) for the 5 bp library or T2-7 (CCGGCGACGUUGGGUCAACU; SEQ IS NO: 143) for the 7 bp library. Spy and Sth3 Cas9 proteins preloaded with sgRNAs targeting the T2 sequence were used to interrogate the 5 bp randomized PAM library while the Sth1 Cas9-T2 sgRNA complexes were used to digest the 7 bp randomized PAM library. (Spy sgRNA T2, SEQ ID NO: 144; Sth3 sgRNA T2, SEQ ID NO: 145 and Spy sgRNA T2, SEQ ID NO: 147). The library was digested with Spy, Sth3 and Sth1 Cas9 proteins preloaded with sgRNAs targeting the T2 sequence and PAM preferences were assayed as described above. The PAM preferences for all 3 Cas9 proteins were nearly identical regardless of spacer and target DNA sequence (FIG. 37 A-C).

Example 11

Identification of Extended PAM Sequences

As shown in FIG. 23 (Example 8), the PAM consensus for the Blat Cas9 protein under the 0.5 nM digest conditions was NNNNCND (N=G, C, A or T; D=A, G or T) with a strong preference for a C at position 5 of the PAM sequence. A moderate preference for an A was observed at position 7 and slight preferences for a C or T at position 4 and G, C or A over T at position 6 were also noted when closely examining FIG. 23. Similarly to Spy, Sth3 and Sth1 Cas9 proteins, the PAM specificity broadens as the Cas9-sgRNA complex concentration increases. This was most evident at position 5 where a larger proportion of PAM sequences containing an A residue support cleavage at 50 nM compared with 0.5 nM digest conditions (FIG. 23).

Since Blat Cas9 may accept any base in the first 3 positions of its PAM sequence (FIG. 23), the spacer domain T1 (and corresponding variable targeting domain in the guide RNA, SEQ ID NO: 141) was shifted by 3 nucleotides to allow PAM identification to be extended from 7 to 10 bp. The shifted T1 variable targeting domain, T1-3 (AAACGC-UAAAGAGGAAGAGG, SEQ ID NO: 148), was incorporated into the Blat "direct" sgRNA resulting in sgRNA of SEQ ID NO: 149 (referred to as Blat sgRNA (T1-3) and PAM identification was performed as described previously for Spy, Sth3, Sth1 and Blat Cas9 proteins. PAM preference analysis revealed the PAM specificity for Blat Cas9 can be extended out to position 8 where there is a moderate preference for an additional A (FIG. 38).

To validate the PAM specificity for Blat Cas9, plasmids were engineered to contain mutations (GTCCCGAA (reference), GTCACGAA, GTCCTGAA, GTCCCGCA, GTCCCGAC, GTCCCGCC with mutations shown in bold and underlined, FIG. 39) in the most conserved residues of the PAM immediately downstream of a 20 base pair region matching the variable targeting domain T1 (SEQ ID NO: 141). In vitro cleavage reactions with the various PAM sequences were initiated by mixing supercoiled plasmid DNA with pre-assembled Blat Cas9-sgRNA complex (1:1 v/v ratio) at 15° C. The final reaction mixture contained 3 nM plasmid, 50 nM Cas9, 10 mM Tris-HCl (pH 7.5 at 37° C.), 100 mM NaCl, 1 mM DTT and 10 mM MgCl2 in a 100 µl reaction volume. Aliquots were removed at timed intervals and quenched with phenol/chloroform. The aqueous phase was mixed with 3× loading dye solution (0.01% (w/v) bromophenol blue and 75 mM EDTA in 50% (v/v) glycerol) and reaction products analyzed by agarose gel electrophoresis. The amount of supercoiled (SC) form was evaluated by densitometric analysis of ethidium bromide stained gels using the software ImageJ. Values of reaction rate constants were obtained as described by Szczelkun et al, 2014, *Proc. Natl. Acad. Sci. U.S.A.* 111: 9798-803). Replacement of the C nucleotide at the 5th position abolished plasmid DNA cleavage confirming its key role in Blat Cas9 PAM recognition (FIG. 39). Replacement of A nucleotides at the 7th and 8th positions significantly reduced (43× and 12×, respectively) the cleavage rate of supercoiled plasmid also indicating the importance of these nucleotides in Blat Cas9 PAM recognition (FIG. 39).

To confirm the cleavage positions for the Blat Cas9 protein with an optimal PAM sequence, a plasmid was engineered that contained a 20 base pair region matching the variable targeting domain T1 (SEQ ID NO: 141) followed by a PAM sequence, GTCCCGAA, falling within the PAM consensus for Blat Cas9, NNNNCNDD. We used direct sequencing to determine the ends of the linear DNA molecule generated by the Blat Cas9 RNP complex. The sequence results confirmed that plasmid DNA cleavage occurred in the protospacer 3 nucleotides away from the PAM sequence (FIG. 40 similar to that observed for Spy, Sth3 and Sth1 Cas9 proteins (Garneau et al, 2010, Nature 468: 67-71; Gasiunas et al, 2012, Proc. Natl. Acad. Sci. U.S.A. 109: E2579-2586; Jinek et al, 2012, Science 337: 816-21).

Example 12

In Planta Genome Editing Using Blat Cas9 and sgRNA

Following elucidation of the sgRNA and PAM preferences for Blat Cas9, maize optimized Cas9 and sgRNA expression cassettes were generated for in planta testing. The Blat cas9 gene was maize codon optimized and intron 2 of the potato ST-LSI gene was inserted to disrupt expression in *E. coli* and facilitate optimal splicing (Libiakova et al, 2001. Plant Cell Rep. 20: 610-615). To facilitate nuclear localization of the Blat Cas9 protein in maize cells, Simian virus 40 (SV40) monopartite (MAPKKKRKV, SEQ ID NO: 150) and *Agrobacterium tumefaciens* bipartite VirD2 T-DNA border endonuclease (KRPRDRHDGELG-GRKRAR, SEQ ID NO: 151) nuclear localization signals were incorporated at the amino and carboxyl-termini of the Cas9 open reading frame, respectively. To express the resulting maize optimized Blat cas9 gene in a robust constitutive manner, it was operably linked to a maize Ubiquitin promoter, 5' UTR and intron (Christensen et al, 1992, Plant Mol. Biol. 18: 675-689) and pin II terminator (An et al, 1989, Plant Cell 1: 115-122) in a plasmid DNA vector. To confer efficient sgRNA expression in maize cells, a maize U6 polymerase III promoter region isolated from *Zea mays* cultivar B73 residing on chromosome 8 at position 165,535,024-165,536,023 (B73 RefGen_v3) and terminator (TTTTTTTT) were isolated and operably fused to the 5' and 3' ends of a modified Blat sgRNA encoding DNA sequence. The modified Blat sgRNA contained two modifications from the sgRNA that was used in the in vitro studies (see Blat sgRNA (T1) direct; SEQ ID NO: 151), a T to G alteration at position 101 and a T to C modification at 159. The changes were introduced to remove potential premature U6 polymerase III signals in the Blat sgRNA. Alterations were introduced to have minimal impact on the secondary structure of the sgRNA compared to the version used in the in vitro studies (FIG. 41, SEQ ID NO: 152 and FIG. 42, SEQ ID NO: 153). For a direct comparison with the Blat Cas9 sgRNA system, equivalent Cas9 and sgRNA DNA expression vectors were also prepared for the Spy Cas9 sgRNA system.

To carefully compare the mutational efficiency resulting from the imperfect non-homologous end-joining (NHEJ) repair of DNA double-strand breaks (DSBs) resulting from Spy and Blat Cas9 cleavage, protospacer identical genomic target sites were selected by identifying targets with Spy and Blat Cas9 compatible PAMs, NGGYCVAA. Since Blat and Spy Cas9 both cleave between the 3 and 4 bp upstream of their respective PAM, genomic targets will be cleaved at the exact same position allowing a tighter correlation between NHEJ mutation frequency and cleavage activity. Identical variable targeting domain sequences were selected for Blat and Spy Cas9 by capturing the 18 to 21 nt sequence immediately upstream of the PAM. To ensure optimal U6 polymerase III expression and not introduce a mismatch within the sgRNA variable targeting domain (spacer), all target sequences were selected to naturally terminate in a G at their 5' end. Targets were selected in exon 1 and 4 of the maize fertility gene Ms45 (referred to as MS45 Exon1 and MS45 Exon 4; see also U.S. Pat. No. 5,478,369 incorporated herein by reference) and within the promoter region of the maize liguleless-1 gene (referred to as LIG34 Promoter target herein; Moreno et al. 1997. Genes and Development 11:616-628).

To rapidly examine the mutational activity of Blat Cas9 with the PAM and sgRNA identified herein, Blat and the equivalent Spy Cas9 and sgRNA DNA expression vectors were independently introduced into maize Hi-II (Armstrong & Green, 1985, Planta 164: 207-214) immature embryos (IEs) by particle gun transformation similar to that described in (Ananiev et al, 2009, Chromosoma 118: 157-177). Since particle gun transformation can be highly variable, a visual marker DNA expression cassette, Ds-Red, was also co-delivered with the Cas9 and sgRNA expression vectors to aid in the selection of evenly transformed IEs. In total, 3 transformation replicates were performed on 60-90 IEs and 20-30 of the most evenly transformed IEs from each replicate were harvested 3 days after transformation. Total genomic DNA was extracted and the region surrounding the target site was PCR amplified and deep sequenced to a read depth in excess of 300,000. The resulting reads were examined for the presence of mutations at the expected site of cleavage by comparison to control experiments where only the Cas9 DNA expression cassette was transformed. As shown in FIG. 43, mutations arising at the expected site of cleavage for Blat Cas9 were detected (in SEQ ID NOs: 155-164) with the most prevalent types of mutations being single base pair insertions or deletions. This pattern of imprecise mutagenic repair of the double-stranded DNA cut introduced by Blat Cas9 was also observed for the Spy Cas9 (FIG. 44; SEQ ID NOs: 165-174) and at other Cas9 sites in maize (data not shown). The mutational activity for Blat Cas9 was robust at 2 of the 3 sites tested and exceeded that of the Spy Cas9 at the Ms45 Exon 4 target site by ~30% (FIG. 45).

In Planta Mutation Detection

The DNA region surrounding the expected site of cleavage for each Cas9-guide RNA was amplified by PCR using Phusion® High Fidelity PCR Master Mix (NEB, USA) "tailing" on the sequences necessary for amplicon-specific barcodes and Illumina sequences through two rounds of PCR each consisting of 20 cycles. The primer pairs used in the primary PCR were JKYX1.1 (SEQ ID NO:181)/JKYS178Rd (SEQ ID NO:182), JKYS1083.1 (SEQ ID NO:183)/JKYS1084 (SEQ ID NO:184) and JKYX2.1 (SEQ ID NO:185)/JKYX3 (SEQ ID NO:186) corresponding to the Ms45 exon 1, Ms45 exon 4 and Lig34 promoter regions, respectively. A set of primers universal to the products from the primary reactions, JKY557 (SEQ ID NO:177)/JKY558 (SEQ ID NO:178), were used in the secondary PCR reaction. The resulting PCR amplifications were purified with a Qiagen PCR purification spin column (Qiagen, Germany), concentration measured with a Hoechst dye-based fluorometric assay, combined in an equimolar ratio, and single read 100 nucleotide-length amplicon sequencing was performed on Illumina's MiSeq Personal Sequencer with a 5-10% (v/v) spike of PhiX control v3 (Illumina, FC-110-3001) to off-set sequence bias. Only those reads with a nucleotide INDEL arising within the 10 nt window centered over the expected site of cleavage and not found in the negative controls were classified as mutations. Mutant reads with an identical mutation were counted and collapsed into a single read and the top 10 most prevalent mutations were visually confirmed as arising within the expected site of cleavage. The total numbers of visually confirmed mutations were then used to calculate the percentage of mutant reads based on the total number of reads of an appropriate length containing a perfect match to the barcode and forward primer.

Example 13

Simplified Construction of Randomized Protospacer-Adjacent-Motif (PAM) Libraries for Assaying Cas Endonuclease PAM Preferences To simplify construction for randomized PAM libraries, a fully double-stranded DNA oligoduplex as described in Example 1 (oligoduplex II) containing a region of randomization immediately adjacent to a DNA target sequence may be used directly as template for Cas endonuclease digestion. This would eliminate the cloning of the oligoduplex II fragment into a plasmid DNA vector allowing randomized PAM libraries to be constructed without the downstream E. coli transformation and plasmid DNA isolation steps. PAM sequences supporting Cas endonuclease cleavage in these linearized double-stranded DNA libraries would be captured and deep sequenced as described in Examples 3, 4 and 8 for Spy, Sth3, Sth1 and Blat Cas9 proteins. To identify those sequences that have truly been cleaved by a Cas endonuclease and not just the result of adaptor ligation to the end of an un-cleaved oligoduplex, an in silico enrichment step may be applied to the resulting deep sequencing reads by selecting for only those reads that contain an appropriate sequence junction resulting for Cas endonuclease cleavage and adapter ligation. Once reads harboring a PAM sequence that supported cleavage have been identified, their nucleotide composition may be analyzed similar to that described for Spy, Sth3, Sth1 and Blat Cas9 proteins in Examples 3, 4 and 8.

Example 14

Cas Endonuclease Proto-Spacer Adjacent Motifs (PAMs) May be Assayed Directly in E. coli Cell Lysate Cas endonuclease protein produced in E. coli may be directly (without subsequent purification steps) used to assay proto-spacer adjacent motif (PAM) recognition and single guide RNA (sgRNA) requirements upon cell lysis.

Streptococcus thermophilus CRISPR1 (Sth1) and Streptococcus thermophilus CRISPR3 (Sth3) Cas9 protein were produced in E. coli cells as described in Example 2 but without the purification steps. In brief, after cultures were grown, induced and allowed to express Cas9 protein, cell lysis was performed via sonication and cell debri was pelleted by centrifugation resulting in a cell lysate containing soluble Cas9 protein. Cas9-guide RNA complexes were assembled by combining 20 µl of resulting cell lysate with RiboLock RNase Inhibitor (40 U; Thermo Fisher Scientific) and 2 µg of T7 in vitro transcribed sgRNA (generated as described in Example 7) and incubated at room temperature for 15 min. To examine PAM preferences at different Cas9 concentrations, 1 µg of the 7 bp randomized PAM library (Example 4) was incubated with 10 µl of various dilutions (1-fold (undiluted), 10-fold and 100-fold) of cell lysate containing assembled Cas9 complexes in a 100 µl reaction buffer (10 mM Tris-HCl pH 7.5 at 37° C., 100 mM NaCl, 10 mM $MgCl_2$, 1 mM OTT) so that E. coli lysate was diluted to a final concentration of either 10-fold, 100-fold or 1000-fold, respectively. Reactions mixtures were incubated for 60 min. at 37°, DNA end repaired with 2.5 U T4 DNA polymerase (Thermo Fisher Scientific), RNA digested with 1 µl RNase A/T1 Mix (Thermo Fisher Scientific) and 3' dA added with 2.5 U of DreamTaq DNA Polymerase (Thermo Fisher Scientific). Finally, DNA was recovered using a GeneJET PCR Purification Kit (Thermo Fisher Scientific). DNA fragments resulting from cleavage by Cas9 were tagged with adapters, captured and prepared for Illumina deep sequencing as described in Example 3 (FIG. 3). The resulting libraries were deep sequenced as described in Example 1. PAM sequences were identified from the resulting sequence data as described in Example 3 by only selecting those reads containing a perfect 12 nt sequence match flanking either side of the 7 nt PAM sequence capturing only those PAM sequences resulting from perfect Cas9-guide RNA target site recognition, cleavage and adapter ligation. The collection of resulting PAM sequences were then collapsed into like sequences, counted, and frequency of each PAM supporting cleavage calculated. To compensate for inherent bias in the initial randomized PAM libraries, the frequency of each PAM sequence was next normalized to its frequency in the starting library. Then, a PAM consensus was calculated using a position frequency matrix (PFM). This was accomplished by first aligning the collapsed PAM sequences. Next, each nucleotide (G, C, A, or T) at each position of the PAM was weighted based on the frequency of the PAM sequence with which it was associated. Finally, the total contribution of each nucleotide (G, C, A, or T) at each PAM position was summed to generate the overall probability of identifying a given nucleotide at each PAM position within the dataset.

Tables 13-18 represent the position frequency matrix (PFM) and resulting PAM consensus at each position of the 7 bp randomized PAM library for the *Streptococcus thermophilus* CRISPR1 (Sth1) and *Streptococcus thermophilus* CRISPR3 (Sth3) Cas9 proteins when assayed at different concentrations of *E. coli* cell lysate. The nucleotide positions of the 7 bp randomized PAM library are indicated by 1, 2, 3, 4, 5, 6, and 7 in a 5' to 3' direction with 1 being the closest to the DNA sequence involved in spacer target site recognition. The frequency of each nucleotide (G, C, A, T) at a respective position is indicated as a %. The consensus PAM preference is listed at the bottom of the table (consensus). The numbers marked with an asterisk (*) indicate the nucleotide preference(s) at each position of the protospacer adjacent motif (PAM). The percentages in the position frequency matrix (PFM) tables represent the probability of finding the corresponding nucleotide at each position of the PAM sequence and can be used to infer the strength of PAM recognition at each position.

TABLE 13

Position frequency matrix (PFM) and PAM consensus for
*Streptococcus thermophilus* CRISPR1 Cas9 with Cas9 protein
provided via 10 fold dilution of *E. coli* cell lysate.

|  | 1 | 2 | 3 | 4 | 5 | 6 | 7 |
|---|---|---|---|---|---|---|---|
| G | 17.69% | 14.97% | 22.16% | 41.47%* | 9.34% | 8.56% | 21.79% |
| C | 27.64% | 29.63% | 5.67% | 17.96% | 28.97% | 10.45% | 13.89% |
| A | 26.54% | 25.79% | 70.38%* | 16.85% | 55.56%* | 64.09%* | 26.22%* |
| T | 28.13% | 29.61% | 1.79% | 23.72% | 6.13% | 16.90% | 38.10%* |
| Consensus | N | N | A | G | A | A | W |

TABLE 14

Position frequency matrix (PFM) and PAM consensus for *Streptococcus thermophilus* CRISPR1 Cas9 with Cas9 protein provided via 100 fold dilution of *E. coli* cell lysate.

|  | 1 | 2 | 3 | 4 | 5 | 6 | 7 |
|---|---|---|---|---|---|---|---|
| G | 19.80% | 16.70% | 27.37% | 43.52%* | 11.01% | 7.87% | 20.20% |
| C | 25.74% | 27.47% | 6.01% | 16.02% | 24.04% | 8.77% | 12.49% |
| A | 29.40% | 25.80% | 64.19%* | 18.73% | 59.60%* | 69.09%* | 27.66%* |
| T | 25.06% | 30.03% | 2.43% | 21.73% | 5.36% | 14.27% | 39.65%* |
| Consensus | N | N | A | G | A | A | W |

TABLE 15

Position frequency matrix (PFM) and PAM consensus for *Streptococcus thermophilus* CRISPR1 Cas9 with Cas9 protein provided via 1000 fold dilution of *E. coli* cell lysate.

|  | 1 | 2 | 3 | 4 | 5 | 6 | 7 |
|---|---|---|---|---|---|---|---|
| G | 19.72% | 16.25% | 24.92% | 53.70%* | 10.39% | 3.79% | 18.40% |
| C | 26.89% | 30.09% | 4.08% | 13.55% | 22.65% | 3.32% | 10.18% |
| A | 27.92% | 26.35% | 70.37%* | 15.20% | 64.60%* | 86.15%* | 33.19%* |
| T | 25.46% | 27.30% | 0.64% | 17.55% | 2.37% | 6.73% | 38.23%* |
| Consensus | N | N | A | G | A | A | W |

TABLE 16

Position frequency matrix (PFM) and PAM consensus for *Streptococcus thermophilus* CRISPR3 Cas9 with Cas9 protein provided via 10 fold dilution of *E. coli* cell lysate.

|  | 1 | 2 | 3 | 4 | 5 | 6 | 7 |
|---|---|---|---|---|---|---|---|
| G | 12.46% | 49.67%* | 80.76%* | 21.03% | 49.94%* | 23.46% | 21.96% |
| C | 26.60% | 9.72% | 5.67% | 15.73% | 10.22% | 20.97% | 24.97% |
| A | 16.71% | 22.42% | 8.85% | 35.35% | 19.75% | 27.10% | 25.69% |
| T | 44.23% | 18.18% | 4.72% | 27.89% | 20.10% | 28.46% | 27.39% |
| Consensus | N | G | G | N | G | N | N |

TABLE 17

Position frequency matrix (PFM) and PAM consensus for *Streptococcus thermophilus* CRISPR3 Cas9 with Cas9 protein provided via 100 fold dilution of *E. coli* cell lysate.

|  | 1 | 2 | 3 | 4 | 5 | 6 | 7 |
|---|---|---|---|---|---|---|---|
| G | 12.06% | 55.16%* | 82.16%* | 23.38% | 53.61%* | 23.02% | 22.39% |
| C | 28.81% | 11.09% | 5.10% | 17.36% | 10.19% | 21.26% | 24.06% |
| A | 22.84% | 17.33% | 9.02% | 31.55% | 18.80% | 25.87% | 25.64% |
| T | 36.28% | 16.42% | 3.72% | 27.71% | 17.40% | 29.84% | 27.91% |
| Consensus | N | G | G | N | G | N | N |

TABLE 18

Position frequency matrix (PFM) and PAM consensus for *Streptococcus thermophilus* CRISPR3 Cas9 with Cas9 protein provided via 1000 fold dilution of *E. coli* cell lysate.

|  | 1 | 2 | 3 | 4 | 5 | 6 | 7 |
|---|---|---|---|---|---|---|---|
| G | 12.26% | 63.66%* | 89.19%* | 27.07% | 54.77%* | 26.19% | 23.09% |
| C | 30.31% | 7.86% | 2.78% | 17.23% | 9.70% | 19.39% | 22.85% |
| A | 21.26% | 15.31% | 6.18% | 29.16% | 17.45% | 26.56% | 26.21% |
| T | 36.17% | 13.17% | 1.86% | 26.55% | 18.08% | 27.87% | 27.86% |
| Consensus | N | G | G | N | G | N | N |

As shown in Tables 13-18, all lysate dilutions yielded the canonical PAM preferences for Sth1 and Sth3 Cas9 proteins, NNAGAAW and NGGNG, respectively. Similar to the results with purified protein in Examples 3, 4 and 8, higher concentrations of lysate and consequentially Cas9 protein resulted in a relaxation of PAM specificity. This was most notable for the Sth3 Cas9 protein at PAM position 2 where the preference for a G residue is reduced from approximately 64% in the PFM in the 1000-fold dilution (final concentration) reaction to around 50% in the 10-fold dilution (final concentration) experiment (Tables 16-18). For Sth1 Cas9 protein, PAM positions 4, 5 and 6 were most particularly affected by different concentrations of Cas9 protein in the lysate dilution experiments.

This data indicates that the in vitro PAM library assay described herein obtained the same results for the PAM preferences for Sth1 and Sth3 Cas9 proteins when compared to assays where the Sth1 and Sth3 Cas9 proteins are stably expressed (in-vivo expressed). Hence, the in vitro PAM library assay described herein, or derivations of it, may be used to assay PAM specificity from any Cas endonuclease using unpurified Cas protein coming directly from *E. coli* lysate. Additionally by diluting *E. coli* lysate containing Cas9 protein, the in vitro PAM library assay permits the measurement of PAM specificity to be examined as a function of Cas endonuclease concentration as is evident by the apparent broadening in PAM specificity as *E. coli* lysate containing Cas9 protein was increased.

Example 15

Cas Endonuclease Proto-Spacer Adjacent Motifs (PAMs) May be Assayed Directly with In Vitro Translated Protein Cas endonuclease protein produced by in vitro translation may be used to directly (without subsequent purification steps) assay proto-spacer adjacent motifs (PAM) and single guide RNA (sgRNA) requirements.

The *Streptococcus pyogenes* (Spy) cas9 gene was codon optimized for expression in eukaryotes (maize) with standard methods known in the art and operably linked to the in vitro translation (IVT) vector pT7CFE1-NHIS-GST-CHA (Thermo Fisher Scientific). To eliminate expression of the HA tag, a stop codon was included between the Spy cas9 gene and C-terminal tag. The resulting plasmid was purified by phenol:chloroform extraction to remove residual RNases and further purified by precipitation with 2 volumes of ethanol in the presence of sodium acetate. Next, Spy protein was produced in vitro using a 1-Step Human Coupled IVT Kit (Thermo Fisher Scientific) per the manufacturer's instruction allowing the reaction to proceed overnight at 30° C. Following the incubation, the reactions were centrifuged at 10,000 rpm for 5 min. 20 µl of supernatant containing soluble Cas9 protein was mixed with 2 µg of T7 in vitro transcribed sgRNA (generated as described in Example 7) and incubated for 15 min. at room temperature. To examine PAM preferences at different Cas9 concentrations, 1 µg of the 7 bp randomized PAM library (Example 4) was incubated with 10 µl of various dilutions (1-fold (undiluted), 10-fold and 100-fold) of in vitro translation mixtures containing assembled Cas9 complexes in a 100 µl reaction buffer (10 mM Tris-HCl pH 7.5 at 37° C., 100 mM NaCl, 10 mM MgCl$_2$, 1 mM DTT) so that IVT supernatant was diluted to a final concentration of either 10-fold, 100-fold or 1000-fold. Reactions mixtures were incubated for 60 min at 37°, DNA end repaired with 2.5 U T4 DNA polymerase (Thermo Fisher Scientific), RNA digested with 1 µl RNase A/T1 Mix (Thermo Fisher Scientific) and 3' dA added with 2.5 U of DreamTaq DNA Polymerase (Thermo Fisher Scientific). Finally, DNA was recovered using a GeneJET PCR Purification Kit (Thermo Fisher Scientific). PAM sequences supporting cleavage were captured by adapter ligation and enriched for as described in Example 3 (FIG. 3). The resulting libraries were deep sequenced as described in Example 1. PAM sequences were identified from the resulting sequence data as described in Example 3 by only selecting those reads containing a perfect 12 nt sequence match flanking either side of the 5 or 7 nt PAM sequence capturing only those PAM sequences resulting from perfect Cas9-guide RNA target site recognition, cleavage and adapter ligation. To compensate for inherent bias in the initial randomized PAM library, the frequency of each PAM sequence was normalized to its frequency in the starting library and a PAM consensus was then calculated with a position frequency matrix (PFM) as described in Example 14.

Tables 19-21 represent the position frequency matrix (PFM) and resulting PAM consensus at each position of the 7 bp randomized PAM library for the *Streptococcus pyogenes* Cas9 protein when assayed at different concentrations of in vitro translated (IVT) supernatant. The nucleotide positions of the 7 bp randomized PAM library are indicated by 1, 2, 3, 4, 5, 6, and 7 in a 5' to 3' direction with 1 being the closest to the DNA sequence involved in spacer target site recognition. The frequency of each nucleotide (G, C, A, T) at a respective position is indicated as a %. The consensus PAM preference is listed at the bottom of the table (consensus). The numbers marked with an asterisk (*) indicate the nucleotide preference(s) at each position of the protospacer adjacent motif (PAM). The percentages in the position frequency matrix (PFM) tables represent the probability of finding the corresponding nucleotide at each position of the PAM sequence and can be used to infer the strength of PAM recognition at each position.

TABLE 19

Position frequency matrix (PFM) and PAM consensus for *Streptococcus pyogenes* Cas9 with Cas9 protein provided via 10 fold dilution of in vitro translated solution (IVT).

|  | 1 | 2 | 3 | 4 | 5 | 6 | 7 |
|---|---|---|---|---|---|---|---|
| G | 24.18% | 53.04%* | 72.63%* | 19.30% | 14.19% | 19.97% | 23.65% |
| C | 25.97% | 7.16% | 8.52% | 24.26% | 25.67% | 28.52% | 27.44% |
| A | 25.21% | 28.71% | 14.69% | 22.57% | 23.80% | 19.66% | 20.39% |
| T | 24.64% | 11.09% | 4.16% | 33.87% | 36.34% | 31.85% | 28.52% |
| Consensus | N | G | G | N | N | N | N |

TABLE 20

Position frequency matrix (PFM) and PAM consensus for *Streptococcus pyogenes* Cas9 with Cas9 protein provided via 100 fold dilution of in vitro translated solution (IVT).

|  | 1 | 2 | 3 | 4 | 5 | 6 | 7 |
|---|---|---|---|---|---|---|---|
| G | 23.84% | 52.07%* | 78.60%* | 21.17% | 14.72% | 19.66% | 22.39% |
| C | 24.16% | 6.26% | 4.34% | 21.69% | 23.72% | 28.60% | 27.09% |
| A | 26.64% | 34.55% | 14.85% | 25.33% | 25.90% | 20.48% | 21.29% |
| T | 25.36% | 7.12% | 2.21% | 31.82% | 35.66% | 31.26% | 29.23% |
| Consensus | N | G | G | N | N | N | N |

TABLE 21

Position frequency matrix (PFM) and PAM consensus for *Streptococcus pyogenes* Cas9 with Cas9 protein provided via 1000 fold dilution of in vitro translated solution (IVT).

|  | 1 | 2 | 3 | 4 | 5 | 6 | 7 |
|---|---|---|---|---|---|---|---|
| G | 23.39% | 81.14%* | 95.35%* | 27.51% | 15.79% | 19.98% | 22.92% |
| C | 22.34% | 2.54% | 0.80% | 14.69% | 23.08% | 26.85% | 25.30% |
| A | 29.08% | 12.52% | 3.07% | 26.65% | 25.51% | 22.87% | 22.57% |
| T | 25.19% | 3.80% | 0.78% | 31.15% | 35.63% | 30.29% | 29.22% |
| Consensus | N | G | G | N | N | N | N |

As illustrated in Tables 19-21, the PAM requirement preferences reported for the Spy Cas9 protein (NGG) may be recapitulated under all IVT dilutions. Similar to the results with purified protein in Examples 3, 4 and 8, higher concentrations of IVT supernatant and consequentially Cas9 protein resulted in a broadening of PAM specificity. This was most notable for Spy Cas9 at PAM position 2 where the frequency for an uncanonical A residue increases from approximately 13% in the PFM with the 1000-fold dilution (final concentration) reaction to around 29% in the 10-fold dilution (final concentration) experiment.

This data indicates that the in vitro translation (IVT) assay described herein obtained the same results for the PAM preferences for the Spy Cas9 protein when compared to assays where the Spy Cas9 protein is stably expressed (in-vivo expressed). Hence, the in vitro translation (IVT) assay described herein, or derivations of it, may be used to assay PAM specificity from any Cas endonuclease. Additionally by diluting IVT products containing Cas9 protein, our assay permits the measurement of PAM specificity to be examined as a function of Cas endonuclease concentration as evident by the apparent broadening in PAM specificity as IVT supernatant containing Cas9 protein was increased.

Example 16

Guide RNA and PAM Requirements for Novel Cas Endonucleases

The single guide RNA (sgRNA) and PAM requirements of the Cas9 endonucleases from *Lactobacillus reuteri* Mlc3 (Lreu), *Lactobacillus nodensis* JCM 14932 (Lnod), *Sulfurospirillum* sp. SCADC (Sspe), *Bifidobacterium thermophilum* DSM 20210 (Bthe), *Loktanella vestfoldensis* (Lves), *Epilithonimonas tenax* DSM 16811 (Eten) and *Sporocytophaga myxococcoides* (Smyx) (Example 9) were determined with the methods described herein.

If purified protein could not be easily obtained as described in Example 2, Cas9 protein from *E. coli* cell lysate as described in Example 14 or in vitro translated (IVT) Cas9 protein as described in Example 15 was utilized. Once a source of Cas9 protein was established, 1 μg of the 7 bp randomized PAM plasmid DNA library (Example 4) was subject to Cas9-guide RNA digestion at various concentrations of either purified protein, lysate, or IVT protein. DNA fragments resulting from cleavage by Cas9 were ligated to adapters, captured and prepared for Illumina deep sequencing as described in Example 3 (FIG. 3). The resulting libraries were deep sequenced as described in Example 1. Since the position of cleavage within target sites for novel Cas9 proteins is unknown, reads were 1$^{st}$ examined for the most predominant cleavage location by examining the junction resulting from cleavage and adapter ligation. After properly defining the position of cleavage, PAM sequences were identified from the resulting sequence data as described in Example 3 by only selecting those reads containing a perfect 12 nt sequence match flanking either side of the 5 or 7 nt PAM sequence. To compensate for inherent bias in the initial randomized PAM library, the frequency of each PAM sequence was normalized to its frequency in the starting library and a PAM consensus was then calculated with a position frequency matrix (PFM) as described in Example 14. To obtain the most accurate read-out on PAM specificity and avoid conditions that are conducive to promiscuous PAM recognition (Examples 3, 4, 8, 14 and 15), the lowest concentration of Cas9 (purified, *E. coli* lysate or IVT supernatant) that supported cleavage was used to ascertain the PAM recognition of each Cas9 protein.

Tables 22-28 represent the position frequency matrix (PFM) and resulting PAM consensus at each position of the 7 bp randomized PAM library for several previously uncharacterized Cas9 proteins. Results derived from the lowest concentration of Cas9 coming from either purified, *E. coli* lysate or in vitro translation (IVT) supernatant that supported cleavage are shown. The nucleotide positions of the 7 bp randomized PAM library are indicated by 1, 2, 3, 4, 5, 6, and 7 in a 5' to 3' direction with 1 being the closest to the DNA sequence involved in spacer target site recognition. The frequency of each nucleotide (G, C, A, T) at a respective position is indicated as a %. The consensus PAM preference is listed at the bottom of the table (consensus). The numbers marked with an asterisk (*) indicate the nucleotide preference(s) at each position of the protospacer adjacent motif (PAM). The percentages in the position frequency matrix (PFM) tables represent the probability of finding the corresponding nucleotide at each position of the PAM sequence and can be used to infer the strength of PAM recognition at each position.

TABLE 22

Position frequency matrix (PFM) and PAM consensus for *Lactobacillus reuteri* Cas9 when purified Cas9 protein was used (0.5 nM Cas9-guide RNA complex and 60 minute digestion time).

|  | 1 | 2 | 3 | 4 | 5 | 6 | 7 |
|---|---|---|---|---|---|---|---|
| G | 15.57% | 83.27%* | 98.90%* | 31.64% | 39.04%* | 25.51% | 15.86% |
| C | 15.96% | 2.44% | 0.12% | 17.94% | 24.13% | 26.77% | 34.32% |
| A | 17.74% | 11.81% | 0.66% | 14.84% | 11.30% | 22.13% | 18.37% |
| T | 50.73% | 2.48% | 0.32% | 35.58% | 25.53% | 25.58% | 31.44% |
| Consensus | N (T > V) | G | G | N | N (G > H) | N | N |

TABLE 23

Position frequency matrix (PFM) and PAM consensus for *Lactobacillus nodensis* Cas9 when purified Cas9 protein was used (50 nM Cas9-guide RNA complex and 60 minute digestion time).

|  | 1 | 2 | 3 | 4 | 5 | 6 | 7 |
|---|---|---|---|---|---|---|---|
| G | 21.47% | 13.95% | 2.62% | 7.92% | 4.07% | 5.67% | 24.14% |
| C | 25.74% | 23.76% | 2.07% | 1.53% | 1.68% | 1.29% | 16.67% |

TABLE 23-continued

Position frequency matrix (PFM) and PAM consensus for *Lactobacillus nodensis* Cas9 when purified Cas9 protein was used (50 nM Cas9-guide RNA complex and 60 minute digestion time).

|   | 1 | 2 | 3 | 4 | 5 | 6 | 7 |
|---|---|---|---|---|---|---|---|
| A | 22.41% | 19.73% | 94.31%* | 89.34%* | 93.77%* | 91.48%* | 33.13% |
| T | 30.38% | 42.56%* | 0.99% | 1.22% | 0.48% | 1.55% | 26.07% |
| Consensus | N | N (T > V) | A | A | A | A | N |

TABLE 24

Position frequency matrix (PFM) and PAM consensus for *Sulfurospirillum* sp. SCADC Cas9 with Cas9 protein provided via 1000 fold dilution of in vitro translated solution (IVT).

|   | 1 | 2 | 3 | 4 | 5 | 6 | 7 |
|---|---|---|---|---|---|---|---|
| G | 16.26% | 97.32%* | 97.67%* | 18.52% | 22.18% | 18.86% | 23.20% |
| C | 24.43% | 0.95% | 0.85% | 20.37% | 20.90% | 25.19% | 22.14% |
| A | 35.19% | 1.11% | 0.74% | 31.97% | 22.61% | 26.12% | 23.94% |
| T | 24.13% | 0.61% | 0.74% | 29.13% | 34.31% | 29.82% | 30.72% |
| Consensus | N | G | G | N | N | N | N |

TABLE 25

Position frequency matrix (PFM) and PAM consensus for *Bifidobacterium thermophilum* Cas9 when purified Cas9 protein was used (0.5 nM Cas9-guide RNA complex and 60 minute digestion time).

|   | 1 | 2 | 3 | 4 | 5 | 6 | 7 |
|---|---|---|---|---|---|---|---|
| G | 18.93% | 16.16% | 20.28% | 0.10% | 0.03% | 2.53% | 3.19% |
| C | 34.69% | 31.11% | 27.80% | 99.55%* | 99.05%* | 5.34% | 47.56%* |
| A | 23.13% | 28.52% | 28.76% | 0.13% | 0.40% | 91.44%* | 1.17% |
| T | 23.24% | 24.20% | 23.17% | 0.21% | 0.52% | 0.69% | 48.08%* |
| Consensus | N | N | N | C | C | A | Y |

TABLE 26

Position frequency matrix (PFM) and PAM consensus for *Loktanella vestfoldensis* Cas9 with Cas9 protein provided via 1000 fold dilution of *E. coli* cell lysate.

|   | 1 | 2 | 3 | 4 | 5 | 6 | 7 |
|---|---|---|---|---|---|---|---|
| G | 21.74% | 62.30%* | 51.21%* | 13.71% | 17.79% | 32.03%* | 23.70% |
| C | 29.99% | 8.00% | 5.94% | 10.17% | 5.73% | 14.72% | 23.82% |
| A | 16.37% | 21.66% | 37.33%* | 63.65%* | 64.49%* | 13.01% | 25.97% |
| T | 31.89% | 8.03% | 5.51% | 12.47% | 11.99% | 40.24%* | 26.51% |
| Consensus | N | G | R (G > A) | A | A | K | N |

TABLE 27

Position frequency matrix (PFM) and PAM consensus for *Epilithonimonas tenax* Cas9 with Cas9 protein provided via 10 fold dilution of *E. coli* cell lysate.

|   | 1 | 2 | 3 | 4 | 5 | 6 | 7 |
|---|---|---|---|---|---|---|---|
| G | 30.87%* | 25.83% | 39.60%* | 18.03% | 14.19% | 87.26%* | 91.40%* |
| C | 30.34%* | 7.27% | 3.14% | 7.13% | 11.68% | 2.31% | 2.27% |

TABLE 27-continued

Position frequency matrix (PFM) and PAM consensus for *Epilithonimonas tenax* Cas9 with Cas9 protein provided via 10 fold dilution of *E. coli* cell lysate.

|  | 1 | 2 | 3 | 4 | 5 | 6 | 7 |
|---|---|---|---|---|---|---|---|
| A | 15.84% | 63.47%* | 54.64%* | 71.53%* | 31.83%* | 3.18% | 2.88% |
| T | 22.95% | 3.43% | 2.61% | 3.30% | 42.29%* | 7.25% | 3.45% |
| Consensus | N (S > W) | A | R | A | N (W > S) | G | G |

TABLE 28

Position frequency matrix (PFM) and PAM consensus for *Sporocytophaga myxococcoides* Cas9 when purified Cas9 protein was used (50 nM Cas9-guide RNA complex and 60 minute digestion time).

|  | 1 | 2 | 3 | 4 | 5 | 6 | 7 |
|---|---|---|---|---|---|---|---|
| G | 10.48% | 19.15% | 2.54% | 4.72% | 1.02% | 7.00% | 23.48% |
| C | 26.01% | 14.45% | 0.56% | 23.74% | 0.80% | 3.23% | 17.02% |
| A | 19.94% | 59.05%* | 96.61%* | 7.74% | 97.97%* | 79.56%* | 28.21% |
| T | 43.58% | 7.35% | 0.29% | 63.80%* | 0.21% | 10.21% | 31.28% |
| Consensus | N (T > V) | A | A | T | A | A | N |

TABLE 29

Summary of sgRNA and PAM requirement for novel Cas endonucleases.

| Bacterial Origin | Abbreviation | PAM consensus | sgRNA SEQ ID NO: |
|---|---|---|---|
| *Lactobacillus reuteri* MIc3 | Lreu | Table 22 | 114 |
| *Lactobacillus nodensis* JCM 14932 | Lnod | Table 23 | 117 |
| *Sulfurospirillum* sp. SCADC | Sspe | Table 24 | 119 |
| *Bifidobacterium thermophilum* DSM 20210 | Bthe | Table 25 | 120 |
| *Loktanella vestfoldensis* | Lves | Table 26 | 121 |
| *Epilithonimonas tenax* DSM 16811 | Eten | Table 27 | 123 |
| *Sporocytophaga myxococcoides* | Smyx | Table 28 | 124 |

Among the Cas9 proteins examined, both the length and composition of PAM recognition was diverse. Two of the Cas9 proteins, Lreu and Sspe (Tables 22-23), exhibited PAM recognition similar to the *Streptococcus pyogenes* (Spy) Cas9 protein which predominantly recognizes a NGG PAM while others exhibited very C-rich (Bthe, Table 25) or A-rich (Lnod and Smyx; Tables 23 and 28) PAM recognition. Additionally, a couple of the Cas9 proteins, Eten and Lves (Tables 26 and 27), yielded characteristics of both G-rich and A-rich PAM recognition.

Unlike the diversity observed for PAM recognition, the position of target site cleavage did not differ greatly and was determined to be between the $3^{rd}$ and 4th bp upstream (5 prime) of the PAM for all Cas9 proteins except for one, the Cas9 protein from *Sulfurospirillum* sp. SCADC. Interestingly, the predominant cleavage location by examining the junction resulting from cleavage and adapter ligation was around the $7^{th}$ bp upstream (5 prime) of the PAM sequence.

Taken together, these data further suggest that the methods described herein can be used to characterize novel Cas endonuclease PAM and guide RNA requirements.

Example 17

In Planta Genome Editing with Novel Cas9 Endonucleases

After determining the proto-spacer adjacent motif (PAM) and guide RNA requirement as described herein, Cas9 proteins with novel PAM recognition were selected and tested for their ability to cleave and mutagenize maize chromosomal DNA as described in Example 12.

To expand the number and diversity of sites available for genome editing, Cas9 proteins with diverse PAM recognition were selected for evaluation in corn by preferentially choosing systems with either A, T or C-rich PAM recognition to best complement the G-rich PAM of the *Streptococcus pyogenes* (Spy) Cas9 protein. Once systems were selected, DNA target sites adjacent to the appropriate PAM sequence were chosen and maize optimized cas9 gene and single guide RNA (sgRNA) expression vectors were constructed and delivered into maize immature embryos as described in Example 12. Embryos were harvested two days after transformation and chromosomal DNA was analyzed for the presence of mutations resulting from DNA target site cleavage and repair as described in Example 12. The frequency of mutations identified at each target site for each Cas9 is listed in Table 30.

Interestingly, the *Bifidobacterium thermophilum* (Bthe) Cas9 protein failed to effectively mutagenize its target sites. However when different spacer lengths were tested for Bthe, the frequency of mutagenesis improved dramatically with a spacer length around 25 nt being the most optimal (FIG. 46). Since the minimal spacer length for the *Streptococcus pyogenes* (Spy) Cas9 sgRNA is approximately 17 nt in length, it seems that the sgRNA spacer DNA target interactions for Bthe Cas9 may provide enhanced specificity relative to the Spy Cas9 protein.

TABLE 30

Maize chromosomal target DNA mutation frequencies two days after transformation by particle gun.

| Origin of cas9 gene | DNA Target Location | sgRNA Spacer Length | Mutation Frequency |
|---|---|---|---|
| *Bifidobacterium thermophilum* DSM 20210 | Chr1: 51.81 cM<br>Chr9: 119.15 cM | 25<br>25 | 0.29%<br>0.05% |

TABLE 30-continued

Maize chromosomal target DNA mutation frequencies two days after transformation by particle gun.

| Origin of cas9 gene | DNA Target Location | sgRNA Spacer Length | Mutation Frequency |
|---|---|---|---|
| *Lactobacillus nodensis* JCM 14932 | Chr1: 51.81 cM<br>Chr9: 119.15 cM | 21<br>22 | 0.06%<br>0.28% |

Taken together, these results indicate that the methods described herein to characterize Cas endonuclease PAM recognition and guide RNA requirements are robust. Ultimately, allowing new Cas endonuclease systems to be characterized for genome editing applications.

That which is claimed:

1. A method for identification of a Protospacer-Adjacent-Motif (PAM) sequence, the method comprising:
   a) providing a library of circular double-stranded plasmid DNA, wherein each one of said plasmid DNA comprises a randomized Protospacer-Adjacent-Motif sequence integrated adjacent to a target sequence that can be recognized by a guide RNA/Cas endonuclease complex;
   b) providing to said library of plasmids a guide RNA and a Cas endonuclease protein, wherein said guide RNA and Cas endonuclease protein can form a complex that is capable of introducing a double strand break into the said target sequence, thereby creating a library of cleavage products;
   c) ligating 3' deoxyAdenine to the cleavage products;
   d) ligating adaptors to the library of cleavage products of (c) allowing for the library of cleavage products to be amplified;
   e) amplifying the library of cleavage products of (d) such that the cleavage products containing the randomized PAM sequence are enriched, thereby producing a library of enriched PAM-sided targets;
   f) sequencing the library of (a) and the library of enriched PAM-sided targets of (e) and identifying the nucleotide sequence adjacent to the target sequences in the cleavage products of (b) on either strand of the plasmid DNA, wherein said nucleotide sequence represents a putative Protospacer-Adjacent-Motif sequences; and,
   g) determining the fold enrichment of each nucleotide within the putative Protospacer-Adjacent-Motif sequence relative to the plasmid DNA library of (a).

2. The method of anyone of claim 1, wherein the randomized PAM sequence comprises at least 1, 2, 3, 4, 5, 6, 7, 8, 9, 10, 11, 12, 13, 14, 15, 16, 17, 18, 19 or 20 randomized nucleotides.

3. The method of claim 1, wherein the target sequence is at least 12, 13, 14, 15, 16, 17, 18, 19, 20, 21, 22, 23, 24, 25, 26, 27, 28, 29 or 30 nucleotides in length.

4. The method of claim 1, wherein the Cas endonuclease protein is provided as a purified protein, a cell lysate comprising said Cas endonuclease, a dilution of a cell lysate comprising said Cas endonuclease, an in-vitro translation mixture or an dilution of an in-vitro translation mixture.

5. The method of claim 1, wherein the Cas endonuclease protein is a Cas9 protein.

6. The method of claim 1, wherein the Cas endonuclease comprises an HNH domain and an RuvC domain.

7. The method of claim 1, wherein the Cas endonuclease, the guide RNA, or both in step (b) is(are) provided as a purified molecule(s).

8. The method of claim 1, wherein the Cas endonuclease, the guide RNA, or both in step (b) is(are) provided as part of a cell lysate.

9. The method of claim 1, wherein the Cas endonuclease, the guide RNA, or both in step (b) is(are) provided as in vitro transcription product(s).

10. The method of claim 5, wherein the Cas9 protein is from *Streptococcus thermophilus*.

* * * * *